(12) United States Patent
Pasternak et al.

(10) Patent No.: US 9,056,859 B2
(45) Date of Patent: Jun. 16, 2015

(54) INHIBITORS OF THE RENAL OUTER MEDULLARY POTASSIUM CHANNEL

(75) Inventors: Alexander Pasternak, Princeton, NJ (US); Reynalda K. deJesus, East Brunswick, NJ (US); Yuping Zhu, Edison, NJ (US); Lihu Yang, Edison, NJ (US); Shawn Walsh, Bridgewater, NJ (US); Haifeng Tang, Metuchen, NJ (US); Dooseop Kim, Seoul (KR); Barbara Pio, Hillsborough, NJ (US); Aurash Shahripour, Rathway, NJ (US); Kevin Belyk, Metuchen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/881,574

(22) PCT Filed: Oct. 24, 2011

(86) PCT No.: PCT/US2011/057421
§ 371 (c)(1),
(2), (4) Date: Apr. 25, 2013

(87) PCT Pub. No.: WO2012/058134
PCT Pub. Date: May 3, 2012

(65) Prior Publication Data
US 2013/0217680 A1    Aug. 22, 2013

Related U.S. Application Data

(60) Provisional application No. 61/408,217, filed on Oct. 29, 2010.

(51) Int. Cl.
| | | |
|---|---|---|
| C07D 257/04 | (2006.01) |
| C07D 405/12 | (2006.01) |
| C07D 405/14 | (2006.01) |
| C07D 413/12 | (2006.01) |
| C07D 413/14 | (2006.01) |
| C07D 495/04 | (2006.01) |
| A61K 31/496 | (2006.01) |
| C07D 311/76 | (2006.01) |
| C07D 311/80 | (2006.01) |
| C07D 403/10 | (2006.01) |
| C07D 307/88 | (2006.01) |
| C07D 311/02 | (2006.01) |
| C07D 405/06 | (2006.01) |
| C07D 471/08 | (2006.01) |
| C07D 487/08 | (2006.01) |

(52) U.S. Cl.
CPC ............ *C07D 405/12* (2013.01); *A61K 31/496* (2013.01); *C07D 405/14* (2013.01); *C07D 413/14* (2013.01); *C07D 311/76* (2013.01); *C07D 311/80* (2013.01); *C07D 403/10* (2013.01); *C07D 413/12* (2013.01); *C07D 471/08* (2013.01); *C07D 257/04* (2013.01); *C07D 487/08* (2013.01); *C07D 495/04* (2013.01); *C07D 307/88* (2013.01); *C07D 311/02* (2013.01); *C07D 405/06* (2013.01)

(58) Field of Classification Search
None
See application file for complete search history.

(56) References Cited

U.S. PATENT DOCUMENTS

| | | | |
|---|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

ACCF/AHA Practice Guideline, 2009 Focused update incorporated into the ACC/AHA 2005 guidelines . . . , Circulation, 2009, e391-e436, 119.

(Continued)

*Primary Examiner* — Emily Bernhardt
(74) *Attorney, Agent, or Firm* — Nicole M. Beeler; Catherine D. Fitch

(57) ABSTRACT

This invention relates to compounds having structural Formula (I); and pharmaceutically acceptable salts thereof which are inhibitors of the Renal Outer Medullary Potassium (ROMK) channel (Kir 1.1). The compounds of Formula I are useful as diuretics and natriuretics and therefore are useful for the therapy and prophylaxis of disorders resulting from excessive salt and water retention, including cardiovascular diseases such as hypertension and chronic and acute heart failure.

(I)

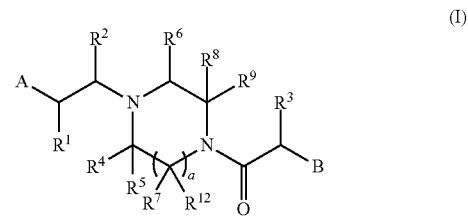

2 Claims, No Drawings

(56) References Cited

U.S. PATENT DOCUMENTS

| | | | |
|---|---|---|---|
| 5,736,546 A | 4/1998 | Kawashima et al. | |
| 6,258,813 B1 | 7/2001 | Arlt et al. | |
| 6,787,543 B2 | 9/2004 | Take et al. | |
| 7,754,724 B2 * | 7/2010 | Lorsbach et al. | 514/253.12 |
| 2004/0204404 A1 | 10/2004 | Zelle et al. | |
| 2005/0215526 A1 | 9/2005 | Hulme et al. | |
| 2005/0267121 A1 | 12/2005 | Li et al. | |
| 2006/0183739 A1 | 8/2006 | Tsaklakidis et al. | |
| 2006/0183742 A1 | 8/2006 | Mederski et al. | |
| 2006/0211692 A1 | 9/2006 | Mederski et al. | |
| 2007/0004750 A1 | 1/2007 | Lorsbach et al. | |
| 2007/0093472 A1 | 4/2007 | Mederski et al. | |
| 2008/0003214 A1 | 1/2008 | Cezanne et al. | |
| 2010/0286123 A1 | 11/2010 | Pasternak et al. | |

FOREIGN PATENT DOCUMENTS

| | | | |
|---|---|---|---|
| EP | 1094063 A1 | 4/2001 | |
| EP | 1939175 A1 | 7/2009 | |
| FR | 2673182 | 8/1992 | |
| GB | 949088 A | 2/1964 | |
| GB | 1575310 A | 9/1980 | |
| GB | 2116967 | 7/1986 | |
| WO | 9744329 | 11/1997 | |
| WO | 0051611 A1 | 9/2000 | |
| WO | 0204314 A1 | 6/2002 | |
| WO | 0250061 A1 | 6/2002 | |
| WO | 02032874 | 11/2003 | |
| WO | 2004020422 A1 | 3/2004 | |
| WO | 2004037817 A1 | 5/2004 | |
| WO | 2004046110 | 6/2004 | |
| WO | 2005037843 | 4/2005 | |
| WO | 2005044797 | 5/2005 | |
| WO | 2006034341 A2 | 3/2006 | |
| WO | 2006034769 A1 | 4/2006 | |
| WO | 2006098342 A1 | 9/2006 | |
| WO | 2006129199 A1 | 12/2006 | |
| WO | 2007075629 A2 | 7/2007 | |
| WO | 2008147864 | 12/2008 | |
| WO | 2009149508 | 11/2009 | |
| WO | 2010129379 A1 | 11/2010 | |
| WO | 2012058116 A1 | 5/2012 | |
| WO | 2013028474 A1 | 2/2013 | |
| WO | 2013039802 A1 | 3/2013 | |
| WO | 2013062892 A1 | 5/2013 | |
| WO | 2013062900 A1 | 5/2013 | |
| WO | 2013066714 A1 | 5/2013 | |
| WO | 2013066717 A1 | 5/2013 | |
| WO | 2013066718 A2 | 5/2013 | |
| WO | 2013090271 A1 | 6/2013 | |
| WO | 2014018764 A1 | 1/2014 | |

OTHER PUBLICATIONS

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave, G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-Isobenzofurandione 5-[[4-[(5-chloro-2-methoxyphenyl) sulfonyl]-1-..."

Cheymol et al., Increase in the effects of epinephrine and acetylcholine . . . , Comptes Rendus des seances de la Societe de Biologie, 1951, 496-499 (English trans.), 145.

Fallen, K., The Kir channel immunoglobuling domain is essential for Kir1.1 (ROMK) thermodynamic stability, trafficking and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report for PCT/US2011/057421, mailed Mar. 9, 2012, 4 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Supplementary European Search Report for PCT/US2011/057421, dated Feb. 21, 2014 , 4 pages.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

RELATED APPLICATIONS

This application is a U.S. National Phase application under 35 U.S.C. §371 from International Application No. PCT/US2011/057421, filed Oct. 24, 2011, which claims the benefit of U.S. Provisional Application No. 61/408,217, filed Oct. 29, 2010. Each of the aforementioned applications is herein incorporated by reference in its entirety.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Banter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103.

SUMMARY OF THE INVENTION

One object of the present invention is to provide compounds of Formula I

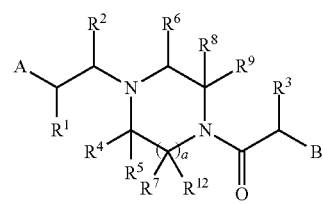

and the pharmaceutically acceptable salts thereof. The compounds of Formula I are inhibitors of the ROMK (Kir1.1) channel and can act as diuretics and natriuretics and are valuable pharmaceutically active compounds for the therapy and prophylaxis of diseases, including, but not limited to, cardiovascular diseases such as hypertension and conditions resulting from excessive salt and water retention. Therefore, an object of the invention is to provide methods of treatment comprising administering a therapeutically or prophylactically effective amount of a compound of Formula I to a patient in need of a diuretic and/or natriuretic agent. A further object is to provide the use of compounds of Formula I in combination with other therapeutically effective agents, including other drugs useful for the treatment of hypertension and conditions resulting from excessive salt and water retention. The invention furthermore relates to processes for preparing compounds of Formula I, and pharmaceutical compositions which comprise compounds of Formula L These and other objects will be evident from the description contained herein.

DETAILED DESCRIPTION OF THE INVENTION

The present invention is directed to compounds having structural Formula I:

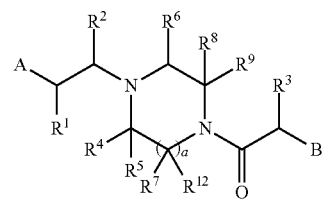

and the pharmaceutically acceptable salts thereof wherein:

A is 
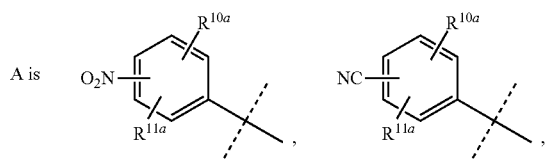

-continued

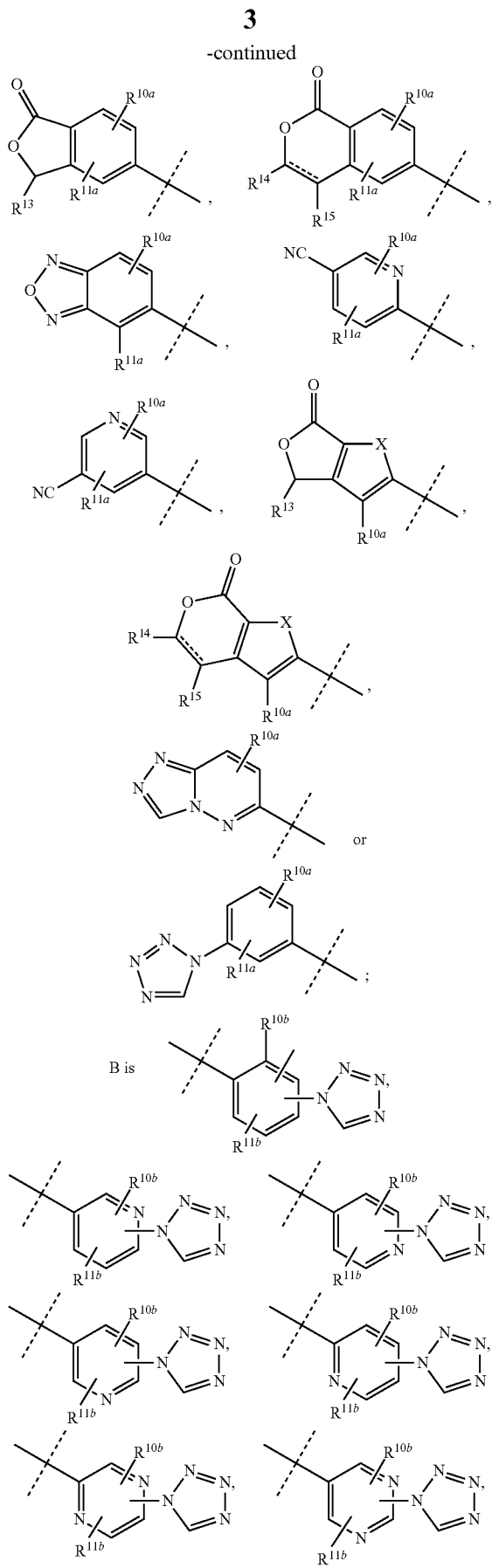

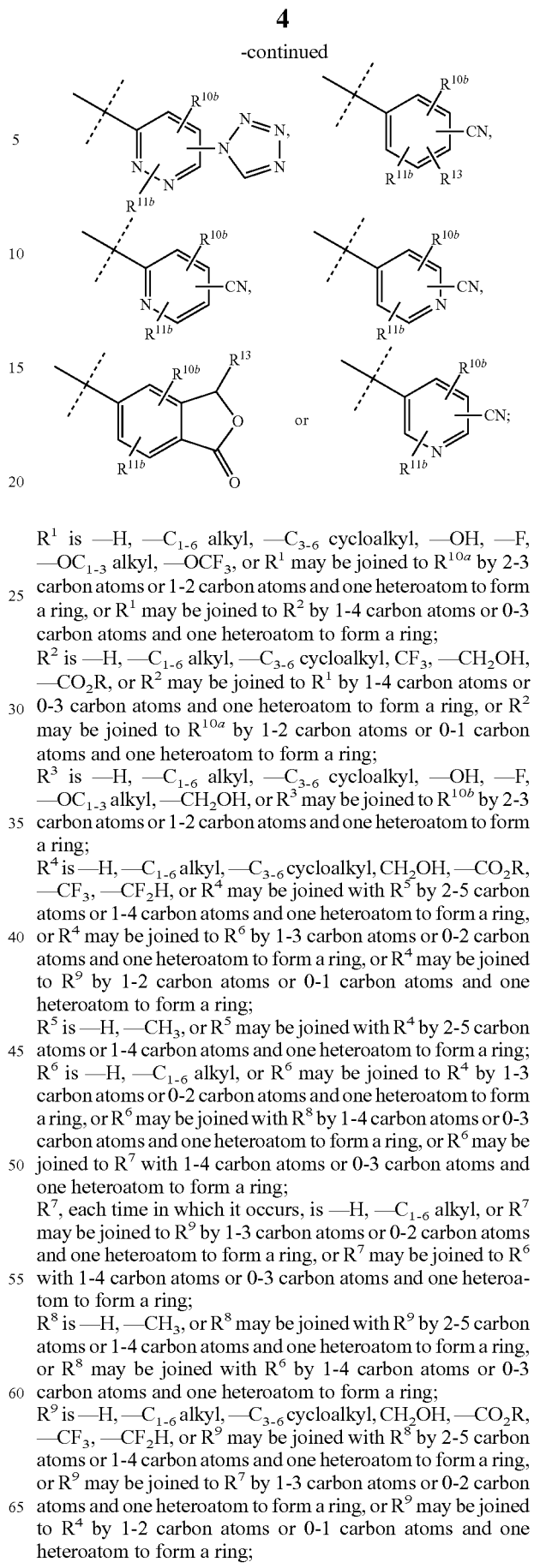

R$^1$ is —H, —C$_{1-6}$ alkyl, —C$_{3-6}$ cycloalkyl, —OH, —F, —OC$_{1-3}$ alkyl, —OCF$_3$, or R$^1$ may be joined to R$^{10a}$ by 2-3 carbon atoms or 1-2 carbon atoms and one heteroatom to form a ring, or R$^1$ may be joined to R$^2$ by 1-4 carbon atoms or 0-3 carbon atoms and one heteroatom to form a ring;

R$^2$ is —H, —C$_{1-6}$ alkyl, —C$_{3-6}$ cycloalkyl, CF$_3$, —CH$_2$OH, —CO$_2$R, or R$^2$ may be joined to R$^1$ by 1-4 carbon atoms or 0-3 carbon atoms and one heteroatom to form a ring, or R$^2$ may be joined to R$^{10a}$ by 1-2 carbon atoms or 0-1 carbon atoms and one heteroatom to form a ring;

R$^3$ is —H, —C$_{1-6}$ alkyl, —C$_{3-6}$ cycloalkyl, —OH, —F, —OC$_{1-3}$ alkyl, —CH$_2$OH, or R$^3$ may be joined to R$^{10b}$ by 2-3 carbon atoms or 1-2 carbon atoms and one heteroatom to form a ring;

R$^4$ is —H, —C$_{1-6}$ alkyl, —C$_{3-6}$ cycloalkyl, CH$_2$OH, —CO$_2$R, —CF$_3$, —CF$_2$H, or R$^4$ may be joined with R$^5$ by 2-5 carbon atoms or 1-4 carbon atoms and one heteroatom to form a ring, or R$^4$ may be joined to R$^6$ by 1-3 carbon atoms or 0-2 carbon atoms and one heteroatom to form a ring, or R$^4$ may be joined to R$^9$ by 1-2 carbon atoms or 0-1 carbon atoms and one heteroatom to form a ring;

R$^5$ is —H, —CH$_3$, or R$^5$ may be joined with R$^4$ by 2-5 carbon atoms or 1-4 carbon atoms and one heteroatom to form a ring;

R$^6$ is —H, —C$_{1-6}$ alkyl, or R$^6$ may be joined to R$^4$ by 1-3 carbon atoms or 0-2 carbon atoms and one heteroatom to form a ring, or R$^6$ may be joined with R$^8$ by 1-4 carbon atoms or 0-3 carbon atoms and one heteroatom to form a ring, or R$^6$ may be joined to R$^7$ with 1-4 carbon atoms or 0-3 carbon atoms and one heteroatom to form a ring;

R$^7$, each time in which it occurs, is —H, —C$_{1-6}$ alkyl, or R$^7$ may be joined to R$^9$ by 1-3 carbon atoms or 0-2 carbon atoms and one heteroatom to form a ring, or R$^7$ may be joined to R$^6$ with 1-4 carbon atoms or 0-3 carbon atoms and one heteroatom to form a ring;

R$^8$ is —H, —CH$_3$, or R$^8$ may be joined with R$^9$ by 2-5 carbon atoms or 1-4 carbon atoms and one heteroatom to form a ring, or R$^8$ may be joined with R$^6$ by 1-4 carbon atoms or 0-3 carbon atoms and one heteroatom to form a ring;

R$^9$ is —H, —C$_{1-6}$ alkyl, —C$_{3-6}$ cycloalkyl, CH$_2$OH, —CO$_2$R, —CF$_3$, —CF$_2$H, or R$^9$ may be joined with R$^8$ by 2-5 carbon atoms or 1-4 carbon atoms and one heteroatom to form a ring, or R$^9$ may be joined to R$^7$ by 1-3 carbon atoms or 0-2 carbon atoms and one heteroatom to form a ring, or R$^9$ may be joined to R$^4$ by 1-2 carbon atoms or 0-1 carbon atoms and one heteroatom to form a ring;

$R^{10a}$ is —H, —$C_{1-6}$ alkyl, —$C_{3-6}$ cycloalkyl, -halogen, $CF_3$, —$CH_2OH$, —$CO_2R$, —OR, —SR, —CN, -aryl, -heterocycle, or $R^{10a}$ may be joined to $R^1$ by 2-3 carbon atoms or 1-2 carbon atoms and one heteroatom to form a ring, or $R^{10a}$ may be joined to $R^2$ by 1-2 carbon atoms or 0-1 carbon atoms and one heteroatom to form a ring, or $R^{10a}$ may be joined to $R^{11a}$ by 3-4 carbon atoms or 2-3 carbon atoms and one heteroatom to form a ring;

$R^{10b}$ is —H, —$C_{1-6}$ alkyl, —$C_{3-6}$ cycloalkyl, -halogen, $CF_3$, —$CH_2OH$, —$CO_2R$, —OR, —SR, —CN, -aryl, -heterocycle, or $R^{10b}$ may be joined to $R^3$ by 2-3 carbon atoms or 1-2 carbon atoms and one heteroatom to form a ring, or $R^{10b}$ may be joined to $R^{11b}$ by 3-4 carbon atoms or 2-3 carbon atoms and one heteroatom to form a ring;

$R^{11a}$ is —H, —$C_{1-6}$ alkyl, —$C_{3-6}$ cycloalkyl, -halogen, $CF_3$, —$CH_2OH$, —$CO_2R$, —OR, —SR, -aryl, -heterocycle, or $R^{11a}$ may be joined to $R^{10a}$ by 3-4 carbon atoms or 2-3 carbon atoms and one heteroatom to form a ring;

$R^{11b}$ is —H, —$C_{1-6}$ alkyl, —$C_{3-6}$ cycloalkyl, -halogen, $CF_3$, —$CH_2OH$, —$CO_2R$, —OR, —SR, —CN, -aryl, -heterocycle, or $R^{11b}$ may be joined to $R^{10b}$ by 3-4 carbon atoms or 2-3 carbon atoms and one heteroatom to form a ring;

X is S or O;
R is —H, —$C_{1-6}$ alkyl, —$C_{3-6}$ cycloalkyl, or -halogen;
a is 1 or 2;
$R^{12}$, each time in which it occurs, is —H or —$C_{1-6}$ alkyl;
$R^{13}$ is —H, —$C_{1-6}$ alkyl, or —O—$C_{1-6}$ alkyl;
$R^{14}$ is —H, —$C_{1-6}$ alkyl, $C_{3-6}$ cycloalkyl, —$CF_3$, or $R^{14}$ and $R^{15}$, together with the atoms to which they are attached, form a phenyl ring; and
$R^{15}$ is —H, —$C_{1-6}$ alkyl, $C_{3-6}$ cycloalkyl, or $R^{15}$ and $R^{14}$, together with the atoms to which they are attached, form a phenyl ring.

In one embodiment of the invention are compounds where, and pharmaceutically acceptable salts thereof.

In another embodiment of the invention are compounds where $R^1$ is —H, methyl, methoxy, hydroxy, or fluoro, or is joined to $R^{10a}$ by 2-3 carbon atoms or 1-2 carbon atoms and one heteroatom to form a ring, and pharmaceutically acceptable salts thereof.

In another embodiment, $R^2$ is —H or methyl, or is joined to $R^{10a}$ by 1-2 carbon atoms or 0-1 carbon atoms and one heteroatom to form a ring, and pharmaceutically acceptable salts thereof.

In another embodiment, $R^3$ is —H or methyl, or is joined to $R^{10b}$ by 2-3 carbon atoms or 1-2 carbon atoms and one heteroatom to form a ring, and pharmaceutically acceptable salts thereof.

In another embodiment, $R^4$ is —H, and pharmaceutically acceptable salts thereof.

In another embodiment, $R^5$ is —H, and pharmaceutically acceptable salts thereof.

In another embodiment, $R^6$ is —H, and pharmaceutically acceptable salts thereof.

In another embodiment, $R^7$ is —H, and pharmaceutically acceptable salts thereof.

In another embodiment, $R^8$ is —H, and pharmaceutically acceptable salts thereof.

In another embodiment, $R^9$ is —H, and pharmaceutically acceptable salts thereof.

In another embodiment, $R^{10a}$ is —H, halogen, methoxy, —$SCH_3$, —$COOCH_3$ or —$CH_3$, or is joined to $R^1$ by 2-3 carbon atoms or 1-2 carbon atoms and one heteroatom to form a ring, or is joined to $R^2$ by 1-2 carbon atoms or 0-1 carbon atoms and one heteroatom, and pharmaceutically acceptable salts thereof.

In another embodiment, $R^{10b}$ is —H, halogen, methoxy, or —$CH_3$, or is joined to $R^3$ by 2-3 carbon atoms or 1-2 carbon atoms and one heteroatom to form a ring, and pharmaceutically acceptable salts thereof.

In another embodiment, $R^{11a}$ is —H, halogen, methoxy, ethoxy, or —$CH_3$, and pharmaceutically acceptable salts thereof.

In another embodiment, $R^{11b}$ is —H, halogen, methoxy, or —$CH_3$, and pharmaceutically acceptable salts thereof In another embodiment, a is 1, and pharmaceutically acceptable salts thereof.

In another embodiment, $R^6$ is joined to $R^8$ by a carbon atom to form a ring, and pharmaceutically acceptable salts thereof.

In another embodiment, $R^{14}$ is —H or —$CH_3$, or $R^{14}$ and $R^{15}$, together with the atoms to which they are attached, form a phenyl ring.

In another embodiment, $R^{15}$ is —H, or $R^{15}$ and $R^{14}$, together with the atoms to which they are attached, form a phenyl ring.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

In some instances the number of substituents which may be optionally present on a moiety is specified, for example but not limited to, 1 to 3 of —F (fluoro). For example, an alkyl group that can be optionally substituted with 1-3 of —F includes, but is not limited to, —$CH_3$, —$CH_2F$, —$CHF_2$, —$CF_3$, —$CH_2CH_3$, —$CH_2$—$CH_2F$, —$CH_2$—$CHF_2$, —CHF—$CH_2F$, —$CH_2CF_3$, —CHF—$CHF_2$, —$(CH_2)_2CH_3$, —$CH(CF_3)$—$CH_3$, —$(CH_2)_3$—$CF_3$, —$(CH_2)_2CH(CF_3)$ $CH_3$, and —$(CH_2)_5$—$CF_3$, as appropriate for the defined number of carbon atoms for the given alkyl group.

Halo or halogen refers to —F (fluoro), —Cl (chloro), —Br (bromo) and —I (iodo). Preferred halogens are —F and —Cl.

Unless expressly depicted or described otherwise, variables depicted in a structural formula with a "floating" bond, such as each of substituents $R^{10a}$, $R^{10b}$, $R^{11a}$ and $R^{11b}$ in structural Formula I, are permitted on any available carbon atom in the ring to which each is attached.

The image "$---$", when present in a ring, represents a single, double or aromatic bond.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulas II-X and all embodiments thereof) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and are therefore useful as diuretic and/or natriuretic agents. ROMK inhibitors help to increase urination and increase urine volume and also to prevent or reduce reabsorption of sodium in the kidneys leading to increased excretion of sodium and water. Therefore, the compounds are useful for treatment or prophylaxis of disorders that benefit from increased excretion of water and sodium from the body. Accordingly, an object of the instant invention is to provide a method for inhibiting ROMK comprising administering a compound of Formula I in a ROMK-inhibitory effective amount to a patient in need thereof. The inhibition of ROMK by the compounds of Formula I can be examined, for example, in any of the activity assays described below. Another object is to provide a method for causing diuresis, natriuresis or both, comprising administering a compound of Formula I in a therapeutically effective amount to a patient in need thereof.

Due to their activity as diuretics and natriuretic agents, this invention further provides the use of compounds of Formula I in methods for treatment of, prevention of or reduction of risk for developing medical conditions that benefit from increased excretion of water and sodium, such as but not limited to one or more of hypertension, heart failure (both acute and chronic, also known as congestive heart failure) and/or other conditions resulting from excessive salt and water retention. It further includes the use of the compounds of Formula I in methods for treatment of, prevention of or reduction of risk for developing one or more disorders such as pulmonary arterial hypertension (PAH), cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute and chronic kidney insufficiency, hypercalcemia, Dent's disease, Meniere's disease, edetamous states, and other conditions for which a diuretic would have therapeutic or prophylactic benefit. The compounds of the invention can be administered to a patient having, or at risk of having, one or more conditions for which a diuretic would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) the $^{86}Rb^+$ Efflux Assay, 2) the Thallium Flux Assay, 3) the Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohhylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a pharmaceutically active agent (or agents) that is active in the body, including pro-drugs that convert to pharmaceutically active form after administration, which is different from the compound of Formula I, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidan); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino dials (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTINTE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Several methods for preparing the compounds of this invention are described in the following Schemes and Examples. Starting materials and intermediates are purchased, made from known procedures, or as otherwise illustrated.

SCHEMES

Compounds of the formula I are prepared in a variety of ways as exemplified by the examples below. Some frequently applied routes to the compounds of the formula I are described by the Schemes below.

Compounds of the formula I may be prepared as shown in Scheme 1 by coupling of appropriately substituted piperazines 1 with carboxylic acids of the structure 2. This can be accomplished in many ways well-known to the chemist, including by using EDC in the presence or absence of HOBt and a base such as triethylamine, or by using a variety of other amide coupling reagents such as HATU.

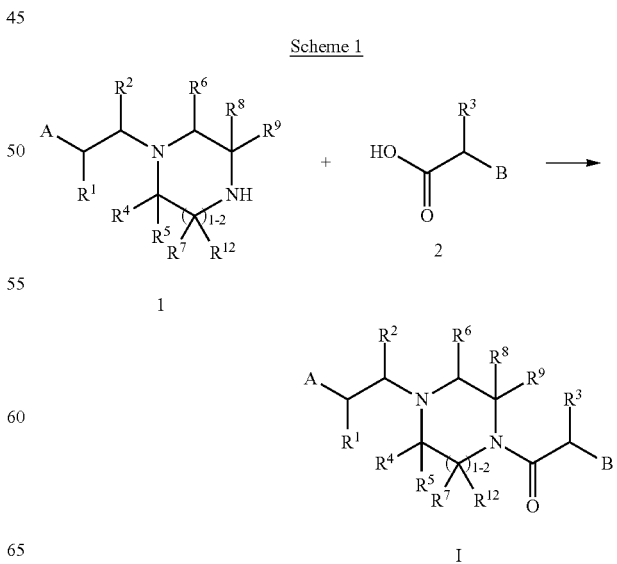

Alternatively, compounds of the formula I may also be prepared as shown in Scheme 2 by reductive alkylation reaction of appropriately substituted acylpiperazines 3 with aldehydes or ketones of the structure 4. This reaction may be accomplished in a wide variety of ways well-known to the chemist, including by use of reagents such as sodium triacetoxyborohydride in dichloromethane or 1,2-dichloroethane, or sodium cyanoborohydride (in the presence or absence of Ti(O-i-Pr)$_4$). In a related approach the ketone or aldehyde 4 may be prepared by ozonolysis of a corresponding alkene and then treated with the piperazine 3 in the same pot using a reducing agent such as sodium triacetoxyborohydride as described above.

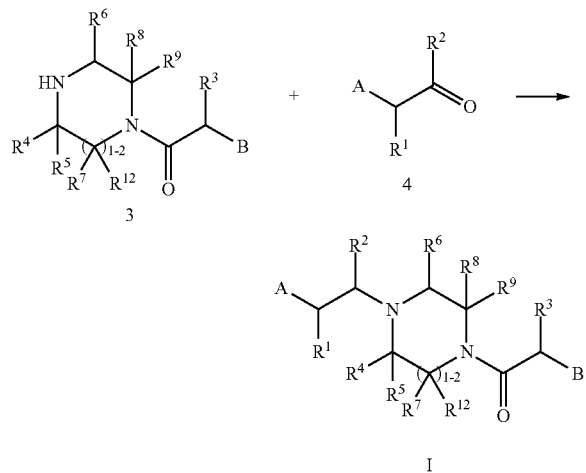

Another route to compounds of the formula I is depicted in Scheme 3 where appropriately substituted piperazines 3 may be alkylated by bromides (or iodides) of the formula 5 in the presence of a base such as triethylamine, and in the presence or absence of a phase transfer catalyst such as tetrabutylammonium iodide.

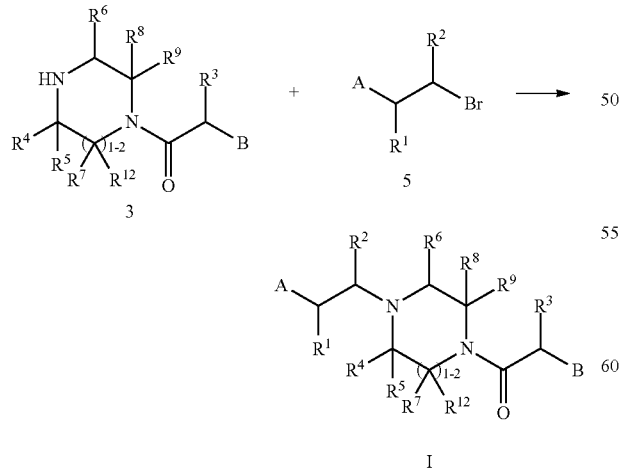

A sub-class of compounds of the present invention having the formula Ia may be prepared as described in Scheme 4 by reaction of appropriately substituted acylpiperazine 3 with epoxides of the structure 6 in the presence or absence of a base such as triethylamine in solvents such as ethanol or DMSO with heating. This transformation may also be performed using microwave irradiation to provide the heating.

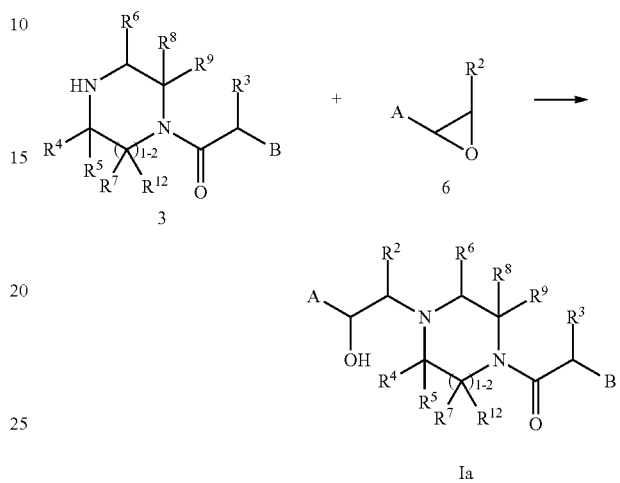

Intermediates of the structure type 1 can be prepared in a variety of ways including by the route depicted in Scheme 5' where aldehydes or ketones of the structure 4 are initially reductively aminated with protected (for example with a Boc protecting group as shown) piperazines of the structure 7 using reagents such as sodium triacetoxyborohydride or sodium cyanoborohydride. Then the protective group can be removed as appropriate to the type of protective group; for example, the Boc group can be removed by treatment with HCl in dioxane or ethyl acetate, or by treatment with TFA.

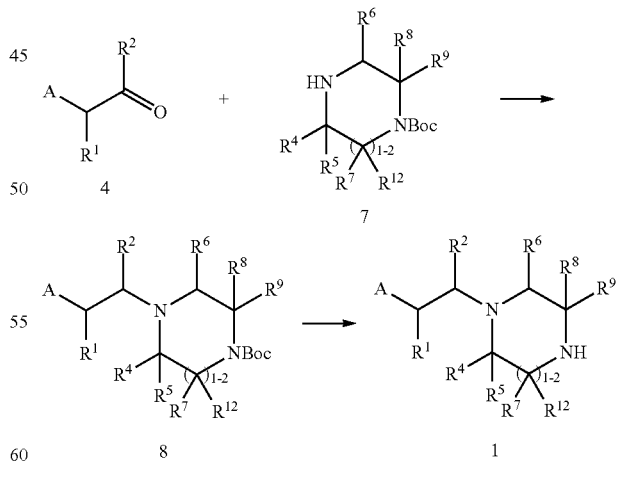

Alternatively, intermediates of the structure type 1 may also be directly prepared according to Scheme 6 by reductive alkylation of piperazines 9 with aldehydes or ketones of the structure 4 using reagents such as sodium triacetoxyborohydride or sodium cyanoborohydride.

Scheme 6

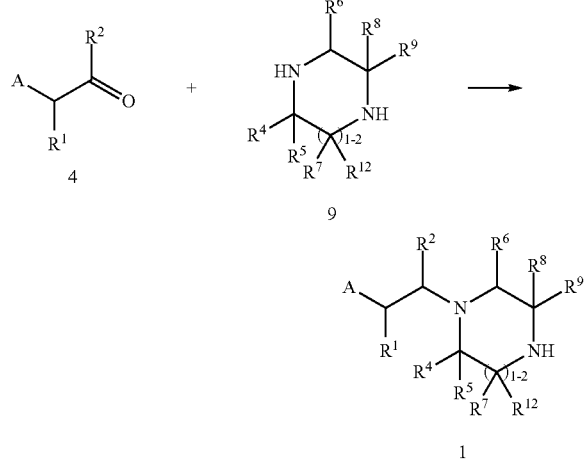

Sub-classes of intermediates of the structures 1a, 1b, and 1c having hydroxyl, alkoxy, or fluoro groups, respectively can be prepared according to Scheme 7. Initially, protected piperazines of the structure 7 (with, for example a Boc protective group) are reacted with epoxides of the structure 6 in solvents such as ethanol or DMSO with heating, alternatively with a microwave apparatus to afford alcohols 8a. The protective group may then be removed as appropriate to the type of protective group to afford intermediates 1a. In the example of a Boc protective group this can be accomplished using HCl or TFA. Alternatively, the alcohols 8a may be treated with alkyl halides (for example iodomethane) in the presence of a base such as sodium hydride to afford alkoxy intermediates 8b, which may then be converted to the corresponding intermediates 1b by removal of the protective group as described above. Another alternative involves treatment of the hydroxyl intermediate 8a with a reagent such as DAST to promote conversion of the hydroxyl group to a fluoro, affording compounds of the structure 8c. Again, the protective group may be removed as described above to afford intermediates of the structure 1c.

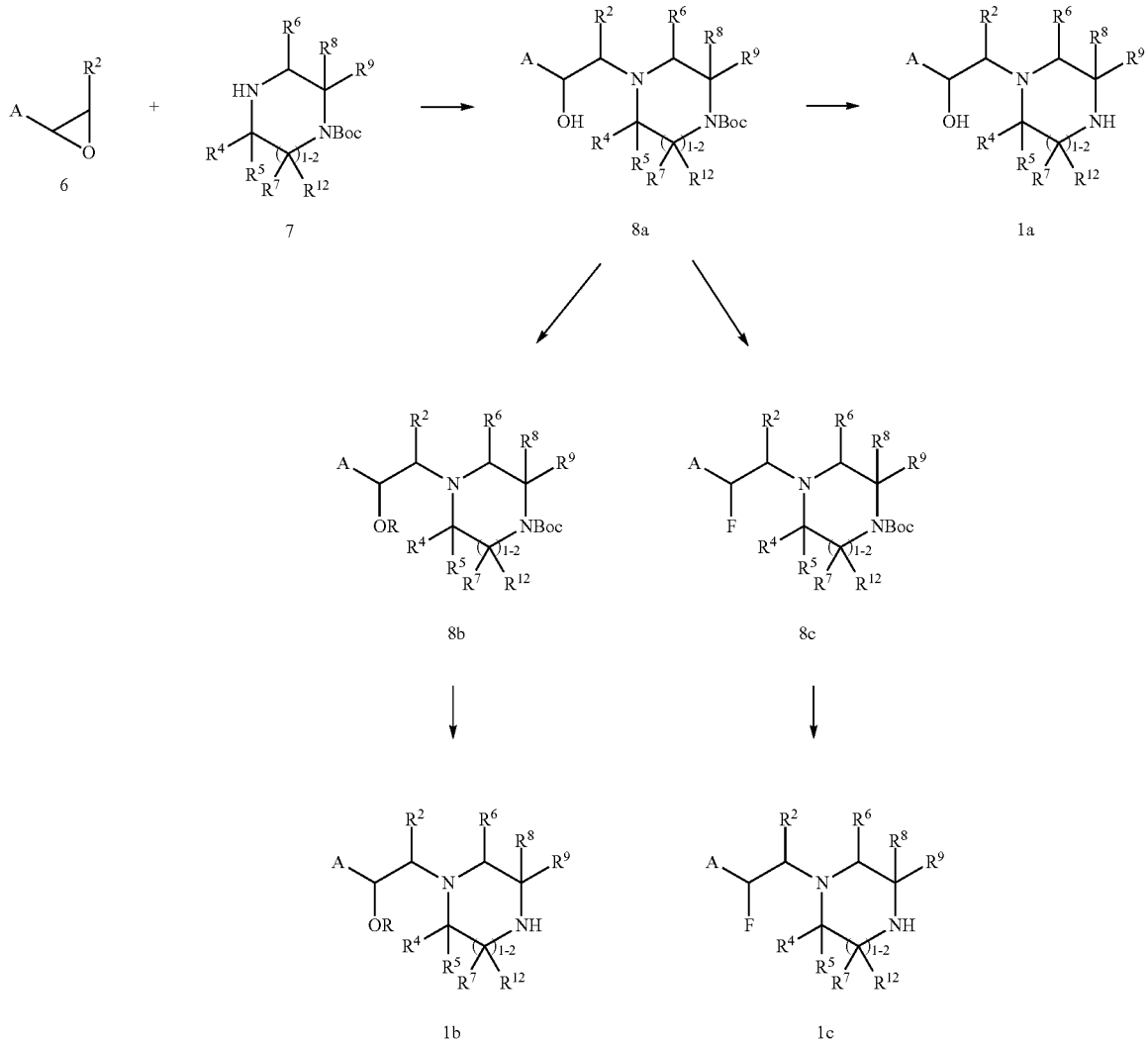

Intermediates of the structure 3 may be prepared according to Scheme 8 by initial coupling of protected piperazines (for example, with a Boc protective group) 10 with carboxylic acids of the structure 2 using any of a number of amide coupling conditions well-known to the chemist. For example EDC in the presence or absence of HOBt in dichloromethane, or HATU may be used to achieve amide coupling. The protective group may then be removed as appropriate to the type of protective group to provide intermediates of the structure 3. In the example shown, where the protective group is Boc, removal can be accomplished in a variety of ways, including by treatment with HCl or TFA.

Scheme 8

Intermediates 2 may be prepared in a variety of ways. A sub-class (2a) of carboxylic acids of the structure 2 may be prepared according to Scheme 9. By this route malonates 12 are reacted in the presence of a base such as sodium hydride with nitro-substituted aromatic or heterocyclic groups bearing a halogen leaving group such as a fluoro or chloro (13 shown). The resulting coupled products 14 are decarboxylated with hydrolysis of the remaining ester to afford carboxylic acids 15. Reduction of the nitro group can be achieved in a variety of ways. One approach is to reduce with hydrogen gas in the presence of a catalyst such as Pd on carbon. The aniline 16 may then be cyclized to the tetrazoles (2a) by a number of different methods, including reaction (often with heating) with sodium azide and triethylorthoformate in a solvent such as acetic acid.

Scheme 9

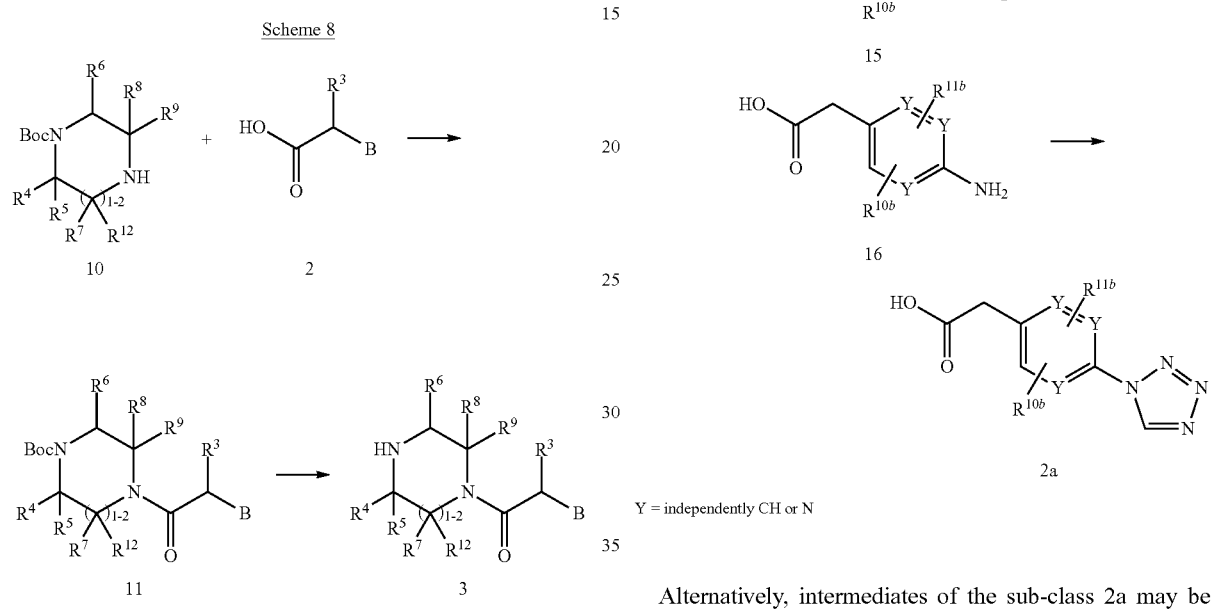

Y = independently CH or N

Alternatively, intermediates of the sub-class 2a may be prepared according to Scheme 10. In this case, a mixed malonate 12a is used to afford compounds 14a in a similar fashion as described in Scheme 9. Decarboxylation under acidic conditions with, for example TFA, provides the esters 17. Reduction, under conditions described for Scheme 9, provides amines 18. Cyclization to afford the tetrazoles 19 again could be accomplished as described above for Scheme 9. Finally ester hydrolysis using a base such as lithium hydroxide or sodium hydroxide with water and an organic solvent such as THF or dioxane affords the intermediates 2a.

Scheme 10

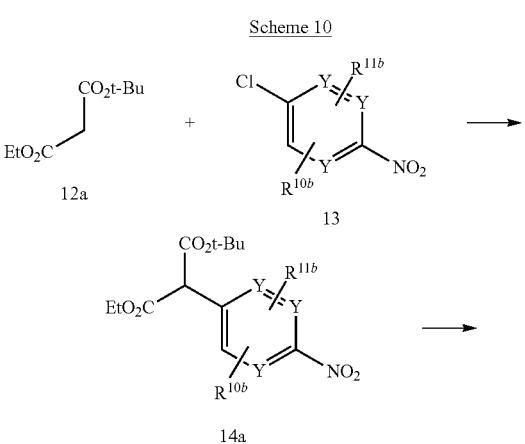

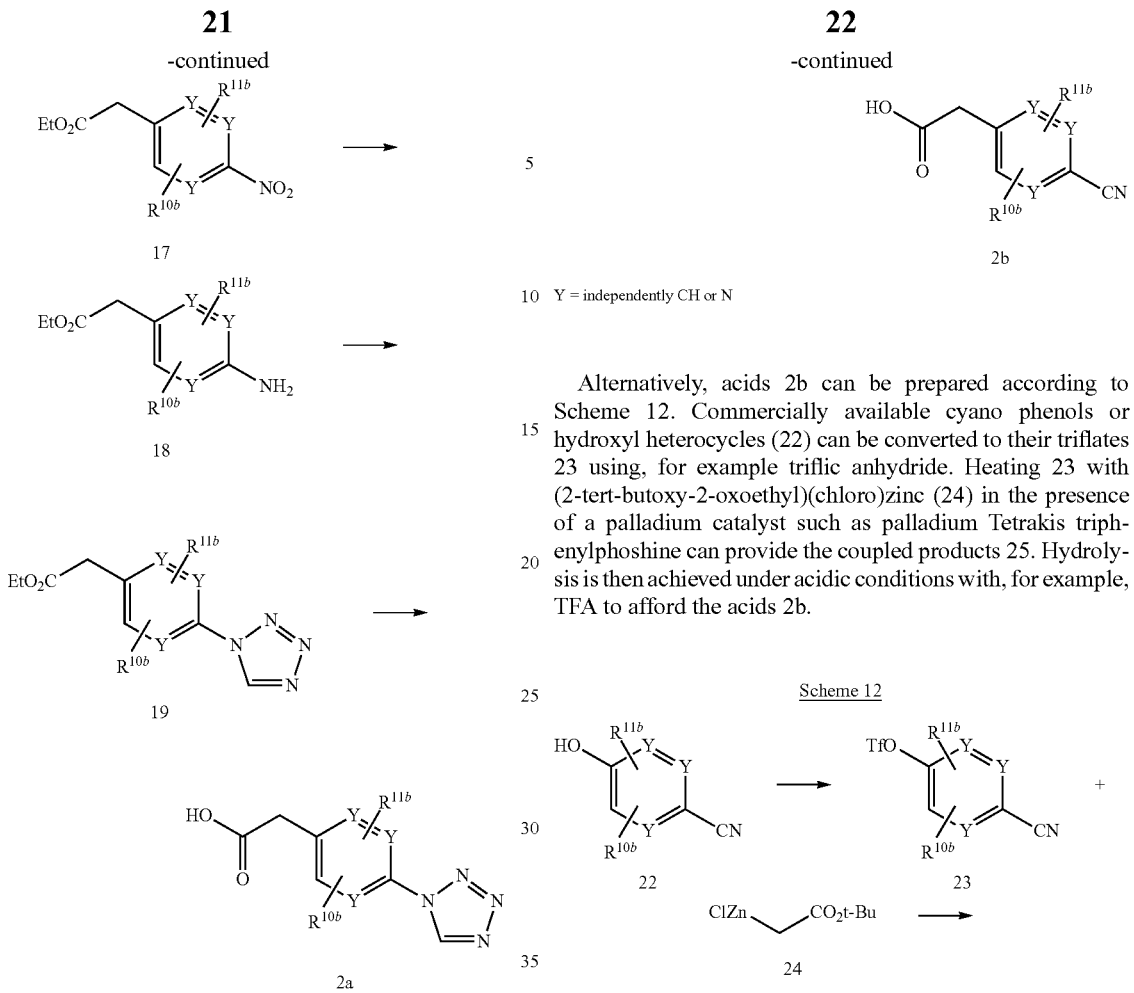

Y = independently CH or N

Alternatively, acids 2b can be prepared according to Scheme 12. Commercially available cyano phenols or hydroxyl heterocycles (22) can be converted to their triflates 23 using, for example triflic anhydride. Heating 23 with (2-tert-butoxy-2-oxoethyl)(chloro)zinc (24) in the presence of a palladium catalyst such as palladium Tetrakis triphenylphoshine can provide the coupled products 25. Hydrolysis is then achieved under acidic conditions with, for example, TFA to afford the acids 2b.

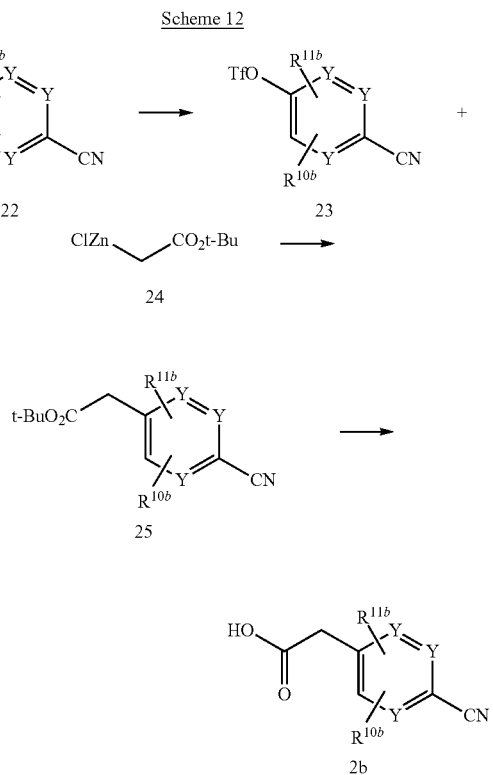

Y = independently CH or N

Another sub-class of acids 2b can be prepared in a variety of ways. One approach is depicted in Scheme 11. Malonate 12b, in the presence of a base such as sodium hydride can be coupled to cyano aryl or heterocycle compounds bearing a halogen leaving group such as a chloride, bromide, or fluoride (for example 20). Hydrolysis and decarboxylation can be achieved under acidic conditions (for example TFA) to provide the acids 2b.

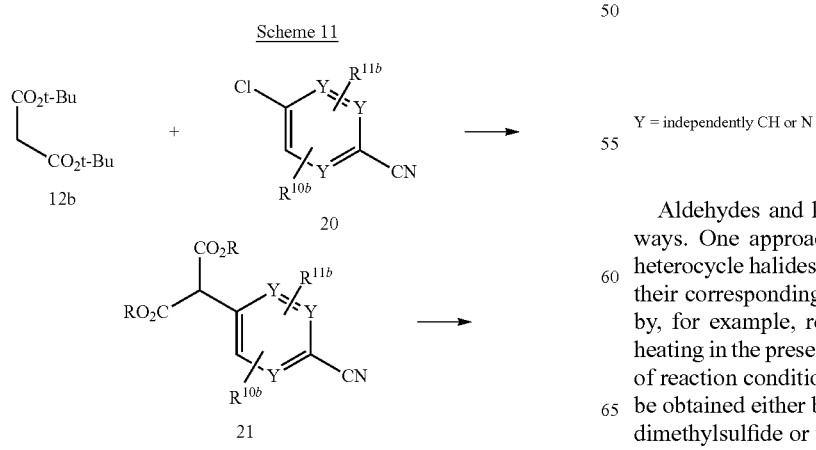

Aldehydes and ketones 4 may be prepared in numerous ways. One approach is described by Scheme 13. Aryl or heterocycle halides (bromide 26 shown) may be converted to their corresponding aryl or heterocycle allyl compounds 27 by, for example, reaction with allyltributylstannane whilst heating in the presence of a palladium catalyst under a variety of reaction conditions. Then the aldehydes and ketones may be obtained either by ozonolysis followed by treatment with dimethylsulfide or triphenylphosphine, or by treatment with osmium tetroxide followed by sodium periodate.

Scheme 13

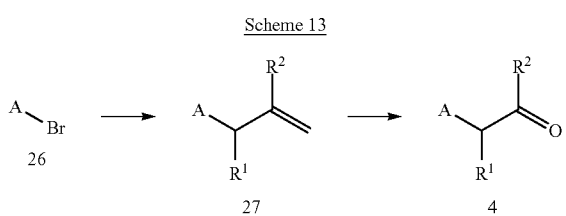

Epoxides 6 may be prepared by a variety of methods. One approach is described by Scheme 14. Aryl or heterocycle halides (bromide 26 shown) may be coupled to form alkene products 28 in a number of ways, for example by Heck reaction or by reaction with vinyl tetrafluoroborate and a metal catalyst. The alkenes 28 can then be converted to the corresponding epoxides 6 by several ways, including treatment with meta-chloroperoxybenzoic acid.

Scheme 14

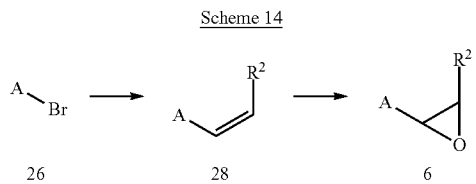

General Procedures

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS). Typically the analytical LC-MS system used consisted of a Waters ZQ platform with electrospray ionization in positive ion detection mode with an Agilent 1100 series HPLC with autosampler. The column was usually a Waters Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TEA) and solvent B (acetonitrile plus 0.05% TFA) with a gradient of 100% solvent A for 0.7 mM changing to 100% solvent B over 3.75 min, maintained for 1.1 mM, then reverting to 100% solvent A over 0.2 min. Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions perfumed using microwave iradiation were normally carried out using an Ermys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was usually conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Celite® (Fluka) diatomite is diatomaceous earth, and can be referred to as "celite". Where retention times are provided, they are not intended to be a definitive characteristic of a particular compound, since retention times will vary depending on the chromatographic conditions and equipment used.

Terminology referencing the process of crystallization, crystals or the like in the Intermediates and Examples section is used to describe the process and product resulting from precipitating a solid product from solution and does not necessarily mean that the precipitated solid was determined to be in a crystalline physical form.

Abbreviations used herein include: —C(O)CH$_3$ (Ac); acetic acid (AcOH); —OC(O)CH$_3$ (OAc); aqueous (aq); Cbz (benzyloxycarbonyl); N;N-diisopropylethylamine (DIEA); diethylamine (DEA); N;N-dimethylformamide (DMF); ethyl acetate (EtOAc); diethyl ether (ether or Et$_2$O); petroleum ether (PE); gram(s) (g); hour(s) (h or hr); 2-propanol (IPA); iso-butyl alcohol (IBA); mass spectrum (ms or MS); microliter(s) (µL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time (t$_R$); room temperature (rt or RT); saturated aq sodium chloride solution (brine); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Bac or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC); diisobutylaluminum hydride (DIBAL-H); Tmax (maximum temperature); nicotinamide adenine dinucleotide phosphate (NADP); solid phase extraction (SPE); N-ethyl-N'-(3-dimethylaminopropyl)carbodiimide (EDC); high-performance liquid chromatography mass spectrometry (HPLC-MS); N-iodosuccinimide (NIS); lithium diisopropylamide (LDA); 1,8-diazabicyclo[5.4.0]undec-7-ene (DBU); sodium hexamethyldisilazane (NaHMDS); lithium aluminum hydride (LAH); N-methylmorpholine N-oxide (NMO); N,N,N',N'-tetramethylethylenediamine (TMEDA); trifluoroacetic anhydride (TFAA); tetramethylsilane (TMS); N-ethyl-N'-(3-dimethylaminopropyl)carbodiimide (EDC); lithium hexamethyldisilazide (LHMDS); neutral mass spectrometer (NMS); O-(7-Azabenzotriazole-1-yl)-1,1,3,3-tetramethyluronium hexafluorophosphate (HATU); 1-Hydroxybenzotriazole (HOBt); medium pressure liquid chromatography (MPLC); dimethylsulfide (DMS); liquid chromatograph-mass spectrometer (LCMS); m-3-Chloroperoxybenzoic acid (mCPBA); triethylamine (TEA); isopropyl acetate (IPAc); phenyl (Ph); trifluoro (TO; 1,1'-bis(diphenylphosphino)ferrocene (dppf); ethyl (Et); hexy lithium (HexLi); 4-Hydroxymethylphenoxyacetic acid (HMPA); starting material (SM); tris(dibenzylideneacetone)dipalladium(0) (Pd$_2$(dbu)$_3$); tri-ortho-tolylphosphine (Pd(oTol)$_3$); toluenesulfonylmethyl isocyanide (TosMIC); and 2,2'-bis(diphenylphosphanyl)-1,1'-binaphthyl (BINAP).

The following are representative procedures for the preparation of the compounds used in the following Examples, or which can be substituted for the compounds used in the following Examples which may not be commercially available.

Intermediate 1

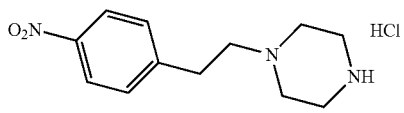 [SMILES: O=[N+]([O-])c1ccc(CCN2CCNCC2)cc1 ; Cl]

1-[2-(4-nitrophenyl)ethyl]piperazine hydrochloride

Triethylamine (22.6 mL, 161 mmol) was added to a stirred solution of BOC-piperazine (10.0 g, 53.7 mmol) and 4-nitrophenethyl bromide (12.4 g, 53.7 mmol) in 100 mL DMF then the mixture was heated at 50° C. for 16 h. The reaction mixture was poured into water and extracted three times with ethyl acetate. The combined organic layers were washed three times with water, three times with 0.1 N HCl, again with water, then finally with brine. The organic layer was dried over MgSO$_4$, filtered, most of the solvent was removed under reduced pressure, and hexane was added. The resulting precipitate was filtered and washed with hexane to yield the Boc-protected intermediate. Analysis by LC-MS showed M+H 336 and M-55 280 for the major peak. The intermediate was treated with 4M HCl in dioxane (Aldrich) to yield 1-[2-(4-nitrophenyl)ethyl]piperazine hydrochloride. $^1$H-NMR (500 MHz, DMSO): δ ppm 9.80 (b, 1H), 8.21 (d, J=8.5 Hz, 2H), 7.59 (d, J=8.5 Hz, 2H), 3.2-3.8 (m, 12H); LC-MS: M+1=236.

Intermediate 2

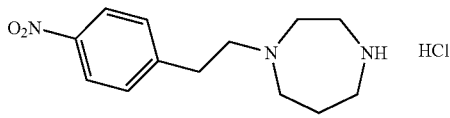 [SMILES: O=[N+]([O-])c1ccc(CCN2CCCNCC2)cc1 ; Cl]

1-[2-(4-nitrophenyl)ethyl]-1,4-diazepane hydrochloride

1-[2-(4-nitrophenyl)ethyl]-1,4-diazepane hydrochloride was prepared in an analogous fashion to that described above for 1-[2-(4-nitrophenyl)ethyl]piperazine hydrochloride starting with 4-nitrophenethyl bromide and tert-butyl 1,4-diazepane-1-carboxylate. LC-MS: M+1=250.2.

Intermediate 3

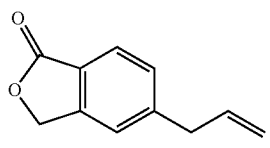

5-(prop-2-en-1-yl)-2-benzofuran-1(3H)-one 5-bromo-2-benzofuran-1(3H)-one (6.68 g, 31.4 mmol) was combined with allyltributylstannane (12.5 g, 37.6 mmol), Pd(PPh$_3$)$_4$ (1.09 g, 0.941 mmol), and lithium chloride (2.66 g, 62.7 mmol) in toluene (100 mL) and the mixture was purged with nitrogen gas. The reaction mixture was then stirred at 100° C. for 4 h. The mixture was cooled to room temperature, filtered, and concentrated. The crude residue was purified by MPLC eluting in stepwise fashion with hexanes, then 10% ethyl acetate/hexanes, then 20% ethyl acetate/hexanes. $^1$H-NMR (500 MHz, CDCl$_3$): δ ppm 7.87 (d, J=8 Hz, 1H), 7.39 (d, J=8 Hz, 1H), 7.35 (s, 1H), 5.96-6.04 (m, 1H), 5.32 (s, 2H), 5.15-5.20 (m, 2H), 3.55 (d, J=6.5 Hz, 2H).

Intermediate 4

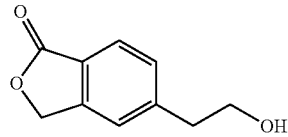 [SMILES: O=C1OCc2cc(CCO)ccc21]

5-(2-hydroxyethyl)-2-benzofuran-1(3H)-one 5-(Prop-2-en-1-yl)-2-benzofuran-1(3H)-one (1.53 g, 8.78 mmol) was dissolved in a mixture of methanol (30 mL) with just enough THF to solubilize the starting material and was cooled to −78° C. Ozone was bubbled through the solution until the reaction mixture color changed (to orange). Then nitrogen gas was bubbled through the reaction mixture for about one min. to remove the residual ozone. Sodium borohydride (0.65 g, 17 mmol) was added and the mixture was allowed to warm to room temperature. The reaction mixture was partially concentrated then was partitioned between ethyl acetate and water. The organic layer was washed with brine, then dried over MgSO$_4$. The crude product was purified by MPLC (silica) eluting with ethyl acetate to afford pure product. LCMS: m/z 179 (M+1)$^+$; $^1$H NMR (500 MHz, CD$_3$OD) δ 7.77 (m, 1H), 7.37-7.41 (m, 2H), 5.23 (s, 2H), 192 (m, 2H), 2.99 (m, 2H).

Intermediate 5 (Method 1)

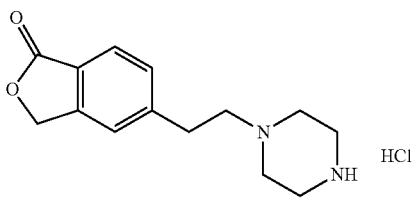 [SMILES: O=C1OCc2cc(CCN3CCNCC3)ccc21 ; Cl]

5-(2-piperazin-1-ylethyl)-2-benzofuran-1(3H)-one hydrochloride

Step A: 5-(1,3-dioxolan-2-ylmethyl)-2-berizofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 469 mmol). DMF (1.88 L) was added to the flask, and the mixture was degassed three times by alternating vacuum and nitrogen purge. Commercially available bromo(1,3-dioxolan-2-ylmethyl)zinc solution (1.033 L, 516 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO$_4$, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one, MS: m/z 221 (M+1)$^+$.

Step B: (1-oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. MS: in/z 177 (M+1)$^+$.

Step C: 1,1-dimethylethyl-4-[2-(1-oxo-1,3-dihydro-2-benzofuran-5-yl)ethyl]piperazine-1-carboxylate A three neck 5 L round bottomed flask equipped with a nitrogen bubbler, thermocouple, and stirbar was charged with (1-oxo-1,3-dihydro-2-benzofuran-5-yl)acetaldehyde (46.1 g, 262 mmol) and dichloromethane (1 L). 1-Boc-piperazine (48.7 g, 262 mmol) in 1 L of dichloromethane was added and the mixture was stirred for 5 min. Sodium triacetoxyborohydride (111 g, 523 mmol) was added in portions at room temperature and the resulting mixture was stirred for 1 h. Water (1 L) was added and the mixture was stirred for 10 min. After gas evolution subsided the organic layer was separated and the aqueous layer was extracted with methylene chloride (1 L). The organic layers were combined, washed with brine, and concentrated. The crude product was purified by silica gel MPLC eluting with a 0-100% gradient of 5% methanol/DCM solution (Solvent A) to pure DCM (Solvent B) to afford 1,1-dimethylethyl-4-[2-(1-oxo-1,3-dihydro-2-benzofuran-5-yl)ethyl]piperazine-1-carboxylate.

Step D: 5-(2-piperazin-1-ylethyl)-2-benzofuran-1(3H)-one hydrochloride

To 1,1-dimethylethyl-4-[2-(1-oxo-1,3-dihydro-2-benzofuran-5-yl)ethyl]piperazine-1-carboxylate (120 g, 347 mmol) in dioxane (800 mL) was added 4 N HCl in dioxane (87.0 mL, 347 mmol) and the resulting mixture was stirred at room temperature over night. The reaction mixture was concentrated and stored under vacuum overnight to afford 5-(2-piperazin-1-ylethyl)-2-benzofuran-1(3H)-one hydrochloride. This can be used as is or converted to the free base by partitioning between an organic solvent and saturated NaHCO$_3$ solution. MS: m/z 247 (M+1)$^+$.

Intermediate 5 (Method 2)

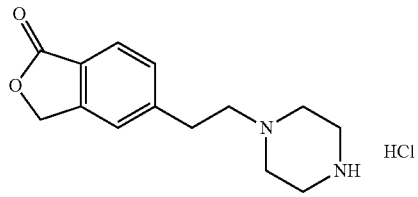 [SMILES: O=C1OCc2cc(CCN3CCNCC3)ccc21 ; Cl]

5-(2-piperazin-1-ylethyl)-2-benzofuran-1(3H)-one hydrochloride 5-(prop-2-en-1-yl)-2-benzofuran-1(3H)-one (2.30 g, 13.2 mmol) was dissolved in DCM (30 mL) and cooled to −78° C. Ozone was bubbled through the solution until the color changed (to orange). Nitrogen was bubbled through the solution for about one minute to remove any residual ozone. tert-Butyl piperazine-1-carboxylate (1.64 g, 8.80 mmol) in DCM was added followed by sodium triacetoxyborohydride (11.2 g, 52.8 mmol). The reaction mixture was permitted to warm to room temperature and was stirred overnight. The reaction mixture was partitioned between DCM and water. The organic layer was washed with brine, then dried over MgSO$_4$. The crude product was purified by preparative TLC eluting with 5% methanol in DCM. The resulting 1,1-dimethylethyl-4-[2-(1-oxo-1,3-dihydro-2-benzofuran-5-yl)ethyl]piperazine-1-carboxylate was deprotected (of Boc) as described in Method 1 of the synthesis of 5.

Intermediate 6

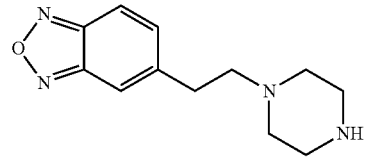 [SMILES: c1cc2nonc2cc1CCN1CCNCC1]

5-[2-(piperazin-1-yl)ethyl]-2,1,3-benzoxadiazole
Step A: 5-(prop-2-en-1-yl)-2,1,3-benzoxadiazole 5-Bromo-2,1,3-benzoxadiazole (10 g, 50 mmol) was combined with lithium chloride (6.39 g, 151 mmol), Pd(PPh$_3$)$_4$ (2.90 g, 2.51 mmol) and allyl-tri-n-butylstannane (18.7 mL, 60.3 mmol) in toluene (300 mL). The mixture was degassed and purged with nitrogen and then stirred under reflux for three h. The reaction mixture was poured into water and extracted with ethyl acetate. The organic layer was washed with brine and dried over MgSO$_4$. Purification by silica MPLC eluting with a 0-10% gradient of ethyl acetate/hexanes over 20 minutes and isocratic 10% ethyl acetate/hexanes for an additional 20-30 minutes afforded the title compound.
$^1$H-NMR (500 MHz, CDCl$_3$) δ ppm 7.96 (d, J=9 Hz, 1H), 7.74 (s, 1H), 7.43 (d, J=9.5 Hz, 1H), 6.00 (m, 1H), 5.16 (m, 2H), 3.50 (d, J=7 Hz, 2H)
Step B: 5-[2-(piperazin-1-yl)ethyl]-2,1,3-benzoxadiazole 5-(Prop-2-en-1-yl)-2,1,3-benzoxadiazole (480 mg, 3.0 mmol) was dissolved in DCM and cooled to −78° C. Ozone was bubbled in until the reaction mixture reached a bluish tint, then nitrogen was bubbled through the mixture to get rid of excess ozone. Boc-piperazine (558 mg, 3.0 mmol) was then added followed by sodium triacetoxyborohydride (2541 mg, 11.99 mmol). The reaction mixture was warmed up to RT and stirred overnight. The reaction mixture was poured into 1 N NaOH and extracted with ethyl acetate twice. The ethyl acetate layer was dried over MgSO$_4$, filtered, and evaporated to dryness. The residue was purified through a 40 g Redi-sep column to yield tert-butyl 4-[2-(2,1,3-benzoxadiazol-5-yp-ethyl]piperazine-1-carboxylate, which was dissolved in dioxane and treated with 7 mL of 4M HCl in dioxane. The reaction mixture was stirred at RT overnight. The solvent was evaporated, then the residue was taken up in ethyl acetate and made alkaline by addition of 1N NaOH. The ethyl acetate was separated, washed with brine, then dried over Na$_2$SO$_4$ and evaporated to dryness. The residue was purified by MPLC chromatography using 5% (1 NH4OH:10 MeOH) in 95% DCM to yield 5-[2-(piperazin-1-yl)ethyl]-2,1,3-benzoxadiazole. $^1$H-NMR (600 MHz, CDCl13): δ 7.72 (d, J=9.2 Hz, 1H), 7.28 (d, J=9.2 Hz, 1H), 2.92 (t, J=4.9 Hz, 2H), 2.88 (t, J=7.6 Hz, 1H), 2.65 (t, J=7.6 Hz, 1H) LC-MS: M+1=233.

Intermediate 7

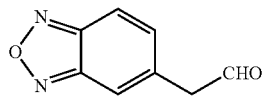 [SMILES: O=CCc1ccc2nonc2c1]

2,1,3-benzoxadiazol-5-ylacetaldehyde 5-(Prop-2-en-1-yl)-2,1,3-benzoxadiazole (2.00 g, 12.5 mmol) was dissolved in DCM and cooled to −78° C. Ozone was bubbled through the reaction mixture until a blue color was observed, then nitrogen was bubbled through the reaction mixture to remove excess ozone. Dimethyl sulfide (9.24 mL, 125 mmol) was added and the reaction mixture was permitted to warm to room temperature and stir for 2 h. The solvent was removed and the crude material was purified by MPLC eluting with ethyl acetate/hexanes, 0-50% gradient, to afford the title compound. $^1$H NMR (500 MHz, CDCl$_3$, δ in ppm): 9.89 (s, 1H), 7.86 (d, J=9.5 Hz, 1H), 7.71 (s, 1H), 7.27 (dd, J=9 Hz, 1 Hz, 1H), 3.91 (s, 2H).

Intermediate 8

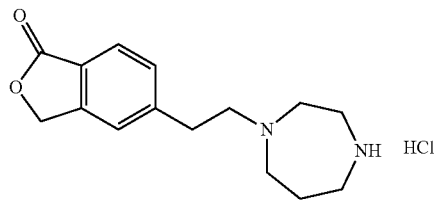 [SMILES: O=C1OCc2cc(CCN3CCCNCC3)ccc21 ; Cl]

5-[2-(1,4-diazepan-1-yl)methyl]-2-benzofuran-1(3H)-one hydrochloride

5-[2-(1,4-Diazepan-1-yl)ethyl]-2-benzofuran-1(3H)-one hydrochloride was prepared from (1-oxo-1,3-dihydro-2-benzofuran-5-yl)acetaldehyde and tert-butyl 1,4-diazepane-1-carboxylate in an analogous fashion to that described above for the synthesis of 5-(2-piperazin-1-ylethyl)-2-benzofuran-1(3H)-one hydrochloride (Method 1, steps C and D). MS: m/z 261 (M+1)$^+$.

The following piperazine intermediates were similarly prepared from (1-oxo-1,3-dihydro-2-benzofuran-5-yl)acetaldehyde or 2,1,3-benzoxadiazol-5-ylacetaldehyde and the known or commercially available Boc-piperazines shown in the Table below in an analogous fashion as described above for the synthesis of 5-(2-piperazin-1-ylethyl)-2-benzofuran-1(3H)-one hydrochloride (Method 1, steps C and D).

| INTERMEDIATE | Precursor | Structure of INTERMEDIATE | MS (M + 1)$^+$ |
|---|---|---|---|
| 9 | ![Me piperazine with NBoc] | ![lactone-ethyl-piperazine with Me] | 261 |
| 10 | ![CF3 piperazine with NBoc] | ![lactone-ethyl-piperazine with CF3] | 315 |
| 11 | ![CHF2 piperazine with NBoc] | ![lactone-ethyl-piperazine with CHF2] | 297 |

| INTER-MEDIATE | Precursor | Structure of INTERMEDIATE | MS (M + 1)+ |
|---|---|---|---|
| 12 | F F HN NBoc | F F N O N N NH | 283 |
| 13 | CF₃ HN NBoc | N O N CF₃ N NH | 301 |
| 14 | O OMe HN NBoc | O O O OMe N NH | |

Intermediate 15

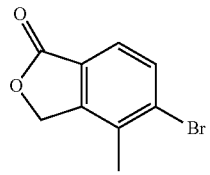

5-bromo-4-methyl-2-benzofuran-1(3H)-one
Step A: (3-bromo-2-methylphenyl)methanol To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl) methanol.

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a Celite® pad, washed with EtOAc, adsorbed onto silica and purified by silica gel chromatography to afford 5-bromo-4-methyl-2-benzofuran-1(3H)-one.

¹H-NMR (500 MHz, CDCl₃) δ ppm 7.71 (d, J=8.0 Hz, 1H), 7.58 (d, J=8.0 Hz, 1H), 5.25 (s, 2H), 2.37 (s, 3H).

Intermediate 16

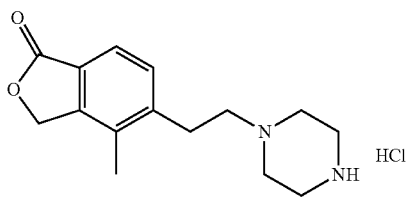 [SMILES: Cc1c(CCN2CCNCC2)ccc2c1COC2=O ; Cl]

4-methyl-5-(2-piperazin-1-ylethyl)-2-benzofuran-1(3H)-one hydrochloride
Step A: 4-methyl-5-prop-2-en-1-yl-2-benzofuran-1(3H)-one To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh₃)₄ (244 mg, 0.211 mmol), lithium chloride (179 mg, 4.23 mmol), and toluene (15 mL). The reaction was purged with nitrogen 2 times then was heated at reflux for 4 hours. The reaction mixture was diluted with DCM, adsorbed onto silica gel, and purified by silica gel chromatography to give 4-methyl-5-prop-2-en-1-yl-2-benzofuran-1(3H)-one.

Step B: (4-methyl-1-oxo-1,3-dihydro-2-benzofuran-5-yl)acetaldehyde

A solution of 4-methyl-5-prop-2-en-1-yl-2-benzofuran-1(3H)-one (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The solvents were removed under reduced pressure. The crude product was purified by flash chromatography to afford (4-methyl-1-oxo-1,3-dihydro-2-benzofuran-5-yl)acetaldehyde. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Step C: 1,1-dimethylethyl-4-[2-(4-methyl-1-oxo-1,3-dihydro-2-benzofuran-5-yl)ethyl]piperazine-1-carboxylate To a solution of (4-methyl-1-oxo-1,3-dihydro-2-benzofuran-5-yl)acetaldehyde (160 mg, 0.84 mmol) and 1-Boc piperazine (234 mg, 1.26 mmol) in MeOH (5 mL) was added NaCNBH$_3$ (149 mg, 2.52 mmol) and a few drops of acetic acid. The reaction was allowed to stir at RT for 16 hours. TLC at that point showed good and complete reaction. The reaction was diluted with EtOAc (100 mL), washed with aq. NaHCO$_3$ solution and brine, dried over Na$_2$SO$_4$, adsorbed onto silica gel, and purified by MPLC. 1,1-Dimethylethyl-4-[2-(4-methyl-1-oxo-1,3-dihydro-2-benzofuran-5-yl)ethyl]piperazine-1-carboxylate was collected after removal of solvents. LCMS: m/z 361 (M+1)$^+$.

Step D: 4-methyl-5-(2-piperazin-1-ylethyl)-2-benzofuran-1(3H)-one hydrochloride 1,1-Dimethylethyl-4-[2-(4-methyl-1-oxo-1,3-dihydro-2-benzofuran-5-yl)ethyl]piperazine-1-carboxylate (245 mg) was treated with 4N HCl in dioxane solution and the reaction was monitored until completion. The mixture was concentrated to afford 4-methyl-5-(2-piperazin-1-ylethyl)-2-benzofuran-1(3H)-one hydrochloride. The hydrochloride can be converted to free base as needed by partitioning between organic solvent (EtOAc, DCM, or 30% IPA/CHCl$_3$) and saturated Na$_2$CO$_3$ solution.

$^1$H-NMR (500 MHz, DMSO) δ ppm 12.4 (broad, 1H), 9.80 (broad, 2H), 7.71 (d, J=7.5 Hz, 1H), 5.53 (d, J=7.5 Hz, 1H), 5.44 (s, 2H), 3.81 (m, 2H), 3.64-3.27 (m, 10H).

Intermediates 17 and 18

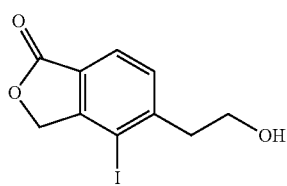

INTERMEDIATE 17

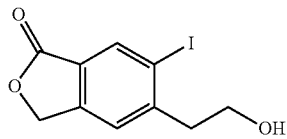

INTERMEDIATE 18

5-(2-hydroxyethyl)-4-iodo-2-benzofuran-1(3H)-one and 5-(2-hydroxyethyl)-6-iodo-2-benzofuran-1(3H)-one 5-(2-Hydroxyethyl)-2-benzofuran-1(3H)-one (1.89 g, 10.6 mmol) was dissolved in trifluoromethanesulfonic acid (3 mL). The mixture was cooled to 0° C. and N-iodosuccinimide (2.39 g, 10.6 mmol) was added. The reaction mixture was permitted to warm to room temperature and was stirred overnight. The reaction mixture was poured into ice water and the resulting mixture was extracted twice with DCM. The combined organic layers were washed with water, 10% NaHSO$_3$, and then brine. The organic layer was dried over MgSO$_4$, filtered, and concentrated. The crude product containing a mixture of two regioisomer products was purified and separated by MPLC eluting with 90% ethyl acetate/hexanes (750 mL), then 95% ethyl acetate/hexanes (750 mL) to afford the individual separated title products. The first isomer to elute was identified by HNMR to 5-(2-hydroxyethyl)-4-iodo-2-benzofuran-1(3H)-one and the second isomer to elute was identified as 5-(2-hydroxyethyl)-6-iodo-2-benzofuran-1(3H)-one. 5-(2-hydroxyethyl)-4-iodo-2-benzofuran-1(3H)-one: LCMS: m/z 305 (M+1)$^+$;

$^1$H-NMR (500 MHz, DMSO) δ ppm 7.86 (d, J=8 Hz, 1H), 7.50 (d, J=8 Hz, 1H), 5.12 (s, 2H), 3.97 (t, J=7 Hz, 2H), 3.20 (t, J=6.5 Hz, 2H), 1.64 (br s, 1H); 5-(2-hydroxyethyl)-6-iodo-2-benzofuran-1(3H)-one: LCMS: m/z 305 (M+1)$^+$;

$^1$H-NMR (500 MHz, DMSO) δ ppm 8.41 (s, 1H), 7.48 (s, 1H), 5.28 (s, 2H), 3.98 (m, 2H), 3.18 (t, J=6 Hz).

Intermediate 19

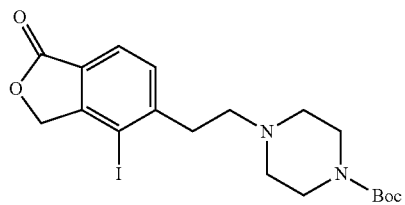 [SMILES: CC(C)(C)OC(=O)N1CCN(CCc2ccc3c(c2I)COC3=O)CC1]

tert-butyl-4-[2-(4-iodo-1-oxo-1,3-dihydro-2-benzofuran-5-yl)ethyl]piperazine-1-carboxylate Step A: (4-iodo-1-oxo-1,3-dihydro-2-benzofuran-5-yl)acetaldehyde To a solution of 5-(2-hydroxyethyl)-4-iodo-2-benzofuran-1(3H)-one (1.2 g, 4.0 mmol) in DCM (50 mL) was added Dess-Martin periodinane reagent (2.1 g, 4.9 mmol). The reaction was allowed to stir at RT for 2 hours. LC showed a major product spot. The reaction was worked up with 10% Na$_2$S$_2$O$_3$ solution (20 mL) and stirred until the layers separated. The DCM layer was separated, and the aqueous layer was extracted with DCM. The extractions were combined, washed with aqueous sodium bicarbonate and brine, dried over magnesium sulfate, and concentrated. The crude product, (4-iodo-1-oxo-1,3-dihydro-2-benzofuran-5-yl)acetaldehyde, was used directly in the next step. LC-MS (IE, m/z): 303 [M+1]$^+$;

Step B: tert-butyl-4-[2-(4-iodo-1-oxo-1,3-dihydro-2-benzofuran-5-yl)ethyl]piperazine-1-carboxylate The crude (4-iodo-1-oxo-1,3-dihydro-2-benzofuran-5-yl) acetaldehyde (1.2 g) was dissolved in DCM (40 mL). Boc-piperazine (1.1 g, 5.9 mmol) was added into the solution, followed by addition of sodium triacetoxyborohydride (4.2 g, 20 mmol). The reaction was allowed to stir at RT overnight. The reaction was diluted with DCM, washed with sodium bicarbonate and brine, dried over MgSO$_4$, and purified by silica gel chromatography to furnish tert-butyl-4-[2-(4-iodo- 1-oxo-1,3-dihydro-2-benzofuran-5-yl)ethyl]piperazine-1-carboxylate. LC-MS (IE, m/z): 473 [M+1]⁺.

Intermediate 20

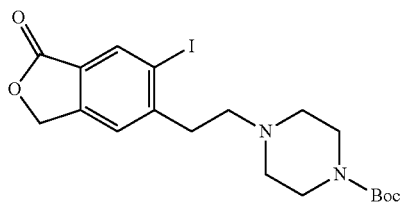 [SMILES: CC(C)(C)OC(=O)N1CCN(CCc2cc3c(cc2I)C(=O)OC3)CC1]

tert-butyl 4-[2-(6-iodo-1-oxo-1,3-dihydro-2-benzofuran-5-yl)ethyl]piperazine-1-carboxylate tert-Butyl 4-[2-(6-iodo-1-oxo-1,3-dihydro-2-benzofuran-5-yl)ethyl]piperazine-1-carboxylate was prepared in an analogous fashion to that described for the preparation of tert-butyl 4-[2-(4-iodo-1-oxo-1,3-dihydro-2-benzofuran-5-yl)ethyl]piperazine-1-carboxylate above starting from 5-(2-hydroxyethyl)-6-iodo-2-benzofuran-1(3H)-one. LC-MS (IE, m/z): 473 [M+1]⁺.

Intermediate 21

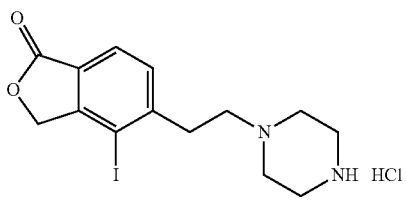 [SMILES: O=C1OCc2c1ccc(CCN1CCNCC1)c2I ; Cl]

4-iodo-5-[2-(piperazin-1-yl)ethyl]-2-benzofuran-1(3H)-one hydrochloride

4-Iodo-5-[2-(piperazin-1-yl)ethyl]-2-benzofuran-1(3H)-one hydrochloride was prepared from tert-butyl-4-[2-(4-iodo-1-oxo-1,3-dihydro-2-benzofuran-5-yl)ethyl]piperazine-1-carboxylate using 4N HCl in dioxane in an analogous fashion to that described for the synthesis of 4-methyl-5-(2-piperazin-1-ylethyl)-2-benzofuran-1(3H)-one hydrochloride above. LC-MS (IE, m/z): 373 [M+1]⁺.

Intermediate 22

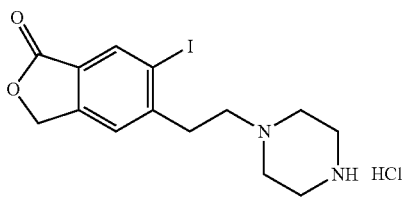 [SMILES: O=C1OCc2cc(CCN3CCNCC3)c(I)cc21 ; Cl]

6-iodo-5-[2-(piperazin-1-yl)ethyl]-2-benzofuran-1(3H)-one hydrochloride

6-Iodo-5-[2-(piperazin-1-yl)ethyl]-2-benzofuran-1(3H)-one hydrochloride was prepared from tert-butyl-4-[2-(6-iodo-1-oxo-1,3-dihydro-2-benzofuran-5-yl)ethyl]piperazine-1-carboxylate using 4N HCl in dioxane in an analogous fashion to that described for the synthesis of 4-methyl-5-(2-piperazin-1-ylethyl)-2-benzofuran-1(3H)-one hydrochloride above. LC-MS (IE, m/z): 373 [M+1]⁺.

Intermediate 23

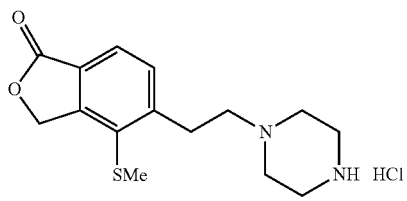 [SMILES: CSc1c(CCN2CCNCC2)ccc2c1COC2=O ; Cl]

4-(methylsulfanyl)-5-[2-(piperazin-1-yl)ethyl]-2-benzofuran-1(3H)-one hydrochloride Step A: tert-butyl 4-(2-[4-(methylsulfanyl)-1-oxo-1,3-dihydro-2-benzofuran-5-yl)ethyl]piperazine-1-carboxylate In a 15 mL microwave reaction vial was added tert-butyl 4-(2-[4-iodo-1-oxo-1,3-dihydro-2-benzofuran-5-yl)ethyl]piperazine-1-carboxylate (30 mg, 0.064 mmol), sodium thiomethoxide (8.9 mg, 0.127 mmol, 2.0 eq) and copper(I) iodide (24.2 mg, 0.127 mmol, 2.0 eq). To above mixture was added DMF (0.5 mL). The reaction was heated to 110° C. in microwave reactor for 30 min. The reaction was cooled down, diluted with EtOAc, washed with brine and water. The organic phase was dried over MgSO₄, filtered and concentrated. The crude was used in next step without purification. LC-MS (IE, m/z): 393.51 [M+1]⁺.

Step B: 4-(2-[4-(methylsulfanyl)-1-oxo-1,3-dihydro-2-benzofuran-5-yl)ethyl]piperazine-1-ium chloride In a 12 mL reaction vial, was added tert-butyl 4-(2-[4-(methylsulfanyl)-1-oxo-1,3-dihydro-2-benzofuran-5-yl)ethyl]piperazine-1-carboxylate (25 mg, 0.064 mmol) and 4 N HCl in dioxane (1 mL). The reaction was stirred at r. t. for 18 hr. The reaction mixture was concentrated to give the desired product.

Intermediates 24 and 25

INTERMEDIATE 24

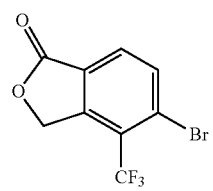

INTERMEDIATE 25

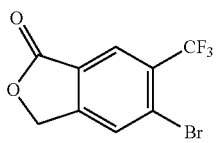

5-bromo-4-(trifluoromethyl)-2-benzofuran-1(3H)-one and 5-bromo-6-(trifluoromethyl)-2-benzofuran-1(3H)-one Step A: 5-bromo-4-iodo-2-benzofuran-1(3H)-one and 5-bromo-6-iodo-2-benzofuran-1(3H)-one 5-Bromo-2-benzofuran-1(3H)-one (5.38 g, 25.2 mmol) was dissolved in trifluoromethanesulfonic acid (sufficient volume to allow magnetic stirring) and the mixture was cooled to 0° C. N-iodo succinimide was added and the mixture was allowed to warm to rt and stir over the weekend. The mixture was poured into ice water and then extracted twice with DCM and twice with ethyl acetate. The combined organic layers were then washed with saturated NaHCO3, 1M NaHSO₃, and brine. The organic layer was dried over MgSO₄, filtered, and concentrated. The crude product was shown to be an approximately 1:1 mixture of regioisomeric products by HNMR analysis, and displayed insufficient solubility for further purification, therefore was used directly in the following step. LC-MS (IE, m/z): 339, 341 [M+1]⁺;

Step B: 5-bromo-4-(trifluoromethyl)-2-benzofuran-1(3H)-one and 5-bromo-6-(trifluoromethyl)-2-benzofuran-1(3H)-one A crude ~1:1 mixture of 5-bromo-4-iodo-2-benzofuran-1(3H)-one and 5-bromo-6-iodo-2-benzofuran-1(3H)-one (6.26 g, 18.5 mmol) was dissolved in DMF and treated with methyl difluoro(fluorosulfonyl)acetate (8.87 g, 46.2 mmol) followed by CuI (0.879 g, 4.62 mmol). The mixture was warmed to 90° C. and stirred for 2 h. An additional 5 mL aliquot of methyl difluoro(fluorosulfonyl)acetate was added and the mixture was stirred at 90° C. for 3 h. The mixture was filtered through Celite® pad. The filtrate was diluted with ethyl acetate and washed three times with water and once with brine. The organic layer was dried over MgSO₄, filtered and concentrated. The crude product was purified by MPLC eluting with 30% ethyl acetate/hexanes whereupon the two regiosimeric products cleanly separated to afford pure 5-bromo-4-(trifluoromethyl)-2-benzofuran-1(3H)-one and 5-bromo-6-(trifluoromethyl)-2-benzofuran-1(3H)-one.

5-bromo-4-(trifluoromethyl)-2-benzofuran-1(3H)-one: LC-MS (IE, m/z): 281, 283 [M+1]⁺;
5-bromo-6-(trifluoromethyl)-2-benzofuran-1(3H)-one: LC-MS (IE, m/z): 281, 283 [M+1]⁺.

Intermediate 26

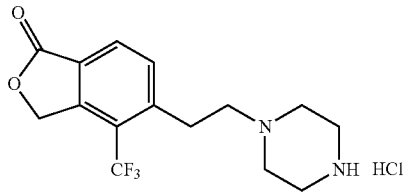 [SMILES: O=C1OCc2c1ccc(CCN1CCNCC1)c2C(F)(F)F ; Cl]

5-[2-(piperazin-1-yl)ethyl]-4-(trifluoromethyl)-2-benzofuran-1(3H)-one hydrochloride 5-[2-(piperazin-1-yl)ethyl]-4-(trifluoromethyl)-2-benzofuran-1(3H)-one hydrochloride was prepared in an analogous fashion to that described for the synthesis of 4-methyl-5-(2-piperazin-1-ylethyl)-2-benzofuran-1(3H)-one hydrochloride above starting from 5-bromo-4-(trifluoromethyl)-2-benzofuran-1(3H)-one. LC-MS (IE, m/z): 315 [M+1]⁺;

Intermediate 27

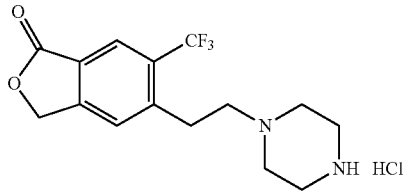 [SMILES: O=C1OCc2cc(CCN3CCNCC3)c(C(F)(F)F)cc21 ; Cl]

5-[2-(piperazin-1-yl)ethyl]-6-(trifluoromethyl)-2-benzofuran-1(3H)-one hydrochloride 5-[2-(piperazin-1-yl)ethyl]-6-(trifluoromethyl)-2-benzofuran-1(3H)-one hydrochloride was prepared in an analogous fashion to that described for the synthesis of 4-methyl-5-(2-piperazin-1-ylethyl)-2-benzofuran-1(3H)-one hydrochloride above starting from 5-bromo-6-(trifluoromethyl)-2-benzofuran-1(3H)-one. LC-MS (IE, m/z): 315 [M+1]⁺.

Intermediate 28

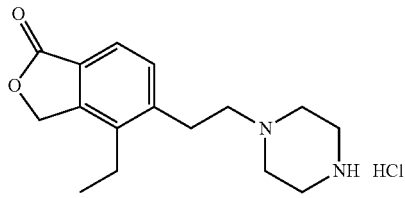 [SMILES: CCc1c(CCN2CCNCC2)ccc2c1COC2=O ; Cl]

4-ethyl-5-[2-(piperazin-1-yl)ethyl]-2-benzofuran-1(3H)-one hydrochloride

Step A: tert-butyl-4-[2-(1-oxo-4-vinyl-1,3-dihydro-2-benzofuran-5-yl)ethyl]piperazine-1-carboxylate To a microwave tube charged with tert-butyl-4-[2-(4-iodo-1-oxo-1,3-dihydro-2-benzofuran-5-yl)ethyl]piperazine-1-carboxylate (100 mg, 0.21 mmol) and a stir bar was added potassium vinyltrifluoroborate (37 mg, 0.28 mmol), PdCl₂(dppf)-DCM complex (8.7 mg, 0.011 mmol), triethylamine (39 mg, 0.38 mmol), and EtOH (4 mL). The mixture was sealed, purged three times with nitrogen, and heated to 120° C. for 20 minutes. LC showed formation of the desired product, which was separated by silica gel chromatography. LC-MS (IE, m/z): 373 [M+1]⁺;

Step B: tert-butyl-4-[2-(4-ethyl-1-oxo-1,3-dihydro-2-benzofuran-5-yl)ethyl]piperazine-1-carboxylate To a solution of tert-butyl-4-[2-(1-oxo-4-vinyl-1,3-dihydro-2-benzofuran-5-yl)ethyl]piperazine-1-carboxylate (30 mg, 0.081 mmol) in MeOH (10 mL) was added palladium on carbon (4.3 mg, 0.040 mmol). The mixture was allowed to stir under an atmosphere of hydrogen for 16 hours. LC showed complete reaction. The crude reaction was filtered through a pad of Celite®, concentrated to deliver tert-butyl-4-[2-(4-ethyl-1-oxo-1,3-dihydro-2-benzofuran-5-yl)ethyl]piperazine-1-carboxylate.

LC-MS (IE, m/z): 375 [M+1]⁺;

Step C: 4-ethyl-5-[2-(piperazin-1-yl)ethyl]-2-benzofuran-1(3H)-one

4-Ethyl-5-[2-(piperazin-1-yl)ethyl]-2-benzofuran-1(3H)-one was prepared in a similar fashion to that described for the synthesis of 4-methyl-5-(2-piperazin-1-ylethyl)-2-benzofuran-1(3H)-one hydrochloride above starting from tert-butyl-4-[2-(4-ethyl-1-oxo-1,3-dihydro-2-benzofuran-5-yl)ethyl]piperazine-1-carboxylate. LC-MS (IE, m/z): 275 [M+1]⁺.

Intermediate 29

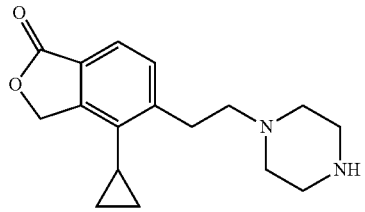 [SMILES: O=C1OCc2c1ccc(CCN1CCNCC1)c2C1CC1]

4-cyclopropyl-5-[2-(piperazin-1-yl)ethyl]-2-benzofuran-1(3H)-one

Step A: tert-butyl-4-[2-(4-cyclopropyl-1-oxo-1,3-dihydro-2-benzofuran-5-yl)ethyl]piperazine-1-carboxylate To a microwave tube charged with tert-butyl-4-[2-(4-iodo-1-oxo-1,3-dihydro-2-benzofuran-5-yl)ethyl]piperazine-1-carboxylate (100 mg, 0.21 mmol) and a stir bar was added palladium acetate (3.6 mg, 0.016 mmol), tricyclohexylphosphine (8.9 mg, 0.032 mmol), cyclopropyl boronic acid (27 mg, 0.32 mmol), and potassium phosphate (160 mg, 0.74 mmol). The tube was sealed, and injected toluene (2 mL) and water (100 uL). The mixture was purged three times with nitrogen, and heated to 100° C. for 30 minutes. LC showed formation of the desired product. The reaction was purified by silica gel chromatography to afford tert-butyl-4-[2-(4-cyclopropyl-1-oxo-1,3-dihydro-2-benzofuran-5-yl)ethyl]piperazine-1-carboxylate. LC-MS (IE, m/z): 387 [M+1]$^+$.

Step B: 4-cyclopropyl-5-[2-(piperazin-1-yl)ethyl]-2-benzofuran-1(3H)-one

4-Cyclopropyl-5-[2-(piperazin-1-yl)ethyl]-2-benzofuran-1(3H)-one was prepared in a similar fashion to that described for the synthesis of 4-methyl-5-(2-piperazin-1-ylethyl)-2-benzofuran-1(3H)-one hydrochloride above starting from tert-butyl-4-[2-(4-cyclopropyl-1-oxo-1,3-dihydro-2-benzofuran-5-yl)ethyl]piperazine-1-carboxylate. LC-MS (IE, m/z): 275 [M+1]$^+$.

Intermediate 30 (Method 1)

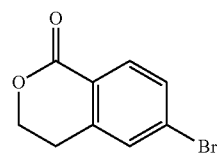

6-bromo-3,4-dihydro-1H-isochromen-1-one

A 250-mL, three-necked, round-bottomed flask equipped with a septum, nitrogen inlet needle, and thermocouple was charged with diisopropylamine (4.36 mL, 30.6 mmol) and 30 mL of THF. The reaction mixture was cooled at −20° C. while n-BuLi (2.5 M, 12.2 mL, 30.6 mmol) was added dropwise via syringe keeping the internal temperature below 0° C. The resulting reaction mixture was stirred at 0° C. for 15 min. The reaction was then cooled at −40° C. while 4-bromo-2-methylbenzonitrile (4.00 g, 20.4 mmol) in 10 mL of THF was added dropwise via syringe over 1 h. An internal temperature of ca. −40° C. was maintained during the addition. The resulting reaction mixture was stirred at −40° C. for 30 min and then charged with DMF (ca. 50 ppm water) in one portion. The reaction mixture was stirred at −40° C. for 15 min. The reaction mixture was quenched with MeOH (5 vol., 20 mL) and then charged with NaBH$_4$ (0.77 g, 20.4 mmol) in one portion and allowed to warm to room temperature. After complete reduction of intermediate aldehyde (as judged by HPLC analysis), the reaction mixture was carefully quenched with 5 M HCl (with cooling) to adjust the pH to 2-3. The reaction mixture was extracted with EtOAc and then solvent-switched to EtOH. H$_2$SO$_4$ (98%, 10.9 mL, 204 mmol) was added in one portion and the resulting reaction mixture was stirred at reflux for 24 h. After complete cyclization (monitored by HPLC analysis), the reaction mixture was cooled to room temperature and then solvent-switched to EtOAc. The resulting organic layer was washed with water, washed with brine, and solvent-switched to MTBE. Crystallization from 1:1 MTBE:heptane afforded 6-bromo-3,4-dihydro-1H-isochromen-1-one.

Intermediate 30 (Method 2)

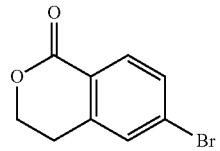 [SMILES: O=C1OCCc2cc(Br)ccc21]

6-bromo-3,4-dihydro-1H-isochromen-1-one

A solution of DIPA (4 M, 270 mL, 1080 mmol) in THF (900 mL) was cooled to −65° C. and HexLi (2.1 M, 505 mL, 1061 mmol) was added dropwise over 15 min maintaining the internal temp <−55° C. Upon completion the reaction mixture was warmed up to −40° C. where it was stirred 30 min. To the resulting solution of LDA was added 4-bromo-2-methylbenzoic acid (90 g, 419 mmol) slowly (over 15 min) as a solution in THF (400 mL) during which time the reaction mixture turned into a bright red suspension. The reaction mixture was stirred for 30 min at −40° C. and then warmed to 15° C. at which point paraformaldehyde (50.3 g, 1674 mmol) was added in 3 portions as a solid keeping the internal temperature (ice water bath) below <18° C. Stirring was then continued at room temperature for 1 hour during which time the mixture turned an orange-yellow colour. After a second hour of stirring, the vessel was immersed in an ice water bath and 3N HCl (650 mL) was added at such a rate to keep the internal temperature less than 30° C. The contents of the reaction vessel was subsequently transferred to a separatory funnel where it was extracted 3× 400 mL EtOAc and the combined organic phases were then concentrated to ~800 mL total volume. To this was added Amberlyst 15 resin (12 g) and the resulting mixture stirred at 48° C. overnight (~14 h). HPLC analysis the following morning indicated that cyclization to the desired halolactone was nearly complete. The resin was removed by filtration and the yellow solution concentrated to ~200 mL total volume at which point the desired product began to crystallize as a yellow solid which was then collected by filtration. The cake was subsequently washed with MTBE (2× 80 mL) to give the first crop of product. Additional material was salvaged by washing the collected supernatant 2× with 200 mL 10% K$_2$CO$_{3,aq}$ followed by 200 mL 1M H$_3$PO$_4$. After concentration to ~100 mL the crystallized material was collected by filtration, washed with MTBE and then combined with the first crop of and dried to afford the title compound. LCMS: m/z 227, 229 (M+1)$^+$;
$^1$H-NMR (500 MHz, CDCl$_3$) δ ppm 7.98 (d, J=8.5 Hz, 1H), 7.57 (dd, J=8.5 Hz, 1.5 Hz, 1H), 7.48 (s, 1H), 4.56 (t, J=6 Hz, 2H), 3.08 (t, J=6 Hz, 2H).

Intermediate 31

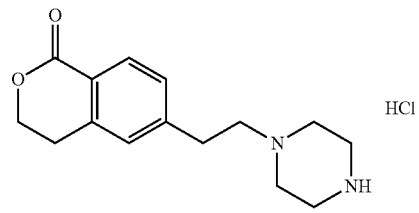 [SMILES: O=C1OCCc2cc(CCN3CCNCC3)ccc21 ; Cl]

6-[2-(piperazin-1-yl)ethyl]-3,4-dihydro-1H-isochromen-1-one hydrochloride

Step A: 6-(1,3-dioxolan-2-ylmethyl)-3,4-dihydro-1H-isochromen-1-one 6-bromo-3,4-dihydro-1H-isochromen-1-one (10 g, 44 mmol) was combined with tri-t-butyl phosphonium tetrafluoroborate (256 mg, 0.881 mmol), palladium (II) acetate (99 mg, 0.44 mmol) and commercially available bromo(1,3-dioxolan-2-ylmethyl)zinc solution (0.5 M, 97 mL, 48 mmol) in DMF (100 mL), and the mixture was degassed three times by alternating vacuum and nitrogen purge. The mixture was then heated at 85° C. for 6 h, then was stirred at room temperature for overnight. Ethyl acetate and ether were added and the mixture was washed with water. The aqueous layer was extracted with ethyl acetate, the organic layers were combined, and washed twice with water and once with brine. The organic layer was dried over $MgSO_4$, filtered and concentrated. The crude product was purified by MPLC (silica) eluting with ethyl acetate in hexanes to afford the title compound. LCMS: m/z 235 (M+1)$^+$.

Step B: (1-oxo-3,4-dihydro-1H-isochromen-6-yl)acetaldehyde 6-(1,3-Dioxolan-2-ylmethyl)-3,4-dihydro-1H-isochromen-1-one (4.42 g, 18.9 mmol) was dissolved in dioxane (25 mL) and treated with 3 M HCl (40 mL). The reaction mixture was stirred at room temperature over night, then was warmed to 50° C. for 2 h to drive the reaction to completion (however this led to increased side product production based on LCMS). Ethyl acetate was added and the layers were separated. The aqueous layer was extracted again with ethyl acetate, and the combined organic layers were washed with brine and dried over $MgSO_4$ to afford the title compound.

LCMS: m/z 191 (M+1)$^+$.

Step C: tert-butyl-4-[2-(1-oxo-3,4-dihydro-1H-isochromen-6-yl)ethyl]piperazine-1-carboxylate (1-Oxo-3,4-dihydro-1H-isochromen-6-yl)acetaldehyde (2.40 g, 12.6 mmol) was combined with 1-Boc-piperazine (3.53 g, 18.9 mmol) and sodium triacetoxyborohydride (13.4 g, 63.1 mmol) in DCM (90 mL). The reaction mixture was stirred at room temperature overnight. Saturated sodium bicarbonate solution was added and the layers were separated. The organic layer was washed with brine, then dried over $MgSO_4$. The crude product was purified first by MPLC (silica), eluting with 3% of a 10% $NH_4OH$/methanol solution in DCM, then a second MPLC purification eluting with ethyl acetate, to afford the title compound. LCMS: m/z 361 (M+1)$^+$.

Step D: 6-[2-(piperazin-1-yl)ethyl]-3,4-dihydro-1H-isochromen-1-one hydrochloride tert-Butyl-4-[2-(1-oxo-3,4-dihydro-1H-isochromen-6-yl)ethyl]piperazine-1-carboxylate (2.24 g, 6.21 mmol) was treated with 4 M HCl in dioxane (Aldrich, 90 mL) and the resulting mixture was stirred at room temperature for 40 minutes. The reaction mixture was then concentrated to afford the title compound. LCMS: m/z 261 (M+1)$^+$.

Intermediate 32

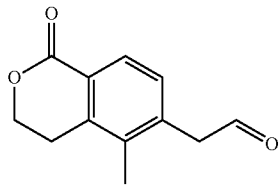

(5-Methyl-1-oxo-3,4-dihydro-1H-isochromen-6-yl)acetaldehyde

Step A: 6-Bromo-5-iodo-3,4-dihydro-1H-isochromen-1-one

To a flask charged with 6-Bromo-3,4-dihydro-1H-isochromen-1-one (50 mg, 0.22 mmol) was added NIS (60 mg, 0.26 mmol) and Triflic acid (3 mL). TLC showed two new product spots within 3 hours. The reaction was poured into ice, extracted with EtOAc, dried over sodium sulfate, and purified by MPLC (Hex/EtOAc gradient) to afford the desired product. LC-MS (IE, m/z): 355 [M+1]$^+$;

Step B: 6-Bromo-5-methyl-3,4-dihydro-1H-isochromen-1-one

To a 20 mL microwave tube was added 6-Bromo-5-iodo-3,4-dihydro-1H-isochromen-1-one (300 mg, 0.85 mmol), Potassium Trifluoromethylborate (114 mg, 0.94 mmol), $PdCl_2(dppf)$-$CH_2Cl_2$ Adduct (69 mg, 0.085 mmol), cesium carbonate (830 mg, 2.6 mmol), and a stir bar. The mixture was sealed and THF (10 mL) and water (1 mL) were added with a syringe. The mixture was purged three times with nitrogen, and then heated to 140° C. for 30 minutes. TLC showed formation of the desired product. The reaction was diluted with EtOAc, washed with water and brine, dried over sodium sulfate, adsorbed onto silica gel, and purified by MPLC (Hex/EtOAc gradient) to furnish the product. LC-MS (IE, m/z): 241 [M+1]$^+$;

Step C: 5-Methyl-6-(prop-2-en-1-yl)-3,4-dihydro-1H-isochromen-1-one

To a flask charged with 6-Bromo-5-methyl-3,4-dihydro-1H-isochromen-1-one (100 mg, 0.42 mmol), Allyl Tri-n-butyltin (165 mg, 0.50 mmol), Palladium Tetrakis (48 mg, 0.041 mmol), and Lithium Chloride (35 mg, 0.83 mmol) was added Toluene (5 ml). The mixture was sealed with a condenser and purged three times with N2. The mixture was then heated to reflux for 6 hours. TLC and LC showed complete reaction. The reaction was diluted with EtOAc (50 mL), washed with brine, dried over sodium sulfate, adsorbed onto silica, and purified by MPLC (Hex/EtOAc gradient) to furnish the product. LC-MS (IE, m/z): 203 [M+1]$^+$.

Step D: (5-Methyl-1-oxo-3,4-dihydro-1H-isochromen-6-yl)acetaldehyde

To a MeOH solution of 5-Methyl-6-(prop-2-en-1-yl)-3,4-dihydro-1H-isochromen-1-one (60 mg, 0.30 mmol) was bubbled ozone until it turned blue. Excess ozone was removed by bubbling nitrogen through. To the reaction was added DMS (0.22 ml, 3.0 mmol), and it was allowed to warm up slowly. The reaction was diluted with EtOAc, washed with water, and purified by MPLC to give the title compound. LC-MS (IE, m/z): 205 [M+1]$^+$.

Intermediate 33

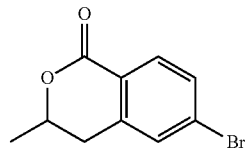

6-bromo-3-methyl-3,4-dihydro-1H-isochromen-1-one

A −78° C. solution of diisopropylamine (13.26 ml, 93 mmol)) in THF (155 ml) was treated with nBuLi (1.6M in Hexanes; 58.1 ml, 93 mmol) over a period of 15 minutes using a syringe pump. In a separate flask, a solution of 2-methyl-4-bromo benzoic acid (10 g, 46.5 mmol) and HMPA (8.33 ml, 46.5 mmol) in THF (155 ml) was cooled to −78° C. Methyl Lithium (29.1 ml, 46.5 mmol) was added slowly via syringe to the cooled solution in order to make the lithio carboxylate. The resulting solution was stirred for 10 minutes and then transferred via cannula to the LDA solution at −78° C. The resulting bright red solution was stirred at −78° C. for an additional 1 hour before being quenched with anhydrous acetaldehyde (7.88 ml, 140 mmol) (color changed from red to orange to clear yellow) and the reaction was then taken out of the dry ice acetone bath and allowed to stir for an additional 1 hour. The flask containing the reaction mixture was then resubmerged in the dry ice acetone bath before it was quenched with 4M HCl in Dioxane (50 mL) followed by 25 mL of MeOH. The reaction was stirred at room temp for an additional 1 hour. The crude reaction was partitioned b/w 200 mL EtOAc and 200 mL water. The organic layer was washed with waster, brine, dried with mag. sulfate, filtered and concentrated. Purification via MPLC (30-70% DCM/Hexanes) afforded 6-bromo-3-methyl-3,4-dihydro-1H-isochromen-1-one.

$^1$H NMR (500 MHz; CDCl$_3$): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-MS (IE, m/z): 241 [M+1]$^+$.

Intermediate 34

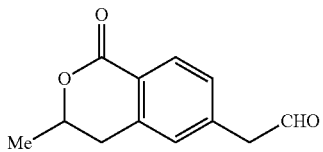 [SMILES: CC1Cc2cc(CC=O)ccc2C(=O)O1]

(3-methyl-1-oxo-3,4-dihydro-1H-isochromen-6-yl)acetaldehyde

Step A: 6-(1,3-dioxolan-2-ylmethyl)-3-methyl-3,4-dihydro-1H-isochromen-1-one

A sealed tube was charged with aryl bromide, palladium (II) acetate (0.028 g, 0.124 mmol) and tri-t-butylphosphine-BF$_4$ complex (0.072 g, 0.249 mmol) and sealed. The tube was evacuated and refilled with nitrogen before DMF (12.44 ml) and 6-bromo-3-methyl-3,4-dihydro-1H-isochromen-1-one (0.75 g, 3.11 mmol) were added followed by bromo(1,3-dioxolan-2-ylmethyl)zinc (6.22 ml, 3.11 mmol). The tube was heated to 110° C. in the microwave for 75 minutes, after which it was cooled, diluted with EtOAc, filtered, concentrated and purified via MPLC (20-50% E/H) to afford 6-(1,3-dioxolan-2-ylmethyl)-3-methyl-3,4-dihydro-1H-isochromen-1-one. $^1$H NMR (500 MHz; CDCl$_3$): δ 8.04 (d, J=7.8 Hz, 1H), 7.32 (d, J=8.0 Hz, 1H), 7.17 (s, 1H), 5.11 (t, J=4.7 Hz, 1H), 4.68 (m, 1H), 3.96 (m, 2H), 3.88 (m, 2H), 3.03 (d, J=4.9 Hz, 2H), 2.93 (m, 2H), 1.54 (d, J=6.4 Hz, 3H); LC-MS (IE, m/z): 249 [M+1]$^+$.

Step B: (3-methyl-1-oxo-3,4-dihydro-1H-isochromen-6-yl)acetaldehyde

A 1:1 solution of dioxane:3N HCl was added to a flask containing of 99 mg (0.49 mmol) of 6-(1,3-dioxolan-2-ylmethyl)-3-methyl-3,4-dihydro-1H-isochromen-1-one; the reaction was then stirred at room temp overnight. The crude reaction mixture was then partitioned between water and DCM. The organic layer was washed with saturated sodium bicarbonate solution, followed by brine. The organic layer was then dried with magnesium sulfate, filtered and concentrated.

Intermediate 35

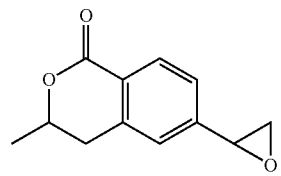

3-methyl-6-(oxiran-2-yl)-3,4-dihydro-1H-isochromen-1-one

Step A: 6-ethenyl-3-methyl-3,4-dihydro-1H-isochromen-1-one

A solution of 6-bromo-3-methyl-3,4-dihydro-1H-isochromen-1-one (2.4 g, 9.96 mmol) and triethylamine (2.78 ml, 19.91 mmol) in EtOH (39.8 ml) was added to a microwave vial containing Cl$_2$Pd(dppf)$_2$-DCM (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave 6-ethenyl-3-methyl-3,4-dihydro-1H-isochromen-1-one.

$^1$H NMR (500 MHz; CDCl$_3$): 8.07 (d, J=8.0 Hz, 1H), 7.44 (dd, J=1.2, 7.1 Hz, 1H), 7.26 (s, 1H), 6.75 (dd, J=10.8, 17.6 Hz, 1H), 5.90 (d, J=17.6 Hz, 1H), 5.44 (d, J=11 Hz, 1H), 4.75 (m, 1H), 2.96 (m, 2H), 1.54 (d, J=6.1 Hz, 3H); LC-MS (IE, m/z): 189 [M+1]$^+$.

Step B: 3-methyl-6-(oxiran-2-yl)-3,4-dihydro-1H-isochromen-1-one

A solution of 6-ethenyl-3-methyl-3,4-dihydro-1H-isochromen-1-one (1.69 g, 8.98 mmol) in DCM (60 mL) was treated with mCPBA (3.10 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give 3-methyl-6-(oxira-2-yl)-3,4-dihydro-1H-isochromen-1-one.

$^1$H NMR (500 MHz; CDCl$_3$): 8.10 (d, J=8.0 Hz, 1H), 7.33 (m, 1H), 7.16 (d, J=4.4 Hz, 1H), 4.71 (m, 1H), 3.92 (dt, J=1.6, 2.5 Hz, 1H), 3.22 (dt, J=1.4, 4.1 Hz, 1H), 2.96 (m, 2H), 2.80 (dd, J=2.3, 3.5 Hz, 1H), 1.55 (d, J=7.6 Hz, 3H); LC-MS (IE, m/z): 205 [M+1]$^4$.

Intermediate 36

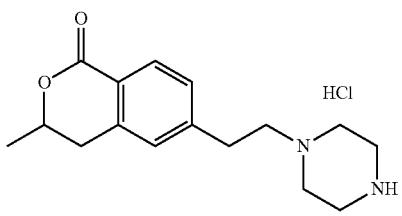 [SMILES: CC1Cc2cc(CCN3CCNCC3)ccc2C(=O)O1 ; Cl]

3-methyl-6-[2-(piperazin-1-yl)ethyl]-3,4-dihydro-1H-isochromen-1-one hydrochloride Step A: tert-butyl 4-[2-(3-methyl-1-oxo-3,4-dihydro-1H-isochromen-6-yl)ethyl]piperazine-1-carboxylate Freshly prepared (3-methyl-1-oxo-3,4-dihydro-1H-isochromen-6-yl)acetaldehyde was dissolved in DCM. To the solution was added Boc-piperazine (671 mg, 3.6 mmol) followed by sodium triacetoxyborohydride (1.91 g, 9.0 mmol), the reaction mixture was allowed to stir overnight before being quenched with 10 mL of MeOH. The excess solvent was removed and the residue was re-redissolved in DCM; washed with water and brine, dried with magnesium sulfate, filtered, concentrated and purified via MPLC (50-100% EtOAc/Hex) to afford tert-butyl 4-[2-(3-methyl-1-oxo-3,4-dihydro-1H-isochromen-6-yl)ethyl]piperazine-1-carboxylate.

$^1$H NMR (500 MHz; CDCL$_3$): 8.02 (d, J=7.8 Hz, 1H), 7.24 (d, J=7.7 Hz, 1H), 7.09 (s, 1H), 4.68 (in, 1H), 3.49 (m, 4H), 2.94 (m, 4H), 2.88 (m, 2H), 2.51 (m, 4H), 1.54 (d, J=6.8 Hz, 3H), 1.48 (s, 9H); LC-MS (IE, m/z): 375 [M+1]$^+$.

Step B: 3-methyl-6-[2-(piperazin-1-yl)ethyl]-3,4-dihydro-1H-isochromen-1-one hydrochloride A solution of tert-butyl 4-[2-(3-methyl-1-oxo-3,4-dihydro-1H-isochromen-6-yl)ethyl]piperazine-1-carboxylate (850 mg, 2.27 mmol) was stirred in 4N HCl in Dioxane for 4 hours. The excess solvent was then removed to give the free amine as the HCl salt. LC-MS (IE, m/z): 275 [M+1]$^+$.

Intermediate 37

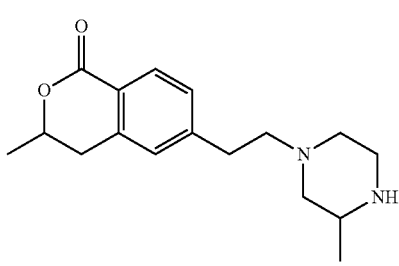 [SMILES: CC1CN(CCc2ccc3c(c2)CC(C)OC3=O)CCN1]

3-methyl-6-[2-(3-methylpiperazin-1-yl)ethyl]-3,4-dihydro-1H-isochromen-1-one

Freshly prepared (3-methyl-1-oxo-3,4-dihydro-1H-isochromen-6-yl)acetaldehyde was dissolved in DCM. To the solution was added 2-methyl piperazine (221 mg, 2.2 mmol) followed by sodium cyanoborohydride (165 mg, 2.64 mmol). The reaction mixture was allowed to stir overnight before being quenched with 10 mL of 1N HCl followed by stirring for 30 minutes. The reaction mixture was then treated with 50 mL of saturated sodium bicarbonate solution and extracted with DCM (3×50 mL). The combined organic layers were washed with water and brine, dried with magnesium sulfate, filtered, concentrated and purified via MPLC (30-100% (10% IPA in DCM/DCM) to afford 3-methyl-6-[2-(3-methylpiperazin-1-yl)ethyl]-3,4-dihydro-1H-isochromen-1-one. LC-MS (IE, m/z): 289 [M+1]$^+$.

The following INTERMEDIATES (Table) were prepared in an analogous fashion to that described for the synthesis of 3-methyl-6-[2-(3-methylpiperazin-1-yl)ethyl]-3,4-dihydro-1H-isochromen-1-one using the indicated substituted piperazines and freshly prepared (3-methyl-1-oxo-3,4-dihydro-1H-isochromen-6-yl)acetaldehyde,

| INTERMEDIATE | Starting substituted piperazine | Structure of INTERMEDIATE | LC/MS (M + 1)$^+$ |
|---|---|---|---|
| 38 | 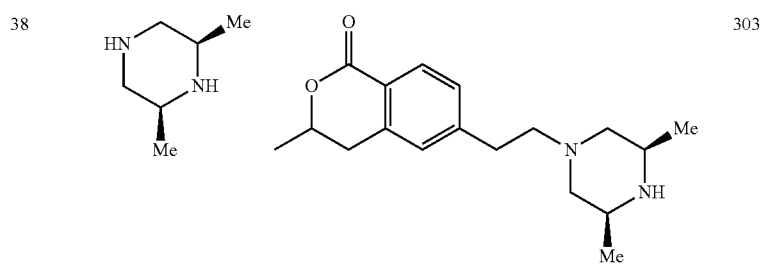 | | 303 |
| 39 | 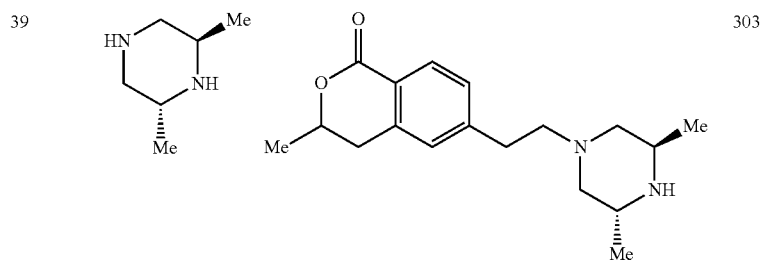 | | 303 |

| INTERMEDIATE | Starting substituted piperazine | Structure of INTERMEDIATE | LC/MS (M + 1)+ |
|---|---|---|---|
| 40 | HN⌐⌐NH, Me Me | Me substituted isochromanone with piperazine-Me,Me | 303 |
| 41 | HN⌐⌐NH, CF₃ | Me substituted isochromanone with piperazine-CF₃ | 343 |

Intermediate 42

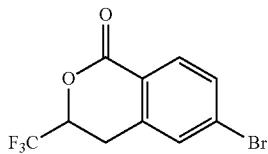

6-bromo-3-(trifluoromethyl)-3,4-dihydro-1H-isochromen-1-one

Step A: 4-bromo-N,N-diethyl-2-methylbenzamide

A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide. ¹H NMR (500 MHz; CDCL₃): 7.39 (s, 1H), 7.36 (dd, J=1.6; 9.7 Hz, 1H), 7.05 (d, J=8.1, 1H), 3.3 (bs, 1H), 3.5 (bs, 1H), 3.13 (q, J=6.8 Hz, 2H), 2.29 (s, 3H), 1.27 (t, J=7.1 Hz, 3H), 1.05 (t, J=7.1 Hz, 3H); LC/MS (M+H)⁺270.

Step B: 4-bromo-N,N-diethyl-2-(trifluoroacetyl)benzamide

A solution of 4-bromo-N,N-diethyl-2-methylbenzamide (500 mg, 1.851 mmol) in Tetrahydrofuran (4.63 ml) was cooled to −78 C and treated with LDA (2.313 ml, 4.63 mmol) for 15 minutes before 2,2,2-trifluoro-N-methoxy-N-methylacetamide (320 mg, 2.036 mmol) in Tetrahydrofuran (4.63 ml) was added to the reaction mixture and allowed to warm to room temperature. The reaction was stirred overnight and then partitioned between 1N HCl (100 mL) and EtOAc (100 mL). The aqueous layer was further extracted with EtOAc (2×50 mL). The combined organic layers were washed with brine (150 mL), dried over magnesium sulfate, filtered and concentrated. Purification using MPLC (0-20% EtOAc/Hex) affords 4-bromo-N,N-diethyl-2-(trifluoroacetyl)benzamide. LC-MS (IE, m/z): 366 [M+1]⁺.

Step C: 6-bromo-3-(trifluoromethyl)-3,4-dihydro-1H-isochromen-1-one

A solution of 4-bromo-N,N-diethyl-2-(trifluoroacetyl)benzamide (480 mg, 1.311 mmol) in Ethanol at room temp was treated with NaBH₄ (49.6 mg, 1.311 mmol) for 1 hour. The reaction was then quenched with 4N HCl in dioxane, transferred to a sealed tube and heated to 60 C for 48 hours. The reaction mixture was cooled, partitioned b/w sat sodium bicarbonate and DCM. The combined organic layers were then washed with water (50 mL), brine (50 mL), dried over magnesium sulfate, filtered and concentrated. The crude material was then purified via MPLC (10-30% EtOAc/Hexane) to afford 6-bromo-3-(trifluoromethyl)-3,4-dihydro-1H-isochromen-1-one. ¹H NMR (500 MHz; CDCL₃): 7.99 (d, J=8.3 Hz, 1H), 7.64 (dd, J=1.1, 8.4 Hz, 1H), 7.54 (s, 1H), 4.89 (m, 1H), 3.33 (m, 1H), 3.16 (m, 1H); LC-MS (IE, m/z): 295 [M+1]⁺.

Intermediate 43

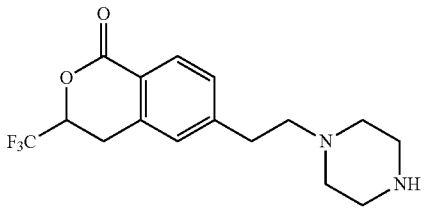 [SMILES: O=C1OC(C(F)(F)F)Cc2cc(CCN3CCNCC3)ccc21]

6-[2-piperazin-1-yl)ethyl]-3-(trifluoromethyl)-3,4-dihydro-1H-isochromen-1-one

6-[2-(Piperazin-1-yl)ethyl]-3-(trifluoromethyl)-3,4-dihydro-1H-isochromen-1-one was prepared in an analogous fashion to that described for the synthesis of 3-methyl-6-[2-(piperazin-1-yl)ethyl]-3,4-dihydro-1H-isochromen-1-one hydrochloride starting from 6-bromo-3-(trifluoromethyl)-3,4-dihydro-1H-isochromen-1-one.

Intermediate 44

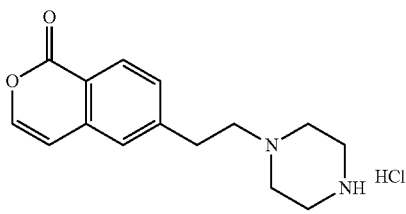 [SMILES: O=c1occc2cc(CCN3CCNCC3)ccc12 ; Cl]

4-[2-(1-oxo-1H-isochromen-6-yl)ethyl]piperazin-1-ium chloride:

Step A: 4,6-dibromo-3,4-dihydro-1H-isochromen-1-one

6-Bromo-3,4-dihydro-1H-isochromen-1-one (3.00 g, 13.2 mmol) was dissolved in $CCl_4$ (150 mL) then added N-bromosuccinimide (2.352 g, 13.21 mmol) followed by benzoyl peroxide (0.0960 g, 0.396 mmol) and refluxed for 3 hrs. Filtered and concentrated then chromatographed through a 120 g ISCO Redi-sep. column and eluted with 0-25% ETOAc/Hexane to yield 4,6-dibromo-3,4-dihydro-1H-isochromen-1-one. LC-MS (IE, m/z): 306.9 [M+1]$^+$; $^1$H-NMR (500 MHz, $CDCL_3$) δ ppm 8.03 (d, J=8.9 Hz, 1H), 7.69 (d, J=7.9 Hz, 1H), 7.68 (s, 1H), 5.32 (t, J=3 Hz, 1H), 4.72-4.81 (q, 1H).

Step B: 6-bromo-1H-isochromen-1-one 4,6-dibromo-3,4-dihydro-1H-isochromen-1-one (1.76 g, 5.75 mmol) was dissolved in DCM (15 mL) then added TEA (20 mL, 143 mmol) and stirred at room temperature for 72 hrs. The mixture was concentrated then took up the residue with DCM and washed with 1N HCl. Repeated the wash with brine then dried over $Na_2SO_4$ and evaporated to dryness. The residue was purified by MPLC with 0-100% ETOAc/hexane to yield 6-bromo-1H-isochromen-1-one. LC-MS (IE, m/z): 227 [M+2]$^+$; $^1$H-NMR (500 MHz, $CDCl_3$) δ ppm 8.18 (d, J=8.5 Hz, 1H), 7.67 (dd, J=1.8, 6.4 Hz, 1H), 7.64 (d, J=1.9 Hz, 1H), 7.33 (d, J=5.7 Hz, 1H), 6.47 (d, J=5.8 Hz, 1H).

Step C: 6-(1,3-dioxolan-2ylmethyl)-1H-isochromen-1-one

6-Bromo-1H-isochromen-1-one (980 mg, 4.35 mmol), tributyl phosphonium tetrafluoroborate (25.3 mg, 0.087 mmol), palladium(ii) acetate (9.78 mg, 0.044 mmol) was suspended in DMF (10 mL) then added Rieki reagent (9.58 mL, 4.79 mmol) and degassed. The reaction was heated to 85° C. for 10 hrs then stirred at RT overnight. Added methyltetrahydrofuran and washed with brine. The organic layer was dried over $MgSO_4$, filtered and evaporated to dryness. The residue was purified thru a 80 g ISCO Redi-sep column and eluted with 0-100% ETOAc/hexane to yield 6-(1,3-dioxolan-2ylmethyl)-1H-isochromen-1-one. LC-MS (IE, m/z): 233 [M+1]$^+$;

Step D: (1-oxo-1H-isochromen-6-yl)acetaldehyde 6-(1,3-dioxolan-2ylmethyl)-1H-isochromen-1-one (410 mg, 1.77 mmol) was dissolved in dioxane (20 mL) and HCl (20 mL, 3M) was added then stirred for 16 hrs. The reaction was extracted with ethyl acetate then separated. The organic layer was washed with brine, dried over $Na_2SO_4$, filtered and concentrated. to yield (1-oxo-1H-isochromen-6-yl)acetaldehyde LC-MS (IE, m/z): 189 [M+1]$^+$; $^1$H-NMR (500 MHz, $CDCl_3$) δ ppm 9.86 (s, 1H), 8.33 (d, J=8 Hz, 1H), 7.41 (d, J=8 Hz, 1H), 734(s, 2H), 6.52 (d, J=5.5 Hz, 1H), 3.89 (s, 2H).

Step E: tert-butyl 4-[2-(1-oxo-1H-isochromen-6-yl)ethyl]piperazine-1-carboxylate (1-oxo-1H-isochromen-6-yl) acetaldehyde (240 mg, 1.275 mmol) and tert-butyl piperazine-1-carboxylate (238 mg, 1.275 mmol) were dissolved in dichloroethane (10 mL) and added sodium triacetoxyborohydride (811 mg, 3.83 mmol) then stirred at RT for 16 hrs. LC-MS showed product peak. The reaction was washed with $NaHCO_3$, brine, dried over $Na_2SO_4$ and evaporated to dryness. The residue was chromatographed through a 80 g. ISCO Redi-Sep column and eluted with 0-100% ethyl acetate/hexane to yield tert-butyl 4-[2-(1-oxo-1H-isochromen-6-yl)ethyl]piperazine-1-carboxylate. $^1$H-NMR (500 MHz, $CDCl_3$) δ ppm 8.25 (d, J=8 Hz, 1H), 7.42 (d, J=9.4 Hz, 2H), 6.49 (d, J=5.7 Hz, 1H), 3.49 (s, 4H), 2.96 (t, J=7.6 Hz, 2H), 2.69 (t, J=7.3 Hz, 2H), 2.51 (s, 4H), 1.50 (s, 9H).

Step F: 4-[2-(1-oxo-1H-isochromen-6-yl)ethyl]piperazin-1-ium chloride tert-Butyl 4-[2-(1-oxo-1H-isochromen-6-yl) ethyl]piperazine-1-carboxylate (370 mg, 1.03 mmol) was stirred in 3N HCl in dioxane (5 mL) for 16 h. The reaction was concentrated to yield 4-[2-(1-oxo-H-isochromen-6-yl)ethyl]piperazin-1-ium chloride. LC-MS (IE, m/z): 259 [M+1]$^+$.

Intermediate 45

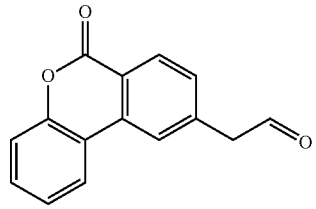 [SMILES: O=CCc1ccc2c(=O)oc3ccccc3c2c1]

(6-oxo-6H-benzo[c]chromen-9-yl)acetaldehyde

Step A: 9-methyl-6H-benzo[c]chromen-6-one

A sealed tube containing methyl 2-bromo-4-methylbenzoate (650 mg, 2.84 mmol), 2-(4,4,5,5-tetramethyl-1,3,2-dioxaborolan-2-yl)phenol (781 mg, 3.55 mmol) and TETRAKIS(TRIPHENYLPHOSPHINE)PALLADIUM(0) (164 mg, 0.142 mmol) was evacuated and backfilled with nitrogen before Toluene (1.29E+04 µl) and Ethanol (1290 µl) were added, followed by $K_2CO_3$ (2838 µl, 5.68 mmol). The tube was heated in the microwave for 25 minutes at 130° C. The mixture was cooled, diluted with chloroform (15 mL), washed with aqueous ammonium chloride (saturated, 10 mL), dried (Na$_2$SO$_4$), filtered and the solvent was evaporated under reduced pressure. The crude product was then purified by column chromatography on silica gel Isolute Flash Si; eluting with 5-10% EtOAc/isohexane to give 9-methyl-6H-benzo[c]chromen-6-one. $^1$H NMR (500 MHz; CDCl$_3$): 8.32 (d, J=8.3 Hz, 1H), 8.09 (d, J=8.0 Hz, 1H), 7.94 (s, 1H), 7.51 (m, 1H), 7.37 (m, 3H), 2.59 (s, 3H); LC-MS (IE, m/z): 211 [M+1]$^+$.

Step B: (6-oxo-6H-benzo[c]chromen-9-yl)acetaldehyde

A solution of 9-methyl-6H-benzo[c]chromen-6-one (100 mg, 0.476 mmol) in dry DMF (2378 μl) Was treated with TERT-BUTOXY BIS(DIMETHYLAMINO)METHANE (99 mg, 0.571 mmol) at 80° C. in a sealed tube for one hour. The solution turned a deep red color and was cooled, diluted with 2M HCl and stirred for 20 minutes. The solution was then extracted with DCM, the combind orgainc layers were dried, filtered and concentrated with out heat. Crude (6-oxo-6H-benzo[c]chromen-9-yl)acetaldehyde was used without further purification. LC-MS (IE, m/z): 239 [M+1]$^+$.

Intermediate 46 (Method 1)

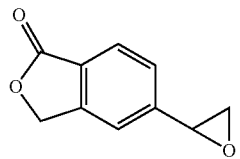 [SMILES: O=C1OCc2cc(C3CO3)ccc21]

5-Oxirane-2-yl-2-benzofuran-1(3H)-one

To a solution of 5-(2-hydroxyethyl)-2-benzofuran-1(3H)-one (0.50 g, 2.8 mmol) and Et$_3$N (0.65 mL, 4.7 mmol) in dichloromethane (5 mL) was added methanesulfonyl chloride (0.24 mL, 3.1 mmol) at 0° C. After 15 min. the reaction mixture was poured into saturated ammonium chloride and extracted with dichloromethane. The combined organics were washed with 1 N HCl, saturated sodium bicarbonate solution, and brine, then dried (MgSO$_4$) and concentrated in vacua. The residue (LC/MS: [(M+1)]$^+$=257.2; t$_R$=0.45 min) was redissolved in dichloromethane (5 mL) and treated with DBU (0.80 mL, 5.3 mmol) and stirred 2 h. TLC monitoring showed conversion to the olefin. The reaction mixture was diluted with water and extracted with dichloromethane. The combined organics were washed with 1 N HCl, saturated sodium bicarbonate solution, and brine, then dried (MgSO$_4$) and concentrated in vacuo. The resulting olefin (LC/MS: [(M+1)]$^+$=161.2) was dissolved in dichloromethane (5 mL) and treated with meta-chloro perbenzoic acid (0.90 g, 3.7 mmol) at 0° C. After 3 h, the mixture was diluted with saturated sodium bicarbonate solution and extracted twice with dichloromethane. The combined organic extracts were washed with brine, dried (MgSO$_4$), filtered and concentrated in vacuo. The crude epoxide was purified by silica gel column chromatography (5→80% EtOAc:hexane) to provide the 5-oxirane-2-yl-2-benzofuran-1(3H)-one. $^1$H NMR (500 MHz, CD$_3$OD) δ 7.84 (d, J=8.0 Hz, 1H), 7.55 (s, 1H), 7.52 (d, J=8.0 Hz, 1H), 5.38 (s, 2H), 4.05 (dd, J=2.6, 3.9 Hz, 1H), 3.21 (dd, J=4.3, 5.4 Hz, 1H), 2.82 (dd, J=2.4, 5.5 Hz, 1H); LC/MS: [(M+1)]$^+$=177.1.

Intermediate 46 (Method 2)

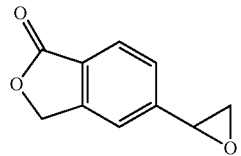

5-Oxirane-2-yl-2-benzofuran-1(3H)-one

5-Bromophthalide (50 g, 235 mmol), potassium vinyl trifluoroborate (62.9 g, 469 mmol), and PdCl$_2$(dppf)-CH$_2$Cl$_2$ Adduct (9.58 g, 11.74 mmol) were added to ethanol (500.0 mL), then TEA (65.4 mL, 469 mmol) was added. The reaction mixture was degassed then heated to reflux for 8 h. The reaction mixture was worked up by diluting with ethyl acetate and washing with brine twice. The organic layer was dried and evaporated to dryness. The crude product was purified by MPLC (silica, 600 g column) with 25% EtOAc/hexane-(3 L) then with 30% EtOAc/Hexane (2 L) to yield the target olefin. The olefin (28.4 g, 177 mmol) was dissolved in DCM (400 mL) then mCPBA (47.7 g, 213 mmol) was added. The mixture was stirred at room temperature overnight. Some SM remained so another 25 g of mCPBA was added and the mixture was stirred overnight. The mixture was poured into ice cold Na$_2$SO$_3$ solution (saturated). The layers were separated and the organic layer was washed with 5% NaOH solution, brine, then was dried (MgSO4). The crude product was purified by MPLC (330 g column, eluting with 40% EtOAc/hexane, 2 L, then with 45% EtOAc/hexane, 2 L to afford the target epoxide. $^1$H-NMR (500 MHz, CDCL$_3$): δ ppm 7.92 (d, J=8 Hz, 1H), 7.50 (d, J=8 Hz, 1H), 7.43 (s, 1H), 5.34 (s, 2H), 4.02 (s, 1H), 3.26 (s, 1H), 2.81 (d, J=3Hz, 1H); LC-MS: M+1=177.

Intermediate 47

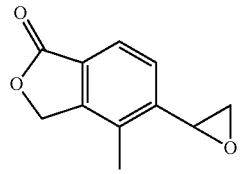

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$ Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl₃): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175.

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na₂S₂O₃, NaHCO₃, and brine. The organic layer was dried over Na₂SO₄, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. ¹H-NMR (500 MHz, CDCl₃): δ ppm 7.77 (d, J=8 Hz, 1H), 7.43 (d, 8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H); LC-MS: M+1=191.

Intermediates 48A and 48B (Method 1)

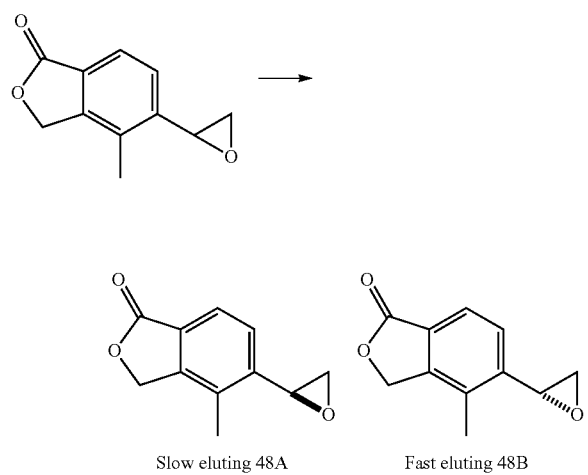

14A: 4-methyl-5-[(2S)-oxiran-2-yl]-2-benzofuran-1(3H)-one
14B: 4-methyl-5-[(2R)-oxiran-2-yl]-2-benzofuran-1(3H)-one Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO2, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 3B) eluted at 5.2 min, and the slow epoxide (4-methyl-5-[(2S)-oxiran-2-yl]-2-benzofuran-1(3H)-one, 3A) eluted at 5.6 min.

Alternatively, the resolution could also be achieved using a mobile phase of 8% MeOH/98% CO₂ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

Intermediate 48B (Method 2)

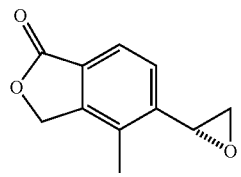

4-methyl-5-[(2R)-oxiran-2-yl]-2-benzofuran-1(3H)-one

StepA: 3-hydroxymethyl-2-methyl phenol

To a 5 L 3 neck RB equipped with overhead stirrer was charged NaBH4 (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF₃—OEt₂ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

¹H-NMR (400 MHz, DMSO-d₆): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C: 5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through Solka-Flok® and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

$^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: Trifluoromethanesulfonic acid 4-methyl-1-oxo-1,3-dihydro-isobenzofuran-5-yl ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka floc, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g, 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

$^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L, erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif.) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

Intermediate 49

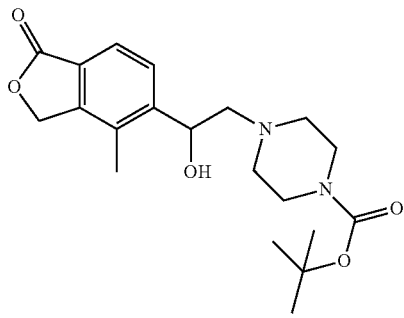 [SMILES: Cc1c(C(O)CN2CCN(C(=O)OC(C)(C)C)CC2)ccc2c1COC2=O]

1,1-dimethylethyl-4-[2-hydroxy-2-(4-methyl-1-oxo-1,3-dihydro-2-benzofuran-5-yl)ethyl]piperazine-1-carboxylate To a 25 mL microwave tube was added 4-methyl-5-oxiran-2-yl-2-benzofuran-1(3H)-one (1.2 g, 6.0 mmol, 1.0 eq) and tert-butyl piperazine-1-carboxylate (1.7 g, 9.0 mmol, 1.5 eq). To the mixture was added EtOH (15 mL). The reaction was heated in a microwave apparatus at 150° C. for 30 min. The reaction mixture was concentrated to dryness. The crude product was purified by flash column chromatography yielding 1,1-dimethylethyl-4-[2-hydroxy-2-(4-methyl-1-oxo-1,3-dihydro-2-benzofuran-5-yl)ethyl]piperazine-1-carboxylate. $^1$H NMR (500 MHz, CDCl$_3$, δ in ppm): 7.80 (1H, s), 7.26 (1H, s), 5.25 (2H, s), 5.10 (1H, dxd, J=3.0 Hz, J=10.8 Hz), 3.50 (4H, m), 2.73 (2H, m), 2.53-2.40 (4H, m), 2.28 (3H, s, Me), 1.47 (9H, s). LC-MS (IE, m/z): 377.1 [M+1]$^+$; $t_R$=2.1 min.

Intermediate 50

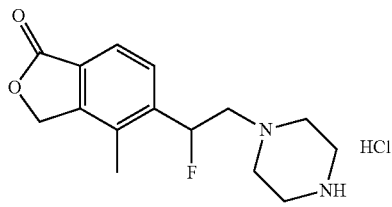 [SMILES: Cc1c(C(F)CN2CCNCC2)ccc2c1COC2=O ; Cl]

5-(1-fluoro-2-piperazin-1-ylethyl)-4-methyl-2-benzofuran-1(3H-one hydrochloride

Step A: 1,1-dimethylethyl-4-[2-fluoro-2-(4-methyl-1-oxo-1,3-dihydro-2-benzofuran-5-yl)ethyl]piperazine-1-carboxylate 1,1-Dimethylethyl-4-[2-hydroxy-2-(4-methyl-1-oxo-1,3-dihydro-2-benzofuran-5-yl)ethyl]piperazine-1-carboxylate (0.500 g, 1.46 mmol) was added to a 25 mL flask containing a stir bar and dissolved in THF (4 mL). To the solution was added DAST (0.232 mL, 1.76 mmol) and triethylamine (0.175 mL, 1.33 mmol) and subsequently stirred for 45 min; LC as well as TLC (hexanes/EtOAc=1/0.3) indicated that reaction had gone to completion. Reaction mixture was concentrated to dryness, absorbed into silica gel and loaded into silica column. Compound 1,1-dimethylethyl-4-[2-fluoro-2-(4-methyl-1-oxo-1,3-dihydro-2-benzofuran-5-yl)ethyl]piperazine-1-carboxylate was obtained.

Step B: 5-(1-fluoro-2-piperazin-1-ylethyl)-4-methyl-2-benzofuran-1(3H)-one hydrochloride 1,1-Dimethylethyl-4-[2-fluoro-2-(4-methyl-1-oxo-1,3-dihydro-2-benzofuran-5-yl)ethyl]piperazine-1-carboxylate (0.18 g) was treated with 4M HCl in dioxane (4 mL) and stirred at room temperature for 1 h. The mixture was then concentrated to dryness. Analysis by LC indicated complete removal of the Boc group and formation of compound 5-(1-fluoro-2-piperazin-1-ylethyl)-4-methyl-2-benzofuran-1(3B)-one hydrochloride. $^1$H-NMR (DMSO, 500 MHz), δ 7.744 (d, J=7.5 Hz, 1H), 7.612 (d, J=7.5 Hz, 1H), 6.264-6.167 (m, 1H), 5.382 (s, 2H), 3.362-3.309 (m, 2H), 3.255-3.125 (m, 8H), 3.078-3.049 (m, 1H), 2.499 (s, 3H)

Intermediate 51

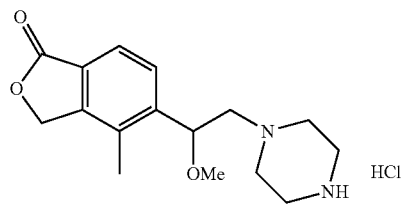 [SMILES: COC(CN1CCNCC1)c1ccc2c(c1C)COC2=O ; Cl]

4-methyl-5-[1-(methyloxy)-2-piperazin-1-ylethyl]-2-benzofuran-1(3H)-one hydrochloride Step A: 1,1-dimethylethyl-4-[2-(4-methyl-1-oxo-1,3-dihydro-2-benzofuran-5-yl)-2-(methyloxy)ethyl]-piperazine-1-carboxylate 1,1-Dimethylethyl-4-[2-hydroxy-2-(4-methyl-1-oxo-1,3-dihydro-2-benzofuran-5-yl)ethyl]piperazine-1-carboxylate (0.10 g, 0.27 mmol) was combined in a 50 mL flask with DMF (2 mL) and DCM (1 mL) and the flask was placed in a cooling bath at −20° C. The mixture was then treated with NaH (0.021 g, 0.53 mmol) and stirred for 30 minute, followed by addition of iodomethane (0.0414 mL, 0.664 mmol) at −20° C. The resulting mixture was stirred for another 1 h after which analysis by LC as well as TLC (5% MeOH in DCM) indicated that reaction had gone to completion. The reaction mixture was quenched by addition of MeOH and stirred for 10 min at room temperature. The reaction mixture was concentrated to dryness, dissolved in EtOAc and absorbed into silica gel where it was separated on silica column; to obtain 1,1-dimethylethyl-4-[2-(4-methyl-1-oxo-1,3-dihydro-2-benzofuran-5-yl)-2-(methyloxy)ethyl]-piperazine-1-carboxylate was isolated.

Step B: 4-methyl-5-[1-(methyloxy)-2-piperazin-1-ylethyl]-2-benzofuran-1(3H)-one hydrochloride 1,1-Dimethylethyl-4-[2-(4-methyl-1-oxo-1,3-dihydro-2-benzofuran-5-yl)-2-(methyloxy) ethyl]-piperazine-1-carboxylate was treated with 4M HCl in dioxane (4 mL) and stirred at room temperature for 1 h. The reaction mixture was concentrated to dryness. Analysis by LC indicated complete removal of the Bac group and formation of compound 4-methyl-5-[1-(methyloxy)-2-piperazin-1-ylethyl]-2-benzofuran-1(3H)-one hydrochloride. $^1$H-NMR (DMSO, 500 MHz), δ 7.747 (d, J=7.5 Hz, 1H), 7.577 (d, J=7.5 Hz, 1H), 5.402-5.388

(m, 2H), 5.113 (d, J=9 Hz, 1H), 3.850 (s, 3H), 3.496-3.327 (m, 8H), 3.228-3.140 (m, 3H), 2.500 (s, 3H).

Intermediate 52

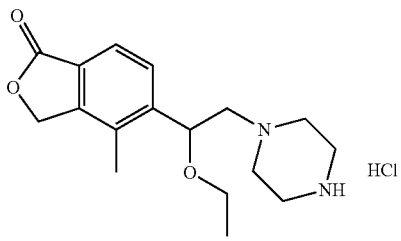 [SMILES: CCOC(CN1CCNCC1)c1ccc2c(c1C)COC2=O ; Cl]

5-[1-(ethyloxy)-2-piperazin-1-ylethyl]-4-methyl-2-benzofuran-1(3H)-one hydrochloride
Step A: 1,1-dimethylethyl-4-[2-(ethyloxy)-2-(4-methyl-1-oxo-1,3-dihydro-2-benzofuran-5-yl)ethyl]piperazine-1-carboxylate
1,1-Dimethylethyl-4-[2-hydroxy-2-(4-methyl-1-oxo-1,3-dihydro-2-benzofuran-5-yl)ethyl]piperazine-1-carboxylate (0.15 g, 0.40 mmol) in a 50 mL flask was dissolved in DMF (1.5 mL) and DCM (1.5 mL) and the flask was placed in a cooling bath at −30° C. The mixture was then treated with NaH (0.023 g, 0.99 mmol) and the resulting mixture was stirred for 30 minutes, followed by treatment with iodoethane (0.080 mL, 0.99 mmol) at −30° C. The resulting mixture was stirred for another 1 h after which LC as well as TLC (5% MeOH in DCM) indicated that reaction had gone to completion. The reaction mixture was quenched with MeOH and stirred for 10 min at room temperature. The reaction mixture was then concentrated to dryness, dissolved in EtOAc, and absorbed into silica gel where it was separated on silica column to afford of 1,1-dimethylethyl-4-[2-(ethyloxy)-2-(4-methyl-1-oxo-1,3-dihydro-2-benzofuran-5-yl)ethyl]piperazine-1-carboxylate. $^1$H-NMR (CDCl3, 500 MHz), δ 7.683 (d, J=8 Hz, 1H), 7.554 (d, J=8 Hz, 1H), 5.200 (s, 2H), 3.356 (s, 1H), 2.899-2.810 (m, 5H), 2.703-2.660 (m, 8H), 2.253 (m, 2H), 1.405 (s, 3H), 1.386 (s, 9H).
Step B: 5-[1-(ethyloxy)-2-piperazin-1-ylethyl]-4-methyl-2-benzofuran-1 (3H)-one hydrochloride
1,1-Dimethylethyl-4-[2-(ethyloxy)-2-(4-methyl-1-oxo-1,3-dihydro-2-benzofuran-5-yl)ethyl]piperazine-1-carboxylate was treated with 4M HCl in dioxane (4 mL) and stirred at room temperature for 1 h. The reaction mixture was concentrated to dryness. Analysis by LC indicated complete removal of the Boc group and formation of 5-[1-(ethyloxy)-2-piperazin-1-ylethyl]-4-methyl-2-benzofuran-1(3H)-one hydrochloride. LC-MS (IE, m/z): 305 [M+1]$^+$; $t_R$=0.69 min Intermediate 53

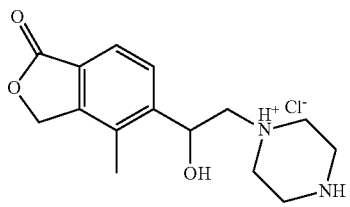

1-[2-hydroxy-2-(4-methyl-1-oxo-1,3-dihydro-2-benzofuran-5-yl)ethyl]piperazin-1-ium chloride
tert-Butyl-4-[2-hydroxy-2-(4-methyl-1-oxo-1,3-dihydro-2-benzofuran-5-yl)ethyl]piperazine-1-carboxylate (800 mg, 2.1 mmol, 1.0 eq) was treated with 4 N HCl in dioxane (4 mL). The reaction was stirred at r.t. for 3 h and then concentrated. The product was dried under high vacuum pump for 6 hr. The intermediate is often converted to the corresponding free base prior to use by partitioning between saturated Na$_2$CO$_3$ solution and CHCl$_3$-IPA (3:1). LC-MS (IE, m/z): 277.1 [M+1]$^+$; $t_R$=0.4 min.

Intermediate (R)-54 (Free Base)

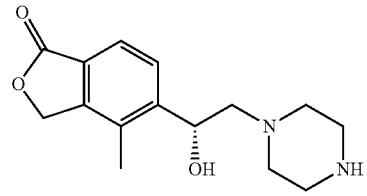 [SMILES: Cc1c([C@@H](O)CN2CCNCC2)ccc2c1COC2=O]

5-[(1R)-1-hydroxy-2-piperazin-1-ylethyl]-4-methyl-2-benzofuran-1(3H)-one
To a 20 mL microwave tube charged with 4-methyl-5-[(2R)-oxiran-2-yl]-2-benzofuran-1(3H)-one (1020 mg, 5.40 mmol) and a stir bar was added 1-Boc Piperazine (800 mg, 4.3 mmol) and EtOH (15 mL). The tube was sealed and heated in a microwave apparatus to 150° C. for 1 hour. The crude product was adsorbed onto silica gel, and purified by flash chromatography (Hexanes-EtOAc with 10% EtOH: 0~100% gradient), and solvent removed to afford tert-butyl-4-[(2R-2-hydroxy-2-(4-methyl-1-oxo-1,3-dihydro-2-benzofuran-5-yl)ethyl]piperazine-1-carboxylate. LCMS M+1 (calc. 377.20, found 377.13). This product was treated with neat TFA for 15 minutes to remove the Boc group. After removal of TFA under reduced pressure, the residue was taken into aq NaHCO$_3$, and back-extracted with CHCl$_3$-IPA (3:1). The organic layers were combined, dried over sodium sulfate, and concentrated to afford 5-[(1R)-1-hydroxy-2-piperazin-1-ylethyl]-4-methyl-2-benzofuran-1(3H)-one. $^1$H NMR (DMSO-d$_6$, 500 MHz) δ 7.68 (d, J=8.0 Hz, 1H), 7.65 (d, J=8.0 Hz, 1H), 5.38, 5.35 (AB system, J=15.4, J=16.7, 2H), 5.06 (dd, J=3.9 Hz, J=3.7 Hz, 1H), 3.76 (m, 1H), 2.72 (m, 4H), 2.42 (m, 4H), 2.34 (d, J=3.8 Hz, 1H), 2.32 (d, J=3.8 Hz, 1H), 2.24 (s, 3H); LC/MS: (IE, m/z) [M+1]$^+$=277.03.

Intermediate 55

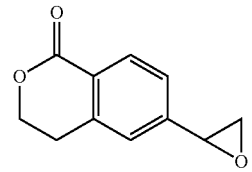 [SMILES: O=C1OCCc2cc(C3CO3)ccc21]

6-(oxiran-2-yl)-3,4-dihydro-1H-isochromen-1-one
Step A: 6-vinyl-3,4-dihydro-1H-isochromen-1-one
To a 100 mL round bottom flask was added 6-bromo-3,4-dihydro-1H-isochromen-1-one (20 g, 88 mmol, 1.0 eq), potassium trifluoro(vinyl)borate (23.6 g, 176 mmol, 2.0 eq),

[1,1′-bis(diphenylposphino)-ferrocene]dichloropalladium (II) complex with dichloromethane(1:1) (7.2 g, 8.8 mmol, 0.1 eq) and triethylamine (24.5 mL, 2.0 eq). To above mixture was added ethanol (400 mL). The flask was degassed and filled with nitrogen. The reaction was heated to reflux under $N_2$ for 10 hr, then cooled and stirred at r.t. for 5 hr. The mixture was then diluted with EtOAc, filtered through a pad of Celite® and washed with brine. The organic phase was dried over $Na_2SO_4$, filtered and purified by flash column chromatography using Biotage and the solvent systems (0-50% EtOAc/Hexane). The fractions containing desired product were collected and concentrated to give 6-vinyl-3,4-dihydro-1H-isochromen-1-one.

LC-MS (IE, m/z): 175.1 [M+1]; $^1$H NMR (500 MHz, $CDCl_3$), δ in ppm: 8.06 (1H, aromatic, d, J=8.2 Hz), 7.43 (1H, aromatic, dxd, J=8.2 Hz, J=1.4 Hz), 7.27 (1H, aromatic, d, J=1.4 Hz), 6.74 (1H, —CH=CH$_2$, dxd, J=11.0 Hz, J=17.6 Hz), 5.89 (1H, —CH=CH$_2$, d, J=17.6 Hz), 5.43 (1H, —CH=CH$_2$, d, J=10.8 Hz), 4.53 (2H, CH$_2$—O—, t, J=6.0 Hz), 3.05 (2H, CH$_2$—CH$_2$—O—, t, J=6.0 Hz).

Step B: 6-(oxiran-2-yl)-3,4-dihydro-1H-isochromen-1-one

6-Vinyl-3,4-dihydro-1H-isochromen-1-one (36.0 g, 207 mmol, 1.0 eq) was added into a 500 mL round bottom flask and dissolved in dichloromethane (500 mL). The solution was cooled to 0° C., added portion wise 3-chloroperoxybenzoic acid (98.0 g, 413 mmol, 2.0 eq). The mixture was then purged with $N_2$ and stirred at r.t. for 18 hr. To above solution was added water (100 mL). The crude product was extracted with dichloromethane. The organic phase was washed with brine (100 mL), dried over anhydrous $Na_2SO_4$, filtered, concentrated and purified by flash column chromatography (hexane/EtOAc 0-50%). The desired product was obtained. LC-MS (IE, m/z): 191.27 [M+1]$^+$; $^1$H NMR (500 MHz, CDCl$_3$, δ in ppm): 8.07 (1H, aromatic, d, J=8.1 Hz), 7.32 (1H, aromatic, d, J=8.0 Hz), 7.16 (1H, br-s, aromatic), 4.52 (2H, C$\underline{H}_2$—O—, t, J=5.7 Hz), 3.90 (1H, br-s), 3.20 (1H, m), 3.05 (2H, C$\underline{H}_2$—CH$_2$—O—, t, J=5.7 Hz), 2.77 (1H, m).

Intermediate 56

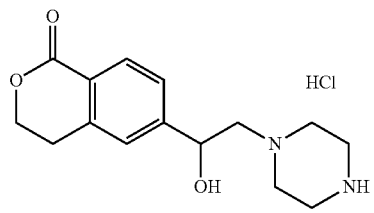 [SMILES: O=C1OCCc2cc(C(O)CN3CCNCC3)ccc21 ; Cl]

6-[1-hydroxy-2-(piperazin-1-yl)ethyl]-3,4-dihydro-1-H-isochromen-1-one hydrochloride 6-[1-Hydroxy-2-(piperazin-1-yl)ethyl]-3,4-dihydro-1-H-isochromen-1-one hydrochloride was prepared in an analogous fashion to that described for the synthesis of 1-[2-hydroxy-2-(4-methyl-1-oxo-1,3-dihydro-2-benzofuran-5-yl)ethyl]piperazin-1-ium chloride starting from 6-(oxiran-2-yl)-3,4-dihydro-1H-isochromen-1-one and tert-butyl piperazine-1-carboxylate. LC-MS (IE, m/z): 277 [M+1]$^+$.

Intermediate 57

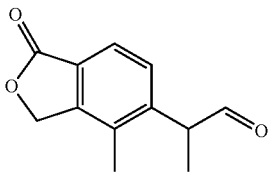

2-(4-Methyl-1-oxo-1,3-dihydro-2-benzofuran-5-yl)propanal

Step A: 4-methyl-5-prop-2-en-1-yl-2-benzofuran-1(3H)-one

A mixture of 5-bromo-4-methyl-2-benzofuran-1(3H)-one (980 mg, 4.3 mmol), allyl-tributyl-stannane (1.7 g, 5.2 mmol), LiCl (550 mg, 12.9 mmol) and Pd(PPh$_3$)$_4$ (0.1 g) in anhydrous toluene was stirred at reflux under $N_2$ overnight. The solvent was removed under reduced pressure, and the residue was purified with silica gel column chromatography to give the product 4-methyl-5-prop-2-en-1-yl-2-benzofuran-1(3H)-one.

Step B: (4-methyl-1-oxo-1,3-dihydro-2-benzofuran-5-yl)acetic acid

To a stirred solution of 4-methyl-5-prop-2-en-1-yl-2-benzofuran-1(3H)-one (2.10 g, 11.2 mmol) in CCl$_4$ (50 mL), acetonitrile (50 mL) and water (75 mL) was added sodium periodate (12 g, 55.8 mmol) and ruthenium oxide hydrate (210 mg) and the resulting mixture was stirred at ambient temperature overnight. The mixture was diluted with 100 mL DCM and 100 mL of water. The organic layer was dried over anhydrous sodium sulfate and concentrated. The residue was purified with silica gel column chromatography to afford (4-methyl-1-oxo-1,3-dihydro-2-benzofuran-5-yl)acetic acid.

Step C: 1,1-dimethylethyl (4-methyl-1-oxo-1,3-dihydro-2-benzofuran-5-yl)acetate

To a solution of (4-methyl-1-oxo-1,3-dihydro-2-benzofuran-5-yl)acetic acid (100 mg, 0.48 mmol) in anhydrous DCM (10 mL) was added 1,1-dimethylethyl-N,N-bis(1-methylethyl)imidocarbamate (485 mg, 2.50 mmol) dropwise at 0° C. under $N_2$. Then the mixture was stirred at r.t. over night. The mixture was filtered and the filtrate was washed with 2N HCl and brine, dried over anhydrous sodium sulfate and concentrated. The residue was purified by preparative TLC to give 1,1-dimethylethyl (4-methyl-1-oxo-1,3-dihydro-2-benzofuran-5-yl)acetate. $^1$H-NMR (400 MHz, CDCl$_3$) δ 6 ppm 7.70 (d, J=7.8 Hz, 1H), 7.38 (d, J=7.0 Hz, 1H), 5.25 (s, 2H), 3.67 (s, 3H), 2.27 (s, 3H), 1.44 (s, 9H).

Step D: 1,1-dimethylethyl-2-(4-methyl-1-oxo-1,3-dihydro-2-benzofuran-5-yl)propanoate A solution of 1,1-dimethylethyl (4-methyl-1-oxo-1,3-dihydro-2-benzofuran-5-yl)acetate (770 mg, 3.1 mmol) in 30 mL of anhydrous THF was cooled to −78° C. NaHMDS (4.0 mmol) was added to the reaction dropwise at −78° C. After the addition, the mixture was stirred at −78° C. for 1 h and then CH$_3$I (462 mg, 3.20 mmol) was added dropwise at −78° C. The reaction was warmed to room temperature slowly and stirred at ambient temperature over night. The reaction was quenched with NH$_4$Cl solution, and extracted with EtOAc. The organic layer was washed with brine, dried over anhydrous sodium sulfate and concentrated. The residue was purified via preparative TLC to afford 1,1-dimethylethyl-2-(4-methyl-1-oxo-1,3-dihydro-2-benzofuran-5-yl)propanoate. $^1$H-NMR (400 MHz, CDCl$_3$) δ ppm 7.67 (d, J=7.8 Hz, 1H), 7.37 (d, J=7.8 Hz, 1H), 5.19 (s, 2H), 3.80 (dd, J=7.0 Hz, 1H), 2.24 (s, 3H), 1.40 (d, J=7.0 Hz, 1H), 1.32 (s, 9H).

Step E: 2-(4-methyl-1-oxo-1,3-dihydro-2-benzofuran-5-yl)propanoic acid

To a solution of 1,1-dimethylethyl-2-(4-methyl-1-oxo-1,3-dihydro-2-benzofuran-5-yl)propanoate (400 mg, 1.4 mmol) in 10 mL of anhydrous DCM was added TFA (2.5 mL) dropwise at r.t. Then the mixture was stirred for 1 hour. The solvent was removed under vacuum to give the crude 2-(4-methyl-1-oxo-1,3-dihydro-2-benzofuran-5-yl)propanoic acid, which was used for next step without purification.

Step F: 5-(2-hydroxy-1-methylethyl)-4-methyl-2-benzofuran-1(3H)-one

To a solution of 2-(4-methyl-1-oxo-1,3-dihydro-2-benzofuran-5-yl)propanoic acid (300 mg, 1.4 mmol) in 18 mL of anhydrous THF was added BH$_3$.THF (2 mL, 2 mmol) dropwise at 0° C. Then the mixture was warmed to room temperature slowly and then stirred for 3 hours. Then the mixture was quenched with MeOH and the solvent was removed under vacuum. The residue was the purified via prep-TLC to give 5-(2-hydroxy-1-methylethyl)-4-methyl-2-benzofuran-1(3H)-one. $^1$H-NMR (400 MHz, CDCl$_3$) δ ppm 7.73 (d, J=7.8 Hz, 1H), 7.40 (d, J=7.8 Hz, 1H), 5.23 (s, 2H), 3.77 (d, J=7.0 Hz, 2H), 3.36~3.42 (m, 1H), 2.30 (s, 3H), 1.27 (d, J=7.0 Hz, 3H).

Step G: 2-(4-Methyl-1-oxo-1,3-dihydro-2-benzofuran-5-yl)propanal 5-(2-Hydroxy-1-methylethyl)-4-methyl-2-benzofuran-1(3H)-one (161 mg, 0.781 mmol, 1.0 eq) was dissolved in DCM (6 mL). To above solution was added Dess-MartinPeriodinane (397 mg, 0.937 mmol, 1.2 eq). The reaction was stirred at rt for 2 hr. To the reaction was added DCM (10 mL), Na$_2$S$_2$O$_3$ (6 mL) and H$_2$O (6 mL). The mixture was stirred at r.t. for 30 minutes and formed two layers. The bottom layer was separated and washed with aqueous NaHCO$_3$, brine and water, dried over Na$_2$SO$_4$, filtered, and concentrated to dryness. The crude product was used to next step without purification. $^1$H NMR (500 MHz, CDCl$_3$, δ in ppm): 9.70 (1H, s, CHO), 7.79 (1H, d, J=7.8 Hz), 7.28 (1H, d, J=7.8 Hz), 5.28 (2H, s), 3.27 (1H, m), 2.32 (3H, s), 1.50 (3H, d, J=7.2 Hz).

Intermediate 58

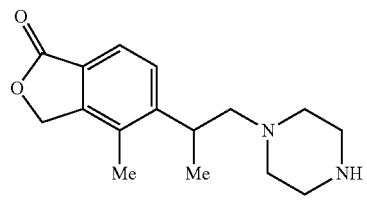 [SMILES: Cc1c(C(C)CN2CCNCC2)ccc2c1COC2=O]

4-methyl-5-(1-methyl-2-piperazin-1-ylethyl)-2-benzofuran-1(3H)-one

Step A: tert-Butyl-4-[2-(4-methyl-1-oxo-1,3-dihydro-2-benzofuran-5-yl)propyl]piperazine-1-carboxylate In a 100 mL round bottom flask, 2-(4-methyl-1-oxo-1,3-dihydro-2-benzofuran-5-yl)propanal (100 mg, 0.49 mmol, 1.0 eq) and Boc-piperazine (91 mg, 0.49 mmol, 1.0 eq) was dissolved in DCM (10 mL). To above solution was added sodium triacetoxyborohydride (208 mg, 0.98 mmol, 2.0 eq). The reaction was stirred at r.t. for 16 hr. The reaction was then diluted with DCM (10 mL), washed with aqueous bicarbonate, water and brine. The organic phase was dried over MgSO$_4$, filtered and concentrated. The product was obtained after purification by flash column chromatography (5% MeOH/DCM). LC-MS (IE, m/z): 375.41 [M+1]$^+$;

Step B: 4-Methyl-5-(1-methyl-2-piperazin-1-ylethyl)-2-benzofuran-1(3H)-one tert-Butyl-4-[2-(4-methyl-1-oxo-1,3-dihydro-2-benzofuran-5-yl)propyl]piperazine-1-carboxylate (160 mg, 0.43 mmol) was stirred in TFA (3 mL) at r.t for 3 hr. The reaction was concentrated and pumped over high vacuum pump overnight to give the desired product, which could be converted to its freebase by partitioning between an organic solvent and saturated NaHCO3 solution. LC-MS (IE, m/z): 275.38 [M+1]$^+$.

Intermediate 59

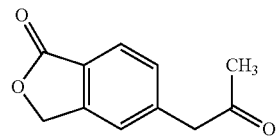

5-(2-oxopropyl)-2-benzofuran-1(3H)-one

Step A: 5-(2-methylprop-2-en-1-yl)-2-benzofuran-1(3H)-one

5-Bromo-2-benzofuran-1(3H)-one (1.0 g, 4.7 mmol) was combined with tributyl(2-methylprop-2-en-1-yl)stannane (1.94 g, 5.63 mmol), lithium chloride (0.597 g, 14.1 mmol) and Pd(PPh$_3$)$_4$ (0.271, 0.235 mmol) in toluene (20 mL) under a nitrogen atmosphere. The resulting mixture was stirred at reflux for 3 h, then was concentrated, diluted with DCM, filtered through a pad of Celite®, and washed in turn with saturated sodium bicarbonate solution, brine and water. The organic layer was dried over MgSO$_4$, and the concentrated filtrate was purified by flash chromatography eluting with 10% ethyl acetate/hexanes to afford the title compound. LC-MS (IE, m/z): 189.3 [M+1]$^+$;

Step B: 5-(2-oxopropyl)-2-benzofuran-1(3H)-one

To a solution of 5-(2-methylprop-2-en-1-yl)-2-benzofuran-1(3H)-one (175 mg, 0.930 mmol) in THF was added osmium tetroxide (295 mg, 0.0460 mmol) and the mixture was stirred for 10 minutes. Then a solution of sodium periodate (497 mg, 2.32 mmol) in water was added and the mixture was stirred at room temperature overnight. The reaction mixture was concentrated, diluted with DCM, and washed with Na$_2$S$_2$O$_3$ solution. The organic layer was dried over MgSO$_4$, filtered, and concentrated. The crude product was purified by flash chromatography (30% ether/hexanes) to afford the title compound. LC-MS (IE, m/z): 191.3 [M+1]$^+$.

Intermediate 60

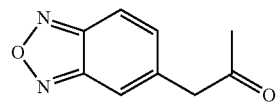

1-(2,1,3-benzoxadiazol-5-yl)propan-2-one 1-(2,1,3-Benzoxadiazol-5-yl)propan-2-one was prepared in an analogous fashion to the synthesis of 5-(2-oxopropyl)-2-benzofuran-1(3H)-one described above starting from 5-bromo-2,1,3-benzoxadiazole.

Intermediate 61

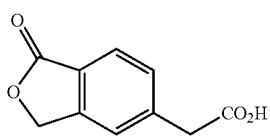 [SMILES: O=C(O)Cc1ccc2c(c1)COC2=O]

(1-oxo-1,3-dihydro-2-benzofuran-5-yl)acetic acid

Step A: tert-butyl (1-oxo-1,3-dihydro-2-benzofuran-5-yl)acetate

To a 20 mL microwave tube charged with 5-bromo-2-benzofuran-1(3H)-one (500 mg, 2.35 mmol) and palladium tetrakis triphenylphosphine (136 mg, 0.117 mmol) in THF (5 mL) was added (2-tert-butoxy-2-oxoethyl) (chloro) zinc (6.57 mL, 0.5 M, 3.29 mmol). The mixture was purged with nitrogen 3 times, and heated to 105° C. for 30 minutes in a microwave reactor. The reaction mixture was poured into water and filtered then extracted with ethyl acetate twice. The organic layer was ashed with brine, dried, and evaporated to dryness. The residue was purified by MPLC on a 40 g ISCO Redi-Sep column to yield tert-butyl (1-oxo-1,3-dihydro-2-benzofuran-5-yl)acetate. $^1$H-NMR (500 MHz, CDCl$_3$) δ ppm 7.89 (d, J=7.7 Hz, 1H), 7.46 (d, J=8.3 Hz, 1H), 7.44 (s, 1H), 5.33 (s, 2H), 3.69 (s, 2H), 1.47 (s, 9H).

Step B: (1-oxo-1,3-dihydro-2-benzofuran-5-yl)acetic acid tert-Butyl (1-oxo-1,3-dihydro-2-benzofuran-5-yl)acetate (1.2 g, 4.8 mmol) was dissolved in TFA and stirred at room temperature for one h. The reaction mixture was concentrated and pumped under vacuum overnight to afford the title compound. LC-MS (IE, m/z): 193.2 [M+1]$^+$.

Example 62

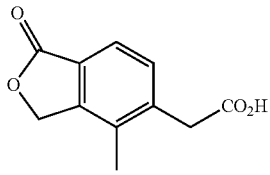

(4-methyl-1-oxo-1,3-dihydro-2-benzofuran-5-yl)acetic acid (4-Methyl-1-oxo-1,3-dihydro-2-benzofuran-5-yl)acetic acid was made in two steps starting from 5-bromo-4-methyl-2-benzofuran-1(3H)-one and (2-tert-butoxy-2-oxoethyl) (chloro) zinc in an analogous fashion to that described above for the synthesis of (1-oxo-1,3-dihydro-2-benzofuran-5-yl) acetic acid. LC-MS: 207 [M+1]$^+$.

Intermediate 63

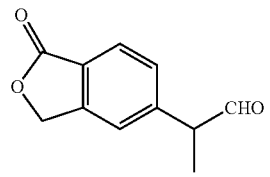

2-(1-oxo-1,3-dihydro-2-benzofuran-5-yl) propanal

Step A: tert-butyl 2-(1oxo-1,3-dihydro-2-benzofuran-5-yl) propanoate

Tert-butyl (1-oxo-1,3-dihydro-2-benzofuran-5-yl)acetate (127 mg, 0.512 mmol) was dissolved in DMF (10 mL) then cooled to 0° C. Sodium hydride (22.5 mg, 0.563 mmol) was added and the mixture was stirred for ½ hr., then methyl iodide (0.128 mL, 2.046 mmol) was added. The reaction mixture was stirred at room temperature for 16 h. The reaction mixture was poured into brine and extracted with ethyl acetate twice. The combined organic layers were dried over MgSO4, filtered, and evaporated to dryness. The residue was purified by MPLC with a 40 g ISCO Redi-Sep column and eluted with 0-25% ethyl acetate/hexane to yield tert-butyl 2-(1-oxo-1,3-dihydro-2-benzofuran-5-yl) propanoate. LC-MS (IE, m/z): 263 [M+1]$^+$; $^1$H-NMR (500 MHz, CDCl$_3$) δ ppm 7.91 (d, J=8.1 Hz, 1H), 7.49 (d, J=8.0 Hz, 1H), 7.47 (s, 1H), 5.34 (s, 2H), 3.79 (q, J=7.1, 14.75 Hz, 1H), 1.54 (d, J=7.1, 3H), 1.44 (s, 9H).

Step B: (1-hydroxypropan-2-yl)-5-2-benzofuran-1(3)-one

Tert-butyl 2-(1-oxo-1,3-dihydro-2-benzofuran-5-yl) propanoate (155 mg, 0.591 mmol) was stirred in TFA (2 mL) then HiVac dried to yield quantitatively 2-(1-oxo-1,3-dihyro-2-benzofuran-5yl) propanoic acid. The propionic acid (125 mg, 0.606 mmol) was dissolved in THF and cooled to −15° C. and treated with BH$_3$.THF (0.606 mL, 0.606 mmol). The reaction was stirred at RT overnight. TLC-showed presence of starting material, so more BH$_3$.THF (1.21 mL, 1.21 mmol) was added and continued to stir for another 1.5 h. The reaction mixture was quenched with methanol then concentrated. The residue was taken up in ethyl acetate and washed with very small amount of brine then dried over MgSO$_4$. The ethyl acetate layer was filtered and concentrated to yield (1-hydroxypropan-2-yl)-5-2-benzofuran-1(3)-one.

$^1$H-NMR (500 MHz, CDCl$_3$) δ ppm 7.89 (d, J=7.8 Hz, 1H), 7.46 (d, J=7.8 Hz, 1H), 7.46 (s, 1H), 5.33 (s, 2H), 3.79-3.85 (m, 2H), 3.11-3.18 (m, 1H), 1.37 (d, J=7.1 Hz, 3H).

Step C: 2-(1oxo-1,3-dihydro-2-benzofuran-5-yl) propanal (1-hydroxypropan-2-yl)-5-2-benzofuran-1(3)-one (116 mg, 0.604 mmol) was dissolved in DCM (30 mL) then added Dess-Martin Periodinane (384 mg, 0.905 mmol) and stirred at room temperature for 2 h. A solution of 10% Na$_2$S$_2$O$_3$ (15 mL) was added and stirred for 1 h. The DCM layer was separated, washed with Na$_2$CO$_3$, dried over Na$_2$SO$_4$, filtered and concentrated to yield 2-(1oxo-1,3-dihydro-2-benzofuran-5-yl) propanal.

Intermediate 64

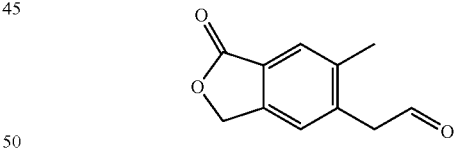

(6-methyl-1-oxo-1,3-dihydro-2-benzofuran-5-yl)acetaldehyde

Step A: 5-bromo-6-methyl-2-benzofuran-1(3H))-one

To a solution of 4-bromo-3-methylbenzoic acid (2.0 g, 9.3 mmol) in THF (20 mL) was added borane-THF solution (27.9 mL, 1.0 M) at 0° C. The mixture was allowed to stir for 16 hours. TLC showed clean conversion. The reaction was quenched with methanol, diluted with EtOAc (100 mL), washed with 1 N HCl, 0.5 N NaOH, and brine, dried over sodium sulfate, filtered and concentrated to give a light yellow oil (1.8 g). To the yellow oil was added Thallium Trifluoroacetate (5.4 g, 9.9 mmol) and TFA (10 mL). The mixture was allowed to stir for 16 hours. The volatiles were removed under reduced pressure. The residue was pumped under high vacuum for 15 minutes before palladium (II) chloride (0.16 g, 0.90 mmol), magnesium oxide (1.1 g, 27 mmol), lithium chloride (0.38 g, 0.90 mmol), and methanol (30 mL) were added. The mixture was stirred under an atmosphere of carbon mono-oxide until the reaction turned black. The reaction was diluted with DCM (100 mL), filtered through a pad of Celite®, adsorbed onto silica gel, and purified by MPLC. After removal of solvent, the desired product was obtained. $^1$H-NMR (500 MHz, CDCl$_3$) δ ppm 7.81 (s, 1H), 7.74 (s, 1H), 5.30 (s, 2H), 2.55 (s, 3H).

Step B: (6-methyl-1-oxo-1,3-dihydro-2-benzofuran-5-yl)acetaldehyde

To a flask charged with 5-bromo-6-methyl-2-benzofuran-1(3H))-one (300 mg, 1.3 mmol) was added allyl tri-n-butyltin (660 mg, 2.0 mmol), palladium tetrakis (153 mg, 0.13 mmol), lithium chloride (168 mg, 4.0 mmol), and toluene (20 mL). The reaction was purged three times with Nitrogen, and then heated to 130° C. for 16 hours. TLC showed complete reaction at that point. The reaction was diluted with EtOAc, washed with water and brine, dried over sodium sulfate, adsorbed onto silica gel, and purified by MPLC to afford a light yellow oil. The yellow oil obtained above was dissolved in methanol (20 mL) and chilled to −78° C. To that solution was bubbled ozone through until it turned light blue. Excess ozone was removed from the reaction by bubbling nitrogen into the solution, followed by addition of dimethyl sulfide (1.1 mL, 16 mmol). LC showed formation of the desired product. The solvent was removed under reduced pressure. The residue was loaded onto a 40 g Isco silica gel column, and separated by MPLC. LC/MS: (IE, m/z) (M+1)$^+$=191.2.

Intermediate 65

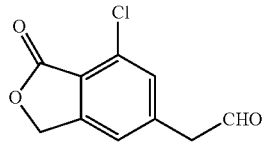 [SMILES: O=CCc1cc(Cl)c2c(c1)COC2=O]

(7-chloro-1-oxo-1,3-dihydro-2-benzofuran-5-yl)acetaldehyde

Step A: 5-bromo-7-chloro-2-benzofuran-1(3H)-one

To a solution of 3-bromo-5-chlorobenzoic acid (1.0 g, 4.3 mmol) in THF (30 mL) was added borane-THF solution (13 mL, 1.0 M) at 0° C. The mixture was allowed to stir for 16 hours. TLC showed clean conversion. The reaction was quenched with methanol, diluted with EtOAc (100 mL), washed with 0.5 N HCl, 0.5 N NaOH, and brine, dried over sodium sulfate, filtered and concentrated to give rise to (3-bromo-5-chlorophenyl)methanol as a waxy solid (680 mg, 72% yield). To the above solid (680 mg, 3.1 mmol) was added thallium trifluoroacetate (1.8 g, 3.4 mmol) and TFA (4 mL). The mixture was allowed to stir at RT for 16 hours. The volatiles were removed under reduced pressure. The residue was pumped under high vacuum for 15 minutes before palladium (II) chloride (0.054 g, 0.31 mmol), magnesium oxide (0.25 g, 6.1 mmol), lithium chloride (0.13 g, 0.31 mmol), and methanol (30 mL) were added. The mixture was stirred under an atmosphere of carbon mono-oxide until the reaction turned black. The reaction was diluted with DCM (50 mL), filtered through a pad of Celite®, adsorbed onto silica gel, and purified by MPLC. Removal of solvent gave rise to a mixture of 5-bromo-7-chloro-2-benzofuran-1(3H)-one and 7-bromo-5-chloro-2-benzofuran-1(3H)-one. LC/MS: (IE, m/z) (M+1)$^+$=249.0;

Step B: (7-chloro-1-oxo-1,3-dihydro-2-benzofuran-5-yl)acetaldehyde

To a round bottom flask charged with a mixture of 5-bromo-7-chloro-2-benzofuran-1(3H)-one and 7-bromo-5-chloro-2-benzofuran-1(3H)-one (120 mg, 0.48 mmol) and a stir bar was added PdCl$_2$(dppf)-DCM complex (40 mg, 0.048 mmol) allyl tri-n-butyltin (241 mg, 0.73 mmol), lithium chloride (41 mg, 0.97 mmol), and toluene (15 mL). The mixture was purged three times with nitrogen, and heated to 120° C. for 4 hours. LC showed formation of the desired product, which was purified by silica gel chromatography (Hexane-EtOAc). The resulting oil yellow oil was then dissolved in methanol (10 mL). The solution was cooled to −78° C. To this solution was bubbled ozone through until it turned light blue. Excess ozone was removed by bubbling nitrogen through the solution, which was followed by addition of dimethyl sulfide (0.21 mL, 2.9 mmol). The reaction was allowed to warm to RT slowly. LC showed formation of the desired product. The reaction was diluted with EtOAc (50 mL), washed with brine, dried over sodium sulfate, adsorbed onto silica gel, and purified by flash chromatography as a mixture of (7-chloro-1-oxo-1,3-dihydro-2-benzofuran-5-yl)acetaldehyde and (6-chloro-3-oxo-1,3-dihydro-2-benzofuran-4-yl)acetaldehyde. LC/MS: (IE, m/z) (M+1)$^+$=211.1.

Intemediate 66

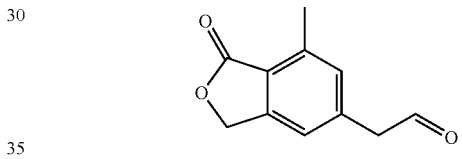

(7-methyl-1-oxo-1,3-dihydro-2-benzofuran-5-yl)acetaldehyde

Step A: (3-bromo-5-methylphenyl)methanol

To a DCM (20 mL) solution of tert-butyl 3-bromo-5-(hydroxymethyl)benzoate (1.2 g, 4.2 mmol) was added methanesulfonyl chloride (0.62 g, 5.5 mmol) and triethylamine (1.2 mL, 8.4 mmol) at 0° C. The mixture was allowed to stir for 16 hours. TLC showed clean conversion. The reaction was diluted with DCM (100 mL), washed with 0.1 N HCl (100 mL) and brine, dried over sodium sulfate, and concentrated to afford tert-butyl 3-bromo-5-{[(methylsulfonyl)oxy]methyl}benzoate as a light yellow oil, which was used without further purification.

The yellow oil (1.8 g, 4.9 mmol) was dissolved in THF (20 mL). To this solution was added LAH solution (16 mL, 1.0 M) at 0° C. The ice bath was removed, and the reaction was allowed to warm to RT for 30 minutes. The reaction was then heated to reflux for 6 hours. TLC showed very clean reaction. The solution was cooled to RT, quenched with saturated Na$_2$SO$_4$ solution. The product was purified by silica gel chromatography. Removal of solvents gave rise to (3-bromo-5-methylphenyl)methanol as a waxy solid. $^1$H-NMR (500 MHz, CDCl$_3$) δ ppm: 7.36 (s, 1H), 7.30 (s, 1H), 7.13 (s, 1H), 4.68 (s, 2H), 2.37 (s, 3H).

Step B: 5-bromo-7-methyl-2-benzofuran-1(3H)-one

To a 100 mL round bottom flask charged with 5-bromo-7-methyl-2-benzofuran-1(3H)-one (815 mg, 4.2 mmol) and a stir bar was added thallium trifluoroacetate (2.5 g, 4.6 mmol) and TFA (5 mL). The mixture was allowed to stir at RT for 16 hours. The volatiles were removed under reduced pressure. The residue was pumped under high vacuum for 15 minutes before palladium (II) chloride (0.074 g, 0.42 mmol), magnesium oxide (0.355 g, 8.3 mmol), lithium chloride (0.035 g, 0.83 mmol), and methanol (30 mL) were added. The mixture was stirred under an atmosphere of carbon mono-oxide until the reaction turned black. The reaction was diluted with DCM (100 mL), filtered through a pad of Celite®, adsorbed onto silica gel, and purified by MPLC. After removal of solvent, the desired product was obtained. LC/MS: (IE, m/z) (M+1)$^+$=229.1;

Step C: (7-methyl-1-oxo-1,3-dihydro-2-benzofuran-5-yl)acetaldehyde

To a flask charged with 5-bromo-7-methyl-2-benzofuran-1(3H)-one (27 mg, 0.12 mmol) and a stir bar was added allyl tri-n-butyltin (79 mg, 0.24 mmol), lithium chloride (15 mg, 0.36 mmol), palladium tetrakis (28 mg, 0.024 mmol), and toluene (4 mL). The reaction was sealed with a condensor, purged three times with nitrogen, and heated to reflux for 16 hours. LC showed good reaction at that point. The reaction was diluted with EtOAc, adsorbed onto silica gel, and purified by flash chromatography. Removal of solvent gave rise to (7-methyl-1-oxo-1,3-dihydro-2-benzofuran-5-yl)acetaldehyde as a light yellow oil. LC/MS: (IE, m/z) (M+1)$^+$=189.2.

Intermediate 67

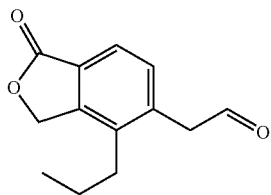 [SMILES: CCCc1c(CC=O)ccc2c1COC2=O]

(1-oxo-4-propyl-1,3-dihydro-2-benzofuran-5-yl)acetaldehyde

Step A: 5-bromo-4-propyl-2-benzofuran-1(3H)-one

To a freshly prepared LDA solution (14 mmol) in THF (14 mL) was dropped a THF solution of 2-methyl-3-(2-oxoethyl) benzoic acid (1.0 g, 4.6 mmol) at −78° C. The reaction turned red right away. The mixture was allowed to stir at −78° C. for 1 hour before iodoethane (3.6 g, 23 mmol) was dropped into the solution. The dark red color faded away slowly. TLC showed a slight less polar spot right away. The reaction was quenched with 1N HCl, and extracted with EtOAc. The extraction was dried over sodium sulfate, concentrated to furnish 3-bromo-2-propylbenzoic acid as a off-white solid.

The above solid (1.0 g, 4.1 mmol) was dissolved in THF (20 mL). To this solution was added borane THF complex (1.0 M, 12 mL) at 0° C. The mixture was allowed to warm to RT slowly. TLC showed complete reduction within 16 hours. The reaction was quenched with 1N HCl, diluted with EtOAc, washed with aqueous sodium carbonate and brine, dried over sodium sulfate, and concentrated to afford (3-bromo-2-propylphenyl)methanol as a light yellow oil. To the flask charged with (3-bromo-2-propylphenyl)methanol (690 mg, 3.0 mmol) and a stir bar was added thallium trifluoroacetate (2.0 g, 3.6 mmol) and TFA (4 mL). The mixture was allowed to stir at RT for 16 hours. The volatiles were removed under reduced pressure. The residue was pumped under high vacuum for 15 minutes before palladium (II) chloride (0.054 g, 0.30 mmol), magnesium oxide (0.364 g, 9.0 mmol), lithium chloride (0.13 g, 3.0 mmol), and methanol (15 mL) were added. The mixture was stirred under an atmosphere of carbon mono-oxide until the reaction turned black. The reaction was diluted with DCM (100 mL), filtered through a pad of Celite®, adsorbed onto silica gel, and purified by MPLC. After removal of solvent, the desired 5-bromo-4-propyl-2-benzofuran-1(3H)-one was collected.

$^1$H-NMR (500 MHz, CDCl$_3$) δ ppm: 7.76 (d, J=8.0 Hz, 1H), 7.64 (d, J=8.0 Hz, 1H), 5.32 (s, 2H), 2.75 (m, 2H), 1.70 (m, 2H), 1.05 (t, J=7.0 Hz, 3H)

Step B: (1-oxo-4-propyl-1,3-dihydro-2-benzofuran-5-yl)acetaldehyde

To a flask charged with 5-bromo-4-propyl-2-benzofuran-1(3H)-one (130 mg, 0.51 mmol) and a stir bar was added allyl tri-n-butyltin (0.24 mL, 0.76 mmol), PdCl$_2$(dppf)-DCM complex (42 mg, 0.051 mmol), lithium chloride (65 mg, 1.5 mmol), and tolene (5 mL). The mixture was sealed with a condensor, purged with nitrogen three times, and heated to reflux for 5 hours. The crude reaction was diluted with EtOAc, adsorbed onto silica gel, and purified by MPLC. Removal of solvent gave rise to 5-allyl-4-propyl-2-benzofuran-1(3H)-one (60 mg, 44% yield) as a light yellow oil.

To the flask charged with 5-allyl-4-propyl-2-benzofuran-1 (3H)-one (60 mg) was added methanol (10 mL). The solution was chilled to −78° C. before ozone was bubbled through. Ozone was stopped when the solution turned light blue. Excess ozone was removed by bubbling nitrogen through the solution, which was followed by addition of dimethyl sulfide (170 mg, 2.8 mmol). The mixture was allowed to warm to RT. The desired product, (1-oxo-4-propyl-1,3-dihydro-2-benzofuran-5-yl)acetaldehyde, was purified by silica gel chromatography.

Intermediate 68

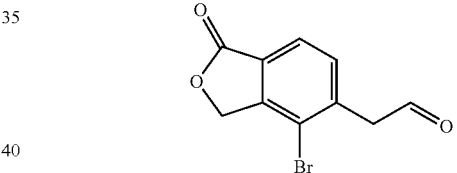

(4-bromo-1-oxo-1,3-dihydro-2-benzofuran-5-yl)acetaldehyde

Step A: 4,5-dibromo-2-benzofuran-1(3H)-one

To a flask containing a stir bar was added 5-bromo-2-benzofuran-1(3H)-one (12.0 g, 56.3 mmol) and NBS (15 g, 84 mmol). Triflic acid (50 mL) was then added at 0° C. and the resulting mixture was allowed to warm to rt and stir for 2 days. TLC analysis of the reaction mixture showed complete reaction. The reaction mixture was poured into ice and the organic layer was separated, washed with brine, water, dried over Na$_2$SO$_4$, filtered, and concentrated to dryness. The residue was then absorbed into silica gel and subjected for purification over a silica MPLC column to give 4,5-dibromo-2-benzofuran-1(3H)-one. LC-MS (IE, m/z): 291 [M+1]$^+$.

Step B: 5-allyl-4-bromo-2-benzofuran-1(3H)-one

To a flask charged with 4,5-dibromo-2-benzofuran-1(3H)-one (170 mg, 0.59 mmol) and a stir bar was added allyl tri-n-butyltin (0.18 mL, 0.59 mmol), palladium tetrakis (68 mg, 0.059 mmol), lithium chloride (50 mg, 1.2 mmol), and toluene (5 mL). The mixture was sealed with a condensor, purged three times with nitrogen, and heated to reflux for 16 hours. The reaction was diluted with EtOAc (50 mL), adsorbed onto silica gel, and purified by silica gel flash chromatography to afford 5-allyl-4-bromo-2-benzofuran-1(3H)-one. LC-MS (IE, m/z): 253 [M+1]$^+$;

Step C: (4-bromo-1-oxo-1,3-dihydro-2-benzofuran-5-yl)acetaldehyde

To a solution of 5-allyl-4-bromo-2-benzofuran-1(3H)-one (120 mg, 0.47 mmol) in methanol (20 mL) was bubbled ozone at −78° C. until the solution turned light blue. Excess ozone was removed by bubbling nitrogen through, which was followed by addition of dimethyl sulfide (0.35 mL, 4.7 mmol). The reaction was allowed to warm to RT, diluted with EtOAc, washed with brine, adsorbed onto silica gel, and purified by MPLC. Removal of solvent gave rise to (4-bromo-1-oxo-1,3-dihydro-2-benzofuran-5-yl)acetaldehyde.

Intermediate 69

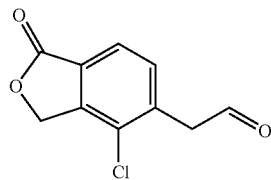 [SMILES: O=CCc1ccc2c(c1Cl)COC2=O]

(4-chloro-1-oxo-1,3-dihydro-2-benzofuran-5-yl)acetaldehyde
Step A: methyl 3-amino-2-chlorobenzoate To a solution of methyl 2-chloro-3-nitrobenzoate (2.1 g, 9.7 mmol) in methanol (100 mL) and THF (20 mL) was added zinc powder (1.9 g, 29 mmol), ammonium formate (3.1 g, 49 mmol), and a few drops of acetic acid. The mixture was allowed to stir at RT for 18 hours. TLC showed complete reaction at that point. Most of the volatiles were removed under reduced pressure. The residue was redissolved in EtOAc (200 mL), washed with brine, concentrated and purified by MPLC to deliver methyl 3-amino-2-chlorobenzoate. LC-MS (IE, m/z): 186 [M+1]$^+$;
Step B: methyl 3-bromo-2-chlorobenzoate To a solution of methyl 3-amino-2-chlorobenzoate (2.0 g, 11 mmol) in 48% HBr (10 mL) and water (20 mL) was added an aqueous solution of sodium nitrite (0.89 g, 13 mmol) at 0° C. The mixture was allowed to stir at 0° C. for 30 minutes before it was added into a suspension of copper(I) bromide (2.3 g, 16 mmol) in water (10 mL) and 48% HBr (5 mL) at 0° C. The reaction was allowed to warm to RT slowly, and then heated to 60° C. for 5 minutes. TLC and LC suggested good reaction. The product was extracted with DCM (100 mL×2). The extractions were combined, dried over sodium sulfate, adsorbed onto silica gel, and purified by MPLC to deliver methyl 3-bromo-2-chlorobenzoate. LC-MS (IE, m/z): 251 [M+1]$^+$;
Step C: (3-bromo-2-chlorophenyl)methanol To a solution of methyl 3-bromo-2-chlorobenzoate (1.9 g, 7.6 mmol) in THF (30 mL) was added Super Hydride (23 mL, 23 mmol) at 0° C. The reaction was allowed to stir for 16 hours. TLC showed clean reaction. The reaction was diluted with EtOAc, washed with brine, dried over sodium sulfate, and purified by MPLC to furnish (3-bromo-2-chlorophenyl)methariol. LC-MS (IE, m/z): 205 [M-17]$^+$;
Step D: 5-bromo-4-chloro-2-benzofuran-1(3H)-one To a flask charged with (3-bromo-2-chlorophenyl)methanol (1.1 g, 4.8 mmol) and a stir bar was added thallium trifluoroacetate (2.9 g, 5.3 mmol) and TFA (6 mL). The mixture was allowed to stir at RT for 16 hours. The volatiles were removed under reduced pressure. The residue was pumped under high vacuum for 15 minutes before palladium (II) chloride (0.085 g, 0.48 mmol), magnesium oxide (0.39 g, 9.6 mmol), lithium chloride (0.20 g, 4.8 mmol), and ethanol (30 mL) were added. The mixture was stirred under an atmosphere of carbon mono-oxide until the reaction turned black. The reaction was diluted with DCM. The suspension was filtered through a pad of Celite® to remove the solids. The filtrate was adsorbed onto silica gel, and purified by MPLC to afford 5-bromo-4-chloro-2-benzofuran-1(3H)-one. LC-MS (IE, m/z): 249 [M+1]$^+$;
Step E: 5-allyl-4-chloro-2-benzofuran-1(3H)-one To a flask charged with 5-bromo-4-chloro-2-benzofuran-1(3H)-one (190 mg, 0.77 mmol) and a stir bar was added allyl tri-n-butyltin (0.36 mL, 1.2 mmol), PdCl$_2$(dppf)-DCM complex, lithium chloride (0.098 mg, 2.3 mmol), and toluene (5 mL). The flask was fitted with a condensor, purged three times with nitrogen, and heated to reflux for 6 hours. LC showed complete reaction, and crude material was purified by MPLC to deliver 5-allyl-4-chloro-2-benzofuran-1(3H)-one. LC-MS (IE, m/z): 209 [M+1]$^+$;
Step E: (4-chloro-1-oxo-1,3-dihydro-2-benzofuran-5-yl)acetaldehyde To a solution of 5-allyl-4-chloro-2-benzofuran-1(3H)-one (80 mg, 0.38 mmol) in MeOH at −78° C. was bubbled ozone through until it turned light blue. After xcess ozone was removed by bubbling nitrogen through the solution, dimethyl sulfide (0.57 mL, 7.7 mmol) was added into the reaction. The solution was allowed to warm to RT. The crude material was purified by MPLC to deliver (4-chloro-1-oxo-1,3-dihydro-2-benzofuran-5-yl)acetaldehyde. LC-MS (IE, m/z): 211 [M+1]$^+$.

Intermediate 70

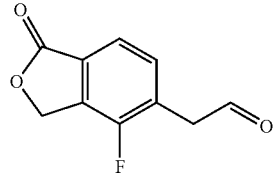 [SMILES: O=CCc1ccc2c(c1F)COC2=O]

(4-fluoro-1-oxo-1,3-dihydro-2-benzofuran-5-yl)acetaldehyde
Step A: 5-bromo-4-fluoro-2-benzofuran-1(3H)-one To a flask charged with (3-bromo-2-fluorophenyl)methanol (840 mg, 4.1 mmol) and a stir bar was added added thallium trifluoroacetate (2.3 g, 4.3 mmol) and TFA (4.0 mL) at 0° C. The mixture was allowed to stir for 16 hours. LC showed no SM left at that point. The volatiles were removed under reduced pressure, and the residue was dissolved in DCM and concentrated twice to affect azeotropic removal of all TFA. After pumping the residue under high vacuum for 20 minutes, palladium chloride (73 mg, 0.41 mmol), lithium chloride (350 mg, 8.2 mmol), magnesium oxide (330 mg, 8.2 mmol), and MeOH (15 mL) were added to the flask. The mixture was treated under an atmosphere of CO for 2 hours. To this mixtue was added EtOAc to precipitate all the inorganic solids. The crude solution was filtered through a Celite® pad, and the filtrate was collected, adsorbed onto silica gel, and purified by silica gel chromatography. Removal of solvents gave rise to 5-bromo-4-fluoro-2-benzofuran-1(3H)-one. LC-MS (IE, m/z): 231 [M+1]$^+$;
Step B: 5-allyl-4-fluoro-2-benzofuran-1(3H)-one To a flask charged with 5-bromo-4-fluoro-2-benzofuran-1(3H)-one (52 mg, 0.22 mmol) and a stir bar was added allyl tri-n-butyltin (0.10 mL, 0.34 mmol), palladium tetrakis (39 mg, 0.034 mmol), lithium chloride (29 mg, 0.68 mmol), and toluene (5 mL). The mixture was purged three times with nitrogen, and heated to reflux for 4 hours. LC showed formation of the desired product, which was purified by silica gel chromatography to deliver 5-allyl-4-fluoro-2-benzofuran-1(3H)-one. LC-MS (IE, m/z): 193 [M+1]$^+$;

Step C: (4-fluoro-1-oxo-1,3-dihydro-2-benzofuran-5-yl)acetaldehyde

To a solution of 5-allyl-4-fluoro-2-benzofuran-1(3H)-one (30 mg, 0.16 mmol) in MeOH at −78° C. was bubbled ozone through until it turned light blue. After excess ozone was removed by bubbling nitrogen through the solution, dimethyl sulfide (0.1 mL, 1.1 mmol) was added into the reaction. The solution was allowed to warm to RT. The crude material was purified by MPLC to deliver (4-fluoro-1-oxo-1,3-dihydro-2-benzofuran-5-yl)acetaldehyde. LC-MS (IE, m/z): 195 [M+1]$^+$.

Intermediate 71

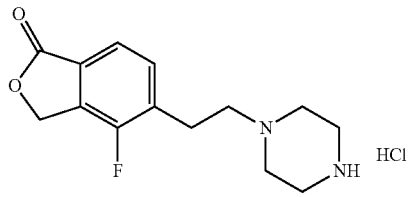 [SMILES: O=C1OCc2c1ccc(CCN1CCNCC1)c2F ; Cl]

4-fluoro-5-[2-piperazin-1-yl)ethyl]-2-benzofuran-1(3H)-one hydrochloride

Step A: tert-butyl 4-[2-(4-fluoro-1-oxo-1,3-dihydro-2-benzofuran-5-yl)ethyl]piperazine-1-carboxylate 4-Fluoro-1-oxo-1,3-dihydro-2-benzofuran-5-yl)acetaldehyde (18 mg, 0.093 mmol) was combined with tort-butyl piperazine-1-carboxylate (17 mg, 0.093 mmol) in methanol (0.5 mL). Sodium cyanoborohydride (8.2 mg. 0.13 mmol) was added and the mixture was permitted to stir for 12 h. The reaction mixture was concentrated, then diluted with water and DCM. The layers were separated and the aqueous layer was extracted twice with DCM. The organic layers were combined, washed with brine, dried over MgSO$_4$, filtered, and concentrated to afford crude title product which was used directly in the next step.

Step B: 4-fluoro-5-[2-(piperazin-1-yl)ethyl]-2-benzofuran-1(3H)-one hydrochloride The crude product from above (~30 mg) was dissolved in dioxane (1 mL) and treated with 0.1 mL of 4M HCl in dioxane. The reaction mixture was stirred for 12 h and concentrated to afford the title compound which was used without purification. LC-MS (IE, m/z): 265 [M+1]$^+$.

Intermediate 72

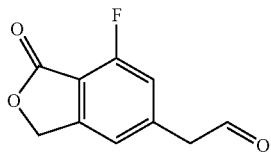 [SMILES: O=CCc1cc(F)c2c(c1)COC2=O]

(7-fluoro-1-oxo-1,3-dihydro-2-benzofuran-5-yl)acetaldehyde

Step A: 5-bromo-7-fluoro-2-benzofuran-1(3H)-one

To a solution of 3-bromo-5-fluorobenzoic acid (0.8 g, 3.7 mmol) in THF (20 mL) was added borane THF complex (11 mL, 11 mmol) at 0° C. The reaction was allowed to stir for 16 hours. TLC showed clean conversion. The reaction was quenched by adding EtOAc. The solution was washed with sodium carbonate and brine, and purified by silica gel chromatography to deliver (3-bromo-5-fluorophenyl)methanol.

To a flask charged with (3-bromo-5-fluorophenyl)methanol (360 mg, 1.8 mmol) and a stir bar was added added thallium trifluoroacetate (1.0 g, 1.8 mmol) and TFA (3.0 mL) at 0° C. The mixture was allowed to stir for 16 hours. LC showed no SM left at that point. The volatiles were removed under reduced pressure, and the residue was dissolved in DCM and concentrated twice to affect azeotropic removal of all TFA. After pumping the residue under high vacuum for 20 minutes, palladium chloride (31 mg, 0.18 mmol), lithium chloride (150 mg, 3.5 mmol), magnesium oxide (140 mg, 3.5 mmol), and MeOH (15 mL) were added to the flask. The mixture was treated under an atmosphere of CO for 2 hours. To this mixtue was added DCM and EtOAc to precipitate all the inorganic solids. The crude solution was filtered through a Celite® pad, and the filtrate was collected, adsorbed onto silica gel, and purified by silica gel chromatography. Removal of solvents gave rise to 5-bromo-7-fluoro-2-benzofuran-1(3H)-one. LC-MS (IE, m/z): 231 [M+1]$^+$;

Step B: 5-allyl-7-fluoro-2-benzofuran-1(3H)-one

To a flask charged with 5-bromo-7-fluoro-2-benzofuran-1(3H)-one (300 mg, 1.3 mmol) and a stir bar was added allyl tri-n-butyltin (0.6 mL, 2.0 mmol), palladium tetrakis triphenylphosphine (230 mg, 0.19 mmol), lithium chloride (170 mg, 3.9 mmol), and toluene (5 mL). The mixture was purged three times with nitrogen, and heated to reflux for 4 hours. LC showed formation of the desired product, which was purified by silica gel chromatography to deliver 5-allyl-7-fluoro-2-benzofuran-1(3H)-one. LC-MS (IE, m/z): 193 [M+1]$^+$;

Step C: (7-fluoro-1-oxo-1,3-dihydro-2-benzofuran-5-yl)acetaldehyde

To a solution of 5-allyl-6-fluoro-2-benzofuran-1(3H)-one (50 mg, 0.26 mmol) in MeOH at −78° C. was bubbled ozone through until it turned light blue. After excess ozone was removed by bubbling nitrogen through the solution, dimethyl sulfide (0.019 mL, 0.26 mmol) was added into the reaction. The solution was allowed to warm to RT. The crude material was purified by MPLC to deliver (7-fluoro-1-oxo-1,3-dihydro-2-benzofuran-5-yl)acetaldehyde. LC-MS (IE, m/z): 195 [M+1]$^+$.

Intermediate 73

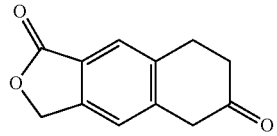 [SMILES: O=C1CCc2cc3c(cc2C1)COC3=O]

7,8-dihydronaphtho[2,3-c]furan-1,6(3H,5H)-dione

Step A: tert-butyl (1-oxo-1,3-dihydro-2-benzofuran-5-yl)acetate

To a sealed 20 mL microwave tube charged with 5-bromo phthalide (500 mg, 2.3 mmol) and palladium tetrakis (136 mg, 0.12 mmol) was added THF (5 mL) and 2-tert-butoxy-2-oxoethyl)(chloro)zinc (0.5 M in ether from Rieke Metals, 6.6 mL, 3.3 mmol). The mixture was purged three times with nitrogen, and then heated to 105° C. for 30 minutes. TLC showed some SM remained, but a few new spots formed. The reaction was diluted with EtOAc, washed with NH$_4$Cl and brine, dried over sodium sulfate, adsorbed onto silica gel, and purified by MPLC. $^1$H NMR (500 MHz, CDCl$_3$, δ in ppm): 7.92 (m, 1H), 7.46 (m, 2H), 5.34 (s, 2H), 3.70 (s, 2H), 1.49 (s, 9H).

Step B: 7,8-dihydronaphtho[2,3-c]furan-1,6(3H,5H)-dione

To a flask charged with tert-butyl (1-oxo-1,3-dihydro-2-benzofuran-5-yl)acetate (375 mg, 2.0 mmol) was added TFA (10 mL). The mixture was allowed to sit at RT for half an hour. LC at that point indicated complete cleavage of the tert-butyl group. The volatiles were removed under reduced pressure. The residue was pumped under high vacuum for 15 minutes before DCM (20 mL) was added to the flask, followed by addition of oxalyl chloride (0.22 mL, 2.5 mmol) and a drop of DMF. The mixture was stirred at RT for 1 hour, and then cooled to 0° C. with an ice bath. Aluminum chloride (780 mg, 5.9 mmol) was added into the reaction. After stirring the solution for 10 minutes, ethylene was bubbled through the reaction with a needle. TLC showed consumption of all material within 1 hour. The crude reaction was dumped into ice, and extracted with DCM (100 mL×3). The extractions were combined, washed with brine, dried over sodium sulfate, adsorbed onto silica gel, and purified by MPLC. The solvent was removed under reduced pressure to afford 7,8-dihydronaphtho[2,3-c]furan-1,6(3H,5H)-dione, $^1$H NMR (500 MHz, CDCl$_3$, δ ppm): 7.83 (s, 1H), 7.36 (s, 1H), 5.36 (s, 2H), 3.78 (s, 2H), 3.23 (m, 1H), 3.09 (m, 1H), 2.70 (m, 1H), 2.63 (m, 1H).

Intermediate 74

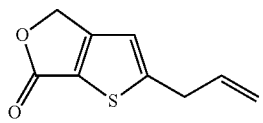

2-(Prop-2-en-1-yl)thieno[2,3-C]furan-6(4H)-one

Step A: Methyl 5-bromo-3-methylthiophene-2-carboxylate

In a 50 mL round bottom flask, methyl 3-methylthiophene-2-carboxylate (1.40 g, 8.96 mmol) was dissolved in chloroform (10 mL). To above solution was added bromine (0.462 mL, 8.96 mmol, 1.0 eq) in chloroform (5 mL) drop wise at r.t. The reaction was heated to reflux for 3 h, cooled and washed with water and aqueous bicarbonate. The organic layer was dried over MgSO$_4$. Crude NMR analysis showed formation of desired product with byproduct methyl 4-bromo-3-methylthiophene-2-carboxylate (ratio: 3:2). The byproduct was not separable from product. Therefore, the above crude was carried over to next step. The organic phase was dried over filtered and concentrated. The product was obtained after purification by flash column chromatography. LC-MS (IE, m/z): 237.05 [M+1]$^+$.

Step B: Methyl 5-bromo-3-(bromomethyl)thiophene-2-carboxylate

In a 100 mL round bottom flask, methyl 5-bromo-3-methylthiophene-2-carboxylate (1.50 g, 6.38 mmol) was dissolved in tetrachloromethane (30 mL). To above solution was added 1-bromopyrrolidine-2,5-dione (1.14 g, 6.38 mmol, 1.0 eq) and diphenylperoxyanhydride (0.155 g, 0.638 mmol, 0.1 eq). The reaction was stirred at 90° C. for 18 hr. To above reaction was added dichloromethane (30 mL), washed with aqueous sodium bicarbonate, brine and water. The organic phase was dried over MgSO$_4$, filtered and concentrated. The crude was used in next step without purification. LC-MS (IE, m/z): 337.4 [M+N]$^+$.

Step C: 5-Bromo-3-(hydroxymethyl)thiophene-2-carboxylic acid

In a 15 mL microwave reaction vial, was added methyl 5-bromo-3-(bromomethyl)thiophene-2-carboxylate (700 mg, 2.23 mmol), THF (4 mL) and MeOH (1 mL). To above solution was added lithium hydroxide (53.4 mg, 2.23 mmol, 1.0 eq) in water (1 mL). The reaction was heated in microwave reactor for 30 min at 90° C. The reaction was cooled down to r.t., neutralized with 1N HCl, extracted with EtOAc, washed with brine and water. The organic phase was dried over MgSO$_4$, filtered and concentrated. The desired product was obtained after purification by flash column chromatography. LC-MS (IE, m/z): 235.2 [M+1]$^+$.

Step D: 2-Bromothieno[2,3-c]furan-6(4H)-one

In a 50 mL round bottom flask, 5-bromo-3-(hydroxymethyl)thiophene-2-carboxylic acid (140 mg, 0.59 mmol) and N-[3-(dimethylamino)propyl]-N'-ethylcarbodiimide hydrochloride (113 mg, 0.59 mmol, 1.0 eq) were dissolved in DCM (5 mL) The solution was stirred at r.t. for 1 hr, concentrated and purified by flash column chromatography to give desired product. LC-MS (IE, m/z): 221.2 [M+1]$^+$. $^1$H NMR (500 MHz, CDCl$_3$, δ in ppm): 7.1 (1H, aromatic), 5.2 (2H, s).

Step E: 2-(Prop-2-en-1-yl)thieno[2,3-C]furan-6(4H)-one

In a 15 mL microwave reaction vial was added 2-bromothieno[2,3-c]furan-6(4H)-one (45 mg, 0.205 mmol), 4,4,5,5-tetramethyl-2-(prop-2-en-1-yl)-1,3,2-dioxaborolane (34.5 mg, 0.205 mmol, 1.0 eq), potassium carbonate (56.8 mg, 0.411 mmol, 2.0 eq) and palladium triphenylphosphane (1:4) (23.7 mg, 0.021 mmol, 0.1 eq). To above mixture was added DMF (1.0 mL), de-gas and filled with N$_2$. The vial was heated to 100° C. for 60 min, cooled down, diluted with EtOAc, washed with aqueous sodium bicarbonate, brine and water. The organic phase was dried over anhydrous Na$_2$SO$_4$, filtered, concentrated. The crude product was purified by flash column chromatography. LC-MS (IE, m/z): 181.2 [M+1]$^+$.

Intermediate 75

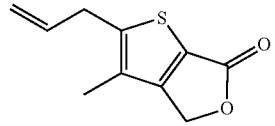

3-methyl-2-(prop-2-en-1-yl)thieno[2,3-c]furan-6(4H)-one

Step A: methyl 3-ethenyl-4-methylthiophene-2-carboxylate

In a 15 mL microwave tube was added methyl 3-iodo-4-methylthiophene-2-carboxylate (1800 mg, 6.38 mmol, 1.0 eq), potassium ethenyl(trifluoro)borate(1-) (1110 mg, 8.29 mmol, 1.3 eq), 1,1'-bis(diphenylposphino)ferrocene]dichloropalladium (II) (261 mg, 0.319 mmol, 0.05 eq) and triethylamine (1162 mg, 11.49 mmol, 1.8 eq). To above mixture was added ethanol (15 mL). The reaction mixture was degassed, filled with N$_2$, stirred at 120° C. for 20 min in microwave reactor. The reaction was diluted with EtOAc, washed with aqueous sodium bicarbonate, brine and water. The organic phase was dried over MgSO$_4$, filtered and concentrated. The desired product was obtained after purification by flash column chromatography. $^1$H NMR (500 MHz, CDCl$_3$, δ in ppm): 7.35 (1H, m), 7.11 (1H), 5.56 (1H), 5.53 (1H, m), 3.85 (3H, s), 2.32 (3H, s);

Step B: methyl 3-(hydroxymethyl)-4-methylthiophene-2-carboxylate

In a 50 mL round bottom flask, methyl 3-ethenyl-4-methylthiophene-2-carboxylate (310 mg, 1.7 mmol, 1.0 eq) was dissolved in dichloromethane (3 mL). The solution was cooled to −78° C. To above solution was bubbled through ozone till color change to purple, then bubbled with $N_2$, and sodium borohydride (77 mg, 2.0 mmol) was added. The reaction was let warmed to r.t. and stirred at this temperature overnight. The reaction was quenched with small amount of water, extracted with dichloromethane, washed with water and brine. The organic phase was dried over $MgSO_4$, filtered and concentrated. LC-MS (IE, m/z): 209.3 [M+Na]$^+$; $^1$H NMR (500 MHz, CDCl$_3$, δ in ppm): 7.14 (1H, s), 4.75 (2H, m), 3.99 (1H, m), 3.90 (3H, s), 2.27 (3H, s);

Step C: 3-(hydroxymethyl)-4-methylthiophene-2-carboxylic acid

In a 15 mL microwave tube, methyl 3-(hydroxymethyl)-4-methylthiophene-2-carboxylate (440 mg, 2.36 mmol, 1.0 eq) was dissolved in THF/MeOH/water (2:1:1, 2 mL). To above solution was added Lithium hydroxide (68 mg, 2.84 mmol). The mixture was heated at 100° C. for 30 min in microwave reactor, neutralized with 1 N HCl, extracted with dichloromethane, washed with brine and water. The organic phase was dried over $MgSO_4$, filtered and concentrated. LC-MS (IE, m/z): 195.3 [M+Na]$^+$; $^1$H NMR (500 MHz, CD$_3$OD, δ in ppm): 7.25 (1H, s), 4.86 (2H, m), 2.28 (3H, s);

Step D: 3-Methylthieno[2,3-c]furan-6-(4H)-one

In a 50 mL round bottom flask, 3-(Hydroxymethyl)-4-methylthiophene-2-carboxylic acid (440 mg, 2.56 mmol, 1.0 eq) was suspended in dichloromethane (5 mL). To above mixture was added N-[3-(dimethylamino)propyl]-N'-ethylcarbodiimide hydrochloride (735 mg, 3.83 mmol, 1.5 eq). The reaction was stirred at r.t. for 18 hr, washed with brine and water. The organic phase was dried over $MgSO_4$, filtered and concentrated. LC-MS (IE, m/z): 155.1 [M+1]$^+$; $^1$H NMR (500 MHz, CDCl$_3$, δ in ppm): 7.44 (1H, s), 5.14 (2H, s), 2.24 (3H, s);

Step E: 2-Bromo-3-methylthieno[2,3-c]furan-6-(4H)-one

In a 50 mL round bottom flask was added 3-methylthieno[2,3-c]furan-6-(4H)-one (130 mg, 0.843 mmol, 1.0 eq) and chloroform (5 mL). To above solution was added bromine (86 μL, 1.08 mmol, 2.0 eq) in chloroform. The reaction was heat to reflux for 3 hr, cooled down, diluted with dichloromethane, washed with water, diluted sodium thiosulfate. The organic phase was dried over $MgSO_4$, filtered and concentrated. The desired product was obtained after purification by flash column chromatography. LC-MS (IE, m/z): 235.2 [M+1]$^+$; $^1$H NMR (500 MHz, CDCl$_3$, δ in ppm): 5.16 (2H, s), 2.19 (3H, s);

Step F: 3-Methyl-2-(prop-2-en-1-yl)thieno[2,3-c]furan-6-(4H)-one

In a 100 mL round bottom flask was added 2-bromo-3-methylthieno[2,3-c]furan-6-(4H)-one (60 mg, 0.257 mmol, 1.0 eq), tributyl (prop-2-en-1-yl)stannane (102 mg, 0.309 mmol, 1.2 eq), palladium triphenylphosphane (1:4) (14.9 mg, 0.013 mmol, 0.05 eq) and lithium chloride (32.7 mg, 0.77 mmol, 3.0 eq). The mixture was dissolved in toluene (20 mL), degassed and filled with $N_2$. The mixture was reflux for 3 hr, concentrated, extracted with EtOAc, washed with water. The organic phase was dried over $MgSO_4$, filtered and concentrated. The desired product was obtained after purification by flash column chromatography. LC-MS (IE, m/z): 195.3 [M+1]$^+$; $^1$H NMR (500 MHz, CDCl$_3$, δ in ppm): 5.16 (2H, s), 2.19 (3H, s).

Intermediate 76

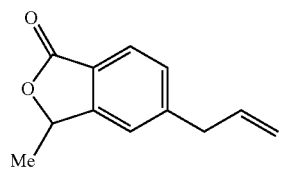

3-methyl-5-(prop-2-en-1-yl)-2-benzofuran-1(3H)-one

Step A: 5-bromo-3-methyl-2-benzofuran-1(3H)-one

To a cooled (0° C.) solution of 5-bromo-2-benzofuran-1(3H)-one (5.00 g, 23.5 mmol) in DMF (100 mL) was added sodium hydride (1.03 g, 25.8 mmol) in portions. The mixture was stirred for 20 minutes, then iodomethane (2.20 mL, 35.2 mmol) was added in one portion. The mixture was stirred at 0° C. for 15 minutes then was permitted to warm to rt and stir overnight. The reaction mixture was poured into a 1N HCl/CHCl$_3$ mixture at 0° C. and was stirred for 1 h. The organic layer was separated, washed with brine, dried over $MgSO_4$, and purified by MPLC eluting with a 0-25% gradient of ethyl acetate/hexanes to afford the title compound.

$^1$H NMR (500 MHz, D-DMSO, δ in ppm): 8.03 (s, 1H), 7.79 (d, J=8 Hz, 1H), 7.76 (d, J=0.8 Hz, 1H), 5.69 (q, J=6.5 Hz, 1H), 1.58 (d, J=6.5 Hz, 3H);

Step B: 3-methyl-5-(prop-2-en-1-yl)-2-benzofuran-1(3H)-one

5-Bromo-3-methyl-2-benzofuran-1(3H)-one (1.00 g, 4.40 mmol) was dissolved in toluene (30 mL) treated with lithium chloride (0.560 g, 13.2 mmol), Pd(Ph$_3$P)$_4$ (0.254 g, 0.220 mmol), and allyl tributylstannane (1.75 g, 5.29 mmol). The reaction mixture was degassed and stirred at reflux under $N_2$ for 3 h. The reaction mixture was poured into water and extracted with ethyl acetate; the organic layer was washed wtih brine 1×, dried and purified by MPLC eluting with 0-10% ethyl acetate/hexanes. to afford the title compound. $^1$H NMR (500 MHz, D-DMSO, δ in ppm): 7.75 (d, J=8 Hz, 1H), 7.50 (s, 1H), 7.42 (d, J=8 Hz, 1H), 6.00 (m, 1H), 5.66 (q, J=6.5 Hz, 1H), 5.13 (m, 2H), 3.53 (d, J=6.5 Hz, 2H), 1.54 (d, J=7 Hz, 3H).

Intermediate 77

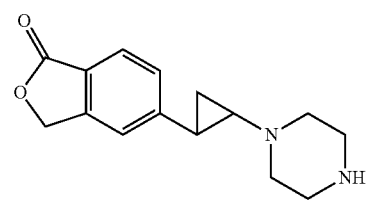 [SMILES: O=C1OCc2cc(C3CC3N3CCNCC3)ccc21]

5-[2-(piperazin-1-yl)cyclopropyl]-2-benzofuran-1(3H)-one

Step A: tert-butyl 4-[(E)-2-(1-oxo-1,3-dihydro-2-benzofuran-5-yl)ethenyl]piperazine-1-carboxylate A mixture of (1-oxo-1,3-dihydro-2-benzofuran-5-yl)acetaldehyde (3.5 g, 20 mmol), Boc-piperazine (3.5 g, 20 mmol) and anhydrous $MgSO_4$ (20 g, 166 mmol) in 100 mL of anhydrous DCM were stirred at room temperature overnight.

The solid was filtered and the solvent was evaporated at reduced pressured to get the crude product. The crude product was purified via column chromatograph to afford tert-butyl 4-[(E)-2-(1-oxo-1,3-dihydro-2-benzofuran-5-yl)ethenyl]piperazine-1-carboxylate. $^1$H-NMR (400 MHz, CDCl$_3$) δ ppm 7.74 (d, J=8.2 Hz, 1H), 7.29~7.34 (m, 2H), 6.88 (d, J=13 Hz, 1H), 5.55 (d, J=14 Hz, 1H), 5.25 (s, 2H), 3.49~3.58 (m, 4H), 3.12~3.17 (m, 4H), 1.50 (s, 9H).

Step B: tert-butyl 4-[2-(1-oxo-1,3-dihydro-2-benzofuran-5-yl)cyclopropyl]piperazine-1-carboxylate To a solution of tert-butyl 4-[(E)-2-(1-oxo-1,3-dihydro-2-benzofuran-5-yl)ethenyl]piperazine-1-carboxylate (1.1 g, 3 mmol) in 30 mL of DCM was added Pd(OAc)$_2$ (100 mg) and was cooled by ice/water. 50 mL of newly prepared CH$_2$N$_2$ solution was added dropwise. The reaction was warmed to room temperature and stirred over night. The solid was filtered off, and the filtrate was evaporated at reduced pressure to get crude product, which was purified via prep-HPLC to afford tert-butyl 4-[2-(1-oxo-1,3-dihydro-2-benzofuran-5-yl)cyclopropyl]piperazine-1-carboxylate.

Step C: 5-[2-(piperazin-1-yl)cyclopropyl]-2-benzofuran-1(3H)-one

A solution of tert-butyl 4-[2-(1-oxo-1,3-dihydro-2-benzofuran-5-yl)cyclopropyl]piperazine-1-carboxylate (30 mg, 0.08 mmol) in 5 mL of DCM was added 3 mL of 4N HCl/dioxane, and then the mixture was stirred at room temperature for 2 hours. The solvents was removed off under vacuum to afford 5-[2-(piperazin-1-yl)cyclopropyl]-2-benzofuran-1(3H)-one.

Intermediate 78

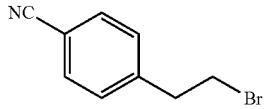 [SMILES: N#Cc1ccc(CCBr)cc1]

4-(2-bromoethyl)benzonitrile 4-(2Hydroxyethyl)benzonitrile (3.0 g, 20 mmol) was combined with triphenylphosphine (6.42 g, 24.5 mmol) imidazole (1.39 g, 20.4 mmol) and carbon tetrabromide (8.11 g, 24.5 mmol) in DCM (10 mL) and stirred at 0° C., monitoring the reaction progress to completion by TLC. Silica gel was added to the mixture and the solvent was removed. Purification by MPLC eluting with 20% ethyl acetate/hexanes afforded the tide compound.

Intermediate 79

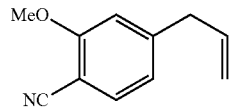

2-(methyloxy)-4-prop-2-en-1-ylbenzonitrile

To a 50 mL flask containing a stir bar were added 2-methoxy-4-bromobenzonitrile (0.30 g, 1.4 mmol), palladium tetrakis (82 mg, 0.071 mmol), allyltri-n-butyltin (0.877 mL, 2.83 mmol), and lithium chloride (0.120 g, 2.83 mmol). The resulting mixture was then dissolved in anhydrous toluene (16 mL); the flask was placed in an oil bath and heated at 130° C.; LC as well as TLC (hexanes/EtOAc=1/0.3) indicated that reaction had gone to completion. The flask was taken out of the oil bath and cooled to room temperature. To the flask was poured EtOAc (40 mL) and the mixture was transferred into a separatory funnel and washed with aqueous NaCl. The organic phase was dried over Na$_2$SO$_4$, filtered and concentrated to dryness. It was then dissolved in DCM and absorbed into silica gel. The slica gel was then loaded onto a silica column for separation with the solvent systems of hexanes/EtOAc (1/0.3); this gave 2-(methyloxy)-4-prop-2-en-1-ylbenzonitrile. LC-MS (IE, m/z): 174 [M+1]$^+$.

The following allyl containing INTERMEDIATES (Table) were prepared from the indicated benzonitrile bromides in an analogous fashion to that described for the synthesis of 2-(methyloxy)-4-prop-2-en-1-ylbenzonitrile.

| INTERMEDIATE | Starting material bromide | Structure of INTERMEDIATE |
|---|---|---|
| 80 | | |
| 81 | | |
| 82 | | |

Intermediate 83

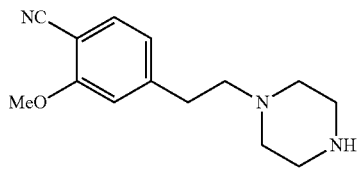 [SMILES: COc1cc(CCN2CCNCC2)ccc1C#N]

2-methoxy-4-[2-(piperazin-1-yl)ethyl]benzonitrile

Step A: 2-(methyloxy)-4-(2-oxoethyl)benzonitrile

To a 25 mL flask containing a stir bar was added compound 2-(methyloxy)-4-prop-2-en-1-ylbenzonitrile (0.150 g, 0.866 mmol) and MeOH (8 mL). The flask was placed in a cold bath of −78° C. Ozone was bubbled through the flask for about 10 min. followed by addition of dimethyl sulfide (1.5 mL, 0.024 mmol). The flask was taken out of the cold bath and stirred at room temperature for 1 h; LC indicated completion of the reaction. The reaction mixture was concentrated to dryness to give 2-(methyloxy)-4-(2-oxoethyl)benzonitrile. LC-MS (IE, m/z): 176 [M+1]$^+$;

Step B: tert-butyl 4-[2-(4-cyano-3-methoxyphenyl)ethyl]piperazine-1-carboxylate 2-(Methyloxy)-4-(2-oxoethyl)benzonitrile (200 mg, 1.142 mmol), tert-butyl piperazine-1-carboxylate (532 mg, 2.85 mmol), and SODIUM CYANOBOROHYDRIDE (717 mg, 11.4 mmol) were combined in a 50 mL Flask and dissolved in MeOH. The resulting mixture was then stirred for 10 minutes followed by addition of few drops of AcOH. The mixture was stirred for overnight. The reaction mixture was concentrated to dryness, re-dissolved in EtOAc and washed with saturated NaHCO$_3$ solution, brine, and the organic layer was dried over Na$_2$SO$_4$, filtered and concentrated to dryness. The residue purified by MPLC to yield the title compound. LC-MS (IE, m/z): 346 [M+1]$^+$;

Step C: 2-methoxy-4-[2-(piperazin-1-yl)ethyl]benzonitrile

Removal of the Boc protecting group to provide 2-methoxy-4-[2-(piperazin-1-yl)ethyl]benzonitrile was accomplished in an analogous fashion to that described for the synthesis of 2-(piperazine-1-yl)-2,3-dihydro-1H-indene-5-carbonitrile.

Intermediate 84

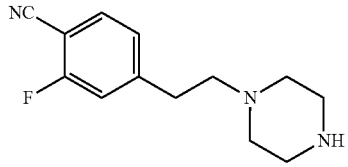 [SMILES: N#Cc1ccc(CCN2CCNCC2)cc1F]

2-fluoro-4-[2-(piperazin-1-yl)ethyl]benzonitrile

2-Fluoro-4-[2-(piperazin-1yl)ethyl]benzonitrile was prepared from 2-fluoro-4-(prop-2-en-1-yl)benzonitrile (described above) in an analogous fashion to that described for 2-methoxy-4-[2-(piperazin-1-yl)ethyl]benzonitrile.

Intermediate 85

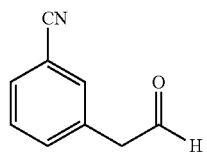 [SMILES: N#Cc1cccc(CC=O)c1]

3-(2-oxoethyl)benzonitrile

Step A: 3-(prop-2-en-1-yl)benzonitrile

To solution of compound 3-bromobenzonitrile (5 g, 27 mmol) and tributyl(prop-2-en-1-yl)stannane (13.5 g, 41.2 mmol) in toluene was added Pd(PPh$_3$)$_4$ (300 mg) and LiCl (2.3 g, 54 mmol) under N$_2$, and then the mixture was stirred at reflux for 18 h. The reaction mixture was quenched by the addition of water. Extracted the mixture with EtOAc and the organic layer was dried and concentrated. The residue was purified by a flash column chromatography to afford 3-(prop-2-en-1-yl)benzonitrile. $^1$H-NMR (300 MHz, CDCl3) δ 7.32~7.82 (m, 4H), 5.85~6.00 (m, 1H), 5.05~5.17 (m, 2H), 3.42 (d, J=6.8 Hz, 2H).

Step B: 3-(2,3-dihydroxypropyl)benzonitrile

To a solution of 3-(prop-2-en-1-yl)benzonitrile (3.8 g, 27 mmol) and NMO (10.85 g, 80 mmol) in MeOH/H$_2$O (v/v=3:1, 133 mL) was added OsO$_4$ (600 mg), and then stirred at room temperature for 18 h. The result mixture was concentrated to dryness and the residue was dissolved in water and extracted with EtOAc. The organic layers were dried and concentrated, and the residue was purified by a flash column chromatography to afford 3-(2,3-dihydroxypropyl)benzonitrile.

$^1$H-NMR (400 MHz, CDCl3) δ 7.38~7.57 (m, 4H), 3.90~3.98 (m, 1H), 3.70 (m, 1H), 2.75~2.86 (m, 2H).

Step C: 3-(2-oxoethyl)benzonitrile

A solution of 3-(2,3-dihydroxypropyl)benzonitrile (2.7 g, 15.3 mmol) in MeOH/H$_2$O (v/v=3:1, 40 mL) was added NaIO$_4$ at 0° C. and then stirred at 0° C. for 1.5 h. The result mixture was filtered and the filtrate was concentrated to afford 3-(2-oxoethyl)benzonitrile, which was used next step without further purification.

Intermediate 86

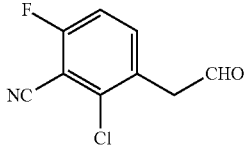 [SMILES: N#Cc1c(F)ccc(CC=O)c1Cl]

2-chloro-6-fluoro-3-(2-oxoethyl)benzonitrile

Step A: 2-chloro-6-fluoro-3-iodobenzonitrile

A suspension of 2-chloro-6-fluoro-3-iodobenzaldehyde (1.08 g, 3.789 mmol) and hydroxylamine-o-sulfomic acid (856 mg, 7.578 mmol) in water (30 mL) was heated at 50° C. for 12 hrs. Then the mixture was cooled to rt. and the solid was collected via filtration to give 2-chloro-6-fluoro-3-iodobenzonitrile. $^1$H-NMR (400 MHz, CDCl$_3$) δ ppm 7.97~8.01 (m, 1H), 6.85~6.89 (m, 1H).

Step B: 2-chloro-6-fluoro-3-(prop-2-en-1-yl)benzonitrile

A mixture of 2-chloro-6-fluoro-3-iodobenzonitrile (800 mg, 2.85 mmol), allyltributylstannane (1.245 mg, 3.761 mmol), LiCl (431 mg, 10.3 mmol) and Pd(PPh$_3$)$_4$ (100 mg) in 50 mL toluene was heated at 100° C. overnight. Cooled to rt. and diluted with 50 mL EtOAc and filtered. The filtrate was washed with water and brine, dried over anhydrous Na$_2$SO$_4$ and concentrated to dryness. The residue was purified via prep-TLC (ethyl acetate/Pet ether=1:5) to give 2-chloro-6-fluoro-3-(prop-2-en-1-yl)benzonitrile. $^1$H-NMR (400 MHz, CDCl$_3$) δ ppm 7.37~7.41 (m, 1H), 7.01~7.06 (m, 1H), 5.78~5.87 (m, 1H), 4.99~5.12 (m, 2H), 3.44 (d, J=6.3 Hz, 2H).

Step C: 2-chloro-6-fluoro-3-(2-oxoethyl)benzonitrile

To a solution of 2-chloro-6-fluoro-3-(prop-2-en-1-yl)benzonitrile (450 mg, 2.296 mmol) in 0.37 mL pyridine (363 mg, 4.592 mmol) and 40 mL DCM/MeOH (V/V=1:1) was bubbled O$_3$ at −78° C. for 15 min. Then N$_2$ was bubbled for another 15 min. at −78° C. and 5 mL of Me$_2$S were added. The mixture was stirred at r.t. overnight and then concentrated to dryness. The residue was dissolve in EtOAc (50 mL) and washed with 1 N HCl (aq.) and brine, dried over anhydrous Na$_2$SO$_4$ and concentrated to dryness to give 2-chloro-6-fluoro-3-(2-oxoethyl)benzonitrile.

The following aldehyde INTERMEDIATES (Table) were prepared from the bromobenzonitriles indicated in an analogous fashion to that described for the synthesis of 2-chloro-6-fluoro-3-(2-oxoethyl)benzonitrile.

| INTERMEDIATE | Starting bromides | Structure of INTERMEDIATE |
|---|---|---|
| 87 | 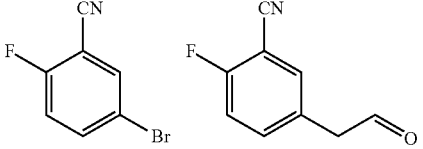 | 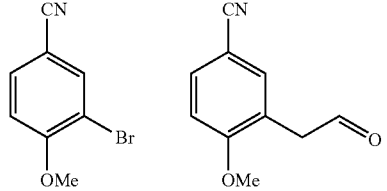 |
| 88 | 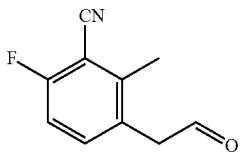 | 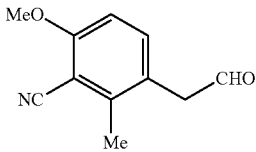 [SMILES: COc1ccc(CC=O)c(C)c1C#N] |

Intermediate 89

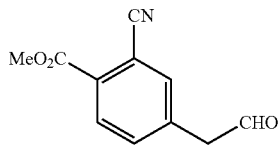 [SMILES: COC(=O)c1ccc(CC=O)cc1C#N]

6-fluoro-2-methyl-3-(2-oxoethyl)benzonitrile
Step A: 3-bromo-6-fluoro-2-methylbenzonitrile Commercially available 2-fluoro-6-methylbenzonitrile (Apollo Scientific, 15.0 g, 111 mmol) was dissolved in triflic acid (75 mL) at 0° C. then NBS (20.7 g, 117 mind) was added. The reaction mixture was stirred at RT for 1 h then poured into ice water and extracted twice with DCM. The organic layer was washed with brine, dried over NaSO4, then filtered and evaporated to dryness to yield the expected aryl bromide (23.6 g, 99% yield). $^1$H-NMR (500 MHz, CDCl$_3$): δ ppm 7.77 (t, J=5.85 Hz, 1H), 6.99 (t, J=8.1 Hz, 1H), 2.65 (s, 3H). LC-MS: M+1=216 at 3.24 RT.
Subsequent Steps: 6-fluoro-2-methyl-3-(2-oxoethyl)benzonitrile 6-Fluoro-2-methyl-3-(2-oxoethyl)benzonitrile was prepared in two steps starting from 3-bromo-6-fluoro-2-methylbenzonitrile in an analogous fashion to that described for the synthesis of 2-chloro-6-fluoro-3-(2-oxoethyl)benzonitrile (Steps B and C) above.

Intermediate 90

6-methoxy-2-methyl-3-(2-oxoethyl)benzonitrile
Step A: 3-bromo-6-methoxy-2-methylbenzonitrile A solution of Br$_2$ (261 mg, 1.63 mmol) in CCl$_4$ (1 mL) was added over 15 min to a solution of 2-methoxy-6-methylbenzonitrile in CCl$_4$ (3 mL) at −10° C. containing 4 mg of Fe powder. After 45 min the reaction was poured into ice water (10 mL). The organic layer was washed with Na$_2$SO$_3$ (aq.) solution (10 mL*2), brine (20 mL) and dried over Na$_2$SO$_4$, concentrated in vacuo to give 3-bromo-6-methoxy-2-methylbenzonitrile.
Subsequent Steps: 6-methoxy-2-methyl-3-(2-oxoethy)benzonitrile 6-methoxy-2-methyl-3-(2-oxoethyl)benzonitrile was prepared in two steps starting from 3-bromo-6-methoxy-2-methylbenzonitrile in an analogous fashion to that described for the synthesis of 2-chloro-6-fluoro-3-(2-oxoethyl)benzonitrile (Steps B and C) above.

Intermediate 91 methyl 2-cyano-4-(2-oxoethyl)benzoate
Step A: methyl 2-amino-4-bromobenzoate

A solution of 2-amino-4-bromobenzoic acid (500 mg, 2.3 mmol) in 20 mL of Et$_2$O was cooled to 0° C. by ice water, and a solution of CH$_2$N$_2$ (145 mg, 3.5 mmol) was added. The reaction was warmed to r.t and stirred for 12 hours. The reaction mixture was concentrated to give methyl 2-amino-4-bromobenzoate $^1$H-NMR (400 MHz, CDCl3) δ 11.45 (s, 1H), 7.95-8.05 (in, 2H), 7.72 (d, J=8.0 Hz, 1H), 3.31 (s, 3H).
Step B: methyl 4-bromo-2-cyanobenzoate A suspension of methyl 2-amino-4-bromobenzoate (500 mg, 2.2 mmol) in 2 mL of conc. HCl was added 5 mL of water and a solution of NaNO$_2$ (159 mg, 2.3 mmol) in water (1 mL) was added over a 10-minute period at 0° C. This diazonium solution was then brought to pH 6 with aqueous NaHCO$_3$. In a separated vail, a solution of CuSO$_4$ (660 mg, 2.75 mmol) in water (2 mL) was added dropwise to a solution of KCN (657 mg, 10.11 mmol) in water (2 mL) at 0° C., then toluene (5 mL) was added and the mixture was stirred and heated to 60° C. The previously prepared diazonium solution was added dropwise to the brown CuCN solution at 60° C. over 40 min. The reaction mixture was heated to 70° C. for 1 hour and cooled to room temperature, and EtOAc (100 mL) was added. The organic phase was washed with brine (20 mL) and concentrated. The crude product was purified via cprep-TLC to afford the methyl 4-bromo-2-cyanobenzoate. $^1$H-NMR (400 MHz, CDCl3) δ 7.75-7.95 (m, 3H), 3.93 (s, 3H).
Step C: methyl 2-cyano-4-(prop-2-en-1-yl)benzoate A mixture of methyl 4-bromo-2-cyanobenzoate (230 mg, 0.96 mmol), allyl-tributyl-stannane (381 mg, 1.2 mmol), LiCl (126 mg, 2.87 mmol) and Pd(PPh$_3$)$_4$ (23 mg) in anhydrous toluene was refluxed under N$_2$ overnight. Distilled off the solvent under reduce pressure, the residue was purified with prep-TLC to give the product methyl 2-cyano-4-(prop-2-en-1-yl)benzoate.
Step D: methyl 2-cyano-4-(2-oxoethyl)benzoate The methyl 2-cyano-4-(prop-2-en-1-yl)benzoate (100 mg, 0.5 mmol) was dissolved in 1:1 CH$_2$Cl$_2$/MeOH (20 mL) containing pyridine (0.25%). The solution was cooled to −78° C., and O$_3$ was passed through until a blue color was present. N$_2$ was then bubbled through to discharge the blue color and Me$_2$S (3 mol) was added. The reaction mixture was allowed to warm and left overnight. The mixture was washed with 1 N HCl and aqueous NaHCO₃ and then dried and evaporated to give methyl 2-cyano-4-(2-oxoethyl)benzoate.

Intermediate 92

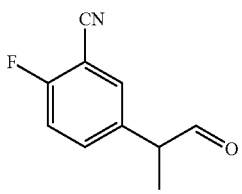

2-fluoro-5-(1-oxopropan-2-yl)benzonitrile
Step A: 2-fluoro-5-(prop-2-en-1-yl)benzonitrile A mixture of compound 5-bromo-2-fluorobenzonitrile (2.5 g, 12.5 mmol), allyl-tributyl-stannane (4.97 g, 12.5 mmol), LiCl (1.6 g, 37.5 mmol) and Pd(PPh₃)₄ (0.2 g) in anhydrous toluene was refluxed under N₂ overnight. Distilled the solution under reduce pressure and the residue was purified with silica gel cloumn chromatography to give the product 2-fluoro-5-(prop-2-en-1-yl)benzonitrile.

Step B: (3-cyano-4-fluorophenyl)acetic acid

A stirred solution of 2-fluoro-5-(prop-2-en-1-yl)benzonitrile (1.9 g, 11.8 mmol) in CCl₄ (25 mL), acetonitrile (25 mL) and water (38 mL) was added sodium periodate (8.83 g, 41.3 mmol) and ruthenium oxide hydrate (200 mg) and the resulting mixture was stirred at ambient temperature overnight. The mixture was diluted with 100 mL DCM and 100 mL of water. The organic layer was dried over anhydrous sodium sulfate and concentrated. The residue was purified with silica gel column chromatography afford crude (3-cyano-4-fluorophenyl)acetic acid.

Step C: methyl (3-cyano-4-fluorophenyl)acetate

A solution of crude (3-cyano-4-fluorophenyl)acetic acid (980 mg, 5.6 mmol) in methanol (10 mL) was added 5 M HCl/MeOH (10 mL). The reaction was stirred at ambient temperature overnight and concentrated. The residue was purified with preparative TLC to afford methyl (3-cyano-4-fluorophenyl)acetate. ¹H-NMR (300 MHz, CDCl3) δ ppm 7.49~7.55 (m, 2H), 7.17 (t, J=8.2 Hz, 1H), 3.71 (s, 3H), 3.63 (s, 2H).

Step D: methyl 2-(3-cyano-4-fluorophenyl)propanoate

A solution of compound methyl (3-cyano-4-fluorophenyl) acetate (200 mg, 1.03 mmol) in 15 mL of anhydrous THF was cooled to −78° C. NaHMDS (1.11 mmol) was added to the reaction dropwise at −78° C. After the addition, the mixture was stirred at −78° C. for 1 h and then CH₃I (160 mg, 1.33 mmol) was added to the reaction dropwise at −78° C. The reaction was warmed to room temperature slowly and stirred at ambient temperature over night. The reaction was quenched with NH₄Cl solution, extracted with EtOAc. The orgianic layer was washed with saturated chloride, dried over anhydrous sodium sulfate and concentrated. The residue was purified via preparative TLC to afford methyl 2-(3-cyano-4-fluorophenyl)propanoate.

Step E: 2-fluoro-5-(1-oxopropan-2-yl)benzonitrile

A solution of compound methyl 2-(3-cyano-4-fluorophenyl)propanoate (50 mg, 0.24 mmol) in 5 mL of anhydrous THF was cooled to 0° C. and then added DIBAL-H (0.3 mmol) was added. The mixture was warmed to ambient temperature and stirred at ambient temperature for 1.5 hours. The reaction was quenched with water, extracte with EtOAc. The organic layer was washed with saturated chloride, dried over anhydrous sodium sulfate and concentrated. The 2-fluoro-5-(1-oxopropan-2-yl)benzonitrile was used for next step without purification.

Intermediate 93

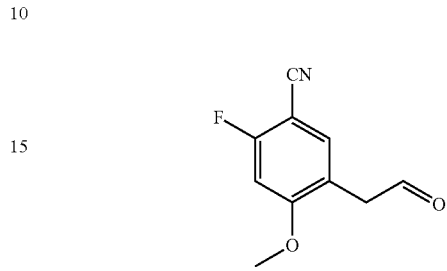

2-fluoro-4-methoxy-5-(2-oxoethyl)benzonitrile
Step A: 5-bromo-2-fluoro-4-methoxybenzonitrile Compound 2-fluoro-4-methoxybenzonitrile (2.97 g, 19.0 mmol) in CHCl₃ (30 mL) was added Br₂ (2 mL), and the mixture was stirred at ambient temperature for 4 days. The mixture was diluted by DCM and washed with saturated NaHCO₃, water, brine, dried over anhydrous sodium sulfate and concentrated. The residue was purified with fast column chromatograph to give 5-bromo-2-fluoro-4-methoxybenzonitrile. ¹H-NMR (300 MHz, CDCl₃) δ ppm 7.76 (d, J=7.2 Hz, 1H), 6.73 (d, J=10.5 Hz, 1H), 3.96 (s, 3H).

Step B: 2-fluoro-4-methoxy-5-(prop-2-en-1-yl)benzonitrile

A mixture of compound 5-bromo-2-fluoro-4-methoxybenzonitrile (10.0 mmol), allyl-tributyl-stannane (12.0 mmol), LiCl (20.0 mmol) and Pd(PPh₃)₄ (0.2 g) in anhydrous toluene was refluxed under N₂ overnight. Distilled off the solvent under reduce pressure, the residue was purified with silica gel cloumn chromatography to give the product 2-fluoro-4-methoxy-5-(prop-2-en-1-yl)benzonitrile.

Step C: 5-(2,3-dihydroxypropyl)-2-fluoro-4-methoxybenzonitrile

A solution of 2-fluoro-4-methoxy-5-(prop-2-en-1-yl)benzonitrile (9 mmol) in a co-solution (methanol/water=3:1, 40 mL) was added OsO₄ (210 mg) and NMO (22.5 mmol) and the resulting mixture was stirred at ambient temperature overnight. Distilled off the solvents under reduced pressure, the residue was dissolved in EtOAc. The organic layer was washed with brine, dried over anhydrous sodium sulfate and concentrated. The residue was purified with fast column chromatograph to give 5-(2,3-dihydroxypropyl)-2-fluoro-4-methoxybenzonitrile.

Step D: 2-fluoro-4-methoxy-5-(2-oxoethyl)benzonitrile

A solution of 5-(2,3-dihydroxypropyl)-2-fluoro-4-methoxybenzonitrile (2.0 mmol) in 10 mL of methanol/water=3:1 was cooled to 0° C. by ice bath, and then NaIO₄ (3.0 mmol) was added. After stirred the reaction at 0° C. for 2 hrs, the mixture was filtered and concentrated. The residue was dissolved in DCM, dried over anhydrous sodium sulfate, and then purified with fast column chromatography to give the product 2-fluoro-4-methoxy-5-(2-oxoethyl)benzonitrile.

Intermediate 94

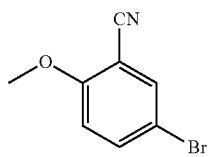

5-bromo-2-methoxybenzonitrile

A mixture of 5-bromo-2-hydroxybenzonitrile (1 g, 5 mmol), MeI (0.85 g, 6 mmol) and K$_2$CO$_3$ (2 g, 15 mmol) in 25 mL of dry CH$_3$CN were heated to refluxed over night. The solvent was evaporated off and the residue was added water. Extracted the mixture with DCM and the organic layer was washed with saturated chloride, dried over Na$_2$SO$_4$. The residue was purified with fast column chromatograph to afford compound 5-bromo-2-methoxybenzonitrile.

Intermediate 95

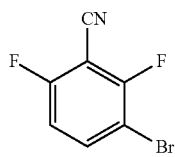

3-bromo-2,6-difluorobenzonitrile

A solution of compound 2,6-difluorobenzonitrile (5 g, 36 mmol) in concentrated sulfuric acid (25 mL) was added with NBS (7 g, 39.6 mmol) at 0° C. and stirred at ambient temperature for 2 days. Ice was added to the reaction solution. The mixture was extracted with EtOAc. The organic layer was washed with water, saturated NaHCO$_3$ solution, brine, dried over anhydrous sodium sulfate and concentrated. The residue was purified with fast column chromatograph to give compound 3-bromo-2,6-difluorobenzonitrile. $^1$H-NMR (400 MHz, CDCl$_3$) δ ppm 7.78~7.83 (m, 1H), 6.98~7.03 (m, 1H).

The following aldehyde intermediates (Table) were prepared from the indicated starting materials in an analogous fashion to that described for the synthesis of 2-fluoro-4-methoxy-5-(2-oxoethyl)benzonitrile above (Steps B to D).

| INTER-MEDIATE | Structure of starting material | Structure of aldehyde intermediate |
|---|---|---|
| 96 | | |
| 97 | | |
| 98 | | |
| 99 | | |
| 100 | | |

Intermediate 101

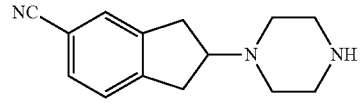

2-(piperazine-1-yl)-2,3-dihydro-1H-indene-5-carbonitrile

Step A: tert-butyl 4-(5-nitro-2,3-dihydro-1H-inden-2-yl) piperazine-1-carboxylate To a solution of 5-nitro-indene-2-one (1.00 g, 5.64 mmol) in methanol (40 mL) containing a stir bar was added sodium cyanoborohydride (1.70 g, 28.2 mmol) and bocpiperazine (1.57 g, 8.47 mmol) followed by addition of few drops of acetic acid; the resulting mixture was stirred for overnight. Analysis of the reaction mixture by LC indicated that reaction had gone to completion. The solution was concentrated in vacuo and the resulting crude was dissolved in EtOAc and washed with saturated sodium bicarbonate solution, and brine, then dried (Na$_2$SO$_4$), filtered and concentrated in vacuo. The crude residue was then subjected for purification by silica gel column chromatography (5% MeOH in DCM) to provide the title product LC/MS: [(M+1)]$^+$=348;

Step B: tert-butyl 4-(5-amino-2,3-dihydro-1H-inden-2-yl) piperazine-1-carboxylate To a solution of 5-nitro-indene bocpiperazine (0.740 g, 2.13 mmol) in methanol (20 mL) was added Pd/C (0.280 g, 2.63 mmol). The reaction mixture was stirred under H$_2$ for 48 h. When the hydrogenation was complete, the reaction mixture was passed through a pad of Celite® and washed several times with methanol. The collected organics were then concentrated in vacuo and gave the title product. LC/MS: [(M+1)]$^+$=318;

Step C: tert-butyl 4-(5-cyano-2,3-dihydro-1H-inden-2-yl) piperazine-1-carboxylate To a solution of CuCN (0.130 g, 1.43 rnmol) in DMSO (3 mL) at 60° C. was added t-butyl nitrite (0.12 mL, 1.3 mmol)

followed by drop by drop addition of a solution of 5-aminoindene bocpiperazine (0.35 g, 1.1 mmol) in DMSO (6 mL) over a course of 10 min. The resulting mixture was stirred for 2 h at 60° C.; LC indicated formation of desired product. The flask was taken out of the oil bath and cooled to rt. To the flask was then poured saturated sodium bicarbonate (5 mL) and water (50 mL); the resulting solution was then transferred into sep. funnel followed by extraction with EtOAc (3×20 mL). The combined organics were then dried (Na$_2$SO$_4$), filtered and concentrated in vacuo to give the title product. LC/MS: [(M+1)]$^+$=328;

Step D: 2-(piperazine-1-yl)-2,3-dihydro-1H-indene-5-carbonitrile

To a flask containing 5-cyano-inden bocpiperazine (0.025 g, 0.076 mmol) and a stir bar was added 4M HCl (2 mL). The resulting mixture was then stirred for 2 h; LC indicated completion of the reaction. The solution was concentrated in vacuo, pumped under reduced pressure and gave the title product (LC/MS: [(M+1)]$^+$=228.

Intrmediate 102

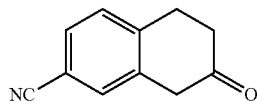 [SMILES: N#Cc1ccc2c(c1)CC(=O)CC2]

7-oxo-5,6,7,8-tetrahydronaphthalene-2-carbonitrile Step A: 7-bromo-3,4-dihydronaphthalen-2(1H)-one To a solution of (3-bromophenyl)acetic acid (~10 g, 50 mmol) in 200 mL of DCM was added DMF (183 mg, 2.5 mmol) and then oxalyl dichloride (6.3 g, 50 mmol) was added dropwise over 30 min. The resulting mixture was stirred at room temperature for 6 hr and then concentrated under reduced pressure. A mixture of prepared acid chloride in 200 mL of DCM was added AlCl$_3$ (13.2 g, 100 mmol) portionwise at 0° C. After the mixture was stirred at 0° C. for 30 min, the solution was bubbled with ethene gas for 2 h and the resulting mixture was warmed to room temperature and stirred overnight. Then 300 mL of water was added dropwise over 30 min with stirring. Then separated the organic layer and extracted the aqueous layer with 200 mL of DCM. The combined organic layers were washed with 1N HCl (200 mL), saturated NaHCO$_3$ (200 mL) and brine (200 mL) and then dried over Na$_2$SO$_4$. Then the organic layer was concentrated under reduced pressure to remove the solvent. The crude product was purified via chromatography (EtOAc/petrol ether 1:20 to 1:5) to give the desired 7-bromo-3,4-dihydronaphthalen-2(1H)-one along with the isomeric side product 5-bromo-3,4-dihydronaphthalen-2(1/1)-one. $^1$H-NMR (400 MHz, CDCl$_3$) δ 7.33 (d, J=8.0 Hz, 1H), 7.27 (s, 1H), 7.10 (d, J=8.0 Hz, 1H), 3.01 (t, J=6.8 Hz, 2H), 2.54 (t, J=6.8 Hz, 2H); MS m/e 225 (M+1)$^+$.

Step B: 7-oxo-5,6,7,8-tetrahydronaphthalene-2-carbonitrile

A solution of 7-bromo-3,4-dihydronaphthalen-2(1H)-one (500 mg, 2.2 mmol) in 5 mL of anhydrous DMF in a 10 mL CEM microwave tube was added Zn(CN)$_2$ (515 mg, 4.4 mmol), Pd$_2$(dba)$_3$ (55 mg, 0.034 mmol), TMEDA (55 mg, 0.47 mmol) and Xantphos (29 mg, 0.05 mmol) sucessively. The reaction tube was sealed and heated to 160° C. under microwave irradiation with a 5 min hold time and 300 W maxium power input. After cooling under a stream of compressed air, the reaction mixture was washed with EtOAc through a Celite® with a thin layer of silica gel in the middle size. The filtrate was washed with saturated bine, dried over anhydrous sodium sulfate and concentrated. The residue was purified by preparative TLC to afford 7-oxo-5,6,7,8-tetrahydronaphthalene-2-carbonitrile (150 mg, yield 40%).

$^1$H-NMR (300 MHz, CDCl$_3$) δ ppm 7.53 (d, J=8.1 Hz, 1H), 7.45 (s, 1H), 7.36 (d, J=8.1 Hz, 1H), 3.15 (t, J=6.8 Hz, 2H), 2.58 (t, J=6.8 Hz, 2H).

Intermediate 103

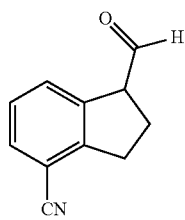 [SMILES: N#Cc1cccc2c1CCC2C=O]

1-formyl-2,3-dihydro-1H-indene-4-carbonitrile

Step A: 1-oxo-2,3-dihydro-1H-indene-4-carbonitrile

To a solution of 4-bromo-2,3-dihydro-1H-inden-1-one (1.00 g, 4.74 mmol) in 5 mL of DMF was added Zn(CN)$_2$ (556 mg, 4.74 mmol) and Pd(PPh$_3$)$_4$ (77 mg, 0.14 mmol), and the reaction mixture was stirred under microwave irradiation for 1 h at 165° C. The solvent was removed in vacuum to afford the crude compound, which was purified via column chromatography to afford 1-oxo-2,3-dihydro-1H-indene-4-carbonitrile.

Step B: (1E)-1-[(methyloxy)methylidene]-2,3-dihydro-1H-indene-4-carbonitrile

Sodium bis(trimethylsilyl)amide (2 mL, 4 mmol, 2M in THF) was added to a stirred suspension of (methoxy methyl)triphenylphosphonium chloride (1.47 g, 4.29 mmol) in dry THF (20 mL) at 0° C. for 35 min and a solution of 1-oxo-2,3-dihydro-1H-indene-4-carbonitrile (450 mg, 2.86 mmol) in THF (10 mL) added over 10 min. The mixture was stirred at 0° C. for 2 h and at room temperature for 1 h. Water was added and the mixture was partitioned between EtOAc and brine. The organic layer was dried and concentrated. The crude product was purified via prep-TLC (PE:EtOAc=10:1) to afford (1E)-1-[(methyloxy)methylidene]-2,3-dihydro-1H-indene-4-carbonitrile. $^1$H-NMR (400 MHz, CDCl$_3$) δ ppm 8.00 (d, J=8.3 Hz, 0.4H), 7.42 (d, J=8.3 Hz, 0.6H), 7.30-7.40 (m, 1H), 7.18-7.22 (m, 1H), 6.70 (s, 0.6H), 6.22 (s, 0.4H), 3.72 (s, 3H), 3.15 (t, J=5.7 Hz, 2H), 2.70-2.82 (m, 2H).

Step C: 1-formyl-2,3-dihydro-1H-indene-4-carbonitrile

A solution of (1E)-1-[(methyloxy)methylidene]-2,3-dihydro-1H-indene-4-carbonitrile (250 mg, 1.05 mmol) in DCM (5 mL) was added BBr$_3$ dropwise at −78° C. under N$_2$. Then the mixture was stirred at this temperature for 3 h. It was poured into ice-saturated NaHCO$_3$ solution, and extracted with DCM. The organic layer was washed with brine and dried over Na$_2$SO$_4$. The solvent was removed in vacuo to give crude 1-formyl-2,3-dihydro-1H-indene-4-carbonitrile, which is used for next step directly. $^1$H-NMR (400 MHz, CDCl$_3$) δ ppm 9.72 (s, 1H), 7.54 (d, J=7.6 Hz, 2H), 7.34 (t, J=7.6 Hz, 1H), 3.76 (s, 1H), 3.18-3.24 (m, 2H), 2.42-2.58 (m, 2H).

Intermediate 104

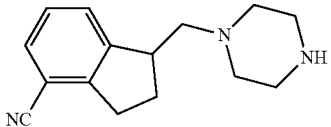 [SMILES: N#Cc1cccc2c1CCC2CN1CCNCC1]

1-(piperazin-1-ylmethyl)-2,3-dihydro-1H-indene-4-carbonitrile 1-(Piperazin-1-ylmethyl)-2,3-dihydro-1H-indene-4-carbonitrile was prepared starting from 1-formyl-2,3-dihydro-1H-indene-4-carbonitrile and tert-butyl piperazine-1-carboxylate in two steps in an analogous fashion to that described for the synthesis of 2-methoxy-4-[2-piperazin-1-yl)ethyl]benzonitrile above. $^1$H-NMR (400 MHz, MeOD) δ ppm 7.68 (d, J=7.8 Hz, 1H), 7.58 (d, J=7.8 Hz, 1H), 7.40 (t, J=7.4 Hz, 1H), 3.64~3.88 (m, 10H), 3.40~3.46 (m, 1H), 3.20~3.30 (m, 1H), 3.07~3.16 (m, 1H), 2.55~2.70 (m, 1H), 2.10~2.25 (m, 1H).

Intermediate 105

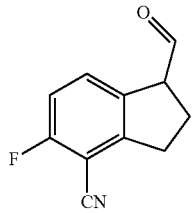 [SMILES: N#Cc1c(F)ccc2c1CCC2C=O]

5-Fluoro-1-formyl-2,3-dihydro-1H-indene-4-carbonitrile

Step A: 5-Fluoro-1-oxo-2,3-dihydro-1H-indene-4-carbonitrile

To a flask charged with 4-Bromo-5-fluoro-2,3-dihydro-1H-inden-1-one (PCT Publ. WO 2007050732. 1.0 g, 4.4 mmol) and a stir bar was added COPPER(I) CYANIDE (0.47 g, 5.2 mmol) and DMF (20 ml). The reaction was sealed with a condensor, purged three times with nitrogen, and heated to 150° C. for 16 hours. TLC at that point showed two new spots. The spot right below SM was the desired product. A small amount of SM was also recovered by MPLC. LC-MS (IE, m/z): 176 [M+1]$^+$.

Step B: 5-Fluoro-1-(methoxymethylidene)-2,3-dihydro-1H-indene-4-carbonitrile

To a suspension of (METHOXYMETHYL)TRIPHENYLPHOSPHONIUM CHLORIDE (1.3 g, 3.8 mmol) in THF (15 ml) was dropped n-Butyl Lithium (3.85 ml, 3.85 mmol) at −20° C. The mixture was stirred for 20 minutes before a THF solution of 5-Fluoro-1-oxo-2,3-dihydro-1H-indene-4-carbonitrile (450 mg, 2.6 mmol) was added into the reaction. TLC showed some green color spot right away. The reaction was then poured into NH$_4$Cl, extracted with EtOAc, and flashed through silica gel. LC-MS (1E, m/z): 204 [M+1]$^+$.

Step C: 5-Fluoro-1-formyl-2,3-dihydro-1H-indene-4-carbonitrile

A solution of 5-Fluoro-1-(methoxymethylidene)-2,3-dihydro-1H-indene-4-carbonitrile (10 mg, 0.049 mmol) in DCM was cooled to −78° C. To this solution was dropped BBr$_3$ (0.492 ml, 0.492 mmol). The mixture was allowed to stir for 15 minutes, and then it was diluted with DCM (10 mL), washed with NaHCO$_3$, dried over Na$_2$SO$_4$, and concentrated. The residue was used directly in the next step.

Intermediate 106

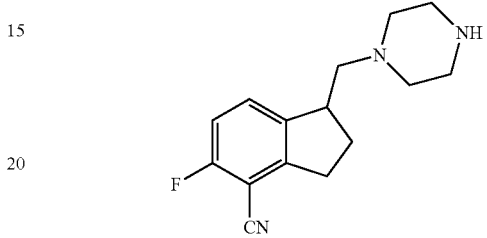

5-Fluoro-1-(piperazin-1-ylmethyl)-2,3-dihydro-1H-indene-4-carbonitrile

Step A: 5-Fluoro-1-methylidene-2,3-dihydro-1H-indene-4-carbonitrile

To a suspension of methyltriphenylphosphonium bromide (1.6 g, 4.45 mmol) in THF (5 ml) was added n-Butyllithium (1.78 ml, 4.45 mmol) at 0° C. The solution turned yellow right away. The mixture was allowed to stir for 15 minutes before a THF solution of 4-Bromo-5-fluoro-2,3-dihydro-1H-inden-1-one (260 mg, 1.48 mmol) was dropped into the reaction. TLC showed formation of the desired product as soon as the addition was done. However, a good portion of the SM remained untouched. The reaction was warmed up to RT slowly, but no significant progress was observed. The reaction was then quenched with NH$_4$Cl, extracted with EtOAc, washed with brine, dried over Na$_2$SO$_4$, and purified by MPLC. LC-MS (IE, m/z): 174 [M+1]$^+$.

Step B: 5-Fluoro-1-(hydroxymethyl)-2,3-dihydro-1H-indene-4-carbonitrile

To a solution of 5-Fluoro-1-methylidene-2,3-dihydro-1H-indene-4-carbonitrile (30 mg, 0.173 mmol) in THF was added BH$_3$.THF (0.173 ml, 0.173 mmol) at 0° C. The mixture was allowed to stir at 0° C. for 15 minutes, and then warm up to RT for 30 minutes. TLC showed little SM left at that point. To this reaction was then added Sodium Hydroxide (2M, 0.173 ml, 0.346 mmol) and Hydrogen peroxide (39.3 mg, 0.346 mmol). The mixture was stirred for another hour at RT. TLC and LC showed good reaction. The reaction was diluted with water, extracted with EtOAc, washed with water and brine, dried over Na$_2$SO$_4$, and concentrated. The resulting oil was used directly in the next step. LC-MS (IE, m/z): 192 [M+1]$^+$.

Step C: 5-Fluoro-1-(piperazin-1-ylmethyl)-2,3-dihydro-1H-indene-4-carbonitrile

A solution of 5-Fluoro-1-(hydroxymethyl)-2,3-dihydro-1H-indene-4-carbonitrile (20 mg, 0.105 mmol) in DCM was treated with Dess-MartinPeriodinane (89 mg, 0.209 mmol) in DCM. When TLC showed the reaction was done, Na$_2$S$_2$O$_3$ was added to the reaction. The solution was stirred vigorously until the two layers turned clear. The mixture was extracted with DCM, and the DCM layer was washed with Na$_2$CO$_3$ and brine, dried over sodium sulfate, and concentrated. The resulting oil was then treated with N-Boc-piperazine (39.0 mg, 0.209 mmol) and Sodium Cyanoborohydride (33 mg, 0.52 mmol) in DCM with a few drops of HOAc. LC showed complete reaction within 6 hours. The reductive amination adduct was then purified by MPLC. Finally, the Boc group was removed by treating the carbamate with 4N HCl in dioxane. After removal of solvent, the title material was obtained. LC-MS (IE, m/z): 260 [M+1]+.

Intermediate 107

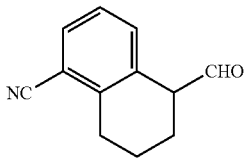 [SMILES: N#Cc1cccc2c1CCCC2C=O]

5-formyl-5,6,7,8-tetrahydronaphthalene-1-carbonitrile

Step A: 5-oxo-5,6,7,8-tetrahydronaphthalen-1-yltrifluoromethanesulfonate

A solution of 5-hydroxy-3,4-dihydronaphthalen-1(2H)-one (5 g, 30.8 mmol) in 30 mL of dry pyridine was cooled to −5° C. and Tf$_2$O (10.4 g, 36.96 mmol) was added dropwise. The reaction was warmed to ambient temperaure slowly and stirred over night. Pyridine was distilled off under reduce pressure, and the residue was purified with silica gel cloumn chromatography to give 5-oxo-5,6,7,8-tetrahydronaphtalen-1-yl trifluoromethanesulfonate.

Step B: 5-oxo-5,6,7,8-tetrahydronaphthalene-1-carbonitrile

A mixture of compound 5-oxo-5,6,7,8-tetrahydronaphthalen-1-yl trifluoromethanesulfonate (8.6 g, 30.8 mmol), Zn(CN)$_2$(7.2 g, 61.6 mmol) and Pd(PPh$_3$)$_4$(0.8 g) in anhydrous DMF was stirred at 120° C. under N$_2$ overnight. The reaction was cooled to ambient temperature, and then diluted with DCM. Filtered off solids and the orgainic filtrate was washed with brine, dried over anhydrous sodium sulfate and concentrated. The residue was purified with silica gel cloumn chromatography to give 5-oxo-5,6,7,8-tetrahydronaphthalene-1-carbonitrile.

Subsequent Steps: 5-formyl-5,6,7,8-tetrahydronaphthalene-1-carbonitrile

5-Formyl-5,6,7,8-tetrahydronaphthalene-1-carbonitrile was prepared from 5-oxo-5,6,7,8-tetrahydronaphthalene-1-carbonitrile in an analogous fashion to that described above for the synthesis of 1-formyl-2,3-dihydro-1H-indene-4-carbonitrile (Steps B and C).

Intermediate 108

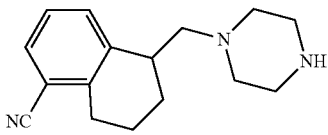 [SMILES: N#Cc1cccc2c1CCCC2CN1CCNCC1]

5-(piperazin-1-ylmethyl)-5,6,7,8-tetrahydronaphthalene-1-carbonitrile 5-(Piperazin-1-ylmethyl)-5,6,7,8-tetrahydronaphthalene-1-carbonitrile was prepared starting from 5-formyl-5,6,7,8-tetrahydronaphthalene-1-carbonitrile and tert-butyl piperazine-1-carboxylate in two steps in an analogous fashion to that described for the synthesis of 2-methoxy-4-[2-(piperazin-1-yl)ethyl]benzonitrile above.

Intermediate 109

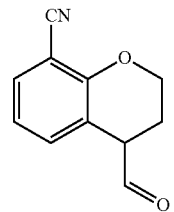 [SMILES: N#Cc1cccc2c1OCCC2C=O]

4-formyl-3,4-dihydro-2H-chromene-8-carbonitrile

Step A: 3-(2-bromophenoxy)propanoic acid

A solution of 2-bromophenol (17.3 g, 100 mmol) in 50 mL of H$_2$O was added NaOH (8 g, 200 mmol), 3-bromopropanoic acid (15.3 g, 100 mmol), and the mixture was stirred at reflux overnight. The reaction solution was diluted with H$_2$O, extracted with EtOAc. The aqueous layer was acidified to pH=1~2 and extracted with EtOAc. The combined organic phase was washed with brine, dried over anhydrous Na$_2$SO$_4$ and concentrated to afford 3-(2-bromophenoxy)propanoic acid.

Step B: 8-bromo-2H-dihydro-4H-chromen-4-one

An ice cold solution of 3-(2-bromophenoxy)propanoic acid (10.14 g, 41.39 mmol) in 150 mL of DCM was added (COCl)$_2$ (7.24 mL) and 3 drops of DMF. The solution was stirred at 0° C. for 2 hours, and then AlCl$_3$ (6.055 g, 45.53 mmol) was added and the solution was stirred overnight at room temperature. The mixture was poured onto ice water, and extracted with DCM. The combined organics were washed with 0.5M NaOH and brine, dried over Na$_2$SO$_4$, and concentrated. The residue was purified by column chromatography (PE: EA=10:1) to give the title compound. $^1$H-NMR (300 MHz, CDCl3) δ ppm 7.84~7.87 (m, 1H), 7.7~7.74 (m, 1H), 6.91 (t, J=8.0 Hz, 1H), 4.65 (t, J=6.2 Hz, 2H), 2.85 (t, J=6.2 Hz, 2H).

Step C: 8-bromo-4-(trimethylsilyl)-3,4-dihydro-2H-chromene-4-carbonitrile

A solution of 8-bromo-2,3-dihydro-4H-chromen-4-one (6.66 g, 29.3 mmol) in (CH$_3$)$_3$SiCN (11.52 g, 117.3 mmol) was added ZnI$_2$ (500 mg, 1.46 mmol) and was stirred at ambient temperature for 48 hours. The reaction was completed, added EA, washed with NaHCO$_3$ aq, the organic layer was dried over anhydrous Na$_2$SO$_4$ and concentrated to give 8-bromo-4-(trimethylsilyl)-3,4-dihydro-2H-chromene-4-carbonitrile.

Step D: 8-bromo-3,4-dihydro-2H-chromene-4-carboxylie acid

A solution of 8-bromo-4-(trimethylsilyl)-3,4-dihydro-2H-chromene-4-carbonitrile (9.6 g, 29.45 mmol) in a mixture of conc. HCl/HOAc (50 mL/40 mL) was added SnCl$_2$.H$_2$O (26.57 g, 117.8 mmol) and the miture was refluxed for 48 hours. The reaction solution was concentrated and the residue was partitioned between water and EtOAc. The combined organic layers were washed with brine, dried over anhydrous Na$_2$SO$_4$ and concentrated to afford 8-bromo-3,4-dihydro-2H-chromene-4-carboxylic acid. $^1$H-NMR (300 MHz, CDCl3) δ ppm 7.15~7.46 (m, 2H), 6.75~6.92 (m, 1H), 4.24~4.4 (m, 2H), 3.78~3.84 (m, 1H), 2.1~2.39 (m, 2H).

Step E: (8-bromo-3,4-dihydro-2H-chromen-4-yl)methanol

A solution of 8-bromo-3,4-dihydro-2H-chromene-4-carboxylic acid (3.1 g, 12 mmol) in 50 mL THF was added $BH_3$ (24 mL, 24 mmol, C=1.0 M in THF) dropwise at 0° C. The mixture was stirred at 0° C. for 2-3 hours before quenched with MeOH (8 mL), and evaporated. The residue was partitioned between water and EtOAc. The organic phase was washed with 3N HCl, saturated $Na_2CO_3$, and brine, dried over anhydrous $Na_2SO_4$ and concentrated to afford (8-bromo-3,4-dihydro-2H-chromen-4-yl)methanol.

Step F: 4-(hydroxymethyl)-3,4-dihydro-2H-chromene-8-carbonitrile

A solution of (8-bromo-3,4-dihydro-2H-chromen-4-yl)methanol (1 g, 4.12 mmol) in 3 mL of DMF was added $Zn(CN)_2$ (481 mg, 4.12 mmol), $Pd_2(dba)_3$ (67 mg, 0.04 mmol), TMEDA (191 mg, 1.6 mmol), Xantphose (48 mg, 0.08 mmol), and the mixture was stirred under microwave irradiation for 5 min at 100° C. The mixture was added with 10 mL of EtOAc, washed with brine, dried over anhydrous $Na_2SO_4$ and concentrated. The residue was purified by prep-TLC to give 4-(hydroxymethyl)-3,4-dihydro-2H-chromene-8-carbonitrile.

Step G: 4-formyl-3,4-dihydro-2H-chromene-8-carbonitrile

A solution of 4-(hydroxymethyl)-3,4-dihydro-2H-chromene-8-carbonitrile (210 mg, 1.11 mmol) in 10 mL of anhydrous DCM was added $NaHCO_3$ (933 mg, 11.1 mmol), Dess-Martin reagent (942 mg, 2.22 mmol) at 0° C. The mixture was stirred at 0° C. for 1-2 hours. The reaction mixture was filtrated and purified by prep-TLC to give 4-formyl-3,4-dihydro-2H-chromene-8-carbonitile. $^1$H-NMR (400 MHz, CDCl3) δ ppm 9.67 (s, 1H), 7.43~7.45 (m, 1H), 7.34~7.36 (m, 1H), 6.93~6.97 (m, 1H), 4.35~4.39 (m, 1H), 4.0~4.06 (m, 1H), 3.58~3.6 (m, 1H), 2.4~2.46 (m, 1H), 2.06~2.14 (m, 1H).

Intermediate 110

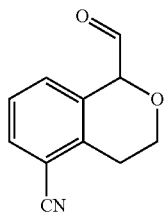 [SMILES: N#Cc1cccc2c1CCOC2C=O]

1-formyl-3,4-dihydro-1H-isochromene-5-carbonitrile

Step A: 2-(2-bromophenyl)ethanol

A solution of (2-bromophenyl)acetic acid (100 g, 0.46 mmol) in dry THF (2 L) was added $NaBH_4$ (29 g, 0.77 mol) in portions. The contents were cooled to 0° C., and $BF_3 \cdot Et_2O$ (123 mL, 0.770 mol) was added drop-wise over 1 h. The mixture was allowed to warm to 25° C. and stirred for 16 h. The reaction was cooled to 0° C. and cautiously quenched with aqueous sodium hydroxide. The contents were stirred for 3 h, and then extracted with EtOAc. The organic layer was dried and concentrated to give 2-(2-bromophenyl)ethanol. $^1$H-NMR (400 MHz, CDCl$_3$) δ 7.54~7.56 (m, 1H), 7.27~7.28 (m, 2H), 7.07~7.11 (m, 1H), 3.88 (s, J=6.6 Hz, 2H), 3.03 (t, J=6.8 Hz, 2H).

Step B: 5-bromo-3,4-dihydro-1H-isochromene-1-carboxylic acid

A solution of 2-(2-bromophenyl)ethanol (40 g, 0.2 mol) and glyoxylic acid (16 g, 0.22 mol) in 100 mL of trifluoacetic acid was refluxed overnight. The solvent was concentrated. Water and ammonium hydroxide was added to the residue to adjust the Ph of the solution over 7. The solution was extracted with diethyl ether, and the aqueous layer was adjusted to about 3 with 1M HCl, and then the solution was extracted with ethyl acetate. The organic layer was dried and evaporated. The residue was without purification to give 5-bromo-3,4-dihydro-1H-isochromene-1-carboxylic acid. $^1$H-NMR (400 MHz, CDCl$_3$) δ 7.52 (d, J=7.6 Hz, 1H), 7.12 (t, J=7.8 Hz, 2H), 5.33 (s, 1H), 4.27~4.33 (m, 1H), 3.99~4.06 (m, 1H), 2.87~2.89 (m, 2H).

Step C: (5-bromo-3,4-dihydro-1H-isochromen-1-yl)methanol

A solution of 5-bromo-3,4-dihydro-1H-isochromene-1-carboxylic acid (0.500 g, 1.94 mmol) in 1 mL of THF was added $BH_3 \cdot THF$ (3.88 mL, 3.88 mmol) dropwise at 0° C. The mixture was stirred at 0° C. for 2 h. The reaction was quenched with water and aqueous sodium hydroxide (1 N, 2 mL). The contents were stirred for 3 h, and then extracted with EtOAc. The organic layer was dried and concentrated to give (5-bromo-3,4-dihydro-1H-isochromen-1-yl)methanol. $^1$H-NMR (400 MHz, CDCl$_3$) δ 7.41 (t, J=2.4 Hz, 1H), 6.97~7.04 (m, 2H), 4.75~4.77 (m, 1H), 3.88~3.92 (m, 1H), 3.73~3.79 (m, 2H), 2.71-2.86 (m, 2H).

Step D: 1-(hydroxymethyl)-3,4-dihydro-1H-isochromene-5-carbonitrile

A mixture of (5-bromo-3,4-dihydro-1H-isochromen-1-yl)methanol (390 mg, 1.6 mmol), $Zn(CN)_2$ (113 mg, 0.960 mmol), TMEDA (0.37 mg), xantphose (4.6 mg) and $Pd(dba)_3$ (2.6 mg) in anhydrous DMF was microwaved 10 min at 100° C. The reaction was quenched with water and extracted with EtOAc. The organic layer was washed with brine, dried and concentrated. The residue was purified with prep-HPLC to give 1-(hydroxymethyl)-3,4-dihydro-1H-isochromene-5-carbonitrile. $^1$H-NMR (400 MHz, CDCl$_3$) δ 7.49~7.50 (m, 1H), 7.24~7.48 (m, 2H), 4.76~4.78 (in, 1H), 4.17~4.22 (m, 1H), 3.76~3.95 (m, 3H), 3.01~3.09 (m, 1H), 2.89~2.95 (m, 1H).

Step E: 1-formyl-3,4-dihydro-1H-isochromene-5-carbonitrile

A solution of 1-(hydroxymethyl)-3,4-dihydro-1H-isochromene-5-carbonitrile (0.16 g, 0.85 mmol) in 4 mL of DCM was added Dess-Martin reagent (0.72 g, 1.7 mmol) in one portion at 0° C. The mixture was stirred at 0° C. for 1 hour, and then stirred at rt. Overnight. The reaction mixture was filtered and the filtrate was concentrated to give 1-formyl-3,4-dihydro-1H-isochromene-5-carbonitrile. $^1$H-NMR (400 MHz, CDCl$_3$) δ 9.71 (s, 1H), 7.93~7.95 (in, 1H), 7.64~7.68 (m, 1H), 4.99 (s, 1H), 4.03~4.09 (m, 2H), 2.99~3.04 (m, 2H).

Intermediate 111

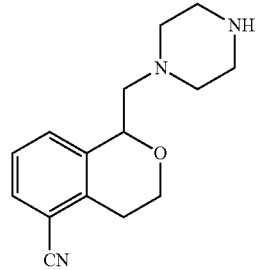 [SMILES: N#Cc1cccc2c1CCOC2CN1CCNCC1]

1-(piperazin-1-ylmethyl)-3,4-dihydro-1H-isochromene-5-carbonitrile

Step A: 2-(2-bromophenyl)ethanol

A solution of (2-bromophenyl)acetic acid (100 g, 0.46 mmol) in dry THF (2 L) was added $NaBH_4$ (29 g, 0.77 mol) in portions. The contents were cooled to 0° C., and BF$_3$·Et$_2$O (123 mL, 0.77 mol) was added drop wise over 1 h. The mixture was allowed to warm to 25° C. and stirred for 16 h. The reaction was cooled to 0° C. and cautiously quenched with aqueous sodium hydroxide. The contents were stirred for 3 h, and then extracted with EtOAc. The organic layer was dried and concentrated to give 2-(2-bromophenyl)ethanol. $^1$H-NMR (400 MHz, CDCl$_3$) δ 7.54~7.56 (in, 1H), 7.23~7.28 (m, 2H), 7.07~7.11 (m, 1H), 3.88 (s, J=6.6 Hz, 2H), 3.03 (t, J=6.8 Hz, 2H).

Step B: methyl 5-bromo-3,4-dihydro-1H-isochromene-1-carboxylate

TiCl$_4$ (76 g, 0.4 mol) was added over a period of 10 min to an ice-cooled mixture of 2-(2-bromophenyl)ethanol (20 g, 0.1 mol) and ethyl bis(ethyloxy)acetate (21.1 g, 0.120 mol) in 120 mL of CH$_3$NO$_2$. After stirring for 10 min, the ice bath was removed and the mixture was allowed to stire at room temperature overnight. The mixture was poured into ice/aqueous 1N HCl. Extracted with DCM and backwashed with 1HCl and brine, dried over anhydrous sodium sulfate and concentrated. The residue was purified with silica gel chromatography to give the product methyl 5-bromo-3,4-dihydro-1H-isochromene-1-carboxylate. $^1$H-NMR (400 MHz, CDCl$_3$) δ 7.42~7.47 (m, 1H), 7.29 (d, J=8.0 Hz, 1H), 7.02 (t, J=8.0 Hz, 1H), 5.22 (s, 1H), 4.16~4.26 (m, 3H), 3.95~4.01 (m, 1H), 3.46~3.63 (m, 1H), 2.99~3.03 (m, 1H), 1.24 (t, J=8.0 Hz, 3H).

Step C: 5-bromo-3,4-dihydro-1H-isochromene-1-carboxylic acid

To a solution of methyl 5-bromo-3,4-dihydro-1H-isochromene-1-carboxylase (12.1 g, 42.4 mmol) in 200 mL of MeOH/THF/H$_2$O (2/2/1) was added LiOH.H$_2$O (5.34 g, 0.127 mol), and the mixture was stirred at ambient temperature for 30 min. The solvents were removed under vacuum, and the residue was added 100 mL of water and extracted with ether. The aqueous layer was then acidified with 4 N HCl to Ph=4~5 in ice bath, and extracted with EtOAc. The combined organic phase was washed with brine, dried over anhydrous sodium sulfate and concentrated to afford 5-bromo-3,4-dihydro-1H-isochromene-1-carboxylic acid. $^1$H-NMR (400 MHz, CDCl$_3$) δ 7.41~7.47 (m, 2H), 7.05 (t, J=8.0 Hz, 1H), 5.27 (s, 1H), 4.19~4.25 (m, 1H), 3.95~4.00 (m, 1H), 2.80 (t, J=6.0 Hz, 2H).

Step D: 5-bromo-N-methyl-N-(methyloxy)-3,4-dihydro-1H-isochromene-1-carboxamide

A mixture of 5-bromo-3,4-dihydro-1H-isochromene-1-carboxylic acid (9.10 g, 35.4 mmol) and CDI (4.14 g, 42.5 mmol) in 200 mL of dry DCM was stirred at r.t. for 30 min and then O,N-dimethyl-hydroxylamine (5.99 g, 42.5 mmol) was added. The result mixture was stirred overnight. The solvents were removed under vacuum, and the residue was purified with silica gel chromatography to give 5-bromo-N-methyl-N-(methyloxy)-3,4-dihydro-1H-isochromene-1-carboxamide. $^1$H-NMR (400 MHz, CDCl$_3$) δ 7.40 (d, J=8.0 Hz, 1H), 6.99 (t, J=8.0 Hz, 1H), 6.93 (d, J=8.0 Hz, 1H), 5.63 (s, 1H), 4.23~4.28 (m, 1H), 3.87~3.92 (m, 1H), 3.71 (s, 3H), 3.19 (s, 3H), 2.71~2.87 (m, 2H).

Step E: 5-bromo-3,4-dihydro-1H-isochromene-1-carbaldehyde

A solution of 5-bromo-N-methyl-N-(methyloxy)-3,4-dihydro-1H-isochromene-1-carboxamide (3.0 g, 10 mmol) in 60 mL of anhydrous THF was cooled to −30° C. and then DIBAL-H (20 mmol) was added. The mixture was stirred at −30° C. for 1 hours. The reaction was quenched with water, extracted with DCM. The organic layer was washed with brine, dried over anhydrous sodium sulfate and concentrated. The crude 5-bromo-3,4-dihydro-1H-isochromene-1-carbaldehyde was used for next step without purification.

Step F: 1,1-dimethylethyl-4-[(5-bromo-3,4-dihydro-1H-isochromen-1-yl)methyl]piperazine-1-carboxylate A solution of 5-bromo-3,4-dihydro-1H-isochromene-1-carbaldehyde (1.62 g, 6.72 mmol), amine (1.25 g, 6.72 mmol) and NaBH(Oac)$_3$ (7.12 g, 33.6 mmol) in 50 mL of anhydrous DCM was stirred at ambient temperature overnight. The reaction mixture was added 50 mL of DCM and washed with brine. The organic layer was dried over anhydrous sodium sulfate and concentrated. The residue was purified with silica gel chromatography to give 1,1-dimethylethyl-4-[(5-bromo-3,4-dihydro-1H-isochromen-1-yl)methyl]piperazine-1-carboxylate.

$^1$H-NMR (400 MHz, CDCl$_3$) δ 7.43 (d, J=8.0 Hz, 1H) 7.14 (d, J=8.0 Hz, 1H), 7.04 (t, J=8.0 Hz, 1H), 4.90 (d, J=8.0 Hz, 1H), 4.15~4.21 (m, 1H), 3.71~3.77 (m, 1H), 3.48~3.49 (m, 4H), 3.36 (t, J=4.0 Hz, 1H), 2.76~2.81 (m, 2H), 2.50~2.54 (m, 4H), 2.41 (s, 1H), 1.45 (s, 9H).

Step G: 1,1-dimethylethyl4-[(5-cyano-3,4-dihydro-1H-isochromen-1-yl)methyl]piperazine-1-carboxylate A solution of 1,1-dimethylethyl-4-[(5-bromo-3,4-dihydro-1H-isochromen-1-yl)methyl]piperazine-1-carboxylate (210 mg, 0.51 mmol), Pd(PPh$_3$)$_4$ (118 mg, 0.100 mmol) and Zn(CN)$_2$ (120 mg, 1.0 mmol) in 10 mL of anhydrous DMF was to 120° C. at N$_2$ atmosphere for 2 hours. After cooled to r.t., the mixture was partitioned between EtOAc and water. The organic layer was dried over anhydrous sodium sulfate and concentrated. The residue was purified with prep-TLC to afford 1,1-dimethylethyl4-[(5-cyano-3,4-dihydro-1H-isochromen-1-yl)methyl]piperazine-1-carboxylate.

Step H: 1-(piperazin-1-ylmethyl)-3,4-dihydro-1H-isochromene-5-carbonitrile

A solution of 1,1-dimethylethyl4-[(5-cyano-3,4-dihydro-1H-isochromen-1-yl)methyl]piperazine-1-carboxylate (150 mg, 0.42 mmol) in 10 mL of DCM was added 5 mL of 4N HCl/dioxane, and the mixture was stirred at room temperature for 2 hours. The solvents was removed off under vacuum to afford 1-(piperazin-1-ylinethyl)-3,4-dihydro-1H-isochromene-5-carbonitrile. $^1$H-NMR (400 MHz, MeOD) δ 7.77 (d, J=8. Hz, 1H), 7.72 (d, J=8.0 Hz, 1H), 7.45 (t, J=8.0 Hz, 1H), 4.11~4.17 (m, 1H), 3.82~3.88 (m, 9H), 3.55~3.61 (m, 2H), 2.87~2.99 (m, 2H).

Intermediate 112

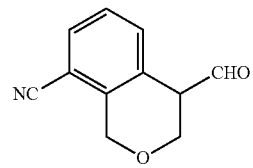

4-formyl-3,4-dihydro-1H-isochromene-8-carbonitrile

Step A: 1-bromo-2-(bromomethyl)-3-nitrobenzene

To a solution of 1-bromo-2-methyl-3-nitrobenzene (50.0 g, 0.231 mol) in CCl$_4$(500 mL) was added NBS (41.2 g, 0.231 mol) and BPO (6.51 g, 0.0231 mol), and the mixture was stirred at reflux for 1 h. Then the mixture was washed with 1 N HCl (300 mL*3), dried over Na$_2$SO$_4$, concentrated in vacuo. The residue was purified via chromatography (petrol ether) to give 1-bromo-2-(bromomethyl)-3-nitrobenzene.

$^1$H-NMR (400 MHz, CDCl$_3$) δ7.86~7.88 (m, 2H), 7.35 (t, J=8.0 Hz, 1H), 4.88 (s, 2H).

Step B: 2-bromo-6-nitrobenzyl (2E)-but-2-en-1-yl ether

To a solution of KOH (0.57 g, 0.099 mol) in (2E)-but-2-en-1-ol (100 mL) was added 1-bromo-2-(bromomethyl)-3-nitrobenzene (10 g, 0.033 mol), and the mixture was stirred at r.t for 30 min. Then the mixture was washed with water (200 mL*4), extracted with EtOAc, dried over $Na_2SO_4$, concentrated in vacuo. The residue was purified via chromatography (petrol ether) to give 2-bromo-6-nitrobenzyl (2E)-but-2-en-1-yl ether. $^1$H-NMR (400 MHz, $CDCl_3$) δ 7.76 (d, J=8.0 Hz, 1H), 7.75 (d, J=8.0 Hz, 1H), 7.25~7.30 (m, 1H), 5.68~5.77 (m, 1H), 5.51~5.58 (m, 1H), 4.82 (s, 2H), 1.69 (d, J=6.0 Hz, 3H).

Step C: 4-ethenyl-8-nitro-3,4-dihydro-1H-isochromene

To a solution of 2-bromo-6-nitrobenzyl (2E)-but-2-en-1-yl ether (3.3 g, 11.19 mmol) in TEA (100 mL) was added P(o-Tol)$_3$ (196 mg, 0.873 mmol) and Pd(OAC)$_2$(1.0 g, 3.21 mmol), and the mixture was stirred at reflux for 16 h. Then the mixture was concentrated in vacuo, and the mixture was partitioned between water and EtOAc. The combined organic layers were washed with HCl (1N) and brine, dried and concentrated in vacuo. The residue was purified with silica gel cloumn chromatography to give 4-ethenyl-8-nitro-3,4-dihydro-1H-isochromene. $^1$H-NMR (400 MHz, $CDCl_3$) δ 7.96 (d, J=8.0 Hz, 1H), 7.45 (d, J=8.0 Hz, 1H), 7.31 (t, J=8.0 Hz, 2H), 5.74~5.82 (m, 1H), 5.14~5.19 (m, 2H), 5.04 (d, J=4.0 Hz, 2H), 3.93~3.98 (m, 1H).

Step D: 4-ethenyl-3,4-dihydro-1H-isochromen-8-amine

A mixture of 4-ethenyl-8-nitro-3,4-dihydro-1H-isochromene (630 mg, 3.07 mmol), Fe (860 mg, 15.3 mmol) and $NH_4Cl$ (1.642 g, 30.7 mmol) in EtOH/$H_2O$ (2:1, 40 mL) was stirred at reflux under $N_2$ protection for 2 h. The mixture was filtered, and the filtrate was evaporated to give 4-ethenyl-3,4-dihydro-1H-isochromen-8-amine. $^1$H-NMR (400 MHz, DMSO) δ 6.88 (t, J=8.0 Hz, 1H), 6.47 (d, J=8.0 Hz, 1H), 6.34 (d, J=8.0 Hz, 1H), 5.74~5.83 (m, 1H), 5.03~5.17 (m, 2H), 4.46 (s, 2H), 3.78~3.82 (m, 1H), 3.61~3.65 (m, 1H), 3.36~3.38 (m, 1H).

Step E: 4-ethenyl-3,4-dihydro-1H-isochromene-8-carbonitrile

A solution of 4-ethenyl-3,4-dihydro-1H-isochromen-8-amine (300 mg, 1.71 mmol) in 4 mL of HCl was added a solution of $NaNO_2$ (121 mg, 1.75 mmol) in 12 mL of $H_2O$ at 0-5° C., and then the mixture was neutralized to pH=6 with $NaHCO_3$. The residue was added to a solution of cuprous cyanide (prepared from 511 mg KCN and 512 mg of $CuSO_4.5H_2O$) at 60° C., and the mxture was stirred at 70° C. for another 2 hours. Then the mxture was cooled to r.t., filtered through Celite®, extracted with EtOAc (20 mL*3). The combined organic layers were washed with $H_2O$, dried over $Na_2SO_4$, concentrated in vacuo to give the desired product 4-ethenyl-3,4-dihydro-1H-isochromene-8-carbonitrile. $^1$H-NMR (400 MHz, DMSO) δ 7.71 (d, J=8.0 Hz, 1H), 7.48 (d, J=8.0 Hz, 1H), 7.41 (t, J8.0 Hz, 1H), 5.80~5.89 (m, 1H), 5.17~5.21 (m, 2H), 4.84 (d, J=3.2 Hz, 2H), 3.90~3.94 (m, 1H), 3.76~3.80 (m, 1H), 3.55~3.60 (m, 1H).

Step F: 4-formyl-3,4-dihydro-1H-isochromene-8-carbonitrile

A solution of 4-ethenyl-3,4-dihydro-1H-isochromene-8-carbonitrile (62 mg, 0.334 mmol) in DCM (10 mL) was bubbled with $O_3$ for 10 mins at −78° C. until the blue color appeared. Then $Me_2S$ (1 mL) was added and the mixture was stirred at r.t. for 5 hours. Then the mixture was concentrated in vacuo to give the desired product 4-formyl-3,4-dihydro-1H-isochromene-8-carbonitrile, which can be used for next step without further purification.

Intermediate 113

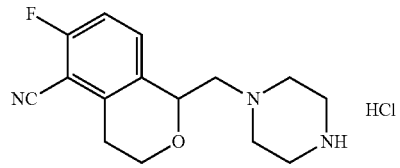 [SMILES: N#Cc1c(F)ccc2c1CCOC2CN1CCNCC1 ; Cl]

6-fluoro-1-(piperazin-1 ylmethyl)-3,4-dihydro-1H-isochromene-5-carbonitrile hydrochloride Step A: diethyl (3-fluoro-2-nitrophenyl)propanedioate A solution of 1,3-difluoro-2-nitrobenzen (5.0 g, 31.4 mmol) in 50 mL of dry DMF was added $K_2CO_3$ (4.41 g, 32 mmol) and diethyl malonate (3.6 mL, 31.4 mmol). The reaction mixture was heated to 65° C. and stirred for 24 hours. After cooling to room temperature, the mixture was neutralized with 2 N HCl and extrated with diethyl ether. The ether layer was dried over anhydrous sodium sulfate and concentrated. The crude product was purified via column chromatograph to afford diethyl (3-fluoro-2-nitrophenyl)propanedioate. $^1$H-NMR (400 MHz, CDCl3) δ 7.50~7.55 (m, 1H), 7.38~7.40 (rn, 1H), 7.23~7.28 (m, 1H), 4.82 (s, 1H), 3.77 (s, 6H).

Step B: (3-fluoro-2-nitrophenyl)acetic acid

A suspension of diethyl (3-fluoro-2-nitrophenyl)propanedioate (5.50 g, 18.3 mmol) in 40 mL of water was added 40 mL of concentrated hydrochloric acid and the mixture was refluxed for 5 hours. Cooled to room temperature, the mixture was extracted with EtOAc, dried over anhydrous sodium sulfate and concentrated to get crude (3-fluoro-2-nitrophenyl)acetic acid, which was used for next step without purification.

Step C: methyl (3-fluoro-2-nitrophenyl)acetate

A solution of (3-fluoro-2-nitrophenyl)acetic acid (5 g, 25 mmol) in 80 mL of 3 N HCl/methonal was stirred at room temperature over night. The mixture was concentrated under vacuum and the crude product was purified via column chromatograph to afford methyl (3-fluoro-2-nitrophenyl)acetate.

Step D: methyl (2-amino-3-fluorophenyl)acetate

A solution of methyl (3-fluoro-2-nitrophenyl)acetate (4.5 g, 21 mmol) in 100 mL of EtOAc was added 500 mg of Pd/C. The reaction was stirred at room temperature at 1 atm of $H_2$ for 4 hours. Filtered off the catalyst and the filtration was concentrated to get methyl (2-amino-3-fluorophenyl)acetate.

Step E: methyl (3-fluoro-2-iodophenyl)acetate

A solution of methyl (2-amino-3-fluorophenyl)acetate (1 g, 5.46 mmol) in 3 mL of conc. $H_2SO_4$ and 18 mL of water was cooled to −5~5° C. and a solution of $NaNO_2$ (0.45 g, 6.55 mmol) in 2 mL of water was added dropwise. The reaction was stirred at −5~5° C. for 1 hour, then a solution of KI (1.4 g, 8.2 mmol) in 20 mL of water was added at 0~5° C. dropwise. The reaction was warmed to room temperature and stirred overnight. The mixture was extracted with EtOAc, washed with $Na_2SO_3$ and brine, dried over anhydrous sodium sulfate and concentrated. The residue was purified via prep-TLC to afford methyl (3-fluoro-2-iodophenyl)acetate. $^1$H-NMR (400 MHz, CDCl3) δ ppm 7.22~7.28 (m, 1H), 7.05~7.07 (m, 1H), 6.92~6.96 (m, 1H), 3.84 (s, 2H), 3.70 (s, 3H).

Step F: 2-(3-fluoro-2-iodophenypl)ethanol

A solution of methyl (3-fluoro-2-iodophenyl)acetate (1.2 g, 4 mmol) in 25 mL of ethanol was cooled to 0~5° C., CaCl$_2$ (900 mg, 8 mmol) was added and the mixture was stirred at 0~5° C. for 10 min. NaBH$_4$(600 mg, 15.7 mmol) was added slowly. The reaction was warmed to room temperature and stirred at room temperature for 2 hours. Recooled to 0~5° C., quenched with aqueous citric acid solution, extracted with EtOAc. The organic layers were washed with water and brine, dried over anhydrous sodium sulfate and concentrated to get 2-(3-fluoro-2-iodophenyl)ethanol. $^1$H-NMR (400 MHz, CDCl3) δ ppm 7.15~7.20 (m, 1H), 6.99~7.00 (m, 1H), 6.84~6.88 (m, 1H), 3.81 (t, J=7.0 Hz, 2H), 3.02 (t, J=7.0 Hz, 2H).

Step G: ethyl 6-fluoro-5-iodo-3,4-dihydro-1H-isochromene-1-carboxylate

TiCl$_4$ (5.6 g, 30 mmol) was added over a period of 10 min to an ice-cooled mixture of 2-(3-fluoro-2-iodophenyl)ethanol (2.5 g, 9.4 mmol) and ethyl diethoxyacetate (2.00 g, 11.7 mmol) in 20 mL of CH$_3$NO$_2$. After stirred for 10 min, the ice bath was removed and the mixture was allowed to stir at room temperature overnight. The mixture was poured into ice/aqueous 1N HCl, extracted with DCM and backwashed by 1N HCl and brine, dried over anhydrous sodium sulfate and concentrated. The residue was purified via column chromatograph to afford ethyl 6-fluoro-5-iodo-3,4-dihydro-1H-isoclupmene-1-carboxylate. $^1$H-NMR (400 MHz, CDCl$_3$) δ ppm 7.35~7.39 (m, 1H), 6.92~6.97 (m, 1H), 5.25 (s, 1H), 4.20~4.29 (m, 3H), 4.01~4.06 (m, 1H), 2.78 (t, J=6.2 Hz, 2H), 1.29 (t, J=7.0 Hz, 3H).

Step H: 6-fluoro-5-iodo-3,4-dihydro-1H-isochromene-1-carboxylic acid

To a solution of ethyl 6-fluoro-5-iodo-3,4-dihydro-1H-isochromene-1-carboxylate (1.6 g, 4.5 mmol) in 25 mL of MeOH/THF/H$_2$O (2/2/1) was added LiOH.H$_2$O (700 mg, 18.3 mmol), and the mixture was stirred at ambient temperature for 30 min. The solvents were removed under vacuum, and the residue was added 50 mL of water and extracted with ether. The aqueous layer was then acidified with 4 N HCl to pH=3 in ice bath, and extracted with EtOAc. The combined organic phase was washed with brine, dried over anhydrous sodium sulfate and concentrated to afford 6-fluoro-5-iodo-3,4-dihydro-1H-isochromene-1-carboxylic acid.

Step I: 6-fluoro-5-iodo-N-methoxy-N-methyl-3,4-dihydro-1H-isochromene-1-carboxamide A mixture of 6-fluoro-5-iodo-3,4-dihydro-1H-isochromene-1-carboxylic acid (1.32 g, 4 mmol) and CDI (690 mg, 4.9 mmol) in 50 mL of dry DCM was stirred at r.t. for 3 hrs and then O,N-dimethyl-hydroxylamine (500 mg, 5.1 mmol) was added. The result mixture was stirred oversight. The solvents were removed under vacuum, and the residue was purified via column chromatograph to afford 6-fluoro-5-iodo-N-methoxy-N-methyl-3,4-dihydro-1H-isochromene-1-carboxamide.

Step J: 6-fluoro-5-iodo-3,4-dihydro-1H-isochromene-1-carbaldehyde

A solution of 6-fluoro-5-iodo-N-methoxy-N-methyl-3,4-dihydro-1H-isochromene-1-carboxamide (700 mg, 0.2 mmol) in 30 mL of anhydrous THF was cooled to –30° C. and then DIBAL-H (0.3 mmol) was added. The mixture was stirred at –30° C. for 1 hours. The reaction was quenched with water, and extracted with DCM. The orgainc layer was washed with brine, dried over anhydrous sodium sulfate and concentrated. The residue was used for the next step without purification.

Step K: tert-butyl 4-[(6-fluoro-5-iodo-3,4-dihydro-1H-isochromen-1-yl)methyl]piperazine-1-carboxylate A solution of 6-fluoro-5-iodo-3,4-dihydro-1H-isochuomene-1-carbaldehyde (500 mg, 1.6 mmol), amine (303 mg, 1.63 mmol) and NaBH(OAc)$_3$ (1.2 g, 6 mmol) in 50 mL of anhydrous DCM was stirred at ambient temperature overnight. The reaction mixture was added 50 mL of DCM and washed with brine. The organic layer was dried over anhydrous sodium sulfate and concentrated. The residue was purified with prep-TLC to afford tert-butyl 4-[(6-fluoro-5-iodo-3,4-dihydro-1H-isochromen-1-yl)methyl]piperazine-1-carboxylate.

Step L: tert-butyl 4-[(5-cyano-6-fluoro-3,4-dihydro-1H-isochromen-1-yl)methyl]piperazine-1-carboxylate A solution of tert-butyl 4-[(6-fluoro-5-iodo-3,4-dihydro-1H-isochromen-1-yl)methyl]piperazine-1-carboxylate (200 mg, 0.42 mmol), Pd(PPh$_3$)$_4$ (200 mg) and Zn(CN)$_2$ (300 mg, 2.6 mmol) in 20 mL of anhydrous DMF was to 110° C. at N$_2$ atmosphere for 2 hours. The reaction was cooled to room temperature, diluted with EtOAc and washed with water and brine. The organic layer was dried over anhydrous sodium sulfate and concentrated. The residue was purified with prep-TLC to afford tert-butyl 4-[(5-cyano-6-fluoro-3,4-dihydro-1H-isochromen-1-yl)methyl]piperazine-1-carboxylate.

Step M: 6-fluoro-1-(piperazin-1-ylmethyl)-3,4-dihydro-1H-isochromene-5-carbonitrile hydrochloride A solution of tert-butyl 4-[(5-cyano-6-fluoro-3,4-dihydro-1H-isochromen-1-yl)methyl]piperazine-1-carboxylate (110 mg, 0.29 mmol) in 10 mL of DCM was added 3 mL of 4N HCl/dioxane, then sirred at room temperature for 2 hours. The solvents was removed off under vacuum to afford 6-fluoro-1-(piperazin-1-ylmethyl)-3,4-dihydro-1H-isochromene-5-carbonitrile hydrochloride. $^1$H-NMR (400 MHz, MeOD) δ ppm 7.63~7.66 (m, 1H), 7.25~7.29 (m, 1H), 5.33~5.30 (m, 1H), 4.25~4.30 (in, 1H), 3.87~3.97 (m, 2H), 3.72~3.83 (m, 3H), 3.58~3.68 (m, 6H), 3.07~3.17 (m, 2H).

Intermediate 114

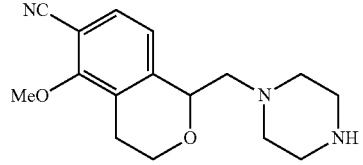 [SMILES: COc1c(C#N)ccc2c1CCOC2CN1CCNCC1]

5-methoxy-1-(piperazin-1-ylmethyl)-3,4-dihydro-1H-isochromene-6-carbonitrile

Step A: methyl (2-hydroxyphenyl)acetate

To a solution of (2-hydroxyphenyl)acetic acid (11 g, 72.3 mmol) in 100 mL of MeOH was added SOCl$_2$ (17.2 g, 144.7 mmol) at 0° C. The mixture was stirred at 50° C. overnight. The reaction was concentrated. The residue was purified column chromatography to give methyl (2-hydroxyphenyl)acetate (14 g).

Step B: methyl (3-bromo-2-hydroxyphenyl)acetate

To a solution of methyl (2-hydroxyphenyl)acetate (14 g, 84.3 mmol) in 100 mL of DCM was added diisopropyl-amine (1.7 g, 16.8 mmol) and NBS (15 g, 84.2 mmol) at 0° C. The mixture was stirred at 0° C. for 1 h. The reaction was poured into 1N HCl, extracted with DCM, and concentrated to give crude methyl (3-bromo-2-hydroxyphenyl)acetate. Step C: methyl (3-bromo-2-methoxyphenyl)acetate To a solution of methyl (3-bromo-2-hydroxyphenyl)acetate (18.7 g, 76.33 mmol) in 200 mL of DMF was added K$_2$CO$_3$ (52.7 g, 381.6 mmol), MeI (14 mL, 228.9 mmol). The mixture was stirred at 50° C. for 3 hours. The reaction solution was diluted with EtOAc and water. The organic layer was dried over anhydrous sodium sulfate and concentrated. The residue was purified column chromatography to give methyl (3-bromo-2-methoxyphenyl)acetate.

Step D: 2-(3-bromo-2-methoxyphenyl)ethanol To a solution of methyl (3-bromo-2-methoxyphenyl)acetate (8.2 g, 31.66 mmol) in 200 mL of dry THF under $N_2$ at room temperature was added $LiBH_4$ (32 mL, 63.32 mmol, 2M THF). After 1.5 hours, the reaction was warmed to reflux for 3 hours, and then cooled to room temperature. The solution was poured into EtOAc/1N HCl solution, and the layers were separated. The organic layer was washed with water, saturated $Na_2CO_3$ and brine, dried over anhydrous $Na_2SO_4$ and concentrated to give 2-(3-bromo-2-methoxyphenyl)ethanol.

Step E: methyl 6-bromo-5-methoxy-3,4-dihydro-1H-isochromene-1-carboxylate $TiCl_4$ (9.84 g, 104 mmol) was added over a period of 20 min to an ice-cooled mixture of 2-(3-bromo-2-methoxyphenyl)ethanol (6 g, 26.0 mmol) and ethyl diethoxyacetate (5.5 g, 31.1 mmol) in 60 mL of $CH_3NO_2$. After stirred for 10 min, the ice bath was removed and the mixture was allowed to stir at room temperature over night. The mixture was poured onto ice/aqueous 1N HCl. Extracted by DCM and backwashed with 1N HCl and brine, dried over anhydrous sodium sulfate and concentrated. The residue was purified via column chromatograph to give methyl 6-bromo-5-methoxy-3,4-dihydro-1H-isochromene-1-carboxylate.

Step F: 6-bromo-5-methoxy-3,4-dihydro-1H-isochromene-1-carboxylic acid To a solution of methyl 6-bromo-5-methoxy-3,4-dihydro-1H-isochromene-1-carboxylate (650 mg, 2.06 mmol) in 20 mL of MeOH/THF/$H_2O$ (2/2/1) was added $LiOH.H_2O$ (347 mg, 8.25 mmol), and the mixture was stirred at ambient temperature overnight. The solvents were removed under vacuum, and the residue was added 50 mL of water and extracted with ether. The aqueous layer was then acidified with 4 N HCl to pH=3 in ice bath, and extracted with EtOAc. The combined organic phase was washed with brine, dried over anhydrous sodium sulfate and concentrated to give 6-bromo-5-methoxy-3,4-dihydro-1H-isochromene-1-carboxylic acid.

Step G: 6-bromo-N,5-dimethoxy-3,4-dihydro-1H-isochromene-1-carboxamide

A mixture of 6-bromo-5-methoxy-3,4-dihydro-1H-isochromene-1-carboxylic acid (600 mg, 2.08 mmol) and CDI (475 mg, 2.93 mmol) in 20 mL of dry DCM was stirred at r.t. for 0.5 hours and then O,N-dimethyl-hydroxylamine (285 mg, 2.93 mmol) was added. The result mixture was stirred oversight. The solvents were removed under vacuum, and the residue was purified by preparative TLC to give 6-bromo-N,5-dimethoxy-3,4-dihydro-1H-isochromene-1-carboxamide.

Step H: 6-bromo-5-methoxy-3,4-dihydro-1H-isochromene-1-carbaldehyde

To a solution of 6-bromo-N,5-dimethoxy-3,4-dihydro-1H-isoehromene-1-carboxamide (300 mg, 0.9 mmol) in 20 mL of anhydrous THF was cooled to −30° C. and then DIBAL-H (1.3 mL, 1.3 mmol, 1M) was added. The mixture was stirred at −30° C. for 2 hours. The reaction was quenched with water and extracte with DCM. The orgainc layer was washed with brine, dried over anhydrous sodium sulfate and concentrated to afford 6-bromo-5-methoxy-3,4-dihydro-1H-isochromene-1-earbaldehyde. The residue was used for next step without purification.

Step I: tert-butyl 4[(6-bromo-5-methoxy-3,4-dihydro-1H-isochromen-1-yl)methyl]piperazine-1-carboxylate To a solution of 6-bromo-5-methoxy-3,4-dihydro-1H-isochromene-1-carbaldehyde (230 mg, 0.85 mmol) in 10 mL of DCM was added Boc-piperazine (189 mg, 1.02 mmol) and $NaBH(OAc)_3$ (720 mg, 3.4 mmol), and the mixture was stirred at room temperature overnight. The reaction was diluted with DCM, and washed with brine. The organic layer was dried over anhydrous $Na_2SO_4$ and concentrated. The residue was purified by prep-TLC to give tert-butyl 4-[(6-bromo-5-methoxy-3,4-dihydro-1H-isochromen-1-yl)methyl]piperazine-1-carboxylate.

Step J: tert-butyl 4-[(6-cyano-5-methoxy-3,4-dihydro-1H-isochromen-1-yl)methyl]piperazine-1-carboxylate To a solution of tert-butyl 4-[(6-bromo-5-methoxy-3,4-dihydro-1H-isochromen-1-yl)methyl]piperazine-1-carboxylate (50 mg, 0.11 mmol), $Pd(PPh_3)_4$ (20 mg) and $Zn(CN)_2$ (26 mg, 0.23 mmol) in 5 mL of anhydrous DMF was to 110° C. at $N_2$ atmosphere overnight. The reaction was cooled to room temperature, extracted by EtOAc, washed by water then by brine. The organic layer was dried over anhydrous sodium sulfate and concentrated. The residue was purified with prep-TLC to afford tert-butyl 4-[(6-cyano-5-methoxy-3,4-dihydro-1H-isochromen-1-yl)methyl]piperazine-1-carboxylate.

Step K: 5-methoxy-1-(piperazin-1-ylmethyl)-3,4-dihydro-1H-isochromene-6-carbonitrile To a solution of tert-butyl 4-[(6-cyano-5-methoxy-3,4-dihydro-1H-isochromen-1-yl)methyl]piperazine-1-carboxylate (30 mg, 0.08 mmol) in 5 mL of DCM was added 5 mL of TFA was stirred at room temperature for 1 hours, and the reaction was concentrated to afford 5-methoxy-1-(piperazin-1-ylmethyl)-3,4-dihydro-1H-isochromene-6-carbonitrile.

Intermediate 115

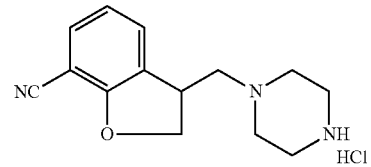 [SMILES: N#Cc1cccc2c1OCC2CN1CCNCC1 ; Cl]

3-(piperazin-1-ylmethyl)-2,3-dihydro-1-benzofuran-7-carbonitrile hydrochloride

Step A: 3-bromo-2-hydroxybenzaldehyde

A solution of 2-bromophenol (48.5 g, 0.28 mol) in 500 mL of THF was added TEA (200 mL) and then $MgCl_2$ (100 g, 1.05 mol) was added portionwise over 90 minutes. The reaction mixture was allowed to stir overnight under a nitrogen atmosphere. The reaction mixture was neutralized with phosphoric, and then exacted with EtOAc (1000 mL). The organic layers were washed with brine (200 mL), dried over $Na_2SO_4$. The solvent was concentrated in vacuo. The residue was purified with silica gel chromatography (petrol ether/EtOAc=5:1) to give product 3-bromo-2-hydroxybenzaldehyde.

Step B: ethyl 7-bromo-1-benzofuran-3-carboxylate

A solution of 3-bromo-2-hydroxybenzaldehyde (20 g, 0.1 mol) in 150 mL of $CH_2Cl_2$ was added $HBF_4.Et_2O$ (1.5 mL, 0.01 mmol). A solution of ethyl diazoacetate (27.36 g, 0.24 mol) in $CH_2Cl_2$ (50 mL) was introduced into the reaction mixture, during about 3-6 min and the evolution of $N_2$ gas observed, and the reaction was not allowed to go above 38° C. Once gas evolution ceased, the reaction mixture was concentrated by rotary evaporator and $H_2SO_4$ (20 mL) was added to the mixture while stirring. After 30 min, the mixture was diluted with $CH_2Cl_2$ (200 mL) and the $H_2SO_4$ was quenched with solid $NaHCO_3$. The mixture was then filtered through silica gel (100 g), and concentrated by rotary evaporator to give an oil, then exacted with EtOAc (500 mL), and washed with brine (100 mL), dried over Na$_2$SO$_4$. The solvent was concentrated in vacuo. The residue was separated and purified with silica gel chromatography to give product ethyl 7-bromo-1-benzofuran-3-carboxylate.

$^1$H-NMR (400 MHz, CDCL3) δ ppm 8.28 (s, 1H), 8.00 (dd, J=8.0, 1.6 Hz, 1H), 7.51 (d, J=7.6 Hz, 1H), 7.22 (t, J=8.0 Hz, 1H), 4.40 (q, J=7.2 Hz, 1H), 1.41 (t, J=7.2 Hz, 1H).

Step C: 7-bromo-1-benzofuran-3-carboxylic acid

To a solution of ethyl 7-bromo-1-benzofuran-3-carboxylate (1.0 g, 3.7 mmol) in 20 mL of MeOH/THF/H$_2$O (2/211) was added LiOH H$_2$O (777 mg, 18.5 mmol), and the mixture was stirred at ambient temperature overnight. The solvents were removed under vacuum, and the residue was added 10 mL of water and extracted with ether (100 mL). The aqueous layer was then acidified with 4 N HCl to pH=3 in ice bath, and extracted with EtOAc. The combined organic phase was washed with brine, dried over anhydrous sodium sulfate and concentrated to give 7-bromo-1-benzofuran-3-carboxylic acid.

Step D: 7-bromo-N-methoxy-N-methyl-1-benzofuran-3-carboxamide

A mixture of 7-bromo-1-benzofuran-3-carboxylic acid (8.9 g, 37 mmol), CDI (9.1 g, 56 mmol) and DCM (200 mL) was stirred for 4 hours at room temperature, and then MeN-HOMe (5.5 g, 56 mmol) was added. The reaction mixture was stirred for 16 hours at room temperature. The reaction mixture was extracted with EtOAc (300 mL). The organic layer was washed with brine (50 mL), dried over Na$_2$SO$_4$. The solvent was concentrated in vacua. The residue was purified with silica gel chromatography to give 7-bromo-N-methoxy-N-methyl-1-benzofuran-3-carboxamide. $^1$H-NMR (400 MHz, CDCL3) δ ppm 8.33 (s, 1H), 8.21 (d, J=8.0, 1 H), 7.51 (d, J=7.6 Hz, 1H), 7.22 (t, J=8.0 Hz, 1H), 3.72 (s, 3H), 3.39 (s, 1H).

Step E: 7-bromo-1-benzofuran-3-carbaldehyde

To a solution of Compound 7-bromo-N-methoxy-N-methyl-1-benzofuran-3-carboxamide (8.98 g, 31.63 mmol) in 150 mL dry toluene at −78° C. was added DIBAL-H (31.63 mL, 31.63 mmol) dropwise. The reaction mixture was stirred for 1 hour at −78° C. under a nitrogen atmosphere, and quenched slowly with saturated aqueous NH4Cl. After warming to room temperature, the mixture was exacted with EtOAc (300 mL), and washed with brine (50 mL), dried over Na$_2$SO$_4$. The solvent was concentrated in vacua. The residue was separated and purified with silica gel chromatography to give product 7-bromo-1-benzofuran-3-carbaldehyde.

Step F: tert-butyl 4-[(7-bromo-1-benzofuran-3-yl)methyl]piperazine-1-carboxylate To a flask charged with Boc-piperazine (130 mg, 0.70 mmol) and 7-bromo-1-benzofuran-3-carbaldehyde (141 mg, 0.63 mmol) was added NaBH(OAc)$_3$ (761 mg, 2.80 mmol). The mixture was stirred at room temperature for 12 hours. Then the reaction was diluted with EtOAc (50 mL), washed with brine (15 mL), dried over Na$_2$SO$_4$ and concentrated. The residue was purified with prep-TLC to obtain the pure product tert-butyl 4-[(7-bromo-1-benzofuran-3-yl)methyl]piperazine-1-carboxylate.

Step G: tert-butyl 4-{[7-methoxycarbonyl)-1-benzofuran-3 yl]methyl}piperazine-1-carboxlate A mixture of tert-butyl 4-[(7-bromo-1-benzofuran-3-yl)methyl]piperazine-1-carboxylate (100 mg, 0.253 mmol), Pd(PPh$_3$)$_2$Cl$_2$ (10 mg, 0.0142 mmol) and TEA (2 mL) in 20 mL of MeOH was heated at 100° C. under CO (3 MPa) overnight. After cooling, the mixture was filtered. The filtrate was then partitioned between EtOAc and water. The combined organics were washed with water (150 mL) and brine (150 mL), dried over Na$_2$SO$_4$ and concentrated to give tert-butyl 4-{[7-(methoxycarbonyl)-1-benzofuran-3-yl]methyl}piperazine-1-carboxylate. $^1$H-NMR (400 MHz, CDCL3) δ ppm 7.88-7.91 (m, 2H), 7.59 (s, 1H), 7.24 (t, J=7.6 Hz, 1H), 3.94 (s, 3H), 3.59 (s, 2H), 3.30-3.50 (m, 4H), 2.30-2.40 (m, 4H), 1.39 (s, 9H); MS m/z 375 (M+1)$^+$.

Step H: tert-butyl 4-{[7-(methoxycarbonyl)-2,3-dihydro-1-benzofuran-3-yl]methyl}piperazine-1-carboxylate A solution of tert-butyl 4-{[7-(methoxycarbonyl)-1-benzofuran-3-yl]methyl}piperazine-1-carboxylate (600 mg, 1.6 mmol) in 100 mL of HOAc was added 300 mg of Pd/C and the mixture was stirred at 65° C. under H$_2$ atmosphere (50 psi) overnight. The reaction mixture was added Na$_2$CO$_3$ (aq.) to pH=8 in ice bath. The mixture was filtered and extracted with EtOAc. The combined organic phase was washed with brine, dried over anhydrous sodium sulfate and concentrated. The residue was purified with silica gel chromatography to give tert-butyl 4-{[7-(methoxycarbonyl)-2,3-dihydro-1-benzofuran-3-yl]methyl}piperazine-1-carboxylate. $^1$H-NMR (400 MHz, CDCL3) δ ppm 7.75 (d, J=8.0, 1 H), 7.38 (d, J=7.6, 1 H), 6.88 (t, J=8.0 Hz, 1H), 4.74 (t, J=9.0 Hz, 1H), 4.57 (dd, J=9.2, 6.2 Hz, 1H), 3.90 (s, 3H), 3.58-3.67 (m, 1H), 3.38-3.50 (m, 4H), 2.36-2.61 (m, 6H), 1.46 (s, 9H); MS m/z 377 (M+1)$^+$.

Step I: 3-{[4-(tert-butoxycarbonyl)piperazin-1-yl]methyl}-2,3-dihydro-1-benzofuran-7-carboxylic acid To a solution of tert-butyl 4-{[7-(methoxycarbonyl)-2,3-dihydro-1-benzofuran-3-yl]methyl}piperazine-1-carboxylate (250 mg, 0.66 mmol) in 20 mL of MeOH/THF/H$_2$O (2/2/1) was added LiOH.H$_2$O (139 mg, 3.32 mmol), and the mixture was stirred at ambient temperature overnight. The solvents were removed under vacuum, and the residue was added 30 mL of water and extracted with ether. The aqueous layer was then acidified with 4 N HCl to pH=7 in ice bath, and extracted with EtOAc. The combined organic phase was washed with brine, dried over anhydrous sodium sulfate and concentrated. The residue was re-crystallized from DCM to give 3-{[4-(tert-butoxycarbonyl)piperazin-1-yl]methyl}-2,3-dihydro-1-benzofuran-7-carboxylic acid.

Step J: tert-butyl 4-[(7-carbamoyl-2,3-dihydro-1-benzofuran-3-yl)methyl]piperazine-1-carboxylate A solution of 3-{[4-(tert-butoxycarbonyl)piperazin-1-yl]methyl}-2,3-dihydro-1-benzofuran-7-carboxylic acid (103 mg, 0.285 mmol) in 5 mL of DCM and two drops of DMF was cooled to 0° C., and then (COCl)$_2$ (64 mg, 0.503 mmol) was added slowly. The reaction mixture was stirred for 3 hours at room temperature. After removing the solvent under vacuum, the residue was added DCM (5 mL), and cooled to −78° C. The mixture was bubbled with NH$_3$ gas for 10 min. The reaction mixture was allowed warm to room temperature, stirred for 5 hours. The solvents were removed under vacuum to give the crude tert-butyl 4-[(7-carbamoyl-2,3-dihydro-1-benzofuran-3-yl)methyl]piperazine-1-carboxylate, which was used for next step without purification.

Step K: tert-butyl 4-[(7-cyano-2,3-dihydro-1-benzofuran-3-yl)methyl]piperazine-1-carboxylate A solution of tert-butyl 4-[(7-carbamoyl-2,3-dihydro-1-benzofuran-3-yl)methyl]piperazine-1-carboxylate in DCM (80 mg, 0.22 mmol) was added Et$_3$N (60 mg, 0.59 mmol). The solution was cooled to 0° C. and TFAA (60 mg, 0.29 mmol) was added dropwise under nitrogen. After 4 hours stirring at room temperature, the solvents were removed under vacuum to give the crude product tert-butyl 4-[(7-cyano-2,3-dihydro-1-benzofuran-3-yl)methyl]piperazine-1-carboxylate (66 g, yield 87%) which was used for next step without purification.

Step L: 3-(piperazin-1-ylmethyl)-2,3-dihydro-1-benzofuran-7-carbonitrile hydrochloride Compound tert-butyl 4-[(7-cyano-2,3-dihydro-1-benzofuran-3-yl)methyl]piperazine-1-carboxylate (76 mg, 0.22 mmol) was added HCl/dioxane (4 N) and the resulting mixture was stirred at room temperature for 3 hours, and then the solvents were removed under vacuum to give the crude 3-(piperazin-1-ylmethyl)-2,3-dihydro-1-benzofuran-7-carbonitrile hydrochloride.

Intermediate 116

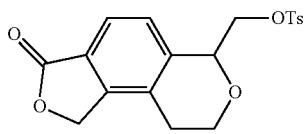 [SMILES: Cc1ccc(S(=O)(=O)OCC2OCCc3c2ccc2c3COC2=O)cc1]

(3-oxo-3,6,8,9-tetrahydro-1H-furo[3,4-f]isochromen-6-yl)methyl-4-methylbenzenesulfonate Step A: 5-bromo-4-iodo-2-benzofuran-1(3H)-one To a solution of 5-bromo-2-benzofuran-1(3H)-one (5.00 g, 23.5 mmol) at 0° C. in TfOH (100 mL) was added NIS (5.55 g, 24.6 mmol). The mixture was stirred at room temperature over night; LC analysis of the reaction mixture indicated completion of the reaction. The reaction mixture was then poured slowly into ice-water (1 L) with stirring. To the solution was then added EtOAc (500 mL) and subsequently stirred for 10 min. The mixture was filtered and the organic layer separated. The aqueous layer was extracted with EtOAc (2×200 mL). The combined organic layers were washed with water (500 mL), brine (500 mL), dried over $Na_2SO_4$, filtered, concentrated to dryness; it was absorbed into silica gel and separated with the solvent systems of (hexanes/EtOAc=1/1) to yield 5-bromo-4-iodo-2-benzofuran-1(3H]-one. $^1$H-NMR (400 MHz, $CDCl_3$) δ ppm 7.80 (d, J=7.8 Hz, 1H), 7.74 (d, J=8.5 Hz, 1H), 5.07 (s, 2H).

Step B: 5-bromo-4-prop-2-en-1-yl-2-benzofuran-1(3H)-one

A mixture of 5-bromo-4-iodo-2-benzofuran-1(3H]-one (2.42 g, 7.13 mmol), allyltributyltin (2.36 g, 7.13 mmol), LiCl (1.50 g, 35.7 mmol) and Pd $(PPh_3)_4$ (200 g, 0.173 mmol) in toluene (50 mL) was heated at 90-100° C. under $N_2$ overnight; LC indicated that reaction had gone to completion, to the solution was poured EtOAc (100 mL) and washed with brine. The organic layer was dried over $Na_2SO_4$, filtered and concentrated to dryness, absorbed into silica gel and was then separated over silica gel column to give 5-bromo-4-prop-2-en-1-yl-2-benzofuran-1(3H)-one. $^1$H-NMR (400 MHz, $CDCl_3$) δ ppm 7.795 (d, J=8 Hz, 1H), 7.680 (d, J=8 Hz, 8.5 Hz, 1H), 5.938-5.925 (m, 1H), 5.302 (s, 2H), 5.192-5.172 (m, 1H), 5.075-5.041 (m, 1H), 3.611-3.599 (m, 2H)

Step C: 5-bromo-4-(2-hydroxyethyl)-2-benzofuran-1(3H)-one

To a solution of 5-bromo-4-prop-2-en-1-yl-2-benzofuran-1(3H)-one (1.27 g, 5.02 mmol) in MeOH (50 mL) and DCM (50 mL) was bubbled $O_3$ at −78° C. until the solution turned blue; excess ozone was removed on high vacuum. After the solution's color changed into colorless, $NaBH_4$ (0.8 g, 20 mmol) was added to the reaction mixture and subsequently stirred at room temperature for 30 min; LC and TLC indicated that reaction had gone to completion; solvent was removed on high vacuum, the residue was then re-dissolved in EtOAc and washed with water, dried over $Na_2SO_4$, filtered and concentrated to dryness. The organic residue was absorbed into silica gel and was separated on silica gel column to give 5-bromo-4-(2-hydroxyethyl)-2-benzofuran-1(3H)-one. $^1$H-NMR (400 MHz, $CDCl_3$) δ ppm 7.7 (d, J=7.8 Hz, 1H), 7.5 (d, J=7.8 Hz, 1H), 5.37 (s, 2H), 3.94 (t, J=6.3 Hz, 2H), 2.98 (t, J=6.3 Hz, 2H)

Step D: 5-ethenyl-4-(2-hydroxyethyl)-2-benzofuran-1(3H)-one

A mixture of 5-bromo-4-(2-hydroxyethyl)-2-benzofuran-1(3H)-one (0.460 g, 1.78 mmol), tributyl(vinyl)tin (0.676 g, 2.13 mmol), LiCl (0.224 g, 5.33 mmol) and Pd $(PPh_3)_4$ (0.10 g, 0.087 mmol) in toluene (50 mL) was heated at 100-110° C. under $N_2$ overnight; TLC indicated that reaction had gone to completion and to the solution was poured EtOAc (100 mL) and washed with brine, water, dried over $Na_2SO_4$, filtered and concentrated to dryness. The residue was then absorbed into silica gel and separated over silica column to give 5-ethenyl-4-(2-hydroxyethyl)-2-benzofuran-1(3H)-one. $^1$H-NMR (400 MHz, $CDCl_3$) δ ppm 7.74 (d, J=7.8 Hz, 1H), 7.67 (d, J=7.8 Hz, 1H), 7.00-7.07 (m, 1H), 5.79-5.84 (m, 1H), 5.50-5.53 (m, 1H), 5.35 (s, 2H), 3.86 (t, J=6.3 Hz, 2H) 2.93 (t, J=6.3 Hz, 2H).

Step E: 4-(2-hydroxyethyl)-5-oxiran-2-yl-2-benzofuran-1(3H)-one

5-Ethenyl-4-(2-hydroxyethyl)-2-benzofuran-1(3H)-one (1.2 g, 5.9 mmol) was added to a flask containing a stir bar. To the flask was then added dichloromethane (20 mL). The flask was placed in a cool bath of 0° C.; to the flask was poured Mcpba (1.5 g, 8.8 mmol) and the resulting mixture was stirred at room temperature for overnight; LC as well as TLC (hexanes/EtOAc=1/1) indicated that reaction had gone to completion. The solution was treated with dichloromethane and washed with $NaHCO_3$, $Na_2S_2O_3$, and water, the organic layer was then dried over $Na_2SO_4$, filtered and concentrated to drynes it was then treated with AcOH (20 mL) and stirred overnight; LC indicated formation of cyclized product. The solvent was removed and the resulting residue was absorbed into silica gel and 6-(hydroxymethyl)-8,9-dihydro-1H-furo[3,4-f]isochromen-3(6I)-one was isolated with the solvent systems of hexanes/EtOAc (1/1). $^1$H-NMR (400 MHz, $CDCl_3$) δ ppm 7.807 (d, J=8 Hz, 1H), 7.337 J=8 Hz, 1H), 5.279 (s, 2H), 4.985 (s, 1H), 4.302-4.302 (m, 1H), 4.183-4.084 (m, 2H), 3.954-3.912 (n 2H), 3.006-2.944 (m, 1H), 2.717-2.686 (m, 1H), 2.179-2.172 (m, 2H)

Step F: (3-oxo-3,6,8,9-tetrahydro-1H-furo[3,4-f]isochromen-6-yl)methyl-4-methylbenzenesulfonate 6-(Hydroxymethyl)-8,9-dihydro-1H-furo[3,4-f]isochromen-3(6H)-one, in DCM (10 mL) was treated with p-Toluenesulfonyl chloride (0.40 g, 2.3 mmol); to the mixture was added pyridine (2 mL) and the resulting mixture stirred at room temperature for 12 h. TLC (hexanes/EtOAc=1/0.5) and LC indicated the consumption of starting material and formation of the desired product. Reaction mixture was treated with dichloromethane and washed with NaCl, water and dried over $Na_2SO_4$, filtered and concentrated to dryness, absorbed into silica gel and was then subjected for purification over silica gel; (3-oxo-3,6,8,9-tetrahydro-1H-furo[3,4-f]isochromen-6-yl)methyl-4-methylbenzenesulfonate was isolated with the solvent system of hexanes/EtOAc (1/0.5). $^1$H-NMR (400 MHz, $CDCl_3$) δ ppm 7.781 (d, J=8 Hz, 1H), 7.727 (d, J=8 Hz, 1H), 7.367 (d, J=8 Hz, 1H), 7.257 (d, J=8.5 Hz, 1H), 7.206 (d, J=8 Hz, 1H), 5.253 (s, 2H), 5.110 (s, 1H), 4.481-4.452 (m, 2H), 4.419-4.385 (m, 2H), 4.196-4.153 (m, 2H), 2.495 (s, 3H).

Intermediate 117

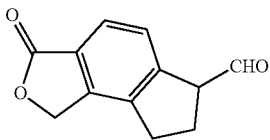 [SMILES: O=CC1CCc2c1ccc1c2COC1=O]

3-oxo-3,6,7,8-tetrah dro-1H-indeno[4,5-c]furan-6-carbaldehyde

Step A: methyl 3-bromo-2-but-3-en-1-ylbenzoate

To a flask charged with freshly prepared LDA (42 mmol) from n-BuLi and i-Pr₂NH was dropped a solution of 3-bromo-2-methylbenzoic acid (3.0 g, 14 mmol) at −78° C. The reaction turned red right away. After stirring the mixture for 15 minutes, allyl bromide (8.4 g, 70 mmol) was dropped into the reaction. The reaction was allowed to warm up to 0° C. The reaction was quenched with 1N HCl, and extracted with EtOAc (100 mL×2). The extracts were combined, washed with brine, dried over sodium sulfate, and concentrated to give a light yellow oil. The oil was dissolved in toluene (30 mL) and methanol (10 mL) and treated with excess TMSdiazo methane (10 mL, 2.0 M in ether). Excess TMSdiazomethane was quenched with acetic acid when TLC indicated the reaction was done. The the mixture was concentrated and crude product was purified by silica gel chromatography to afford methyl 3-bromo-2-but-3-en-1-ylbenzoate.

$^1$H-NMR (500 MHz, CDCl₃) δ ppm 7.78 (d, J=8.0 Hz, 1H), 7.76 (d, J=8.0 Hz, 1H), 7.15 (t, J=8.0 Hz, 1H), 5.98 (m, 1H), 5.12 (d, 17 Hz, 1H), 5.04 (d, J=10 Hz, 1H), 3.94 (s, 3H), 3.18 (m, 2H), 2.41 (m, 2H).

Step B: methyl 1-methylidene-2,3-dihydro-1H-indene-4-carboxylate

To a microwave tube charged with methyl 3-bromo-2-but-3-en-1-ylbenzoate (800 mg, 3.0 mmol) and a stir bar was added palladium(II) acetate (67 mg, 0.30 mmol), triphenylphoshphine (310 mg, 1.19 mmol), potassium carbonate (2.46 g, 18.0 mmol), and acetonitrile (20 mL). The reaction tube was sealed, and the solution was purged three times with nitrogen, and heated in a microwave apparatus to 120° C. for 10 minutes. TLC showed a big blue spot right below the SM. The product was isolated by silica gel chromatography. LC-MS M+1 (calc. 189, found 189).

Step C: 2,3-dihydro-1H-indene-1,4-diyldimethanol

To a solution of methyl 1-methylidene-2,3-dihydro-1H-indene-4-carboxylate (1.4 g, 7.4 mmol) in THF (15 mL) was added borane THF complex (1.0 M, 9.7 mL, 9.7 mmol) at 0° C. The mixture was allowed to stir for 3 hours. To the reaction was added 2N sodium hydroxide (7.5 mL, 15 mmol) and 30% hydrogen peroxide (1.7 mL, 15 mmol). The mixture was then allowed to warm to RT. LC analysis showed complete reaction within 30 minutes. The reaction was neutralized with NH4Cl, diluted with water, extracted with EtOAc, dried over sodium sulfate, and purified by silica gel chromatography. The intermediate hydroxyester (1.1 g) was collected after removal of solvents. To a DCM (10 mL) solution of the hydroxyester (750 mg, 3.6 mmol) was added DIBAL-H (18 mL, 18 mmol) at −78° C. The reaction was allowed to stir for 16 h, warming to RT slowly. The reaction was diluted with DCM (30 mL), and worked up with Roschelle's salt. The organic layer was separated using a separatory funnel, dried over sodium sulfate, and the crude product was purified by silica gel chromatography to afford 2,3-dihydro-1H-indene-1,4-diyldimethanol. $^1$H-NMR (500 MHz, CDCl₃) δ ppm 7.25-7.30 (m, 3H), 4.72 (s, 3H), 3.85 (m, 2H), 3.42 (m, 1H), 3.03 (m, 1H), 2.95 (m, 1H), 2.34 (m, 1H), 2.04 (m, 1H).

Step D: 6-(hydroxymethyl)-1,6,7,8-tetrahydro-3H-indeno[4,5-c]furan-3-one

To a flask charged with 2,3-dihydro-1H-indene-1,4-diyldimethanol (210 mg, 1.2 mmol) and a stir bar was added thallium trifluoroacetate (770 mg, 1.4 mmol) and TFA (2 mL) at 0° C. The mixture was allowed to stir for 16 hours. LC showed no SM left at that point. The volatiles were removed under reduced pressure, and the residue was dissolved in DCM and concentrated twice to affect azeotropic removal of all TFA. After pumping the residue under high vacuum for 20 minutes, palladium chloride (21 mg, 0.18 mmol), lithium chloride (75 mg, 1.8 mmol), magnesium oxide (190 mg, 4.7 mmol), and MeOH (10 mL) were added to the flask. The mixture was treated under an atmosphere of CO for 2 hours. To this mixture was added DCM and EtOAc to precipitate all the inorganic solids. The crude solution was filtered through a Celite® pad, and the filtrate was collected, adsorbed onto silica gel, and purified by MPLC to afford 6-(hydroxymethyl)-1,6,7,8-tetrahydro-3H-indeno[4,5-c]furan-3-one. $^1$H-NMR (500 MHz, CDCl₃) δ ppm 7.79 (d, J=8.0 Hz, 1H), 7.52 (d, J=8.0 Hz, 1H), 5.27 (s, 2H), 3.91 (d, J=6.0 Hz, 2H), 3.85 (dd, J=6.0, 3.5 Hz, 1H), 3.50 (m, 1H), 3.00 (m, 1H), 2.93 (m, 1H), 2.45 (m, 1H), 2.14 (m, 1H).

Step E: 3-oxo-3,6,7,8-tetrahydro-1H-indeno[4,5-c]furan-6-carbaldehyde

To a solution of 6-(hydroxymethyl)-1,6,7,8-tetrahydro-3H-indeno[4,5-c]furan-3-one (55 mg, 0.27 mmol) in DCM (5 mL) was added Dess-Martin Periodate (171 mg, 0.400 mmol). The reaction was allowed to stir at RT for 3 hours. LC analysis showed formation of the desired product, and there was little SM left. The solution was diluted with DCM (30 mL), and to that was added Na₂S₂O₃ (10% aq solution, 15 mL) to consume the excess Dess-Martin reagent. The mixture was stirred until the two layers separated. The bottom DCM layer was collected, washed with aq Na₂CO₃, dried over sodium sulfate, and concentrated to give 3-oxo-3,6,7,8-tetrahydro-1H-indeno[4,5-c]furan-6-carbaldehyde. LC-MS (IE, m/z): 203 [M+1]⁺.

Intermediate 118

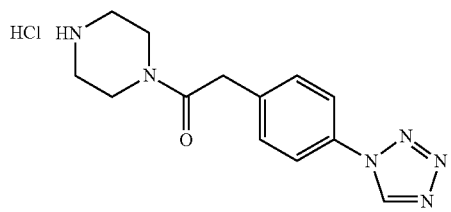 [SMILES: Cl ; O=C(Cc1ccc(-n2cnnn2)cc1)N1CCNCC1]

1-(piperazin-1-yl)-2-[4-(1H-tetrazol-1-yl)phenyl]ethanone hydrochloride

Step A: tert-butyl 4-{[4-(1H-tetrazol-1-yl)phenyl]acetyl}piperazine-1-carboxylate[4-(1H-Tetrazol-1-yl)phenyl]acetic acid (commercially available, 4.91 g, 24.1 mmol) was combined with tert-butyl piperazine-1-carboxylate (5.37 g, 28.9 mmol) and EDC (6.91 g, 36.1 mmol) in DCM (75 mL) and stirred overnight at room temperature. The reaction mixture was diluted with DCM and washed with water, then brine. The organic layer was dried over MgSO$_4$, filtered, and concentrated. The crude product was triturated with ether to afford pure title compound. LC/MS: [(M+1)]$^+$=373.3;

Step B: 1-(piperazin-1-yl)-2-[4-(1H-tetrazol-1-yl)phenyl]ethanone hydrochloride tert-Butyl 4-{[4-(1H-tetrazol-1-yl)phenyl]acetyl}piperazine-1-carboxylate (4.14 g, 11.1 mmol) was suspended in 4 M HCl in dioxane solution (Aldrich, 50 mL). Methanol (8 mL) was added to solubilize the starting material. The mixture was stirred at room temperature for 1 h, then was concentrated to afford the title compound. LC/MS: [(M+1)]$^+$=273.4.

Intermediate 119 (Method 1)

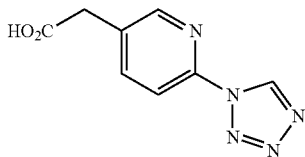 [SMILES: O=C(O)Cc1ccc(-n2cnnn2)nc1]

[6-(1H-tetrazol-1-yl)pyridin-3-yl]acetic acid

Step A: 5-chloro-2-nitro ridine

To concentrated H$_2$SO$_4$ (50 mL) was added 30% H$_2$O$_2$ (25 mL) at 0° C. and a solution of 5-chloropyridin-2-amine (5.0 g, 39 mmol) in concentrated H$_2$SO$_4$. (20 mL) was added at 0° C. The mixture was stirred for 20 hours at room temperature. The mixture was poured into ice water under vigorously stirring and the resulting solid was filtered. The solid was recrystallized from ethanol to give 5-chloro-2-nitropyridine. MS m/z 159 (M+1)$^+$; $^1$H-NMR (400 MHz, CDCl$_3$) δ 8.58 (d, J=2.8 Hz, 1H), 8.23 (d, J=8.8 Hz, 1H), 8.00 (dd, J=2.8 Hz, 8.8 Hz, 1H).

Step B: tert-butyl ethyl (6-nitropyridin-3-yl)propanedioate

To a suspension of NaH (60% in oil, 0.650 g, 16.4 mmol) in DMF (40 mL) was added tert-butyl ethyl propanedioate (2.8 g, 15.1 mmol) at room temperature. The mixture was stirred for 30 min. A solution of 5-chloro-2-nitropyridine (2.00 g, 12.6 mmol) in DMF (10 mL) was added. The mixture was heated to 80° C. and stirred for 4 hours. The solvent was removed under reduce pressure. Water was added and the mixture was extracted with EtOAc. The combined organic layer was washed with brine, dried over anhydrous Na$_2$SO$_4$, concentrated and the residue was purified by column chromatography with silca gel to give tert-butyl ethyl (6-nitropyridin-3-yl)propanedioate. $^1$H-NMR (400 MHz, CDCl$_3$) δ 8.58 (s, 1H), 8.20~8.27 (m, 2H), 4.69 (s, 1H), 4.21~4.26 (m, 2H), 1.45 (s, 9H), 1.28 (t, J=7.2 Hz, 2H).

Step C: ethyl (6-nitropyridin-3-yl)acetate

A mixture of tert-butyl ethyl (6-nitropyridin-3-yl)propanedioate (1.4 g, 4.5 mmol) in a mixed solution of TFA/DCM (10 mL/10 mL) was stirred for 5 hours at room temperature. The mixture was concentrated under reduce pressure. The residue was dissolved with DCM, washed with sat. NaHCO$_3$, dried over anhydrous Na$_2$SO$_4$ and concentrated to give ethyl (6-nitropyridin-3-yl)acetate. $^1$H-NMR (400 MHz, CDCl$_3$) δ 8.57 (s, 1H), 8.27 (d, J=8.4 Hz, 1H), 8.03 (dd, J=2.4 Hz, 8.4 Hz, 1H), 4.22 (q, J=7.2 Hz, 2H), 3.81 (s, 2H), 1.30 (t, J=7.2 Hz, 3H).

Step D: ethyl (6-aminopyridin-3-yl)acetate

A mixture of ethyl (6-nitropyridin-3-yl)acetate (0.9 g, 4.28 mmol), Pd/C (10%, 0.1 g) in MeOH (50 mL) was stirred for 2 hours under H$_2$ atmosphere at room temperature. The mixture was filtered and concentrated to give ethyl (6-aminopyridin-3-yl)acetate. $^1$H-NMR (400 MHz, CDCl$_3$) δ 7.93 (s, 1H), 7.38 (dd, J=2.4 Hz, 8.4 Hz, 1H), 6.46 (d, J=8.4 Hz, 1H), 4.48 (br, 2H), 4.13 (q, J=7.2 Hz, 2H), 3.44 (s, 2H), 1.23 (t, J=7.2 Hz, 3H).

Step E: ethyl [6-(1H-tetrazol-1-yl)pyridin-3-yl]acetate

To a mixture of ethyl (6-aminopyridin-3-yl)acetate (0.55 g, 3.05 mmol), CH(OEt)$_3$ (1.35 g, 9.15 mmol) in AcOH (20 mL) was added NaN$_3$ (0.24 g, 3.7 mmol) at room temperature. The mixture was heated to 80° C. and stirred for 3 hours. The mixture was concentrated under reduce pressure. Water was added, and the mixture was extracted with EtOAc. The combined organic layer was washed with brine, dried over anhydrous Na$_2$SO$_4$, concentrated and the residue was purified by column chromatography via silica gel to give ethyl [6-(1H-tetrazol-1-yl)pyridin-3-yl]acetate. $^1$H-NMR (400 MHz, CDCl$_3$) δ 9.52 (s, 1H), 8.44 (s, 1H), 8.06 (d, J=8.4 Hz, 1H), 7.94 (dd, J=2.4 Hz, 8.4 Hz, 1H), 4.20 (q, J=7.2 Hz, 2H), 3.72 (s, 2H), 1.27 (t, J=7.2 Hz, 3H).

Step F: [6-(1H-tetrazol-1-yl)pyridin-3-yl]acetic acid

To a mixture ethyl [6-(1H-tetrazol-1-yl)pyridin-3-yl]acetate (0.42 g, 1.8 mmol) in THF (3 mL) was added 1.4 M LiOH (aq.) (5 mL) at room temperature. The mixture was stirred 3 hours at room temperature. The reaction was acidified with citric acid until Ph about 3~4. The mixture was extracted with EtOAc. The combined organic layer was washed with brine, dried over anhydrous Na$_2$SO$_4$, concentrated to give [6-(1H-tetrazol-1-yl)pyridin-3-yl]acetic acid. $^1$H-NMR (400 MHz, DMSO) δ 12.62 (s, 1H), 10.16 (s, 1H), 8.54 (s, 1H), 8.01-8.09 (m, 2H), 3.80 (s, 2H).

Intermediate 119 (Method 2)

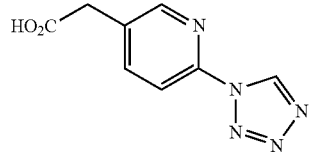 [SMILES: O=C(O)Cc1ccc(-n2cnnn2)nc1]

[6-(1H-tetrazol-1-yl)pyridin-3-yl]acetic acid

Step A: ethyl (6-nitropyridin-3-yl)acetate

To a suspension of NaH (60% in mineral oil, 13.8 g, 345 mmol) in 250 mL DMF in a 1 flask with a magnetic stir bar was added tert-butyl ethyl propanedioate (65.3 mL, 345 mmol) maintaining the temperature below +12° C. in an ice bath over ~20 min (gas evolution). After 20 min, the ice bath was removed, allowed to warm to rt over 30 min. Solid commercially available 5-bromo-2-nitropyridine (50 g, 246 mmol) was added. A red suspension formed immediately. After 15 min, the reaction flask was placed in a 60° C. oil bath. After 1 h, the heating was turned off. The red-black slurry was allowed to stir overnight while cooling down. After 15 h at rt, the mixture was cooled in an ice bath. Additional 0.7 equiv NaH (60% in mineral oil, 6.90 g, 172 mmol) was added in ~10 portions below +10° C. (internal) to keep the foaming under control. After 30 min and ⅔ through the addition of NaH, the mixture turned very thick. Additional 100 mL DMF (2 volumes) was added to facilitate stirring. The rest of NaH was added over 10 min. Stirring in the ice bath was continued for additional 10 min. It is important to add NaH slowly in order to keep the exotherm and foaming under control. If all of NaH is added at the beginning of the reaction, it results in low yield and extensive decomposition. The cooling bath was removed, the mixture was allowed to stir to rt for 1 h. The reaction mixture was heated to 60° C. over 30 min, then heated for the total of 3.5 h at 60° C. whereupon ~95% of the bromide had been consumed. The flask was then cooled in an ice bath. After 20 min in the ice bath, 100 mL MTBE was added followed by 300 mL of 1 M aqueous H$_3$PO$_4$ below +15° C. (pH=5). The red-black color of the reaction mixture sharply turned to light brown. The mixture was combined with 750 mL EtOAc, washed with 4×1 L water. The organic phase was concentrated to an oil and carried directly into the next step.

The resulting crude tert-butyl ethyl (6-nitropyridin-3-yl) propanedioate was dissolved in 153 mL DCM, and TFA (95 mL, 1230 mmol) was added. The mixture was stirred at 25° C. for 2 h, then was heated at 35° C. for 2 h, (80% conversion). An additional 2 equiv of TFA (39 mL, 492 mmol) was added. The mixture was heated at 35° C. for 1 h, then was kept at rt overnight (>95% conversion). The reaction was quenched with 1.0 L of 1 M aq K$_3$PO$_4$ in an ice bath below +20° C. to pH=6. The layers were separated, and the aqueous phase was extracted with an additional 200 mL of DCM. The organic phase was dried (MgSO$_4$), filtered, and concentrated. The residue was dissolved in 200 mL MTBE and the solution was filtered through 20 g of silica gel to remove tar. The silica plug was eluted with additional 750 mL MTBE. The filtrate was concentrated, the oily residue was suspended in ~100 mL of 3:1 Hexane/EtOAc. Crystallized occurred upon stirring/seeding. The suspension was filtered, and the filter cake washed with 100 mL of 5:1 hexane/EtOAc to provide the desired product. The mother liquors were concentrated, purified by flash chromatography on 7.5×18 cm silica (Hexane:EtOAc 3:1 to 3:2). The purest fractions were collected, concentrated to an oil, and treated with ~100 mL hexane to crystallize additional product. The slurry was stirred at rt for 1 h, filtered, the filter cake was washed with hexane to afford additional ethyl (6-nitropyridin-3-yl)acetate.

Step B: ethyl (6-aminopyridin-3-yl)acetate

A suspension of 10% Pd on carbon (9.21 g, 8.66 mmol) in a solution of the ethyl (6-nitropyridin-3-yl)acetate (36.4 g, 173 mmol) in EtOH (364 mL) was hydrogenated at 20 psi and 25° C. for 2 h. The suspension was filtered through Solka Floc eluting with 200 mL EtOH. The filtrate was concentrated and solvent switched with EtOAc, then concetrated to afford the title compound.

Step C: ethyl [6-(1H-tetrazol-1-yl)pyridin-3-yl]acetate

A 1 L 3-neck flask was purged with nitrogen and charged with a solution of ethyl (6-aminopyridin-3-yl)acetate (31.7 g, 176 mmol) in EtOAc (317 mL) at +22° C. Then 30 mL of TMS trifluoroacetate was added (1.0 equiv) while cooling in a water bath. A mild exotherm to +25° C. and partial crystallization was observed. After 5 min, triethylorthoformate was added (44.0 mL, 264 mmol) followed by TMS-azide (28.0 mL, 211 mmol). The resulting suspension was stirred at +23° C. After 15 min, an additional 10 mL of TMS trifluoroacetate was added (0.30 equiv). A clear soln formed after ~10 min. The mixture was stirred for 3 days at +20° C. whereupon a thin, light yellow suspension had formed. The mixture was cooled in an ice bath, and 200 mL of 1M aq K$_3$PO$_4$ was added while maintaining the temperature below +20° C. Then 465 mL EtOAc was added to solubilize the product. The layers were separated (pH of aq~8), then the organic phase was washed with 2×250 mL water, and concentrated to a thick slurry. Then 400 mL of n-heptane was added to the concentrated organic phase over 20 min. After 30 rnM, the suspension was filtered to afford the title tetrazole product.

Step D: [6-(1H-tetrazol-1-yl)pyridin-3-yl]acetic acid

To a suspension of ethyl [6-(1H-tetrazol-1-yl)pyridin-3-yl] acetate (30.0 g, 129 mmol) in 150 mL of water was added 28 mL of 5M aq NaOH (141 mmol) over 5 min while cooled in a water bath. A very mild exotherm to +22° C. was observed. The mixture was stirred for 40 min at rt whereupon 106 mL of 2M aq H$_3$PO$_4$ was added over 30 min at rt. The resulting suspension was filtered, and the filter cake was washed with 2×50 mL water and dried on the frit under a stream of nitrogen overnight to afford [6-(1H-tetrazol-1-yl)pyridin-3-yl]acetic acid. This material was identical by H NMR to that synthesized according to method 1 above.

Intermediate 120

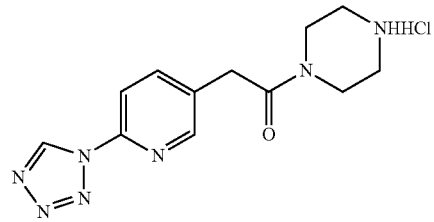

1-(piperazin-1-yl)-2[6-(1H-tetrazol-1-yl)pyridin-3-yl]ethanone hydrochloride

Step A: tert-butyl 4-{[6-(1H-tetrazol-1-yl)pyridin-3-yl] acetyl}piperazine-1-carboxylate A mixture of [6-(1H-tetrazol-1-yl)pyridin-3-yl]acetic acid (65 mg, 0.31 mmol), N-Boc-piperazine (88 mg, 0.47 mmol), HOBt (64 mg, 0.47 mmol), EDC (90 mg, 0.47 mmol) and Et$_3$N (96 mg, 0.95 mmol) in DCM (2 mL) was stirred 12 hours at room temperature. Water was added and the mixture was extracted with DCM. The combined organic layers were washed with brine, dried over anhydrous Na$_2$SO$_4$, concentrated and the residue was purified by prep-TLC to give tert-butyl 4-{[6-(1H-tetrazol-1-yl)pyridin-3-yl] acetyl}piperazine-1-carboxylate. MS m/z 374 (M+1)$^+$. $^1$H-NMR (400 MHz, CDCl$_3$) δ 9.45 (s, 1H), 8.33 (s, 1H), 7.98~8.01 (m, 1H), 7.82~7.85 (m, 1H), 3.73 (s, 2H), 3.56~3.58 (m, 2H), 3.46~3.47 (m, 2H), 3.36~3.39 (m, 4H).

Step B: 1-(piperazin-1-yl)-2-[6-(1H-tetrazol-1-yl)pyridin-3-yl]ethanone hydrochloride A mixture of tert-butyl 4-{[6-(1H-tetrazol-1-yl)pyridin-3-yl]acetyl}piperazine-1-carboxylate (60 mg, 0.16 mmol) in HCl/EtOAc (3 mL) was stirred for 3 hours at room temperature. The reaction mixture was concentrated under reduce pressure to give 1-(piperazin-1-yl)-2-[6-(1H-tetrazol-1-yl) pyridin-3yl]ethanone hydrochloride. MS m/z 274 (M+1)$^+$. $^1$H-NMR (400 MHz, MeOD) δ 9.89 (s, 1H), 8.46 (s, 1H), 8.05~8.07 (m, 1H), 7.99~8.00 (m, 1H), 3.99 (s, 2H), 3.85~3.92 (m, 4H), 3.24~3.30 (m, 4H).

Intermediate 121

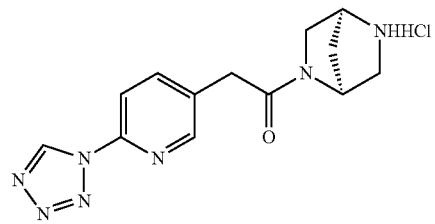

1[(1S,4S)-2,5-diazabicyclo[2.2.1]hept-2-yl]-2-[6-(1H-tetrazol-1-yl)pyridin-3yl]ethanone hydrochloride 1-[(1S,4S)-2,5-Diazabicyclo[2.2.1]hept-2-yl]-2-[6-(1H-tetrazol-1-yl)pyridin-3-yl]ethanone hydrochloride was prepared in two steps starting from [6-(1H-tetrazol-1-yl)pyridin- 3-yl]acetic acid and commercially available tert-butyl (1S, 4S)-2,5-diazabicyclo[2.2.1]heptane-2-carboxylate in an analogous fashion as described for the synthesis of 1-(piperazin-1-yl)-2-[6-(1H-tetrazol-1-yl)pyridin-3-yl]ethanone hydrochloride. MS m/z 286 (M+1)$^+$.

Intermediate 122

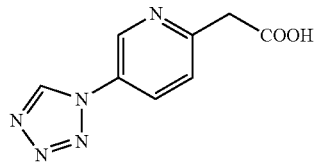 [SMILES: O=C(O)Cc1ccc(-n2cnnn2)cn1]

[5-(1H-tetrazol-1-yl)pyridin-2-yl]acetic acid
Step A: tert-butyl ethyl (5-nitropyridin-2-yl)propanedioate To a suspension of NaH (60% in oil, 1.89 g, 47 mmol) in 20 mL of DMF was added tert-butyl ethyl propanedioate (6.5 g, 34.7 mmol) at room temperature. The mixture was stirred for 30 min. A solution of 2-chloro-5-nitropyridine (5.0 g, 31.5 mmol) in 10 mL of DMF was added. The mixture was stirred at r.t. overnight. The solvent was removed under reduce pressure. Water was added and the mixture was extracted with EtOAc. The combined organic layer was washed with brine, dried over anhydrous Na$_2$SO$_4$, concentrated and the residue was purified by column chromatography with silca gel to give tert-butyl ethyl (5-nitropyridin-2-yl)propanedioate. $^1$H-NMR (400 MHz, CDCl$_3$) δ 9.39 (s, 1H), 8.51 (d, J=8.8 Hz, $^1$H), 7.76 (d, J=8.8 Hz, 1H), 5.00 (s, 1H), 4.28 (q, J=7.2 Hz, 2H), 1.49 (s, 9H), 1.31 (t, J=7.2 Hz, 3H).
Step B: ethyl (5-nitropyridin-2-yl)acetate A mixture of tert-butyl ethyl (5-nitropyridin-2-yl)propanedioate (4.10 g, 13.2 mmol) in a mixed solution of TFA/DCM (4 mL/20 mL) was stirred for 5 hours at room temperature. The mixture was concentrated under reduce pressure. The residue was dissolved with DCM, washed with sat. NaHCO$_3$, dried over anhydrous Na$_2$SO$_4$ and concentrated to give ethyl (5-nitropyridin-2-yl)acetate. $^1$H-NMR (400 MHz, CDCl$_3$) δ 9.41 (s, 1H), 8.58 (d, J=8.4 Hz, 1H), 7.64 (d, J=8.4 Hz, 1H), 4.16 (q, J=7.2 Hz, 2H), 4.02 (s, 2H), 1.22 (t, J=7.2 Hz, 3H).
Step C: ethyl (5-aminopyridin-2-yl)acetate A mixture of ethyl (5-nitropyridin-2-yl)acetate (2.40 g, 11.4 mmol), Raney-Ni (50 mg) in 100 mL of MeOH was stirred at room temperature overnight. The mixture was filtered and concentrated to give ethyl (5-aminopyridin-2-yl) acetate. $^1$H-NMR (400 MHz, CDCl$_3$) δ 8.03 (s, 1H), 7.06 (dd, J=8.4 Hz, 1H), 6.95 (d, J=8.4 Hz, 1H), 4.15 (q, J=7.2 Hz, 2H), 3.71 (s, 2H), 3.65 (br, 2H), 1.24 (t, J=7.2 Hz, 3H).
Step D: ethyl [5-(1H-tetrazol-1-yl)pyridin-2-yl]acetate To a mixture of ethyl (5-aminopyridin-2-yl)acetate (1.0 g, 5.5 mmol), CH(OEt)$_3$ (1.31 g, 8.80 mmol) in AcOH (10 mL) was added NaN$_3$ (0.54 g, 8.3 mmol) at room temperature. The mixture was heated to 80° C. and stirred for 3 hours. The mixture was concentrated under reduce pressure. Water was added, and the mixture was extracted with EtOAc. The combined organic layer was washed with brine, dried over anhydrous Na$_2$SO$_4$, concentrated and the residue was purified by column chromatography via silica gel to give ethyl [5-(1H-tetrazol-1-yl)pyridin-2-yl]acetate. $^1$H-NMR (400 MHz, CDCl$_3$) δ 9.03 (s, 1H), 8.90 (s, 1H), 8.06 (d, J=8.4 Hz, 1H), 7.58 (d, J=8.4 Hz, 1H), 4.21 (q, J=7.2 Hz, 2H), 3.96 (s, 2H), 1.29 (t, J=7.2 Hz, 3H).

Step E: [5-(1H-tetrazol-1-yl)pyridin-2-yl]acetic acid

To a mixture ethyl [5-(1H-tetrazol-1-yl)pyridin-2-yl]acetate (0.19 g, 0.81 mmol) in THF (4 mL) was added 1.4 M LiOH (aq.) (2.9 mL) at room temperature. The mixture was stirred 3 hours at room temperature. The reaction was acidified with citric acid until pH about 3-4. The mixture was extracted with EtOAc. The combined organic layer was washed with brine, dried over anhydrous Na$_2$SO$_4$, concentrated to give [5-(1H-tetrazol-1-yl)pyridin-2-yl]acetic acid. $^1$H-NMR (400 MHz, MeOD) δ 9.83 (s, 1H), 9.02 (s, 1H), 8.28 (d, J=8.8 Hz, 1H), 7.68 (d, J=8.8 Hz, 1H), 3.95 (s, 2H).

Intermediate 123

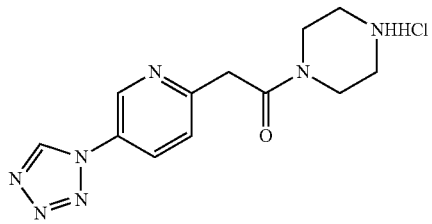

1-(piperazin-1-yl)-2-[5-(1H-tetrazol-1-yl)pyridin-2-yl]ethanone hydrochloride
Step A: tert-butyl 4-{[5-(1H-tetrazol-1-yl)pyridin-2-yl]acetyl}piperazine-1-carboxylate A mixture of [5-(1H-tetrazol-1-yl)pyridin-2-yl]acetic acid (100 mg, 0.49 mmol), N-Boc-piperazine 7 (109 mg, 0.59 mmol), HOBt (79 mg, 0.59 mmol), EDC (112 mg, 0.59 mmol) and Et$_3$N (198 mg, 1.96 mmol) in DCM (2 mL) was stirred 12 hours at room temperature. Water was added and the mixture was extracted with DCM. The combined organic layers were washed with brine, dried over anhydrous Na$_2$SO$_4$, concentrated and the residue was purified by prep-TLC to give tert-butyl 4-{[5-(1H-tetrazol-1-pyridin-2-yl] acetyl}piperazine-1-carboxylate. $^1$H-NMR (400 MHz, CDCl$_3$) δ 8.97 (s, 1H), 8.84 (s, 1H), 7.98 (d, J=8.4 Hz, 1H), 7.56 (d, J=8.4 Hz, 1H), 3.98 (s, 2H), 3.50~3.60 (m, 4H), 3.30~3.40 (m, 4H), 1.40 (s, 9H). MS m/z 374 (M+1)$^+$.
Step B: 1-(piperazin-1-yl)-2-[5-(1H-tetrazol-1-yl)pyridin-2-yl]ethanone hydrochloride A mixture of tert-butyl 4-{[5-(1H-tetrazol-1-yl)pyridin-2-yl]acetyl}piperazine-1-carboxylate (30 mg, 0.08 mmol) in HCl/EtOAc (5 mL) was stirred for 3 hours at room temperature. The reaction mixture was concentrated under reduce pressure to give 1-(piperazin-1-yl)-2-[5-(1H-tetrazol-1-yl) pyridin-2-yl]ethanone hydrochloride. MS m/z 274 (M+1)$^+$.

Intermediate 124

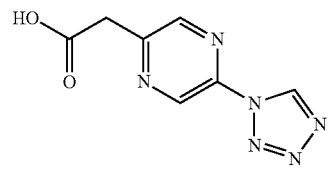 [SMILES: O=C(O)Cc1cnc(-n2cnnn2)cn1]

[5-(1H-tetrazol-1-yl)pyrazin-2-yl]acetic acid
Step A: 5-bromopyrazin-2-amine

To a solution of pyrazin-2-amine (20 g, 210 mmol) in 1.5 L of DCM was added NBS (37.4 g, 210 mmol) at 0° C. The resulting mixture was stirred for 3 hours at 0° C. then filtrated through Celite®. The filtrate was washed with saturated Na₂CO₃ and brine, dried over Na₂SO₄ and evaporated to afford a brown solid. The crude material was purified on silica gel (eluting with 20-40 percent ethyl acetate in hexane) to give 5-bromopyrazin-2-amine. ¹H-NMR (CDCl₃, 400 MHz) δ 8.05 (s, 1H), 7.75 (s, 1H), 4.65 (brs, 1H).

Step B: 2-bromo-5-[(dimethyl-λ⁴-sulfanylidene)amino]pyrazine

To a solution of DMSO (11 g, 138 mmol) in 100 mL of DCM was added Tf₂O (42 g, 149 mmol) at −70° C. The resulting mixture was stirred at −70° C. for 15 minutes then a solution of 5-bromopyrazin-2-amine (20 g, 115 mmol, in 100 mL of DCM and 50 mL of DMSO) was added dropwise. The mixture was stirred at −60° C. for 3 hours and diluted with 500 mL of DCM and washed with water. The water layer was basified to pH=11 with aq. Na₂CO₃ and extracted with DCM twice. The combined DCM layer was washed with brine, dried over Na₂SO₄ and evaporated to afford 2-bromo-5-[(dimethyl-λ⁴-sulfanylidene)amino]pyrazine. ¹H-NMR (CDCl₃, 400 MHz) δ 7.89 (s, 1H), 7.78 (s, 1H), 2.72 (s, 6H).

Step C: 2-bromo-5-nitropyrazine

To a solution of mCPBA (85%, 37.4 g, 184.2 mmol) in 1 L of DCM was added a solution of 2-bromo-5-[(dimethyl-λ⁴-sulfanylidene)amino]pyrazine (26.7 g, 114 mmol) in 800 mL of DCM at 0° C. The resulting mixture was stirred at 0° C. for 45 minutes and 30 mL of DMSO was added. Ozone was bubbled through the mixture for 45 minutes then diluted with 2 L of DCM, washed subsequently with water, aq. Na₂CO₃ and brine, dried over Na₂SO₄ and evaporated. The crude material was purified on silica gel (eluting with 20 percent ethyl acetate in hexane) to give 2-bromo-5-nitropyrazine. ¹H-NMR (CDCl3, 400 MHz) δ 9.27 (s, 1H), 8.70 (s, 1H).

Step D: tert-butyl ethyl (5-nitropyrazin-2-yl)propanedioate

A suspension of NaH (60%, 3.0 g, 75 mmol) in 100 mL of DMF was added text-butyl ethyl propanedioate (14.1 g, 75 mmol) dropwise at 25° C. The mixture was stirred at 40° C. for 30 minutes and 2-bromo-5-nitropyrazine (10.2 g, 50 mmol) in 50 mL of DMF was added dropwise. The resulting suspension was stirred at 50° C. for 2 hours and diluted with 500 mL of EtOAc. The mixture was washed with water (100 mL*3), brine, dried over anhydrous Na₂SO₄ and concentrated. The residue was purified by column chromatography (petrol ether: EtOAc=5:1) to afford tert-butyl ethyl (5-nitropyrazin-2-yl)propanedioate. ¹H-NMR (400 MHz, CDCl3) δ ppm 9.41 (s, 2H), 8.81 (s, 1H), 5.01 (s, 1H), 4.28 (q, J=7.2 Hz, 2H), 1.46 (s, 9H), 1.26 (t, J=7.2 Hz, 3H).

Step E: ethyl (5-nitropyrazin-2-yl)acetate

A mixture of tert-butyl ethyl (5-nitropyrazin-2-yl)propanedioate (10.7 g, 34.4 mmol) in 30 mL of TFA and 30 mL DCM was stirred at 35° C. for 3 hours before concentrated to dryness. The residue was dissolved in 200 mL of EtOAc and washed with water (25 mL) and brine (25 mL), dried over anhydrous Na₂SO₄ and concentrated to afford ethyl (5-nitropyrazin-2-yl)acetate.

Step F: ethyl [5-(hydroxyamino)pyrazin-2-yl]acetate

A mixture of ethyl (5-nitropyrazin-2-yl)acetate (6.7 g, 31.7 mmol) and Pd/C (1 g, 10%) in 300 mL of EtOAc was stirred at room temperature under hydrogen baloon for 6 hours before filtration. The filtrate was concentrated to afford ethyl [5-(hydroxyamino)pyrazin-2-yl]acetate (incomplete reduction). ¹H-NMR (400 MHz, CDCl3) δ ppm 8.35 (s, 1H), 8.05 (s, 1H), 4.17 (q, J=7.2 Hz, 2H), 3.75 (s, 2H), 1.24 (t, J=7.2 Hz, 3H).

Step G: ethyl (5-aminopyrazin-2-yl)acetate

A mixture of ethyl [5-(hydroxyamino)pyrazin-2-yl]acetate (2.8 g, 14.2 mmol) and Pd(OH)₂ (3 g, 10%) in 150 mL of methanol was stirred at room temperature under 50 psi of H₂ for 2 hours before filtration. The filtrate was concentrated to afford ethyl (5-aminopyrazin-2-yl)acetate. ¹H-NMR (400 MHz, CDCl3) δ ppm 7.96 (s, 1H), 7.94 (s, 1H), 4.59 (brs, 2H), 4.18 (q, J=7.2 Hz, 2H), 3.71 (s, 2H), 1.25 (t, J=7.2 Hz, 3H).

Step H: ethyl [5-(1H-tetrazol-1-yl)pyrazin-2-yl]acetate

A solution of the ethyl (5-aminopyrazin-2-yl)acetate (2.0 g, 11.0 mmol) and triethyl orthoformate (4.9 g, 33.1 mmol) in 60 mL of HOAc was added sodium azide (0.9 g, 13.8 mmol) and heated to 100° C. for 1 hour. The reaction was completed which was checked by TLC. The reaction mixture was cooled to r.t. The solvent was removed under vacuum. The residue was dissolved in EtOAc, washed with water, dried over anhydrous sodium sulfate, and concentrated. The residue was purified by column chromatograph to afford the product ethyl [5-(1H-tetrazol-1-yl)pyrazin-2-yl]acetate. ¹H-NMR (400 MHz, CDCl3) δ ppm 9.50 (s, 1H), 9.35 (s, 1H), 8.54 (s, 1H), 4.21 (q, J=7.2 Hz, 2H), 3.98 (s, 2H), 1.27 (t, J=7.2 Hz, 3H).

Step I: [5-(1H-tetrazol-1-yl)pyrazin-2-yl]acetic acid

A mixture of ethyl [5-(1H-tetrazol-1-yl)pyrazin-2-yl]acetate (2.0 g, 8.5 mmol) in 60 mL of THF/MeOH/H₂O (2:2:1) was added LiOH.H₂O (540 mg, 12.8 mmol) portionwise and stirred for 30 minutes before diluted with 200 mL of water and washed with ether (30 mL*3). The water layer was acidified to pH=4 with diluted hydrochloric acid and extracted with EtOAc (50 mL*5). The combined organic layer was washed with brine, dried over anhydrous Na₂SO₄ and concentrated to afford [5-(1H-tetrazol-1-yl)pyrazin-2-yl]acetic acid. ¹H-NMR (400 MHz, d6-DMSO) δ ppm 12.93 (brs, 1H), 10.22 (s, 1H), 9.25 (d, J=1.2 Hz, 1H), 8.71 (d, J=1.2 Hz, 1H), 3.98 (s, 2H).

Intermediate 125

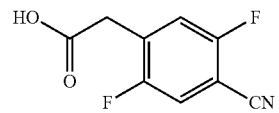 [SMILES: N#Cc1cc(F)c(CC(=O)O)cc1F]

(4-cyano-2,5-difluorophenyl)acetic acid

Step A: di-text-butyl (4-cyano-2,5-difluorophenyl)propanedioate

A suspension of NaH (60% in mineral oil, 2.6 g, 64 mmol) in dry DMF (120 mL) was stirred and cooled to 0° C., and di-tert-butyl malonate (9.0 g, 41 mmol) was added over 30 min. The mixture was allowed to warm to room temperature before addition of 2,4,5-trifluorobenzonitrile (5.0 g, 32 mmol). After being heated at 80° C. for 8 h with stirring, the reaction mixture was cooled to room temperature and poured into a mixture of ice-water (100 mL) and AcOEt (200 mL). Layers were separated, and the organic layer was washed successively with water, and brine, then dried over MgSO₄ and concentrated. The residue was purified by flash chromatography (silica gel, EtOAc/hexanes, 2:8) to give the di-tert-butyl (4-cyano-2,5-difluorophenyl) propanedioate. ¹H NMR (500 MHz, CDCl₃) δ 7.51 (dd, J=5.5 Hz, J=5.4 Hz, 1H), 7.37 (dd, J=5.0 Hz, J=6.0 Hz, 1H), 4.84 (s, 1H), 1.52 (s, 18H); LCMS: [(M+1)-t-Bu]⁺=239.3.

Step B: (4-cyano-2,5-difluorophenyl)acetic acid

TFA (30 mL) was added to a solution of di-tert-butyl (4-cyano-2,5-difluorophenyl) propanedioate (10.0 g, 28.3 mmol) in dichloromethane (30 mL) at room temperature. The reaction mixture was stirred over night, then concentrated under reduced pressure, and the residue was treated with Et₂O (100 mL) to induce crystallization. The crystals were collected by filtration to give 4-cyano-2,5-difluorophenyl)acetic acid. $^1$H NMR (500 MHz, DMSO-$d_6$) δ 12.7 (bs, 1H), 7.96 (dd, J=5.3 Hz, J=5.3 Hz, 1H), 7.61 (dd, J=5.9 Hz, J=5.7 Hz, 1H), 3.76 (s, 2H); LC/MS: [(M+1)+H$_2$O]$^+$=216.2.

Intermediate 126

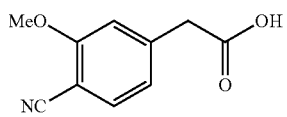

(4-cyano-3-methoxyphenyl)acetic acid

Step A: Ethyl (3-methoxy-4-{[(trifluoromethyl)sulfonyl]oxy}phenyl)acetate

Ethyl (4-hydroxy-3-methoxyphenyl)acetate, 12.0 g, 57 mmol was dissolved in anhydrous dichloromethane (200 mL). 4-Dimethylaminopyridine (0.70 g, 0.10 equiv) was added, followed by triethylamine (9.6 mL, 69 mmol). The solution was then cooled to in a dry ice and acetone bath while under nitrogen. Trifluoromethanesulfonic anhydride (9.6 mL, 57 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure to yield the triflate. LC/MS [(M+1)-CO$_2$Et]$^+$=269.0;

Step B: Ethyl (4-cyano-3-methoxyphenyl)acetate

The crude triflate (16.6 g) was dissolved in anhydrous dimethylformamide (100 mL). Zinc cyanide (3.4 g, 29 mmol) was added, and the solution was purged thoroughly with nitrogen. Tetrakis(triphenylphosphine)palladium(0) (5.6 g, 4.9 mmol) was then added and the reaction mixture was heated to 80° C. for 4 h. After allowing to cool to ambient temperature and diluting with water (200 mL), ethyl acetate (400 mL) was added. The combined layers were filtered to remove any solids, the filtrate transferred to a separatory funnel, and the layers separated. The aqueous layer was re-extracted with ethyl acetate (2×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound. The crude product was purified through silica gel chromatography (ethyl acetate/hexanes, 2:3) to yield the title nitrile. NMR (500 MHz, DMSO-$d_6$), δ 7.67 (d, J=8.0 Hz, 1H), 7.18 (s, 1H), 7.0 (d, J=8.0 Hz, 1H), 4.10 (q, J=7.1 Hz, 2H), 3.89 (s, 3H), 3.78 (s, 2H), 1.19 (t, J=7.1 Hz, 3H); LC/MS (M+1)$^+$=220.17;

Step C: (4-Cyano-3-methoxyphenyl) acetic acid

Aqueous LiOH (0.096 g, 2.9 mmol, in 2 mL of water) was added to a stirred solution of ethyl (4-cyano-3-methoxyphenyl)acetate (0.50 g, 2.9 mmol) in THF:CH$_3$OH) 5:1 (23 mL), and the solution was stirred at room temperature overnight. After acidification to pH 3 with 1 N HCl, the aqueous was extracted with AcOEt (2×50 mL). The organic phase was washed with brine, dried (MgSO$_4$), and evaporated under reduced pressure to give the (4-cyano-3-methoxyphenyl) acetic acid, which was used in the next step without further purification. NMR (500 MHz, DMSO-$d_6$), δ 12.52 (s, 1H), 7.65 (d, J=8.0 Hz, 1H), 7.17 (s, 1H), 7.0 (d, J=7.8.0 Hz, 1H), 3.89 (s, 3H), 3.69 (s, 2H); LC/MS (M+1)$^+$=192.16; $t_R$=0.52 min.

Intermediate 127

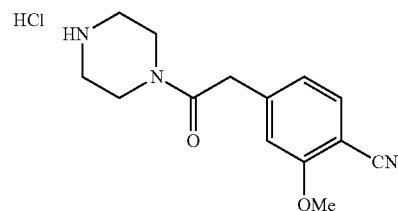 [SMILES: Cl ; COc1cc(CC(=O)N2CCNCC2)ccc1C#N]

2-methoxy-4-[2-oxo-2-(piperazin-1-yl)ethyl]benzonitrile hydrochloride 2-Methoxy-4-[2-oxo-2-(piperazin-1-yl)ethyl]benzonitrile hydrochloride was prepared in two steps from (4-cyano-3-methoxyphenyl) acetic acid in an analogous fashion to that described for 1-(piperazin-1-yl)-2-[6-(1H-tetrazol-1-yl)pyridin-3-yl]ethanone hydrochloride. MS m/z 260 (M+1)$^+$.

Intermediate 128

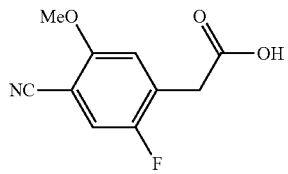 [SMILES: COc1cc(CC(=O)O)c(F)cc1C#N]

(4-cyano-2-fluoro-5-methoxyphenyl)acetic acid

Step A: di-tert-Butyl (4-cyano-2-fluoro-5-methoxyphenyl)propanedioate

A suspension of NaH (60% in mineral oil, 0.33 g, 8.3 mmol) in dry DMF (20 mL) was stirred and cooled to 0° C., and di-tert-butyl malonate (1.5 g, 7.1 mmol) was added. The mixture was allowed to warm to room temperature before addition of 4,5-difluoro-2-methoxybenzonitrile (1.0 g, 5.9 mmol). The mixture was heated at 80° C. for 4 h with stirring, then the reaction mixture was cooled to room temperature and poured into a mixture of ice-water (100 mL) and AcOEt (100 mL). The layers were separated, and the organic layer was washed successively with water, and brine, then dried over Na$_2$SO$_4$ and concentrated. The residue was purified by flash chromatography (silica gel, EtOAc/hexanes, 0→10%) to give the di-tert-butyl (4-cyano-5-fluoro-2-methoxyphenyl) propanedioate. LCMS: [(M+1)-t-Bu,CO2-t-Bu]$^+$=210.1; $t_R$=2.2 min.

Step B: (4-cyano-2-fluoro-5-methoxyphenyl) acetic acid

TFA (5 mL) was added to a solution of di-cert-butyl (4-cyano-5-fluoro-2-methoxyphenyl) propanedioate (1.3 g, 28.3 mmol) in of dichloromethane (5 mL) at room temperature. The reaction mixture was stirred over night, then concentrated under reduced pressure, and the residue was treated with Et$_2$O (10 mL) to induce crystallization. The crystals were collected by filtration to give 4-cyano-2,5-difluorophenyl)acetic acid. $^1$H NMR (500 MHz, CD$_3$OD) δ 7.44 (d, J=5.3 Hz, 1H), 7.19 (d, J=5.4 Hz, 1H), 3.96 (s, 3H), 3.78 (s, 2H); LC/MS: [(M+1)]$^+$=210.1.

Intermediate 129

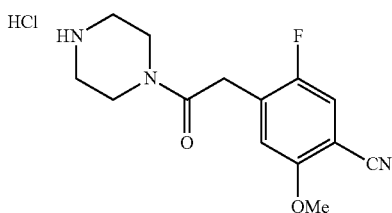 [SMILES: Cl ; COc1cc(CC(=O)N2CCNCC2)c(F)cc1C#N]

5-fluoro-2-methoxy-4-[2-oxo-2-(piperazin-1-yl)ethyl]benzonitrile hydrochloride

5-Fluoro-2-methoxy-4-[2-oxo-2-(piperazin-1-yl)ethyl] benzonitrile hydrochloride was prepared in two steps from (4-cyano-2-fluoro-5-methoxyphenyl) acetic acid in an analogous fashion to that described for the synthesis of 1-(piperazin-1-yl)-2-[6-(1H-tetrazol-1-yl)pyridin-3-yl]ethanone hydrochloride. MS m/z 278 (M+1)$^+$.

Intermediate 130

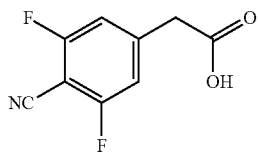 [SMILES: N#Cc1c(F)cc(CC(=O)O)cc1F]

(4-cyano-3,4-difulorophenyl)acetic acid

Step A: 4-Cyano-3,5-difluorophenyl trifluoromethanesulfonate

In a 100 mL round bottom flask was added 2,6-difluoro-4-hydroxybenzonitrile (500 mg, 3.22 mmol), triethylamine (0.45 mL, 3.22 mmol, 1.0 eq) and DCM (10 mL). The solution was cooled to 0° C. To above solution was added trifluorosulfonyl anhydride (0.545 mL, 3.22 mmol, 1.0 eq). The reaction was stirred at 0° C. for 1 hr, quenched with addition of aqueous sodium bicarbonate, extracted with DCM, washed with brine and water. The organic phase was dried over MgSO$_4$, filtered and concentrated. The product was obtained after purification by flash column chromatography. $^1$H NMR (500 MHz, CDCl$_3$, δ in ppm): 7.10 (2H, m).

Step B: tert-Butyl (4-cyano-3,5-difluorophenyl)acetate

In a 15 mL microwave reaction vial was added 4-cyano-3,5-difluorophenyl trifluoromethanesulfonate (250 mg, 0.871 mmol) and THF (2 mL). To above solution was added palladium triphenylphosphane (1:4) (101 mg, 0.087 mmol, 0.1 eq). The vial was sealed, de-gas and filled with N$_2$. To above solution was added (2-tert-butoxy-2-oxoethyl)(chloro)zinc (2.61 mL, 1.31 mmol, 1.5 eq). The reaction was heated to 105° C. for 30 min, concentrated and purified by flash column chromatography to afford the target compound. $^1$H NMR (500 MHz, CDCl$_3$, δ in ppm): 7.0 (2H, aromatic, m), 3.6 (2H, s), 1.4 (9H, s).

Step C: (4-Cyano-3,4-difulorophenyl)acetic acid

In a 12 mL reaction vial, was added tert-butyl (4-cyano-3,5-difulorophenyl)acetate (125 mg, 0.494 mmol) and 4 N HCl in dioxane (1 mL). The reaction was stirred at r.t. for 18 hr. The reaction mixture was concentrated to give the desired product. LC-MS (IE, m/z): 198.2 [M+1]$^+$.

The following carboxylic acids were prepared in an analogous fashion to that described for the synthesis of 4-cyano-3,4-difulorophenyl)acetic acid from the commercially available precursors indicated in the Table below.

| INTERMEDIATE | Commercially available precursor | Structure of carboxylic acid intermediate | LC-MS (M + 1)$^+$ |
| --- | --- | --- | --- |
| 131 | | | 198 |
| 132 | | | |
| 133 | | | |

| INTERMEDIATE | Commercially available precursor | Structure of carboxylic acid intermediate | LC-MS (M + 1)+ |
|---|---|---|---|
| 134 | | | 206 |
| 135 | | | 177 |
| 136 | | | 226 |

Intermediate 137

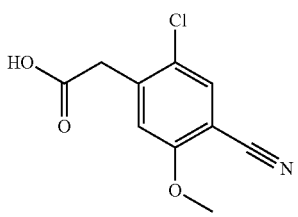

(2-chloro-4-cyano-5-methoxyphenyl)acetic acid

Step A: [4-(acetyloxy)-3-methoxyphenyl]acetic acid

A mixture of (4-hydroxy-3-methoxyphenyl)acetic acid (380 mg, 2.088 mmol) and $H_3PO_4$ (2 drops) in about 20 mL of Hac/$Ac_2O$ (v/v=1:1) was refluxed overnight, and then concentrated to dryness in vacuo. The residue was diluted with water (50 mL), and the result mixture was extracted with ethyl acetate (2*50 mL). The combined organic phase was washed with brine (100 mL) and dried over $Na_2SO_4$ and concentrated to give [4-(acetyloxy)-3-methoxyphenyl]acetic acid. $^1$H-NMR (400 MHz, $CDCl_3$) δ ppm 6.97 (d, J=7.8 Hz, 1H), 6.84~6.89 (m, 2H), 3.81 (s, 3H), 3.61 (s, 2H), 2.29 (s, 3H).

Step B: [4-(acetyloxy)-2-chloro-5-methoxyphenyl]acetic acid

To a solution of [4-(acetyloxy)-3-methoxyphenyl]acetic acid (650 mg, 2.90 mmol) in DMF (10 mL) was added a solution of NCS (428 mg, 3.192 mmol) in DMF (5 mL) dropwise at 0° C. The mixture was stirred at ambient temperature for 6 hrs, and then poured into water (100 mL) and extracted with EtOAc (3*100 mL). The combined organic layers were washed with 1 N HCl, brine, dried over $Na_2SO_4$ and then concentrated to obtain [4-(acetyloxy)-2-chloro-5-methoxyphenyl]acetic acid.

Step C: methyl (2-chloro-4-hydroxy-5-methoxyphenyl)acetate

To a solution of [4-(acetyloxy)-2-chloro-5-methoxyphenyl]acetic acid (670 mg, 2.587 mmol) in 30 mL of MeOH was added dropwise $SOCl_2$ at 0° C. The resulting mixture was stirred at 50~60° C. overnight and concentrated to dryness.

The residue was dissolved in EtOAc (50 mL), washed with water (50 mL), brine (50 mL), dried over anhydrous $Na_2SO_4$ and concentrated to give methyl (2-chloro-4-hydroxy-5-methoxyphenyl)acetate. $^1$H-NMR (400 MHz, $CDCl_3$) δ ppm 6.94 (s, 1H), 6.75 (s, 1H), 3.86 (s, 3H), 3.70 (s, 3H), 3.68 (s, 2H).

Step D: methyl(2-chloro-5-methoxy-4-{[(trifluoromethyl)sulfonyl]oxy}phenyl)acetate To a solution of methyl (2-chloro-4-hydroxy-5-methoxyphenyl)acetate (570 mg, 2.468 mmol) in 10 mL of pyridine was added $Tf_2O$ (853 mg, 2.962 mmol) dropwise at 0° C. The resulting mixture was stirred at rt overnight and concentrated to dryness. The residue was dissolved in EtOAc (50 mL), washed with 1 N HCl (50 mL), brine (50 mL), dried over anhydrous $Na_2SO_4$ and concentrated to give methyl(2-chloro-5-methoxy-4-{[(trifluoromethyl)sulfonyl]oxy}phenyeacetate.

Step E: methyl (2-chloro-4-cyano-5-methoxyphenyl)acetate

A mixture of methyl(2-chloro-5-methoxy-4-{[(trifluoromethyl)sulfonyl]oxy}phenyl)acetate (200 mg, 0.551 mmol), $Zn(CN)_2$ (39 mg, 0.331 mmol) and $Pd(PPh_3)_4$ (50 mg, 0.043 mmol) in 10 mL of DMF was heated at 110~120° C. under $N_2$ overnight. Cooled to ambient temperature and the mixture was poured into brine (50 mL) and extracted with EtOAc (3*50 mL). The combined organic layers were washed with water (50 mL), brine (50 mL), dried over anhydrous $Na_2SO_4$ and concentrated. The residue was purified by prep-TLC to give methyl (2-chloro-4-cyano-5-methoxyphenyl)acetate.

Step F: (2-chloro-4-cyano-5-methoxyphenyl)acetic acid

To a mixture of methyl (2-chloro-4-cyano-5-methoxyphenyl)acetate (30 mg, 0.125 mmol) in 15 mL of THF/MeOH/$H_2O$ (V/V/V=2:2:1) was added LiOH $H_2O$ (11 mg, 0.250 mmol). The mixture was stirred at rt. For 1 hr, and then most of the solvent was concentrated. The residue was diluted with water, adjusted pH=3 with 3 N HCl, and then extracted with EtOAc. The combined organic layers were washed with brine, dried over anhydrous $Na_2SO_4$ and concentrated to give

Intermediate 138

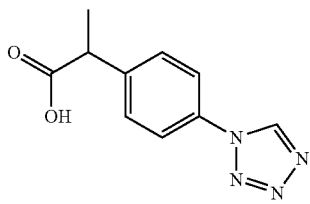 [SMILES: CC(C(=O)O)c1ccc(-n2cnnn2)cc1]

2-[4-(1H-tetrazol-1yl)phenyl]propanoic acid
Step A: 2-(4-aminophenyl) propionic acid 2-(4-nitrophenyl) propionic acid (5 g, 25.6 mmol) was dissolved in ethyl acetate (50 ml) and palladium on carbon (1 g, 9.40 mmol) was added then stirred under hydrogen balloon overnight. The product precipitated out. Added methanol to dissolved product then filtered off the palladium catalyst. The filtrate was concentrated and the residue was triturated with ethyl acetate to yield 2-(4-aminophenyl) propionic acid. LC-MS (IE, m/z): 166 [M+1]$^+$;

Step B: 2-[4-(1H-tetrazol-1yl)phenyl]propanoic acid

Triethyl orthoformate (5.29 ml, 31.8 mmol) and 2-(4-aminophenyl) propionic acid (3.26 g, 19.73 mmol) were suspended in acetic acid (50 ml) then added sodium azide (1.924 g, 29.6 mmol). The mixture was refluxed for 3 hours then let stirred at room temperature overnight. The reaction was poured into water (60 ml) and extracted with ethyl acetate (60 ml). The organic layer was separated and dried over MgSO4. The mixture was filtered and concentrated to yield 2-[4-(1H-tetrazol-1yl)phenyl]propanoic acid (4.2 g, 98%). LC-MS (IE, m/z): 219 [M+1]$^+$.

Intermediate 139

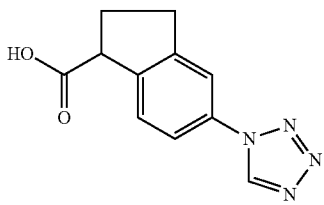 [SMILES: O=C(O)C1CCc2cc(-n3cnnn3)ccc21]

5-(1H-tetrazol-1-yl)indane-1-carboxylic acid
Step A: N-(2,3-dihydro-1H-inden-5-yl)acetamide A solution of indan-5-amine (43 g, 0.31 mol) and TEA (51.3 mL, 0.370 mol) in 400 mL of anhydrous DCM was added a solution of AcCl (23.6 mL, 0.340 mol) in 100 mL of anhydrous DCM dropwise at 0° C. then and stirred for 0.5 h at r.t. After the reaction was completed, the reaction mixture was added 500 mL of DCM, washed with water, 10% HCl solution, 10% NaHCO$_3$ and brine. The organic phase was dried over anhydrous Na$_2$SO$_4$ and concentrated to give N-(2,3-dihydro-1H-inden-5-yl)acetamide. $^1$H-NMR (300 MHz, CDCl$_3$) δ ppm 7.43 (s, 1H), 7.13~7.14 (m, 2H), 2.86 (q, J=7.9 Hz, 4H), 2.15 (s, 3H), 2.0~2.10 (m, 2H);

Step B: N-(1-oxo-2,3-dihydro-1H-inden-5-yl)acetamide

A solution of N-(2,3-dihydro-1H-inden-5-yl)acetamide (50 g, 0.29 mol) in 150 mL of acetic acid and 40 mL of actic anhydride was added a solution of chromium trioxide in a mixed solution (30 mL of water and 140 mL of acetic acid) dropwise at 10° C. by external cooling. After stirring overnight, the solution was poured into 2 L of ice water under vigorously stirring. The resulting solid was filtered, washed with cooled EtOH to give N-(1-oxo-2,3-dihydro-1H-inden-5-yl)acetamide. $^1$H-NMR (300 MHz, CDCl$_3$) δ ppm 7.90 (s, 1H), 7.66~7.70 (m, 2H), 7.22~7.25 (m, 1H), 3.09~3.13 (m, 2H), 2.66~2.70 (m, 2H), 2.22 (s, 3H);

Step C: N-(1-cyano-2,3-dihydro-1H-inden-5-yl)acetamide

To a stirring ice-cooled mixture of N-(1-cyano-2,3-dihydro-1H-inden-5-yl)acetamide (10.00 g, 52.9 mmol), TosMIC (15.50 g, 80.0 mmol) in 100 mL of anhydrous DME was added a solution of NaOMe (1.84 g of Na in 20 mL of anhydrous of MeOH) dropwise. After the addition was completed, the mixture was stirred overnight at ambient temperature. The reaction mixture was quenched with 4 N HCl at 0° C. and extracted with DCM. The extract was washed with bine, dried over anhydrous Na$_2$SO$_4$ and concentrated. The residue was purified with silica gel column chromatograph to give N-(1-cyano-2,3-dihydro-1H-inden-5-yl)acetamide. $^1$H-NMR (300 MHz, CDCl$_3$) δ ppm 7.90 (s, 1H), 7.66~7.70 (m, 2H), 7.22~7.25 (m, 1H), 4.03~4.05 (m, 1H), 3.10~3.15 (m, 2H), 2.35~2.43 (m, 2H), 2.17 (s, 3H).

Step D: 5-aminoindane-1-carboxylic acid

A mixture of N-(1-cyano-2,3-dihydro-1H-inden-5-yl)acetamide (19.7 g, 0.105 mol) in 175 mL of concentrated hydrogen chloride was refluxed for two days. The reaction mixture was concentrated under reduce pressure, and the residue was basified with saturated NaOH to pH 4~5. The mixture was extracted with EtOAc and the extract was dried over anhydrous Na$_2$SO$_4$ and concentrated. The residue was purified with silica gel column chromatograph to afford 5-aminoindane-1-carboxylic acid. $^1$H-NMR (300 MHz, CDCl$_3$) δ ppm 6.95~7.05 (m, 1H), 6.66~6.68 (m, 1H), 6.5~6.53 (m, 1H), 4.11~4.16 (m, 1H), 3.06~3.27 (m, 4H).

Step E: 5-(1H-tetrazol-1-yl)indane-1-carboxylic acid

A solution of 5-aminoindane-1-carboxylic acid (2.95 g, 16.7 mmol), sodium azide (1.20 g, 18.3 mmol) and triethyl orthoformate (7.42 g, 50.1 mmol) in 20 mL of actic acid was heated to 100° C. for 3 hrs. After the reaction was completed, the mixture was cooled to ambient temperature. The solution was removed under vacuum and the residue was diluted with EtOAc, washed with brine, dried over anhydrous Na$_2$SO$_4$ and concentrated. The residue was purified with silica gel column chromatograph to give the crude product, then re-crystalization from DCM to yield 5-(1H-tetrazol-1-yl)indane-1-carboxylic acid. $^1$H-NMR (400 MHz, DMSO) δ ppm 10.0 (s, 1H), 7.75 (s, 1H), 7.66~7.69 (m, 1H), 7.55 (d, J=8.1 Hz, 1H), 4.02~4.06 (m, 1H), 2.88~3.08 (m, 2H), 2.31 (q, J=8.1 Hz, 2H).

Intermediate 140

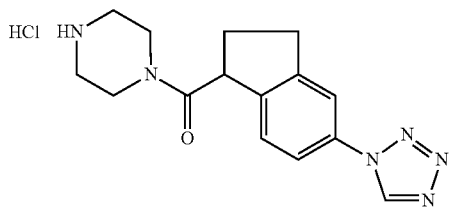 [SMILES: Cl ; O=C(C1CCc2cc(-n3cnnn3)ccc21)N1CCNCC1]

piperazin-1-yl[5-(1H-tetrazol-1-yl)-2,3-dihydro-1H-inden-1-yl]methanone hydrochloride piperazin-1-yl[5-(1H-tetrazol-1-yl)-2,3-dihydro-1H-inden-1-yl]methanone hydrochloride was prepared in two steps in an analogous fashion as described above for the synthesis of 1-(piperazin-1-yl)-2-[4-(1H-tetrazol-1-yl)phenyl]ethanone hydrochloride, starting from tert-butyl piperazine-1-carboxylate and 5-(1H-tetrazol-1-yl)-2,3-dihydro-1H-indene-1-carboxylic acid. LC/MS: [(M+1)]⁺=299.

Intermediate 141

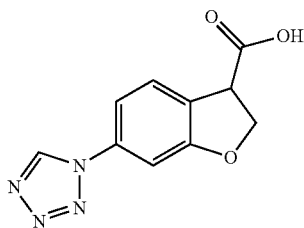 [SMILES: O=C(O)C1COc2cc(-n3cnnn3)ccc21]

6-(1H-tetrazol-1-yl)-2,3-dihydro-1-benzofuran-3-carboxylic acid

Step A: 4-bromo-2-hydroxybenzaldehyde

A solution of 3-bromophenol (100.00 g, 0.576 mol) in a mixture of 600 mL of toluene/acetonitile (2:1) was added MgCl₂ (110.6 g, 3.68 mol), paraformaldehyde (40.00 g) and the mixture was maintained at 80° C. for 1.5 h while the by-product was distilled off. A second portion of paraformaldehyde (40.00 g) was added and the mixture was stirred for 2.5 h at 80° C., and the third portion of paraformaldenhyde (30.6 g) was added and stirred for 2 h at 80° C. The reaction was quenched with cool 2.5 N hydrochloride acid, and the mixture was stirred at room temperature for 1 h to afford a biphasic solution. The aqueous phase was extracted with EtOAc. And the combined organic extracts were washed with brine, dried over anhydrous sodium sulfate and concentrated. The residue was purified by silica gel column chromatography to afford 4-bromo-2-hydroxybenzaldehyde. ¹H-NMR (400 MHz, CDCl₃) 11.10 (s, 1H), 9.86 (s, 1H), 7.40~7.43 (d, J=8.4 Hz, 1H), 7.15~7.20 (m, 2H).

Step B: ethyl 6-bromo-1-benzofuran-3-carboxylate

A solution of 4-bromo-2-hydroxybenzaldehyde (40.00 g, 0.199 mmol) in 200 mL of anhydrous DCM was added HBF₄/Et₂O (3.0 mL, 0.020 mmol), and the reaction mixture became dark. Then a solution of N₂CH₂COOEt (50 mL, 0.48 mmol) in 50 mL of dry DCM was added dropwise, kept the reaction mixture temperature below 38° C. After the addition, the mixture was stirred at ambient temperature for 1 h. The reaction mixture was concentrated under vacuum at room temperature. The residue was added 20 mL of concentrated H₂SO₄ dropwise, stirred at room temperature for 1 h before poured into ice water. Extracted with DCM and the extracts were washed with 5% NaHCO₃ solution and brine, dried over anhydrous sodium sulfate and concentrated to afford ethyl 6-bromo-1-benzofuran-3-carboxylate. ¹H-NMR (300 MHz, CDCl₃) 7.75 (s, 1H), 7.25~7.54 (m, 2H), 4.40-4.47 (q, J=7.2 Hz, 2H), 1.39~1.44 (t, J=7.2 Hz, 3H).

Step C: ethyl 6-(1,3-dioxo-1,3-dihydro-2H-isoindol-2-yl)-1-benzofuran-3-carboxylate A solution of ethyl 6-bromo-1-benzofuran-3-carboxylate (14.90 g, 55.4 mmol) in 200 mL of DMA was added potassium phthalimide (10.3 g, 55.4 mmol) and CuI (10.6 g, 55.4 mmol) and the mixture was stirred at 150° C. under nitrogen atmosphere overnight. The reaction mixture was concentrated under vacuum, and the residue was dissolved in DCM, filtered through Celite®. The filtration was concentrated and purified with silica gel column chromatograph to give ethyl 6-(1,3-dioxo-1,3-dihydro-2H-isoindol-2-yl)-1-benzofuran-3-carboxylate.

Step D: ethyl 6-amino-1-benzofuran-3-carboxylate

A mixture of ethyl 6-(1,3-dioxo-1,3-dihydro-2H-isoindol-2-yl)-1-benzofuran-3-carboxylate (4.7 g, 14.0 mmol) in 200 mL of EtOH was added NH₂NH₂H₂O (6.3 mL, 107.1 mmol, 85% in water) dropwise and the mixture was stirred for 2 h at room temperature. The solvent was removed under vacuum and the residue was dissolved in water. The mixture was extracted with EtOAc, and the combined organic phase was washed with brine, dried over anhydrous sodium sulfate and concentrated. The residue was purified with silca gel column chromatograph to give ethyl 6-amino-1-benzofuran-3-carboxylate.

Step E: methyl 6-amino-2,3-dihydro-1-benzofuran-3-carboxylate

A mixture of ethyl 6-amino-1-benzofuran-3-carboxylate (2.0 g, 9.8 mmol) in 50 mL of MeOH was added Mg filings (1.17 g, 49 mmol) ans the mixtrue was stired overnight at room temperature. The mixture was filtered and the filtrate was concentrated. The residue was then partitioned between EtOAc and water. The combined organic phase was washed with brine, dried over anhydrous sodium sulfate and concentrated. The residue was purified with silca gel column chromatograph to give methyl 6-amino-2,3-dihydro-1-benzofuran-3-carboxylate.

¹H-NMR (400 MHz, CDCl₃) δ ppm 7.02 (d, J=8.0 Hz, 1H), 6.10-6.20 (m, 2H), 4.76-4.83 (m, H), 4.54 (t, J=9.2 Hz, 1H), 4.10-4.20 (m, 1H), 3.67 (s, 3H), 3.30-3.50 (M, 2H).

Step F: methyl 6-(1H-tetrazol-1-yl)-2,3-dihydro-1-benzofuran-3-carboxylate

A solution of methyl 6-amino-2,3-dihydro-1-benzofuran-3-carboxylate (2.51 g, 13 mmol), sodium azide (1.01 g, 15.6 mmol) and triethyl orthoformate (5.92 g, 40 mmol) in 30 mL of acetic acid was heated to 100° C. for 3 hrs. After the reaction was completed, the mixture was cooled to ambient temperature and the solvent was removed under vacuum. The residue was diluted with EtOAc, washed with brine, dried over anhydrous Na₂SO₄ and concentrated. The residue was purified with silica gel column chromatograph to give the crude product, then re-crystalization from DCM to give methyl 6-(1H-tetrazol-1-yl)-2,3-dihydro-1-benzofuran-3-carboxylate.

Step G: 6-(1H-tetrazol-1-yl)-2,3-dihydro-1-benzofuran-3-carboxylic acid

To a solution of methyl 6-(1H-tetrazol-1-yl)-2,3-dihydro-1-benzofuran-3-carboxylate (3.3 g, 13.6 mmol) in 100 mL of MeOH/THF/H₂O (2/2/1) was added LiOH.H₂O (2.84 g, 67.5 mmol), and the mixture was stirred at ambient temperature overnight. The solvents were removed under vacuum, and the residue was added 50 mL of water and extracted with ether. The aqueous layer was then acidified with 4 N HCl to pH=3 in ice bath, and extracted with EtOAc. The combined organic phases were washed with brine, dried over anhydrous sodium sulfate and concentrated. The residue was re-crystallized from DCM to give 6-(1H-tetrazol-1-yl)-2,3-dihydro-1-benzofuran-3-carboxylic acid. ¹H-NMR (300 MHz, DMSO) δ ppm 7.58 (d, J=7.8 Hz, 1H), 7.32-7.50 (m, 2H), 4.71-4.92 (m, 2H), 4.45-4.55 (m, 1H); MS m/z 233 (M+1)+.

Intermediate 142

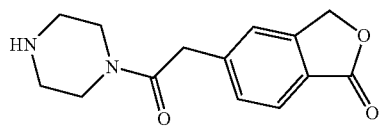 [SMILES: O=C1OCc2cc(CC(=O)N3CCNCC3)ccc21]

5-[2-oxo-2-(piperazin-1-yl)ethyl]-2-benzofuran-1(3H)-one

5-[2-Oxo-2-(piperazin-1-yl)ethyl]-2-benzofuran-1(3H)-one was prepared in an analogous fashion as described above in the synthesis of 1-(piperazin-1-yl)-2-[4-(1H-tetrazol-1-yl)phenyl]ethanone hydrochloride starting from tert-butyl piperazine-1-carboxylate and (1-oxo-1,3-dihydro-2-benzofuran-5-yl)acetic acid.

Intermediate 143

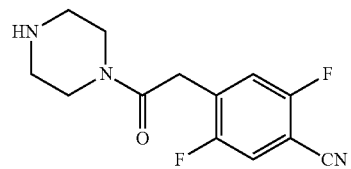 [SMILES: N#Cc1cc(F)c(CC(=O)N2CCNCC2)cc1F]

2,5-difluoro-4-[2-oxo-2-(piperazin-1-yl)ethyl]benzonitrile 2,5-difluoro-4-[2-oxo-2-(piperazin-1-yl)ethyl]benzonitrile was prepared in an analogous fashion as described above in the synthesis of 1-(piperazin-1-yl)-2-[4-(1H-tetrazol-1-yl)phenyl]ethanone hydrochloride starting from tert-butyl piperazine-1-carboxylate and (4-cyano-2,5-difluorophenyl)acetic acid. LC/MS: [(M+1)]+=266.

Intermediate 144

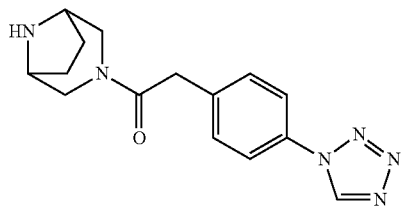 [SMILES: O=C(Cc1ccc(-n2cnnn2)cc1)N1CC2CCC(C1)N2]

1-(3,8-diazabicyclo[3.2.1]oct-3-yl)-2-[4-(1H-tetrazol-1-yl)phenyl]ethanone 1-(3,8-Diazabicyclo[3.2.1]oct-3-yl)-2-[4-(1H-tetrazol-1-yl)phenyl]ethanone was prepared in an analogous fashion as described above in the synthesis of 1-(piperazin-1-yl)-2-[4-(1H-tetrazol-1-yl)phenyl]ethanone hydrochloride starting from [4-(1H-tetrazol-1-yl)phenyl]acetic acid and tert-butyl 3,8-diazabicyclo[3.2.1]octane-8-carboxylate. LC/MS: [(M+1)]+=299.

Intermediate 145

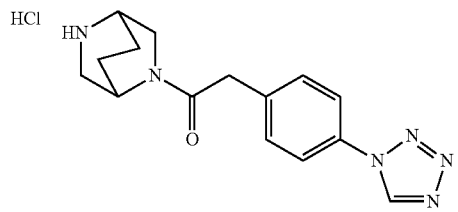 [SMILES: Cl ; O=C(Cc1ccc(-n2cnnn2)cc1)N1CC2CCC1CN2]

1-(2,5-diazabicyclo[2.2.2]oct-2-yl)-2-[4-(1H-tetrazol-1-yl)phenyl]ethanone hydrochloride 1-(2,5-Diazabicyclo[2.2.2]oct-2-yl)-2-[4-(1H-tetrazol-1-yl)phenyl]ethanone hydrochloride was prepared in an analogous fashion as described above in the synthesis of 1-(piperazin-1-yl)-2-[4-(1H-tetrazol-1-yl)phenyl]ethanone hydrochloride starting from [4-(1H-tetrazol-1-yl)phenyl]acetic acid and commercially available tert-butyl 2,5-diazabicyclo[2.2.2]octane-2-carboxylate. LC/MS: [(M+1)]+=299

Intermediate 146

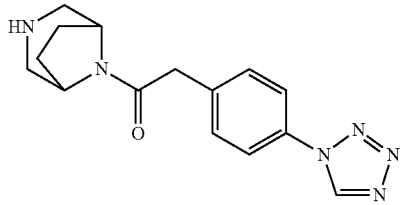 [SMILES: O=C(Cc1ccc(-n2cnnn2)cc1)N1C2CCC1CNC2]

1-(3,8-diazabicyclo[3.2.1]oct-8-yl)-2-[4-(1H-tetrazol-1-yl)phenyl]ethanone

Step A: 1-(3-benzyl-3,8-diazabicyclo[3.2.1]oct-8-yl)-2-[4-(1H-tetrazol-1-yl)phenyl]ethanone Commercially available 3-benzyl-3,8-diazabicyclo[3.2.1]octane (500 mg, 2.45 mmol) was combined with [4-(1H-tetrazol-1-yl)phenyl]acetic acid (500 mg, 2.45 mmol), EDC (469 mg, 2.45 mmol), and triethylamine (1.02 mL, 7.34 mmol) in DCM (10 mL) and the resulting mixture was stirred at room temperature for 18 h. The reaction mixture was diluted with DCM and washed with saturated sodium bicarbonate and brine. The organic layer was dried over MgSO4, filtered, and concentrated. Purification by MPLC eluting with a 0-100% ethyl acetate/hexanes gradient over 20 minutes followed by 100% ethyl acetate for 10 minutes afforded the title compound. LC/MS: [(M+1)]+=389.

Step B: 1-(3,8-diazabicyclo[3.2.1]oct-8-yl)-2-[4-(1H-tetrazol-1-yl)phenyl]ethanone 1-(3-Benzyl-3,8-diazabicyclo[3.2.1]oct-8-yl)-2-[4-(1H-tetrazol-1-yl)phenyl]ethanone (580 mg, 1.49 mmol) was dissolved in ethanol (20 mL), concentrated HCl solution was added (37%, 2.0 mL, 24.4 mmol), followed by palladium on carbon (200 mg). The mixture was degassed and stirred under hydrogen gas at room temperature overnight. The reaction mixture was filtered through a Celite® plug and the filtrate was concentrated. The product was partitioned between DCM and saturated sodium bicarbonate solution, then the organic layer was dried over MgSO₄. Purification by MPLC eluting with 10% methanol in DCM afforded the title compound. LC/MS: [(M+1)]⁺=299.

Intermediate 147

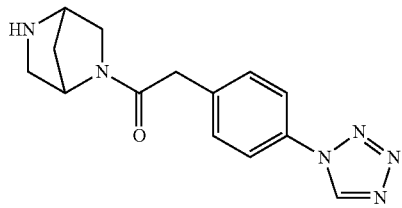 [SMILES: O=C(Cc1ccc(-n2cnnn2)cc1)N1CC2CC1CN2]

1-(2,5-diazabicyclo[2.2.1]hept-2-yl)-2-[4-(1H-tetrazol-1-yl)phenyl]ethanone
Step A: benzyl 5-{[4-(1H-tetrazol-1-yl)phenyl]acetyl}-2,5-diazabicyclo[2.2.1]heptane-2-carboxylate

[4-(1H-Tetrazol-1-yl)phenyl]acetic acid (303 mg, 1.48 mmol) was combined with benzyl 2,5-diazabicyclo[2.2.1]heptane-2-carboxylate (399 mg, 1.48 mmol), EDC (341 mg, 1.78 mmol), and triethylamine (0.248 mL, 1.78 mmol) in DCM (30 mL) and stirred overnight at room temperature. The mixture was washed with 1 M HCl solution, saturated sodium bicarbonate solution, and brine. The organic layer was dried over MgSO₄, filtered and concentrated. The crude product was purified by MPLC eluting with a 0-5% gradient of methanol in ethyl acetate to afford benzyl 5-{[4-(1H-tetrazol-1-yl)phenyl]acetyl}-2,5-diazabicyclo[2.2.1]heptane-2-carboxylate. LC/MS: [(M+1)]⁺=419;

Step B: 1-(2,5-diazabicyclo[2.2.1]hept-2-yl)-2-[4-(1H-tetrazol-1-yl)phenyl]ethanone Benzyl 5-{[4-(1H-tetrazol-1-yl)phenyl]acetyl}-2,5-diazabicyclo[2.2.1]heptane-2-carboxylate (517 mg, 1.24 mmol) and palladium on carbon (131 mg) in methanol (50 mL) were stirred under a hydrogen atmosphere (balloon) for overnight. The reaction mixture was filtered and concentrated to afford 1-(2,5-diazabicyclo[2.2.1]hept-2-yl)-2-[4-(1H-tetrazol-1-yl)phenyl]ethanone. LC/MS: [(M+1)]⁺=285.

Intermediate 148

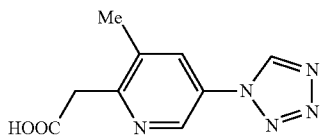 [SMILES: Cc1cc(-n2cnnn2)cnc1CC(=O)O]

[1-methyl-5-(1H-tetrazol-1-yl)pyridin-2-yl]acetic acid

[3-Methyl-5-(1H-tetrazol-1-yl)pyridin-2-yl]acetic acid was prepared in five steps starting from commercially available 2-chloro-3-methyl-5-nitropyridine in an analogous fashion as described for the synthesis of [6-(1H-tetrazol-1-yl)pyridin-3-yl]acetic acid (Method 1, Steps B-F). This compound was more stable stored as the Li salt. LC-MS (IE, m/z): 192 [M+1-N2]⁺, small peak 220 [M+1]⁺.

Intermediate 149

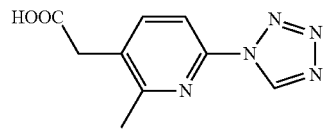

[2-methyl-6-(1H-tetrazol-1-yl)pyridin-3-yl]acetic acid
Step A: 5-chloro-6-methylpyridin-2-amine A solution of 6-methylpyridin-2-amine (10.80 g, 100 mmol) in 50 mL of dry DMF was added a solution of NCS (13.4 g, 100 mmol) in 60 mL of dry DMF dropwise at 0° C. over 20 min. The resulting brown yellow solution was stirred at 0° C. for 1 hour, and at room temperature for 3 hours, then poured to 300 mL of ice-water. The resulting mixture was extracted with EtOAc, washed with water and brine, dried over anhydrous sodium sulfate and concentrated. The residue was purified via column chromatograph to afford 5-chloro-6-methylpyridin-2-amine.
Subsequent steps: [2-methyl-6-(1H-tetrazol-1-yl)pyridin-3-yl]acetic acid

[2-Methyl-6-(1H-tetrazol-1-yl)pyridin-3-yl]acetic acid was prepared from 5-chloro-6-methylpyridin-2-amine in six steps in an analogous fashion to that described for the synthesis of [6-(1H-tetrazol-1-yl)pyridin-3-yl]acetic acid (Method 1, Steps A-F). LC-MS (IE, m/z): 192 [M+1-N2]⁺, 220 [M+1]⁺. ¹H-NMR (400 MHz, CDCl₃) δ 9.88 (s, 1H), 7.9 (d, 1H), 7.85 (d, 1H), 3.79 (s, 2H), 2.59 (s, 3H).

Intermediate 150

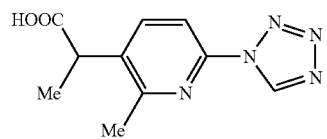

2-[2-methyl-6-(1H-tetrazol-1-yl)pyridin-3-yl]propanoic acid
Step A: 3-chloro-2-methyl-6-nitropyridine A flask containing 100 mL of conc. H₂SO₄ was added 30% H₂O₂ (50 mL) at 0° C. and then a solution of 5-chloro-6-methylpyridin-2-amine (10.0 g, 70 mmol) in 50 mL of conc. H₂SO₄ was added at 0° C. The mixture was stirred for 20 hours at room temperature. The mixture was poured into ice water under vigorously stirring. The resulting solid was filtered. The solid was recrystallized with ethanol to give 3-chloro-2-methyl-6-nitropyridine.
Step B: tert-butyl ethyl (2-methyl-6-nitropyridin-3-yl)propanedioate To a suspension of NaH (60% in oil, 1.4 g, 36 mmol)) in DMF (50 mL) was added 3 (6.8 g, 36 mmol) at room temperature. The mixture was stirred for 30 min. A solution of 3-chloro-2-methyl-6-nitropyridine (4.8 g, 28 mmol) in DMF (10 mL) was added. The mixture was heated to 80° C. and stirred for 5 hours. Cooled to ambient temperature, poured to ice/water, extracted with EtOAc. The combined organic layer was washed with brine, dried over anhydrous Na₂SO₄, concentrated and the residue was purified by column chromatograph silca gel to give tert-butyl ethyl (2-methyl-6-nitropyridin-3-yl)propanedioate. $^1$H-NMR (400 MHz, CDCl$_3$) δ 8.06-8.13 (m, 2H), 4.85 (s, 1H), 2.68 (s, 3H), 1.45 (s, 9H), 1.28 (t, J=7.2 Hz, 3H).

Step C: tert-butyl ethyl methyl(2-methyl-6-nitropyridin-3-yl)propanedioate

To a suspension of NaH (60% in oil, 0.8 g, 19 mmol) in DMF (50 mL) was added tert-butyl ethyl (2-methyl-6-nitropyridin-3-yl)propanedioate (4 g, 13 mmol) at room temperature. The mixture was stirred for 1 hour and CH$_3$I (3.7 g, 26 mmol) was added. The mixture was heated to 40° C. for 2 hours. Cooled to ambient temperature, the mixtue was poured to ice/water, extracted with EtOAc. The combined organic layer was washed with brine, dried over anhydrous Na$_2$SO$_4$, concentrated and the residue was purified by column chromatograph silca gel to give tert-butyl ethyl rnethyl(2-methyl-6-nitropyridin-3-yl)propanedioate. $^1$H-NMR (400 MHz, CDCl$_3$) δ 8.01 (d, J=8.6 Hz, 1H), 7.79 (d, J=8.6 Hz, 1H), 4.19-4.27 (m, 2H), 2.59 (s, 3H), 1.85 (s, 3H), 1.45 (s, 9H), 1.28 (t, J=7.0 Hz, 3H).

Step D: ethyl 2-(2-methyl-6-nitropyridin-3-yl)propanoate

A mixture of tert-butyl ethyl methyl(2-methyl-6-nitropyridin-3-yl)propanedioate (2.8 g, 8 mmol) in a mixed solution of TFA/DCM (30 mL/30 mL) was stirred over night at room temperature. The mixture was concentrated under reduce pressure to give ethyl 2-(2-methyl-6-nitropyridin-3-yl)propanoate.

Step E: ethyl 2-(6-amino-2-methylpyridin-3-yl)propanoate

A mixture of ethyl 2-(2-methyl-6-nitropyridin-3-yl)propanoate (1.6 g, 6.7 mmol), 10% Pd/C (0.1 g) and AcOH (3 mL) in MeOH (50 mL) was stirred over night under 1 atm of H$_2$ at room temperature. The mixture was filtered and concentrated to give the crude product ethyl 2-(6-amino-2-methylpyridin-3-yl)propanoate.

Step F: ethyl 2-[2-methyl-6-(1H-tetrazol-1-yl)pyridin-3-yl]propanoate

To a mixture of ethyl 2-(6-amino-2-methylpyridin-3-yl)propanoate (1.6 g, 7.6 mmol), CH(OEt)$_3$ (3.4 g, 22.8 mmol) in AcOH (50 mL) was added NaN$_3$ (0.6 g, 9.2 mmol) at room temperature. The mixture was heated to 90° C. and stirred for 50 min. The mixture was cooled to ambient temperature and stand over night. The mixture was concentrated under reduce pressure. Water was added, and the mixture was extracted with EtOAc. The combined organic layer was washed with brine, dried over anhydrous Na$_2$SO$_4$, concentrated and the residue was purified by column chromatograph to give compound ethyl 2-[2-methyl-6-(1H-tetrazol-1-yl)pyridin-3-yl]propanoate.

Step G: 2-[2-methyl-6-(1H-tetrazol-1-yl)pyridin-3-yl]propanoic acid

A mixture of ethyl 2-[2-methyl-6-(1H-tetrazol-1-yl)pyridin-3-yl]propanoate (300 mg, 1.1 mmol) in 8 mL of MeOH/THF/H$_2$O (2:2:1) was added LiOH.H$_2$O (75 mg, 1.8 mmol) and stirred for 30 min at room temperature. The reaction was acidified with citric acid until pH about 3~4. Extracted with EtOAc, the combined organic layer was washed with brine, dried over anhydrous Na$_2$SO$_4$, concentrated to give 2-[2-methyl-6-(1H-tetrazol-1-yl)pyridin-3-yl]propanoic acid. $^1$H-NMR (400 MHz, CDCl$_3$) δ ppm 9.51 (s, 1H), 7.86-7.91 (m, 2H), 4.00-4.05 (m, 1H), 2.64 (s, 3H), 1.57 (d, J=7.8 Hz, 3H).

Intermediate 151

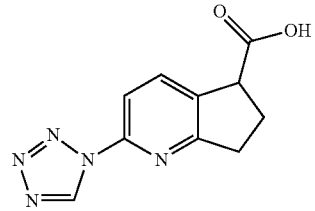 [SMILES: O=C(O)C1CCc2nc(-n3cnnn3)ccc21]

2-(1H-tetrazol-1-yl)-6,7-dihydro-5H-cyclopenta[b]pyridine-5-carboxylic acid

Step A: 6,7-Dihydro-5H-cyclopenta[b]pyridin-5-ol

To a solution of 6,7-dihydro-5H-cyclopenta[b]pyridine (5.0 g, 42 mmol) and MgSO$_4$ (10 g, 84 mmol) in Acetone (250 mL) was added a solution of KMnO$_4$ (13 g, 84 mmol) in water (500 mL) at 60 degrees. The mixture was allowed to stir for 30 minutes at 60° C. IPA was slowly added to quench excess KMnO$_4$. The reaction was filtered through a pad of Celite®. The filtrate was concentrated under reduced pressure, and pumped on a high vacuum pump to ensure complete removal of water. The residue was dissolved in ethanol (200 mL), and cooled with an ice bath. To this solution was slowly added NaBH$_4$ (3.2 g, 84 mmol). When TLC showed complete reduction, water was added to quench excess NaBH$_4$. Ethanol was removed on a rotavapor. The crude material was dissolved in EtOAc, washed with aq. NaHCO$_3$, dried over sodium sulfate, and purified by MPLC (MeOH-DCM: 0-7%). The desired 6,7-dihydro-5H-cyclopenta[b]pyridin-5-ol was collected. LC-MS (IE, m/z): 136 [M+1]$^+$;

Step B: 6,7-dihydro-5H-cyclopenta[b]pyridine-5-carbonitrile

To a solution of 6,7-Dihydro-5H-cyclopenta[b]pyridin-5-ol (2.7 g, 20 mmol) in CHCl$_3$ (30 mL) was dropped thionyl chloride (4.4 mL, 60 mmol) slowly at 0° C. The mixture was allowed to stir at 0° C. for an additional 3 hours when the addition was done. The solvent was removed under reduced pressure, and the residue was pumped under high vacuum for 15 more minutes. The crude material was dissolved in CHCl$_3$ (300 mL), and washed with pH=7 buffer (200 mL). The buffer was extracted once with IPA-CHCl$_3$ (1:3, 100 mL). The organic extractions were combined, dried over sodium sulfate, and concentrated. To the flask was added tetrabutylammonium cynanide (6.4 g, 24 mmol) and acetonitrile (40 mL). The mixture was heated to 50° C. for 16 hours. LC at that point showed complete reaction. After removing acetonitrile on a rotary evaporator, the residue was dissolved in water, extracted three times with IPA-CHCl$_3$ (1:3, 100 mL each). The extractions were combined and purified by MPLC (DCM-MeOH). The desired 6,7-dihydro-5H-cyclopenta[b]pyridine-5-carbonitrile was collected after removal of solvent. LC-MS (IE, m/z): 154 [M+1]$^+$.

Step C: Methyl 6,7-dihydro-5H-cyclopenta[b]pyridine-5-carboxylate 1-oxide

To a flask charged with 6,7-dihydro-5H-cyclopenta[b]pyridine-5-carbonitrile (2.6 g, 18 mmol) and a stir bar was added concentrated HCl (5 mL). The mixture was heated to 70° C. for 15 minutes. LC suggested complete hydrolysis. The volatiles were removed under reduced pressure, and the residue was pumped under high vacuum for 15 minutes. To the flask was added MeOH (20 mL) and toluene (40 mL). The solution was cooled to 0° C. with an ice bath, which was followed by addition of TMS-diazomethane (36 mL, 72 mmol). When LC showed complete reaction, excess TMS-diazomethane was decomposed with HOAc, and the crude product was purified by MPLC. LC-MS (IE, m/z): 179 [M+1]$^+$; The adduct obtained above was dissolved in CHCl$_3$ (50 mL) and cooled to 0° C. To the solution was added m-CPBA (3.1 g, 18 mmol). The mixture was allowed to stir for 3 hours. LC at that point showed complete reaction. Sodium thiosulfate solution was added to consume excess m-CPBA, and the crude product was extracted with IPA-CHCl$_3$ (1:3, 100 mL) three times. The extractions were combined, dried over sodium sulfate, adsorbed onto silica gel, and purified by MPLC (DCM: MeOH with 10% aq NH$_4$OH). After removal of solvent, methyl 6,7-dihydro-5H-cyclopenta[b]pyridine-5-carboxylate 1-oxide was collected. LC-MS (IE, m/z): 194 [M+1]$^+$;

Step D: methyl 2-amino-6,7-dihydro-5H-cyclopenta[b]pyridine-5-carboxylate

To a solution of methyl 6,7-dihydro-5H-cyclopenta[b]pyridine-5-carboxylate 1-oxide (700 mg, 3.6 mmol) in CF$_3$-toluene (20 mL) and CHCl$_3$ (20 mL) was added tert-butylamine (3.8 mL, 36 mmol). The solution was cooled to 0° C. in an ice bath. To the solution was added p-toluenesulfonic anhydride (3.5 g, 10.9 mmol) in small portions until all SM was consumed according to LC-MS. The volatiles were removed under reduced pressure, and the residue was redissolved in TFA (20 mL). The dark solution was heated to 70° C. for 2 hours. LC showed mostly product, with a little bit SM remaining. The reaction was stopped at that point. TFA was removed on a rotavapor, and the residue was taken up in saturated sodium carbonate, extracted three times with IPA-CHCl$_3$ (1:3, 50 mL each). The extractions were combined, dried over sodium sulfate, adsorbed onto silica gel, and purified by MPLC (DCM:MeOH with 10% aq NH$_4$OH). After removal of solvent was collected as the desired methyl 2-amino-6,7-dihydro-5H-cyclopenta[b]pyridine-5-carboxylate. LC-MS (IE, m/z): 193 [M+1]$^+$;

Step E: methyl 2-(1H-tetrazol-1-yl)-6,7-dihydro-5H-cyclopenta[b]pyridine-5-carboxylate To a flask charged with methyl 2-amino-6,7-dihydro-5H-cyclopenta[b]pyridine-5-carboxylate (500 mg, 2.6 mmol) and a stir bar was added sodium azide (340 mg, 5.2 mmol), triethyl orthoformate (2.2 mL, 13 mmol), and HOAc (10 mL). The mixture was heated to 100° C. for 2 hours. The solvent was removed on a rotavapor, and the residue was taken into aq. Sodium carbonate, extracted with EtOAc (50 Mk×3), dried over sodium sulfate, and purified by MPLC (DCM-MeOH). After removal of solvent, an off-white solid was collected as the desired methyl 2-(1H-tetrazol-1-yl)-6,7-dihydro-5H-cyclopenta[b]pyridine-5-carboxylate. LC-MS (IE, m/z): 248 [M+1]$^+$;

Step F: 2-(1H-tetrazol-1-yl)-6,7-dihydro-5H-cyclopenta[b]pyridine-5-carboxylicacid To a solution of methyl 2-(1H-tetrazol-1-yl)-6,7-dihydro-5H-cyclopenta[b]pyridine-5-carboxylate (460 mg, 1.9 mmol) in THF (6 mL) was added lithium hydroxide (1.0 N aq. 3.8 mL, 3.8 mmol). The mixture was allowed to stir at 0° C. for 2 hours. LC at that point showed complete reaction. The reaction was diluted with water (10 mL). The pH was carefully adjusted to about 5 with 1N HCl. The solution was then extracted with EtOAc (30 mL×3). The extractions were combined, dried over sodium sulfate, and concentrated to furnish the title compound. LC-MS (IE, m/z): 231 [M+1]$^+$; $^1$H-NMR (500 MHz, CD$_3$OD) δ ppm 9.87 (s, 1H), 8.09 (d, J=8.0 Hz, 1H), 7.90 (d, J=8.0 Hz, 1H), 4.20 (t, J=8.0 Hz, 1H), 3.15 (m, 1H), 3.08 (m, 1H), 2.51 (m, 2H).

Intermediate 152

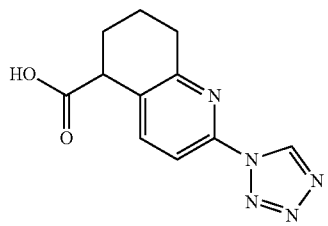 [SMILES: O=C(O)C1CCCc2nc(-n3cnnn3)ccc21]

2-(1H-tetrazol-1-yl)-5,6,7,8-tetrahydroquinoline-5-carboxylic acid

Step A: methyl 5,6,7,8-tetrahydroquinoline-5-carboxylate

Methyl quinoline-5-carboxylate (3.67 g, 19.61 mmol) was dissolved in TFA (60 ml) and added platinum oxide (0.49 g, 2.16 mmol) then hydrogenated at room temperature overnight. Filtered off the catalyst and evaporated to dryness. The residue was chromatographed through a 120 g ISCO Redi-sep column and eluted with 5% of (10% NH4OH in MeOH) in DCM to yield methyl 5,6,7,8-tetrahydroquinoline-5-carboxylate $^1$H-NMR (600 MHz, CDCl$_3$): δ ppm 8.42 (d, J=3.7 Hz, 1H), 7.485 (d, J=7.7 Hz, 1H), 7.06-7.08 (m, 1H), 3.82 (t, J=5.6 Hz, 1H), 3.72 (d, J=3.2 Hz, 3H), 3.02-2.93 (m, 1H), 2.88-2.93 (m, 1H), 2.16-2.20 (m, 1H), 1.97-2.05 (m, 2H), 1.85-1.90 (m, 1H); LC-MS: M+1=192.

Step B: methyl 5,6,7,8-tetrahydroquinoline-5-carboxylate-1-oxide 5,6,7,8-tetrahydroquinoline-5-carboxylate (2.05 g, 10.72 mmol) was dissolved in chloroform (100 ml) and added m-chloroperbenzoic acid (2.77 g, 16.08 mmol). The reaction was stirred at room temperature for 1½ hr. The reaction was washed with NaHCO$_3$ 2×, brine 1×, dried over Na$_2$SO$_4$ filtered and evaporated to dryness. The residue chromatographed through 120 g ISCO Redi-sep column and eluted with gradient solvent system of 100% ethyl acetate to 10% MeOH/90% ETOAc to yield methyl 5,6,7,8-tetrahydroquinoline-5-carboxylate-1-oxide. $^1$H-NMR (600 MHz, CDCl$_3$): δ ppm 8.24 (d, J=6 Hz, 1H), 7.11-7.16 (m, 2H), 3.84 (t, J=3.8 Hz, 1H); H), 3.74 (s, 3H), 3.04-3.09 (m, 1H), 2.86-2.92 (m, 1H), 2.19-2.24 (m, 1H), 1.90-2.0 (m, 2H), 1.78 (b, 1H); LC-MS: M+1=208

Step C: methyl 2-amino-5,6,7,8-tetrahydroquinoline-5-carboxylate

Methyl 5,6,7,8-tetrahydroquinoline-5-carboxylate-1-oxide (2.05 g, 9.89 mmol) and t-butyl amine (5.22 ml, 49.5 mmol) were dissolved in benzotrifluoride (50 ml) and cooled with an ice bath. The p-toluenesulfonic anhydride (6.46 g, 19.79 mmol) was added portionwise keeping the reaction's internal temperature below 5° C. The reaction was monitored and after 10 mins. when the LC-MS showed M+1=263 and 207 (M-56) at 1.20 indicating formation of intermediate methyl 2-(tert-butylamino)-5,6,7,8-tetrahydroquinoline-5-carboxylate. Trifluoroacetic acid (10 ml) was then added to the reaction mixture and heated at 70° C. for 5 hrs. The reaction was cooled and evaporated to dryness. The residue was taken up with water and the pH was adjusted to pH ~8 with 5N NaOH. The reaction was extraction with DCM 2×. The combined DCM layers were washed with brine and dried over Na$_2$SO$_4$, filtered and evaporated to dryness. The residue was chromatographed through a 80 g ISCO Redi-sep column and eluted with solvent system of 5%(10% NH₄OH in MeOH)/DCM to yield methyl 2-amino-5,6,7,8-tetrahydroquinoline-5-carboxylate. ¹H-NMR (600 MHz, CDCl₃): δ ppm 7.27 (d, J=8.3 Hz, 1H), 6.35 (d, J=8.3 Hz, 1H), 4.40 (b, 2H), 3.73 (s, 3H), 3.70 (t, J=6.9 Hz, 1H), 2.68-2.82 (m, 2H) 2.12-2.17 (m, 1H), 1.93-2.12 (m, 2H), 1.81-1.86 (m, 1H); LC-MS: M+1=207;

Step D: methyl 2-(1H-tetrazol-1-yl)-5,6,7,8-tetrahydroquinoline-5-carboxylate

Methyl 2-amino-5,6,7,8-tetrahydroquinoline-5-carboxylate (850 mg, 4.12 mmol) was stirred in acetic acid (15 ml) and tri-ethyl orthoformate (1.373 ml, 8.24 mmol) followed by sodium azide (482 mg, 7.42 mmol) then heated to 80° C. for 3 hrs. The reaction was cooled and evaporated to dryness. The mixture was taken up in DCM and washed with saturated NaHCO₃ solution, then with brine. The organic layer was dried over Na₂SO₄, filtered and evaporated to dryness. The residue was chromatographed through a 40 g ISCO Redi-sep column and eluted with ethyl acetate:hexane (2:3) to yield methyl 2-(1H-tetrazol-1-yl)-5,6,7,8-tetrahydroquinoline-5-carboxylate. ¹H-NMR (600 MHz, DMSO): δ ppm 10.07 (s, 1H), 7.92 (d, J=8.4 Hz, 1H), 7.82 (d, J=8.4 Hz, 1H), 4.06 (t, J=5.4 Hz, 1H), 3.65 (s, 3H), 2.83-2.93 (m, 2H), 2.07-2.12 (b, 1H), 1.95-2.0 (m, 1H), 1.86-1.90 (m, 2H).

Step E: 2-(1H-tetrazol-1-yl)-5,6,7,8-tetrahydroquinoline-5-carboxylic acid

Methyl 2-(1H-tetrazol-1-yl)-5,6,7,8-tetrahydroquinoline-5-carboxylate (1.04 g, 4.01 mmol) and lithium hydroxide (0.202 g, 4.81 mmol) were stirred in a mixture of tetrahydrofuran (10 ml)/water (10.00 ml) for 75 mins. The tlc showed some 20% starting material so more LiOH (50 mg, 1.19 mmol) was added and stirred for another 1 hr. The reaction was adjusted with 2N HCl (3 ml, 6 mmol) to pH 4-5 then extracted with ethyl acetate 2×. The ethyl acetate layers were combined and dried over Na₂SO₄, filtered and evaporated to dryness to yield 2-(1H-tetrazol-1-yl)-5,6,7,8-tetrahydroquinoline-5-carboxylic acid. ¹H-NMR (600 MHz, CDCl₃): δ ppm 9.53 (s, 1H), 7.85-7.89 (q, 2H), 3.945 (t, J=5.46 Hz, 1H), 3.01-3.05 (m, 1H), 2.90-2.96 (m, 1H), 2.29-2.44 (m, 1H), 2.04-2.13 (m, 2H), 1.95-2.01 (m, 1H); LC-MS: (M+1)-28=218.

Intermediate 153

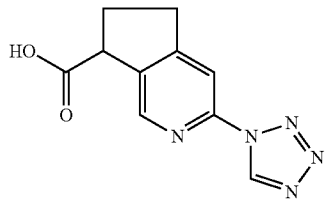 [SMILES: O=C(O)C1CCc2cc(-n3cnnn3)ncc21]

3-(1H-tetrazol-1-yl)-6,7-dihydro-5H-cyclopenta[c]pyridine-7-carboxylic acid

Step A: N-(5-bromo-4-methylpyridin-2-yl)-2,2-dimethylpropanamide

To a solution of 5-bromo-4-methylpyridin-2-amine (20.6 g, 110 mmol) in 80 mL of pyridine was added trimethylacetyl chloride (19.9 g, 165 mmol) dropwise. The reaction mixture was allowed to stir at room temperature for 12 hours. The mixture was diluted with water and extracted with dichloromethane (3×). The organic layers were washed with water (2×), and brine, dried over Na₂SO₄ and concentrated to provide an oil, which was purified by chromatography. On elution with 2→20% EtOAc/hexanes N-(5-bromo-4-methylpyridin-2-yl)-2,2-dimethylpropanamide was obtained. ¹H NMR (500 MHz, CDCl₃), δ 8.30 (s, 1H), 8.27 (s, 1H), 8.22 (br s, 1H), 2.43 (s, 3H), 1.35 (s, 9H); LC/MS (M+1)⁺=270.9;

Step B: N-[5-bromo-4-(2-hydroxyethyl)pyridin-2-yl]-2,2-dimethylpropanamide

A solution of N-(5-bromo-4-methylpyridin-2-yl)-2,2-dimethylpropanamide (30.0 g, 111 mmol) in THF (80 mL) was cooled in an ice bath and treated dropwise with a solution of lithium diisopropylamide in heptane/tetrahydrofuran/ethylbenzene (2.0 M, 138 mL) After stirring 1 h, the solution was treated with paraformaldehyde (24.9 g, 277 mmol) and allowed to warm gradually to room temperature while stirring 12 h. The mixture was diluted with saturated sodium bicarbonate solution and extracted with ethyl acetate (3×). The combined organic layers were washed with brine, dried (Na₂SO₄), filtered and concentrated. Purification by MPLC (eluent 6-50% ethyl acetate/hexanes) afforded N-[5-bromo-4-(2-hydroxyethyl)pyridin-2-yl]-2,2-dimethylpropanamide. ¹H NMR (500 MHz, CDCl₃), δ 8.33 (s, 1H), 8.30 (s, 1H), 8.02 (br s, 1H), 3.98 (dd, J=6.5, 6.5 Hz, 2H), 3.04 (dd, J=6.5, 6.5 Hz, 2H), 1.34 (s, 9H); LC/MS (M+1)⁺=300.87;

Step C: tert-butyl{6-[(2,2-dimethylpropanoyl)amino]-4-(2-hydroxyethyl)pyridin-3-yl}acetate A 250 mL round bottomed flask was charged with N-[5-bromo-4-(2-hydroxyethyl)pyridin-2-yl]-2,2-dimethylpropanamide (1.9 g, 6.31 mmol), tris(dibenzylideneacetone)dipalladium(0) (0.173 g, 0.189 mmol), and 2-(dicyclohexylphosphino)-2',4',6'-triisopropylbiphenyl (0.180 g, 0.379) and the mixture was flushed with nitrogen for 30 min. tetrahydrofuran was added, followed by a solution of 2-tert-butoxy-2-oxoethylzinc chloride in diethyl ether (0.5 M, 47.9 mL) and the mixture was placed in an oil bath maintained at 45° C. After 12 h, the reaction was recharged with tris(dibenzylideneacetone)dipalladium(0) (0.173 g, 0.189 mmol) and 2-(dicyclohexylphosphino)-2',4',6'-triisopropylbiphenyl (0.180 g, 0.379) and an additional quandity of 2-tert-butoxy-2-oxoethylzinc chloride in diethyl ether (0.5 M, 12.6 mL) was added. After stirring an additional 2 h in the 45° C. bath, the reaction mixture was diluted with ethyl acetate and 10% ammonium hydroxide solution, filtered to remove solids, and the layers separated. The organic layer was washed with water and brine, dried (Na₂SO₄), filtered and concentrated. Purification by MPLC (eluent 9-90% ethyl acetate/hexanes) afforded tert-butyl{6-[(2,2-dimethylpropanoyl)amino]-4-(2-hydroxyethyl)pyridin-3-yl}acetate. ¹H NMR (500 MHz, CDCl₃), δ 8.30 (br s, 1H), 8.17 (s, 1H), 7.99 (s, 1H), 3.88 (dd, J=6.5, 6.5 Hz, 2H), 3.55 (s, 2H), 2.88 (dd, J=6.5, 6.5 Hz, 2H), 1.40 (s, 9H), 1.28 (s, 9H); LC/MS (M+1)⁺=337.0;

Step D: tert-butyl{4-(2-bromoethyl)-6-[(2,2-dimethylpropanoyl)amino]pyridin-3-yl}acetate A mixture of tert-butyl{6-[(2,2-dimethylpropanoyl)amino]-4-(2-hydroxyethyl)pyridin-3-yl}acetate (2.30 g, 6.84 mmol) with imidazole (0.558 g, 8.20 mmol) in dichloromethane (50 mL) was treated with triphenylphosphine (1.79 g, 6.84 mmol) and carbon tetrabromide (2.72 g, 8.20 mmol). The reaction mixture was allowed to stir at room temperature for 2 h, then was diluted with water and the layers separated. The organic layer was washed successively with 5% hydrochloric acid, saturated sodium bicarbonate solution, and brine, then dried (Na₂SO₄), filtered and concentrated. The residue was filtered through a short silica plug (20% EtOAc:hexanes eluent) to afford tert-butyl{4-(2-bromoethyl)-6-[(2,2-dimethylpropanoyl)amino]pyridin-3-yl}acetate which was used immediately in the next step. LC/MS (M+1)⁺=398.9;

Step E: tert-butyl 3-[(2,2-dimethylpropanoyl)amino]-6,7-dihydro-5H-cyclopenta[c]pyridine-7-carboxylate A solution of tert-butyl{4-(2-bromoethyl)-6-[(2,2-dimethylpropanoyl)amino]pyridin-3-yl}acetate (6.5 g, 16.3 mmol) in tetrahydrofuran (50 mL) cooled in a dry ice-acetone bath was treated with a solution of lithium diisopropylamide in tetrahydrofuran (50 mL) (prepared from diisopropylamine (3.79 g, 34.7 mmol) and n-butyllithium (2.5 M, 13.7 mL) dropwise via addition funnel over 1 h. After complete addition, the reaction stirred an additional 1 h, then was quenched with saturated sodium bicarbonate solution and allowed to warm to room temperature. The resulting mixture was diluted with ethyl acetate and water and transferred to a reparatory funnel. The layers were separated and the aqueous extracted with ethyl acetate (2×). The combined organics were washed with brine, dried ($Na_2SO_4$), filtered and concentrated. Purification of the resulting residue (2–>25% EtOAc/hexanes eluent) provided tert-butyl 3-[(2,2-dimethylpropanoyl)amino]-6,7-dihydro-5H-cyclopenta[c]pyridine-7-carboxylate. $^1$H NMR (500 MHz, $CDCl_3$), δ 8.27 (s, 1H), 8.16 (s, 1H), 8.06 (br s, 1H), 3.96 (dd, J=5.0, 5.5 Hz, 1H), 3.06 (m, 1H), 2.90 (m, 1H), 2.45 (m, 1H), 2.32 (m, 1H)-1), 1.47 (s, 9H), 1.32 (s, 9H); LC/MS $(M+1)^+=319.0$;

Step F: 3-amino-6,7-dihydro-5H-cyclopenta[c]pyridine-7-carboxylic acid

A solution of 3-[(2,2-dimethylpropanoyl)amino]-6,7-dihydro-5H-cyclopenta[c]pyridine-7-carboxylate (0.624 mg, 1.96 mmol) in 6N hydrochloric acid (25 mL) was heated to reflux for 24 h. The solution was cooled and concentrated to provide 3-amino-6,7-dihydro-5H-cyclopenta[c]pyridine-7-carboxylic acid which was used without further purification in the next step. LC/MS $(M+1)^+=179.0$;

Step G: methyl 3-amino-6,7-dihydro-5H-cyclopenta[c]pyridine-7-carboxylate

To a solution of 3-amino-6,7-dihydro-5H-cyclopenta[c]pyridine-7-carboxylic acid from Step F in methanol (10 mL) was treated dropwise with a solution of trimethylsilyl diazomethane in diethyl ether (2.0 M, 1.96 mL) at 0° C. After complete addition, the reaction warmed to room temperature and stirred 30 min, then was concentrated. The resulting residue was dried under high vacuum to afford methyl 3-amino-6,7-dihydro-5H-cyclopenta[c]pyridine-7-carboxylate. $^1$H NMR (500 MHz, $CDCl_3$), δ 8.26 (s, 1H), 8.19 (s, 1H), 8.05 (br s, 2H), 4.00 (m, 1H), 3.75 (s, 3H), 3.01 (m, 1H), 2.83 (m, 1H), 2.44 (m, 1H), 2.32 (m, 1H); LC/MS $(M+1)^+=193.0$;

Step H: methyl 3-(1H-tetrazol-1-yl)-6,7-dihydro-5H-cyclopenta[c]pyridine-7-carboxylate A mixture of methyl 3-amino-6,7-dihydro-5H-cyclopenta[c]pyridine-7-carboxylate (365 mg, 1.90 mmol), triethyl orthoformate (451 mg, 3.04 mmol), and sodium azide (185 mg, 2.85 mmol) in acetic acid (8 mL) was maintained in an oil bath heated at 80° C. for 3 h. After cooling to room temperature, the mixture was diluted with water and ethyl acetate and the layers separated. The aqueous was extracted with ethyl acetate (2×) and the combined organic layers were washed with brine, dried ($Na_2SO_4$), filtered and concentrated. Purification of the resulting residue (8–>80% EtOAc/hexanes eluent) provided methyl 3-(1H-tetrazol-1-yl)-6,7-dihydro-5H-cyclopenta[c]pyridine-7-carboxylate. $^1$H NMR (500 MHz, $CDCl_3$), δ 9.54 (s, 1H), 8.55 (s, 1H), 8.00 (s, 1H), 4.22 (m, 1H), 3.82 (s, 3H), 3.30-3.06 (m, 2H), 2.66-2.49 (m, 2H); LC/MS $(M+1)^+=193.0$;

Step I: 3-(1H-tetrazol-1-yl)-6,7-dihydro-5H-cyclopenta[c]pyridine-7-carboxylic acid A solution of 3-(1H-tetrazol-1-yl)-6,7-dihydro-5H-cyclopenta[c]pyridine-7-carboxylate (235 mg, 0.958 mmol) in tetrahydrofuran (5 mL) and water (1.5 mL) at room temperature was treated with lithium hydroxide solution (1 M, 1.44 mL). After 30 min. the solution was concentrated to remove tetrahydrofuran and the remaining aqueous acidified with 1 N hydrochloric acid solution (to Ph ~4) and extracted with ethyl acetate (3×). The combined organics were washed with brine, dried ($Na_2SO_4$), filtered and concentrated to provide 3-(1H-tetrazol-1-yl)-6,7-dihydro-5H-cyclopenta[c]pyridine-7-carboxylic acid. $^1$H NMR (500 MHz, $CD_3OD$), δ 9.89 (s, 1H), 8.58 (s, 1H), 8.01 (s, 1H), 4.25 (dd, J=5.0, 5.0 Hz, 1H), 3.27-3.05 (m, 2H), 2.47-2.57 (m, 2H); LC/MS $(M+1)^+=232.2$.

Intermediate 154

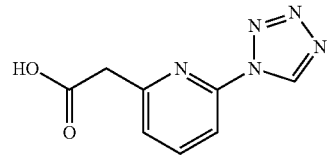 [SMILES: O=C(O)Cc1cccc(-n2cnnn2)n1]

[6-(1H-tetrazol-1-yl)pyridin-2yl]acetic acid

Step A: methyl {6-[(diphenylmethylidene)amino]pyridin-2-yl}acetate

To a solution of $Pd_2(dba)_3$ (4.0 mg, 0.0040 mmol), BINAP (41 mg, 0.065 mmol), and potassium tert-butoxide (490 mg, 4.35 mmol) in toluene (10 mL) was added methyl (6-bromopyridin-2-yl)acetate (1 g, 4.35 mmol) and benzophenone imine (1.1 mL, 6.52 mmol). The reaction was degassed for 15 minutes and then heated at 100° C. for 15 hours in a sealed tube. The reaction was then cooled to room temperature and concentrated in vacua. The crude residue was taken up in ethyl acetate (200 mL), filtered over Celite®, and washed with water. The organic layers were dried over sodium sulfate, filtered and concentrated in vacua. The crude material was purified via MPLC (0-100% EtOAc/Hex gradient) to afford {6-[(diphenylmethylidene)amino]pyridin-2-yl}acetate. LC/MS $(M+H)^+331$.

Step B: methyl (6-aminopyridin-2-yl)acetate {6-[(diphenylmethylidene)amino]pyridin-2-yl}acetate (13 g, 3.93 mmol) was dissolved in 1:1 mixture of THF/water (20 mL) and treated with 4.5 mL of a 1N aqueous hydrochloric acid solution. The reaction was allowed to stir at ambient temperature for 30 minutes and then concentrated in vacuo. The crude residue was dissolved in DCM and washed with a saturated aqueous sodium bicarbonate solution. The organic layers were dried over sodium sulfate, filtered and concentrated to afford crude methyl (6-aminopyridin-2-yl)acetate which, was used without further purification. LC/MS $(M+H)^+167$.

Step C: methyl [6-(1H-tetrazol-1-yl)pyridin-2-yl]acetate

To a solution of (6-aminopyridin-2-yl)acetate (375 mg, 2.26 mmol) in glacial acetic acid (5 mL) was added triethyl orthoformate (1.13 mL, 6.77 mmol) and sodium azide (440 mg, 6.77 mmol). The reaction mixture was heated at 80° C. for 3 hours in a sealed vial and then cooled to ambient temperature. Once cooled, water (5 mL) and solid sodium bicarbonate were added until a pH range of 6-7 was achieved. The aqueous layer was extracted with ethyl acetate (3×20 mL). The combined organic layers were then dried over sodium sulfate, filtered and concentrated in vacuo. The crude residue was purified via MPLC (0-100% EtOAc/Hex gradient) to afford methyl [6-(1H-tetrazol-1-yl)pyridin-2-yl]acetate. $^1$H NMR (500 MHz, DMSO-$d_6$): 10.1 (s, 1H), 8.2 (t, 1H), 8 (d, 1H), 7.6 (d, 1H), 4.0 (s, 3H), 3.6 (s, 2H). $(M+H-28)^+192$.

Step D: [6-(1H-tetrazol-1-yl)pyridin-2-yl]acetic acid

To a solution of methyl [6-(1H-tetrazol-1-yl)pyridin-2-yl]acetate (367 mg, 1.67 mmol) in THF (5 mL) was added 1.5 mL of 1N aqueous lithium hydroxide solution. The reaction mixture was allowed to stir at ambient temperature for 30 minutes and then concentrated in vacuo. The crude residue was dissolved in 4 mL of a 1N aqueous hydrochloric acid solution and extracted with DCM (3×20 mL). The combined organic layers were then dried over sodium sulfate, filtered and concentrated in vacuo to afford crude [6-(1H-tetrazol-1-yl) pyridin-2-yl]acetic acid which was used without further purification. LC/MS (M+H−28)⁺178.

Intermediate 155

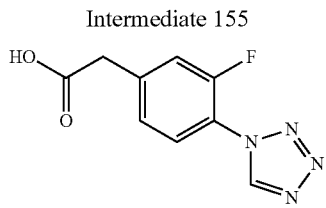

[3-fluoro-4-(1H-tetrazol-1-yl)phenyl]acetic acid
Step A: (3-fluoro-4-nitrophenyl)acetic acid To a stirred solution of $HNO_3$ (0.55 mL) was added a mixture of (3-fluorophenyl)acetic acid (2 g, 13 mmol) and $H_2SO_4$ (4 mL) at 0° C. dropwise. After 2 hours, the mixture was diluted with ice-water and extracted with EtOAc. The combined organic layers were washed with brine, dried over anhydrous $Na_2SO_4$ and concentrated. The residue was purified by prep-TLC to give (3-fluoro-4-nitrophenyl)acetic acid. ¹H-NMR (400 MHz, MeOD) δ ppm 8.2~8.24 (m, 1H), 7.26~7.3 (m, 2H), 4.06 (s, 2H).
Step B: (4-amino-3-fluorophenyl)acetic acid To a solution of (3-fluoro-4-nitrophenyl)acetic acid (1 g, 5 mmol) in 30 mL of EtOAc was added 180 mg of Pd/C was stirred at room temperature under $H_2$ atmosphere overnight. The reaction mixture was filtrated and concentrated to give (4-amino-3-fluorophenyl)acetic acid.
Step C: [3-fluoro-4-(1H-tetrazol-1-yl)phenyl]acetic acid A solution of (4-amino-3-fluorophenyl)acetic acid (450 mg, 2.66 mmol) and triethyl orthoformate (1.18 g, 7.98 mmol) in HOAc (10 mL) was added sodium azide (208 mg, 3.19 mmol), and the mixture was heated to 100° C. for 3 hours. After the reaction was completed, the reaction mixture was cooled to ambient temperature. The solvent was removed under vacuum. The residue was dissolved in EtOAc, washed with water, dried over anhydrous sodium sulfate, and concentrated. The residue was directly used in next step.

Intermediate 156

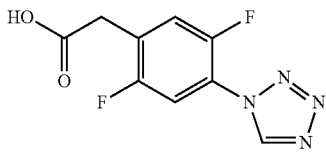 [SMILES: O=C(O)Cc1cc(F)c(-n2cnnn2)cc1F]

[2,5-difluoro-4-(1H-tetrazol-1-yl)phenyl]acetic acid
Step A: diethyl (2,5-difluoro-4-nitrophenyl)propanedioate To an ice-cooled slurry of NaH (475 mg, 11.8 mmol, 60%) in dry DMF (10 mL) was added $CH_2(COOEt)_2$ dropwise under an $N_2$ atmosphere. After 20 minutes, 1,2,4-trifluoro-5-nitrobenzene (1 g, 5.6 mmol) was added dropwise over 10 minutes and the mixture was stirred at −6° C. overnight. After the reaction was completed, the mixture was diluted with water and extracted with EtOAc. The organic layer washed with brine, dried over anhydrous $Na_2SO_4$ and concentrated. The residue was purified chromatography to give diethyl (2,5-difluoro-4-nitrophenyl)propanedioate. ¹H-NMR (400 MHz, CDCl3) δ ppm 7.87~7.84 (m, 1H), 7.54~7.58 (m, 1H), 4.98 (s, 1H), 4.23~4.27 (m, 4H), 1.28 (t, J=7.0 Hz, 6H).
Step B: (2,5-difluoro-4-nitrophenyl)acetic acid A mixture of diethyl (2,5-difluoro-4-nitrophenyl)propanedioate (700 mg, 2.2 mmol) with HOAc (10 mL) and HCl (6 N, 10 mL) was heated under $N_2$ at 120° C. for 2.5 hours and then allowed to cool and stirred overnight. Most of the solvent was removed by evaporation and then water was added. The mixture was extracted with EtOAc. The organic layer washed with brine, dried over anhydrous $Na_2SO_4$ and concentrated to give (2,5-difluoro-4-nitrophenyl)acetic acid.
Step C: (4-amino-2,5-difluorophenyl)acetic acid To a solution of (2,5-difluoro-4-nitrophenyl)acetic acid (440 mg, 2.03 mmol) in 20 ml of EtOAc was added HOAc (121 mg, 2.03 mmol) and 200 mg of Pd/C was stirred at room temperature under $H_2$ atmosphere for 3 hours. The reaction mixture was filtrated and concentrated to give (4-amino-2,5-difluorophenyl)acetic acid.
Step D: [2,5-difluoro-4-(1H-tetrazol-1-yl)phenyl]acetic acid A solution of (4-amino-2,5-difluorophenyl)acetic acid (380 mg, 2.0 mmol) and triethyl orthoformate (902 mg, 6.1 mmol) in HOAc (10 mL) was added sodium azide (158 mg, 2.44 mmol) and the mixture was heated to 100° C. for 3 hours. After the reaction was completed, the reaction mixture was cooled to ambient temperature. The solvent was removed under vacuum. The residue was dissolved in EtOAc, washed with water, dried over anhydrous sodium sulfate, and concentrated. The [2,5-difluoro-4-(1H-tetrazol-1-yl)phenyl]acetic acid was directly used in next step.

Intermediate 157

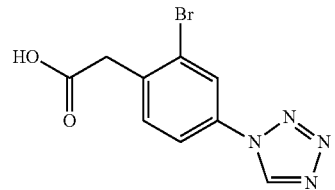 [SMILES: O=C(O)Cc1ccc(-n2cnnn2)cc1Br]

[2-bromo-4-(1H-tetrazol-1-yl)phenyl]acetic acid
Step A: diethyl (2-bromo-4-nitrophenyl)propanedioate A solution of diethylmalonate (3.3 g, 25 mmol) in 70 mL of dry DMF was cooled to 0° C. by ice water, NaH (1 g, 28 mmol) was added, and then the reaction was warmed to ambient temperature and stirred at ambient temperature for 1.5 hours. The reaction was cooled to 0° C. and 2-bromo-1-chloro-4-nitrobenzene (5 g, 23 mmol) was added to the reaction. The reaction was warmed to ambient temperature and heated to 80° C. for 3 hours. The reaction was cooled to ambient temperature and poured to ice water, adjusted pH to 3 with 2N HCl. Extracted with EtOAc and the oranic layers were washed with water, brine, dried over anhydrous sodium sulfate and concentrated. The crude product was purified via column chromatograph to afford diethyl (2-bromo-4-nitrophenyl)propanedioate.
Step B: (2-bromo-4-nitrophenyl)acetic acid A solution of diethyl (2-bromo-4-nitrophenyl)propanedioate (5.6 g, 17 mmol) in 120 mL of methanol and 100 mL of water was added KOH (2.8 g, 50 mmol), and the mixture was heated to 70° C. for 3.5 hours. The reaction was cooled to ambient temperature, distilled off methanol under reduce pressure and adjusted pH to 2 with conc. HCl. Extracted with EtOAc and the organic layers were washed with water, brine and dried over anhydrous sodium sulfate, concentrated to get (2-bromo-4-nitrophenyl)acetic acid. $^1$H-NMR (300 MHz, CDCl$_3$) δ ppm 8.39 (s, 1H), 8.07~8.11 (m, 1H), 7.43 (d, J=8.3 Hz, 1H), 3.88 (s, 2H).

Step C: 4-amino-2-bromophenyl)acetic acid

A solution of (2-bromo-4-nitrophenyl)acetic acid (500 mg, 2 mmol) in 11 mL of concentrated ammonium hydroxide was added a solution of FeSO$_4$.7H$_2$O (3.4 g, 12 mmol) in 11 mL of water over 5 minutes, and then the mixture was heated to reflux for 1 hour. Cooled to ambient temperature, filtered off solids and the filtrate was adjusted to pH to 5 with 2N HCl. Extracted with EtOAc and combined organic layers were washed with water, dried over anhydrous sodium sulfate, and concentrated to get (4-amino-2-bromophenyl)acetic acid. $^1$H-NMR (300 MHz, CDCl$_3$) δ ppm 7.01 (d, J=8.0 Hz, 1H), 6.92 (d, J=2.0 Hz, 1H), 6.62 (dd, J=2.5 Hz, 1H), 3.61 (s, 2H).

Step D: [2-bromo-4-(1Htetrazol-1-yl)phenyl]acetic acid

A solution of (4-amino-2-bromophenyl)acetic acid (230 mg, 1 mmol) and triethyl orthoformate (444 mg, 3 mmol) in 8 mL of HOAc was added sodium azide (80 mg, 1.2 mmol), and the mixture was heated to 100° C. for 3 hours. The reaction mixture was cooled to ambient temperature and the solvent was removed under vacuum. The residue was dissolved in EtOAc, washed with water, dried over anhydrous sodium sulfate, and concentrated. The residue was purified by prep-TLC to afford [2-bromo-4-(1H-tetrazol-1-yl)phenyl]acetic acid. $^1$H-NMR (300 MHz, MeOD) δ ppm 9.78 (s, 1H), 8.16 (s, 1H), 7.83~7.87 (m, 1H), 7.60~7.63 (m, 1H), 3.89 (s, 2H).

Intermediate 158

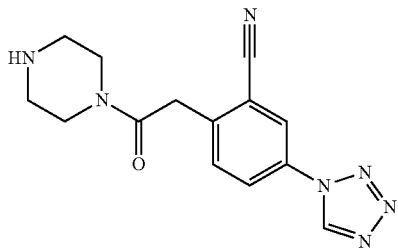 [SMILES: N#Cc1cc(-n2cnnn2)ccc1CC(=O)N1CCNCC1]

2-[2-oxo-2-(piperazin-1-yl)ethyl]-5-(1H-tetrazol-1-yl)benzonitrile

Step A: tert-butyl 4-{[2-bromo-4-(1H-tetrazol-1-yl)phenyl]acetyl}piperazine-1-carboxylate A solution of [2-bromo-4-(1H-tetrazol-1-yl)phenyl]acetic acid (500 mg, 1.77 mmol), Boc-piperazine (329 mg, 1.77 mmol), EDC (418 mg, 2.12 mmol), HOBt (286 mg, 2.12 mmol) and TEA (530 mg, 5.31 mmol) in 20 mL of DCM was stirred at room temperature overnight. The solvent was removed under reduce pressure and the crude was purified via prep-TLC to afford tert-butyl 4-{[2-bromo-4-(1H-tetrazol-1-yl)phenyl]acetyl}piperazine-1-carboxylate.

$^1$H-NMR (400 MHz, MeOD) δ ppm 9.79 (s, 1H), 8.18 (d, J=1.6 Hz, 1H), 7.84~7.87 (m, 1H), 7.55 (d, J=7.8 Hz, 1H), 4.03 (s, 2H), 3.44~3.69 (m, 8H), 1.48 (s, 9H).

Step B: tert-butyl 4-{[2-cyano-4-(1H-tetrazol-1-yl)phenyl]acetyl}piperazine-1-carboxylate A mixture of tert-butyl 4-{[2-bromo-4-(1H-tetrazol-1-yl)phenyl]acetyl}piperazine-1-carboxylate (380 mg, 0.84 mmol), Zn(CN)$_2$ (59 mg, 0.51 mmol), Pd$_2$(dba)$_3$ (7 mg, 0.0042 mmol), TMEDA (20 mg, 0.17 mmol), and xantphos (5 mg, 0.0084 mmol) in 3 mL of DMF was stirred under microwave irradiation for 3 min at 160° C. The solvent was removed in vacuum to afford the crude compound, which was purified via prep-TLC to afford tert-butyl 4-{[2-cyano-4-(1H-tetrazol-1-yl)phenyl]acetyl}piperazine-1-carboxylate. $^1$H-NMR (400 MHz, MeOD) δ ppm 9.82 (s, 1H), 8.31 (d, J=1.6 Hz, 1H), 8.12~8.16 (m, 1H), 7.68 (d, J=7.8 Hz, 1H), 4.14 (s, 2H), 3.43~3.72 (m, 8H), 1.48 (s, 9H).

Step C: 2-[2-oxo-2-(piperazin-1-yl)ethyl]-5-(1H-tetrazol-1-yl)benzonitrile

To a solution of tert-butyl 4-{[2-cyano-4-(1H-tetrazol-1-yl)phenyl]acetyl}piperazine-1-carboxylate (160 mg, 0.4 mmol) in 10 mL of dioxane was added 10 mL of 5 M HCl/EtOH, then the mixture was stirred at room temperature for 3 h. The solvent was removed under reduce pressure. The crude compound was suspension in 20 mL of MeCN and added Na$_2$CO$_3$ (102 mg, 0.96 mmol), then the mixture was stirred at room temperature overnight. After filtration, the filtrate was concentrated in vacua to give crude 2-[2-oxo-2-(piperazin-1-yl)ethyl]-5-(1H-tetrazol-1-yl)benzonitrile, which was used for next step without further purification.

Intermediate 159

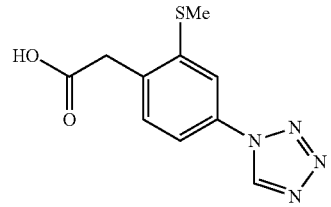 [SMILES: CSc1cc(-n2cnnn2)ccc1CC(=O)O]

[2-(methylsulfanyl)-4-(1H-tetrazol-1-yl)phenyl]acetic acid

Step A: 2-(methylsulfanyl)-4-nitrobenzoic acid

A stirred mixture of 2-chloro-4-nitrobenzoic acid (24.2 g, 120 mmol), methyldisulfide (5.6 mL), copper powder (7.6 g) in 160 mL of DMA was heated to 135° C. during 1 hours, kept at that temperature for 90 minutes, and then heated at 165° C. for 2 hours. After the reaction was completed, the solvent was removed in vacuum to afford the crude compound, which was poured into 40% w/v aqueous sodium hydroxide solution. The mixture was filtered and the filtrate was washed with EtOAc and the aqueous layer was acidified with concentrated aqueous hydrochloric acid and filtered. The solid residue was washed with water and then dissolved in EtOAc, and the solution was dried over anhydrous Na$_2$SO$_4$ and evaporated to dryness under reduced pressure. The residue was crystallized from aqueous EtOH to give 2-(methylsulfanyl)-4-nitrobenzoic acid. $^1$H-NMR (400 MHz, MeOD) δ ppm 8.2~8.33 (m, 1H), 8.12~8.17 (m, 1H), 7.95~7.98 (m, 1H), 2.53 (s, 3H).

Step B: [2-(methylsulfanyl)-4-nitrophenyl]acetic acid

A solution of 2-(methylsulfanyl)-4-nitrobenzoic acid (5.3 g, 24.9 mmol) in 50 mL of THF was treated with (CoCL)$_2$ (17.5 ml) and then DMF (2 drops). After stirring at room temperature for 2 hours, the mixture was evaporated. The residue was dissolved in 50 mL of DCM and added a solution of CH$_2$N$_2$ in 80 mL Et$_2$O at 0° C. and stirred overnight. After the reaction was completed, the Et$_2$O was partly evaporated and the product (3.7 g) filtered. A solution of the product (3.7 g, 15.6 mmol) in 90 mL dioxane was treated at 50° C. with 10 mL of water and added over 30 min with a suspension of Ag$_2$O prepared from 3.98 g AgNO$_3$. The mixture was stirred for 30 min at 85° C. and cooled. The precipitated product was filtered. It was decomposed with hydrochloric acid and the released acid was extracted with EtOAc. The combined organic layers were washed with 5% NaHCO$_3$. Then the aqueous layer was acidified to pH=1~2, extracted with EtOAc. The combined organic phase was washed with brine, dried over anhydrous Na$_2$SO$_4$ and concentrated to afford [2-(methylsulfanyl)-4-nitrophenyl]acetic acid. $^1$H-NMR (400 MHz, MeOD) δ ppm 8.06~8.07 (m, 1H), 7.93~7.96 (m, 1H), 7.44 (d, J=8.6 Hz, 1H), 3.82 (s, 2H), 2.56 (s, 3H).

Step C: [4-amino-2-(methylsulfanyl)phenyl]acetic acid

A solution of [2-(methylsulfanyl)-4-nitrophenyl]acetic acid (230 mg, 1.0 mmol) in 10 mL of water and 0.6 mL of NH$_3$.H$_2$O was added a solution of FeSO$_4$.7H$_2$O (2.25 g, 8.1 mmol) in 10 mL of water and another 1.6 mL of NH$_3$.H$_2$O were added dropwise. The mixture was stirred at 60~80° C. overnight. The mixture was filtered and the filtrate was acidified to pH 4~5 with HOAc. Extracted with EtOAc and the combined organic layers were washed with brine, dried over anhydrous Na$_2$SO$_4$ and concentrated to afford [4-amino-2-(methylsulfanyl)phenyl]acetic acid.

Step D: [2-(methylsulfanyl)-4-(1H-tetrazol-1-yl)phenyl]acetic acid

A solution of [4-amino-2-(methylsulfanyl)phenyl]acetic acid (200 mg, 1 mmol) and triethyl orthoformate (451 mg, 3 mmol) in 10 mL of HOAc was added sodium azide (99 mg, 1.5 mmol), and the mixture was heated to 100° C. for 3 hours. The reaction mixture was cooled to ambient temperature. The solvent was removed under vacuum. The residue was dissolved in EtOAc, washed with water, dried over anhydrous sodium sulfate, and concentrated. The residue was purified by preparative TLC to give [2-(methylsulfanyl)-4-(1H-tetrazol-1-yl)phenyl]acetic acid.

Intermediate 160

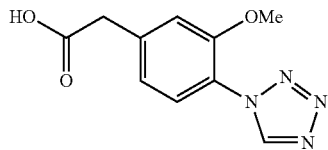 [SMILES: COc1cc(CC(=O)O)ccc1-n1cnnn1]

[3-methoxy-4-(1H-tetrazol-1-yl)phenyl]acetic acid

Step A: diethyl (3-methoxy-4-nitrophenyl)propanedioate

A solution of 5-chloro-2-nitrophenyl methyl ether (5 g, 26.596 mmol) in dry DMF (150 mL) was cooled to 0° C. by ice water and NaH (3.51 g, 87.750 mmol, 60% purity) was added portionwise, and then the reaction was warmed to ambient temperature and stirred for 1.5 hours. The reaction was cooled to 0° C. and CH$_2$(COOEt)$_2$ (14.04 g, 87.768 mmol) was added. The result mixture was warmed to ambient temperature and heated to 80° C. for 13 hours. The reaction was cooled to ambient temperature and poured into ice water and added 2N HCl to adjust pH to 3. Extracted with EtOAc and the organic layer was washed with water, brine, dried over anhydrous sodium sulfate and concentrated. The crude product was purified via column chromatograph to afford diethyl (3-methoxy-4-nitrophenyl)propanedioate. $^1$H-NMR (400 MHz, CDCl$_3$) δ ppm 7.86 (d, J=8.3 Hz, 1H), 7.25 (s, 1H), 7.07 (d, J=8.3 Hz, 1H), 4.67 (s, 1H), 4.23~4.29 (m, 4H), 4.00 (s, 3H), 1.31 (t, J=7.0 Hz, 6H).

Step B: (3-methoxy-4-nitrophenyl)acetic acid

A solution of diethyl (3-methoxy-4-nitrophenyl)propanedioate (3.8 g, 12.219 mmol) in 30 mL of methanol and 20 mL of water was added KOH (2.05 g, 36.657 mmol) and the mixture was heated to 70° C. for 4 hours. Cooled to ambient temperature and removed the solvents under reduce pressure. The residue was added 100 mL of water and adjusted to pH=2 with conc. HCl. Extracted with EtOAc and the organic layer was washed with water, brine and dried over anhydrous sodium sulfate, concentrated to give (3-methoxy-4-nitrophenyl)acetic acid. $^1$H-NMR (400 MHz, MeOD) δ ppm 7.75 (d, J=8.6 Hz, 1H), 7.21 (d, J=1.6 Hz, 1H), 6.98 (dd, J=7.8 Hz, J=1.6 Hz, 1H), 3.93 (s, 3H), 3.70 (s, 2H).

Step C: (4-amino-3-methoxyphenyl)acetic acid

A solution of (3-methoxy-4-nitrophenyl)acetic acid (2.08 g, 9.86 mmol) in 100 mL of EtOAc was added 600 mg of Pd/C under Ar, and the mixture was stirred at ambient temperature under H$_2$ atmosphere overnight. The reaction mixture was filtered and the filtrate was concentrated to give (4-amino-3-methoxyphenyl)acetic acid.

Step D: [3-methoxy-4-(1H-tetrazol-1-yl)phenyl]acetic acid

A solution (4-amino-3-methoxyphenyl)acetic acid (1.63 g, 9.006 mmol) and triethyl orthoformate (4.0 g, 27.018 mmol) in 100 mL of HOAc was added sodium azide (644 mg, 9.907 mmol) and heated to 100° C. overnight. The solvent was removed under vacuum. The residue was dissolved in EtOAc, washed with water, dried over anhydrous sodium sulfate, and concentrated to give [3-methoxy-4-(1H-tetrazol-1-yl)phenyl]acetic acid, which was used for next step without purification.

Intermediate 161

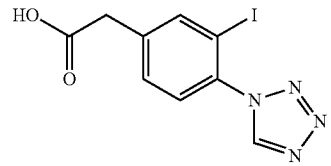 [SMILES: O=C(O)Cc1ccc(-n2cnnn2)c(I)c1]

[3-iodo-4-(1H-tetrazol-1-yl)phenyl]acetic acid

Step A: (4-amino-3-iodophenyl)acetic acid

A solution of (4-aminophenyl)acetic acid (25.94 g, 171 mmol) in 400 mL of dry DCM was cooled to 10° C. by ice water and iodine mononochloride (25 g, 154 mmol) in 120 mL of dry DCM was added by dropwise. The reaction then stirred at ambient temperature for 4 hours. Filtered to get solids and the solids was washed with 20 mL of cold DCM. The crude (4-amino-3-iodophenyl)acetic acid was used for next step without purification.

Step B: methyl (4-amino-3-iodophenyl)acetate

The crude (4-amino-3-iodophenyl)acetic acid (about 40 g, about 171 mmol) in methanol (110 mL) was added 100 mL of 4 M MeOH/HCl and the solution was stirred at ambient temperature over night. Distilled the solution under reduce pressure, and the residue was purified by silica gel cloumn chromatography to give methyl (4-amino-3-iodophenyl)acetate. $^1$H-NMR (300 MHz, CDCl$_3$) δ ppm 7.54 (s, 1H), 7.04 (d, J=7.9 Hz, 1H), 6.68 (d, J=7.9 Hz, 1H), 3.67 (s, 3H), 3.46 (s, 2H).

Step C: methyl [3-iodo-4-(1H-tetrazol-1-yl)phenyl]acetate

A solution of methyl (4-amino-3-iodophenyl)acetate (5 g, 17.2 mmol) and triethyl orthoformate (7.6 mg, 51.5 mmol) in 40 mL of HOAc was added sodium azide (1.2 g, 17.2 mmol), and the mixture was heated to 100° C. for 3 hours. The reaction mixture was cooled to ambient temperature. The solvent was removed under vacuum. The residue was dissolved in EtOAc, washed with water, dried over anhydrous sodium sulfate, and concentrated. The residue was purified by column chromatograph to afford methyl [3-iodo-4-(1H-tetrazol-1-yl)phenyl]acetate. $^1$H-NMR (300 MHz, CDCl$_3$) δ ppm 8.90 (s, 1H), 7.96 (s, 1H), 7.47 (d, J=8.2 Hz, 1H), 7.38 (d, J=7.9 Hz, 1H), 3.74 (s, 3H), 3.70 (s, 2H).

Step D: [3-iodo-4-(1H-tetrazol-1-yl)phenyl]acetic acid

A solution of methyl [3-iodo-4-(1H-tetrazol-1-yl)phenyl]acetate (1 g, 2.9 mmol) in a co-solution 50 mL of THF/methanol/water (2:2:1) was added added LiOH.H$_2$O (0.6 g, 14.5 mmol), and the mixture was stirred at ambient temperature over night. Concentrated and the residue was dissolved in water and then adjusted pH=3 with 2N HCl. Extracted with DCM, and orgianc layers were washed with water, brine and dried over anhydrous sodium sulfate, concentrated to get crude product [3-iodo-4-(1H-tetrazol-1-yl)phenyl]acetic acid, which was used for the next step without purification.

Intermediate 162

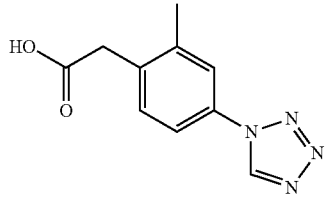 [SMILES: Cc1cc(-n2cnnn2)ccc1CC(=O)O]

[2-Methyl-4-(1H-tetrazol-1-yl)phenyl]acetic Acid

To a solution of (4-amino-2-methylphenyl)acetic acid (0.10 g, 0.61 mmol) and triethyl orthoformate (0.16 ml, 0.97 mmol) in acetic acid (1 ml) was added sodium azide (0.059 g, 0.91 mmol). The resulting mixture was heated to reflux for 4 hours. The mixture was poured into ice water and the resulting solid collected by filtration and dried, under vacuum to provide [2-methyl-4-(1H-tetrazol-1-yl)phenyl]acetic acid. LC-MS (IE, m/z): 219 [M+1]$^+$.

Intermediate 163

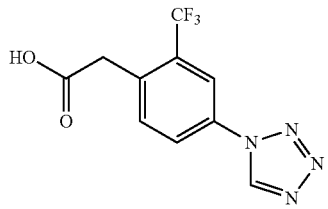 [SMILES: O=C(O)Cc1ccc(-n2cnnn2)cc1C(F)(F)F]

[4-(1H-Tetrazol-1-yl)-2-(trifluoromethyl)phenyl]acetic acid

[4-(1H-tetrazol-1-yl)-2-(trifluoromethyl)phenyl]acetic acid was prepared in a similar fashion to that described for the synthesis of [2-methyl-4-(1H-tetrazol-1-yl)phenyl]acetic acid starting from [4-amino-2-(trifluoromethyl)phenyl]acetic acid. LC-MS (IE, m/z): 273 [M+1]$^+$.

Intermediate 164

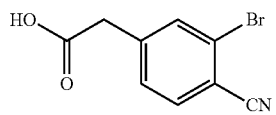 [SMILES: N#Cc1ccc(CC(=O)O)cc1Br]

(3-Bromo-4-cyanophenyl)acetic acid (3-Bromo-4-cyanophenyl)acetic acid was prepared in a similar fashion to the previously described synthesis of (4-cyano-2-fluoro-5-methoxyphenyl)acetic acid starting from di-tert-butyl malonate and 3-bromo-4-fluorobenzonitrile. LC-MS (IE, m/z): 239, 241 [M+1]$^+$.

Intermediate 165

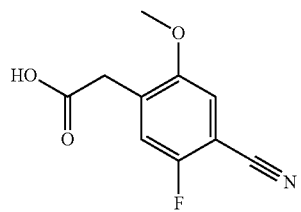

(4-Cyano-5-fluoro-2-methoxyphenyl)acetic acid (4-Cyano-5-fluoro-2-methoxyphenyl)acetic acid was prepared in a similar fashion to the previously described synthesis of (4-cyano-2-fluoro-5-methoxyphenyl)acetic acid starting from di-tert-butyl malonate and 2,4-difluoro-5-methoxybenzonitrile. LC-MS (IE, m/z): 208 [M−1]$^+$.

Intermediate 166

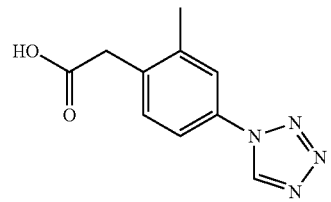 [SMILES: Cc1cc(-n2cnnn2)ccc1CC(=O)O]

[4-Methyl-6-(1H-tetrazol-1-yl)pyridin-3-yl]acetic Acid

Step A: tert-Butyl Ethyl (6-Nitro-4-methylpyridin-3-yl)propanedioate

A dry flask was charged with sodium hydride (60% suspension in mineral oil, 1.29 g, 32.3 mmol) and 100 ml of dry DMF, and cooled to 0° C. followed by dropwise addition of tert-butyl ethyl propanedioate (5.20 g, 27.6 mmol) via syringe. After 30 min at 0° C., a solution of 3-chloro-2,4-difiuorobenzonitrile (5.00 g, 23.0 mmol) in DMF (10 ml) was added over a period of 15 minutes. The ice bath was removed and the reaction mixture was subjected to heating at 80° C. in an oil bath for 12 hrs. The mixture was cooled to RT, quenched with saturated ammonium chloride, and partitioned between water and ethyl acetate. The organic layer was concentrated and the resulting tert-butyl ethyl (6-nitro-4-methylpyridin-3-yl)propanedioate was used directly in the next step without further purification. LC-MS (IE, m/z): 295 [M+1]⁺.

Step B: Ethyl (4-Methyl-6-nitropyridin-3-yl)acetate tert-Butyl ethyl (6-nitro-4-methylpyridin-3-yl)propanedioate (7.4 g, 22.8 mmol) was dissolved in DCM (100 mL) and treated with trifluoromethanesulfonic acid (25 mL). The reaction mixture stirred 12 h, then was concentrated in vacuo and dried under high vacuum. The resulting residue purified by flash chromatography (eluted with 2→10% hexanes/ethyl acetate) to provide ethyl (4-methyl-6-nitropyridin-3-yl)acetate. ¹H-NMR (400 MHz, CDCl₃) δ ppm 8.48 (s, 1H), 8.15 (s, 1H), 4.29 (m, 2H), 3.81 (s, 2H), 2.53 (s, 3H), 1.27 (m, 3H).

Step C: Ethyl (4-Methyl-6-aminopyridin-3-yl)acetate

A mixture of ethyl (4-methyl-6-nitropyridin-3-yl)acetate (1.65 g, 7.36 mmol) and palladium on carbon (10%, 1.57 g, 1.47 mmol) in Ethanol (10 mL) was evacuated and refilled with nitrogen (3×), then stirred under an atmosphere of hydrogen for 2 h. The reaction mixture was filtered through Celite® and concentrated in vacuo to provide ethyl (4-methyl-6-aminopyridin-3-yl)acetate which was used directly in the next reaction without further purification. LC-MS (IE, m/z): 195 [M+1]⁺.

Step D: Ethyl [4-Methyl-6-(1H-tetrazol-1-yl)pyridin-3-yl]acetate

Sodium azide (0.712 g, 11.0 mmol) was added to a stirred mixture of triethyl orthoformate (1.95 ml, 11.7 mmol) and ethyl (4-methyl-6-aminopyridin-3-yl)acetate (1.42 g, 7.30 mmol) in acetic acid (10 ml) and the mixture was stirred at 80° C. for 24 h. The reaction mixture was cooled, diluted with water, and extracted with EtOAc (2×). The combined organic layers were washed with brine, dried (Na₂SO₄), filtered, and concentrated to provide ethyl [4-methyl-6-(1H-tetrazol-1-yl)pyridin-3-yl]acetate. ¹H-NMR (400 MHz, CDCl₃) δ ppm 9.57 (s, 1H), 8.35 (s, 1H), 7.98 (s, 1H), 4.23 (m, 2H), 3.78 (s, 2H), 2.71 (s, 3H), 1.27 (m, 3H). LC-MS (IE, m/z): 248 [M+1]⁺.

Step E: [4-Methyl-6-(1H-tetrazol-1-yl)pyridin-3-yl]acetic Acid

A solution of lithium hydroxide (1 N, 4.75 ml) was added to a stirred mixture of [4-methyl-6-(1H-tetrazol-1-yl)pyridin-3-yl]acetate (1.00 g, 4.29 mmol) in THF (10 ml) and the mixture was stirred at room temperature for 2 h. The reaction mixture was acidified to pH ~3-4 and extracted with EtOAc (3×). The combined organic layers were washed with brine, dried (Na₂SO₄), filtered and concentrated to provide [4-methyl-6-(1H-tetrazol-1-yl)pyridin-3-yl]acetic acid which was used directly in the next step without further purification. LC-MS (IE, m/z): 206 [M+1]⁺.

Intermediate (R)-167

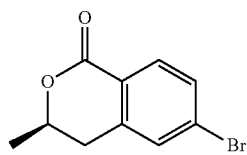

(3R)-6-bromo-3-methyl-3,4-dihydro-1H-isochromen-1-one

Step A: 4-bromo-N,N-diethyl-2-methylbenzamide

A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide.

¹H NMR (500 MHz; CDCl₃): 7.39 (s, 1H), 7.36 (dd, J=1.6; 9.7 Hz, 1H), 7.05 (d, J=8.1, 1H), 3.3 (bs, 1H), 3.5 (bs, 1H), 3.13 (q, J=6.8 Hz, 2H), 2.29 (s, 3H), 1.27 (t, J=7.1 Hz, 3H), 1.05 (t, J=7.1 Hz, 3H). (M+H)⁺270.

Step B: 4-bromo-N,N-diethyl-2-(2-oxopropyl)benzamide

A 2M solution of LDA (35.2 ml, 70.3 mmol) in THF (176 ml) cooled to −78° C. was treated with slow addition of 4-bromo-N,N-diethyl-2-methylbenzamide (19.0 g, 70.3 mmol) in dry THF (176 ml). The reaction was allowed to stir at −78° C. for 1 hour before it was quenched with N-methoxy-N-methylacetamide (22.43 ml, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an orange/brown oil out of which the product crystallizes.

The oil was decanted off and the solid was washed with hexanes and dried using a buchner funnel to afford 4-bromo-N,N-diethyl-2-(2-oxopropyl)benzamide. ¹H NMR (500 MHz; CDCl₃): 7.44 (dd, J=1.7; 8.1 Hz, 1H), 7.37 (d, J=1.6 Hz, 1H), 7.11 (d, J=8.0 Hz, 1H), 3.81 (bs, 2H), 3.52 (bs, 2H), 3.18 (q, J=7.1 Hz, 2H), 2.21 (s, 3H), 1.21 (t, J=7.1 Hz, 3H), 1.10 (t, J=7.1 Hz, 3H). (M+H)⁺312.

Step C: 4-bromo-N,N-diethyl-2-[(2R)-2-hydroxypropyl]benzamide

A flask equipped with an overhead stirrer was charge with pH=8 Phosphate Buffer (156 ml, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg Codexis ketoreductase P1B2 was added to the reaction vessel and stirred at 500 rpm at 30° C. until enzyme is wetted (about 40 min). Lastly, a solution of 4-bromo-N,N-diethyl-2-(2-oxopropyl)benzamide (1.5 g, 4.80 mmol) dissolved in DMSO (14.56 ml) (pre-warmed on stir plate to 30° C.) was added to the reaction over ~3 min and agitate at 30° C. (400 rpm) overnight.

After 48 hours the reaction was cooled to room temperature and then 75 g of potassium carbonate was added to the reaction in portions and stirred for 15 minutes until enzyme clumps together when stirring is stopped. Next acetonitrile (50 mL) was poured into the reaction flask and the layers were thoroughly mixed. Stirring was stopped after 15-20 minutes, the layers allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 ml MTBE. The combined organic extracts were dried over magnesium sulfate, filtered and concentrated. Purification via MPLC (30-70% EtOAc/Hex) afforded 4-bromo-N,N-diethyl-2-[(2R)-2-hydroxypropyl]benzamide.

Step D: (3R)-6-bromo-3-methyl-3,4-dihydro-1H-isochromen-1-one

A solution of 4-bromo-N,N-diethyl-2-[(2R)-2-hydroxypropyl]benzamide (12.2 g, 38.8 mmol) dissolved in 4N HCl in Dioxane (200 mL) was stirred at room temperature and monitored by tlc. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one.

$^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). (M+1)$^+$241.

Intermediate (S)-167

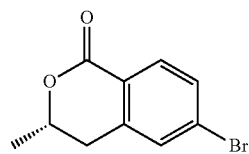

(3S)-6-bromo-3-methyl-3,4-dihydro-1H-isochromen-1-one (3S)-6-Bromo-3-methyl-3,4-dihydro-1H-isochromen-1-one was prepared in a similar manner as (3R)-6-bromo-3-methyl-3,4-dihydro-1H-isochromen-1-one except using Codexis ketoreductase P1H9 in Step C. $^1$H NMR (500 MHz; CDCl$_3$): 8.07 (d, J=8.1 Hz, 1H), 7.35 (d, J=8.0 Hz, 1H), 7.28 (s, 1H), 4.72 (dd, J=1.8, 10.5 Hz, 1H), 4.68 (m, 1H), 4.1-3.8 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.54 (d, J=6.2 Hz, 3H), 1.49 (s, 9H). (M+1)$^+$403.

Intermediate (3R)-168

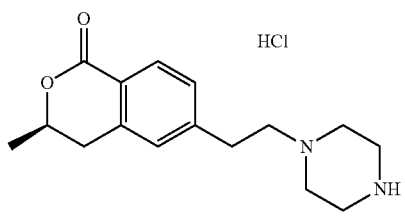 [SMILES: C[C@@H]1Cc2cc(CCN3CCNCC3)ccc2C(=O)O1 ; Cl]

(3R)-3-methyl-6-[2-(piperazin-1-yl)ethyl]-3,4-dihydro-1H-isochromen-1-one hydrochloride Step A: (3R)-6-(1,3-dioxolan-2-ylmethyl)-3-methyl-3,4-dihydro-1H-isochromen-1-one A sealed tube was charged with aryl bromide, palladium (II) acetate (0.028 g, 0.124 mmol) and tri-t-butylphosphine-BF$_4$ complex (0.072 g, 0.249 mmol) and sealed. The tube was evacuated and refilled with nitrogen before DMF (12.44 ml) and (3R)-6-bromo-3-methyl-3,4-dihydro-1H-isochromen-1-one (0.75 g, 3.11 mmol) were added followed by bromo(1,3-dioxolan-2-ylmethyl)zinc (6.22 ml, 3.11 mmol). The tube was heated to 110° C. in the microwave for 75 minutes, after which it was cooled, diluted with EtOAc, filtered, concentrated and purified via MPLC (20-50% E/H) to afford (3R)-6-(1,3-dioxolan-2-ylmethyl)-3-methyl-3,4-dihydro-1H-isochromen-1-one. $^1$H NMR (500 MHz; CDCl$_3$): 8.04 (d, J=7.8 Hz, 1H), 7.32 (d, J=8.0 Hz, 1H), 7.17 (s, 1H), 5.11 (1, J=4.7 Hz, 1H), 4.68 (m, 1H), 3.96 (m, 2H), 3.88 (m, 2H), 3.03 (d, J=4.9 Hz, 2H), 2.93 (m, 2H), 1.54 (d, J=6.4 Hz, 3H); LC-MS (IE, m/z): 249 [M+1]$^+$.

Step B: tert-butyl 4-{2-[(3R)-3-methyl-1-oxo-3,4-dihydro-1H-isochromen-6-yl]ethyl}piperazine-1-carboxylate A 1:1 solution of dioxane:3N HCl was added to a flask containing (3R)-6-(1,3-dioxolan-2-ylmethyl)-3-methyl-3,4-dihydro-1H-isochromen-1-one (782 mg, 3.15 mmol). The reaction was then stirred at room temp overnight. The crude reaction mixture was then partitioned between water and DCM. The organic layer was washed with saturated sodium bicarbonate solution, followed by brine. The organic layer was then dried with mag. sulfate, filtered and concentrated to afford [(3R)-3-methyl-1-oxo-3,4-dihydro-1H-isochromen-6-yl]acetaldehyde. The crude aldehyde was redissolved in DCM. To the solution was added Boc-piperazine (671 mg, 3.6 mmol) followed by sodium triacetoxyborohydride (1.91 g, 9.0 mmol). The reaction mixture was allowed to stir overnight before being quenched with 10 mL of MeOH. The excess solvent was removed and the residue was re-redissolved in DCM; washed with water and brine, dried with magnesium sulfate, filtered, concentrated and purified via MPLC (50-100% EtOAc/Hex) to afford tert-butyl 4-{2-[(3R)-3-methyl-1-oxo-3,4-dihydro-1H-isochromen-6-yl]ethyl}piperazine-1-carboxylate. $^1$H NMR (500 MHz; CDCl$_3$): 8.02 (d, J=7.8 Hz, 1H), 7.24 (d, J=7.7 Hz, 1H), 7.09 (s, 1H), 4.68 (m, 1H), 3.49 (m, 4H), 2.94 (m, 4H), 2.88 (m, 2H), 2.51 (m, 4H), 1.54 (d, J=6.8 Hz, 3H), 1.48 (s, 9H); LC-MS (IE, m/z): 375 [M+1]$^+$;

Step C: (3R)-3-methyl-6[2-(piperazin-1-yl)ethyl]-3,4-dihydro-1H-isochromen-1-one hydrochloride A solution of tert-butyl 4-{2-[(3R)-3-methyl-1-oxo-3,4-dihydro-1H-isochromen-6-yl]ethyl}piperazine-1-carboxylate (850 mg, 2.27 mmol) was stirred in 4N HCl in dioxane for 4 hours. The excess solvent was then removed to give the free amine as the HCl salt. LC-MS (IE, m/z): 275 [M+1]$^+$.

Intermediate (3S)-168

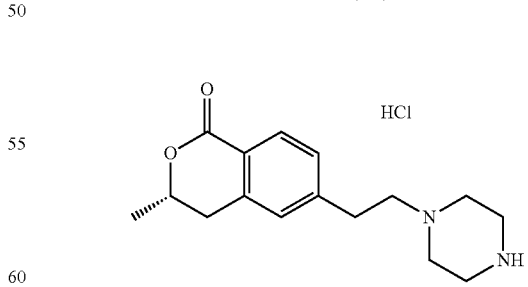

(3S)-3-methyl-6-[2-(piperazin-1-yl)ethyl]-3,4-dihydro-1H-isochromen-1-one hydrochloride (3S)-3-methyl-6-[2-(piperazin-1-yl)ethyl]-3,4-dihydro-1H-isochromen-1-one hydrochloride was prepared in a similar manner as (3R)-3-methyl-6-[2-(piperazin-1-yl)ethyl]-3, 4-dihydro-1H-isochromen-1-one hydrochloride except starting from (3S)-6-bromo-3-methyl-3,4-dihydro-1H-isochromen-1-one.

Intermediate (3R)-169

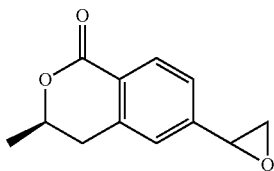

(3R)-3-methyl-6-(oxiran-2-yl)-3,4-dihydro-1H-isochromen-1-one
Step A: (3R)-6-ethenyl-3-methyl-3,4-dihydro-1H-isochromen-1-one A solution of (3R)-6-bromo-3-methyl-3,4-dihydro-1H-isochromen-1-one (2.4 g, 9.96 mmol) and triethylamine (2.78 ml, 19.91 mmol) in EtOH (39.8 ml) was added to a microwave vial containing $Cl_2Pd(dppf)_2$-DCM (0.406 g, 0.498 mmol) and potassium vinyltrifluoroborate (2,000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave 6-ethenyl-3-methyl-3,4-dihydro-1H-isochromen-1-one. $^1$H NMR (500 MHz; CDCl$_3$): 8.07 (d, J=8.0 Hz, 1H), 7.44 (dd, J=1.2, 7.1 Hz, 1H), 7.26 (s, 1H), 6.75 (dd, J=10.8, 17.6 Hz, 1H), 5.90 (d, J=17.6 Hz, 1H), 5.44 (d, J=11 Hz, 1H), 4.75 (m, 1H), 2.96 (m, 2H), 1.54 (d, J=6.1 Hz, 3H); LC/MS (M+H)$^+$189;
Step B: (3R)-3-methyl-6-(oxiran-2-yl)-3,4-dihydro-1H-isochromen-1-one A solution of 6-ethenyl-3-methyl-3,4-dihydro-1H-isochromen-1-one (1.69 g, 8.98 mmol) in DCM (60 mL) was treated with m-CPBA (3.10 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give 3-methyl-6-(oxiran-2-yl)-3,4-dihydro-1H-isochromen-1-one.

$^1$H NMR (500 MHz; CDCl$_3$): 8.10 (d, J=8.0 Hz, 1H), 7.33 (m, 1H), 7.16 (d, J=4.4 Hz, 1H), 4.71 (m, 1H), 3.92 (dt, J=1.6, 2.5 Hz, 1H), 3.22 (dt, J=1.4, 4.1 Hz, 1H), 2.96 (m, 2H), 2.80 (dd, J=2.3, 3.5 Hz, 1H), 1.55 (d, J=7.6 Hz, 3H); LC/MS (M+H)$^+$205.

Intermediate (3S)-169

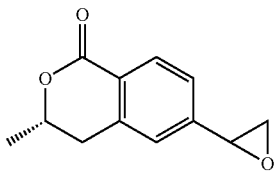

(3S)-3-methyl-6-(oxiran-2-yl)-3,4-dihydro-1H-isochromen-1-one
(3S)-3-Methyl-6-(oxiran-2-yl)-3,4-dihydro-1H-isochromen-1-one was prepared in an analogous fashion to that described for the synthesis of (3R)-3-methyl-6-(oxiran-2-yl)-3,4-dihydro-1H-isochromen-1-one except starting from (3S)-6-bromo-3-methyl-3,4-dihydro-1H-isochromen-1-one.

Intermediate 170

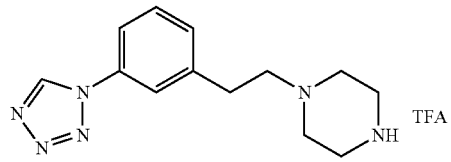 [SMILES: c1cc(CCN2CCNCC2)cc(-n2cnnn2)c1]

4-{2-[3-(1H-tetrazol-1yl)phenyl]ethyl}piperazin-1-ium trifluoroacetate
Step A: [3-(1H-tetrazol-1yl)phenyl]acetic acid 3-Aminophenylacetic acid (1.0 g, 6.62 mmol) was stirred in acetic acid (15 ml) and added triethyl orthoformate (2.203 ml, 13.23 mmol) followed by sodium azide (0.774 g, 11.91 mmol) then heated to reflux for 3 hrs. The reaction was concentrated and added water then extracted with ethyl acetate and tetrahydrofuran (2x). The organic layers were combined and washed with brine (1x), then dried over $Na_2SO_4$ and evaporated to dryness. The residue was triturated with ether, filtered and dried to yield [3-(1H-tetrazol-1yl)phenyl]acetic acid. LC-MS (IE, m/z): 205 [M+1]$^+$; $^1$H-NMR (500 MHz, DMSO) δ ppm 12.45 (b, 1H), 10.1 (s, 1H), 7.84 (s, 1H), 7.79 (dd, J=8 Hz, 1.4 Hz, 1H), 7.59 (t, J=7.9 Hz, 1H), 3.73 (s, 2H);
Step B: tert-butyl 4-{[3-(1H-tetrazol-1-yl)phenyl]acetyl}piperazine-1-carboxylate BOC-piperazine (502 mg, 2.69 mmol) was stirred in DCM (10 ml) and added the [3-(1H-tetrazol-1yl)phenyl]acetic acid (500 mg, 2.449 mmol) followed by HOBT (562 mg, 3.67 mmol) and EDC (939 mg, 4.90 mmol). The reaction was stirred at RT for 1 hr. The reaction was then poured into brine/NaHCO$_3$ mixture and extracted with DCM. The organic layer was washed with 1 N HCl then dried over NaSO$_4$, filtered and concentrated. The residue was purified by MPLC with 40 g ISCO Redi-sep column and eluted with 5% MeOH: 95% DCM solvent system to yield tert-butyl 4-{[3-(1H-tetrazol-1yl)phenyl]acetyl}piperazine-1-carboxylate. LC-MS (IE, m/z): 373 [M+1]$^+$; $^1$H-NMR (500 MHz, CDCl3) δ ppm 9.025 (s, 1H), 7.67 (s, 1H), 7.64 (d, J=8.1 Hz, 1H), 7.58 (t, J=8.8 Hz, 1H), 7.44 (d, J=7.6 Hz, 1H), 3.87 (s, 2H), 3.66 (t, J=5 Hz, 2H), 3.53-3.47 (m, 4H), 1.49 (s, 9H);
Step C: tert-butyl 4-{2-[3-(1H-tetrazol-1yl)phenyl]ethyl}piperazine-1-carboxylate tert-Butyl 4-{[3-(1H-tetrazol-1yl)phenyl]acetyl}piperazine-1-carboxylate (0.80 g, 2.148 mmol) was dissolved in THF (20 ml) and added the borane-tetrahydrofuran complex (4.30 ml, 4.30 mmol) then stirred at RT overnight. TLC showed a less polar spot but still has SM. Added another 2 equiv of borane-THF complex and followed the reaction with TLC. The reaction was first shaken with 1N HCl then basified with 1N NaOH and extracted with ETOAc. The organic layer was dried over Na$_2$SO$_4$, filtered and evaporated to dryness. The residue was chromatographed by MPLC-using 40 g ISCO Redi-sep column and eluted with 50% ethyl acetate/50% hexane to yield t-butyl 4-{2-[3-(1H-tetrazol- 1yl)phenyl]ethyl}piperazine-1-carboxylate. LC-MS (IE, m/z): 359 [M+1]+; 1H-NMR (500 MHz, CDCl3) δ ppm 9.04 (s, 1H), 7.64 (s, 1H), 7.60 (t, J=8.2 Hz, 1H), 7.57 (t, J=7.9 Hz, 1H), 7.44 (d, J=7.3 Hz, 1H), 3.87 (b, 4H), 3.32-3.36 (m, 2H), 3.12 (d, J=11.9 Hz, 2H), 3.024-3.06 (m, 2H), 2.70-2.75 (m, 2H), 1.49 (s, 9H);

Step D: 4-{2-[3-(1H-tetrazol-1yl)phenyl]ethyl}piperazin-1-ium trifluoroacetate

The t-butyl 4-{2-[3-(1H-tetrazol-1yl)phenyl]ethyl}piperazine-1-carboxylate (280 mg, 2.15 mmol) was stirred in TFA (5 ml) for ½ hr then concentrated and dried to yield 4-{2-(1h-tetrazol-1yl)phenyl]ethyl}piperazin-1-ium trifluoroacetate. LC-MS (IE, m/z): 259 [M+1]+.

The following INTERMEDIATES (Table) were prepared as described for 6-[1-Hydroxy-2-(piperazin-1-yl)ethyl]-3,4-dihydro-1-H-isochromen-1-one hydrochloride starting from either (3S)-3-methyl-6-(oxiran-2-yl)-3,4-dihydro-1H-isochromen-1-one or (3R)-3-methyl-6-(oxiran-2-yl)-3,4-dihydro-1H-isochromen-1-one and Boc-piperazine where the intermediate Boc-precursors were separated by preparative chiral SFC-HPLC (30% EtOH (w/0.05% DEA) as the co-solvent on AD-H chiral column) prior to final Boc protective group removal to provide single isomer final intermediates.

Intermediate 175

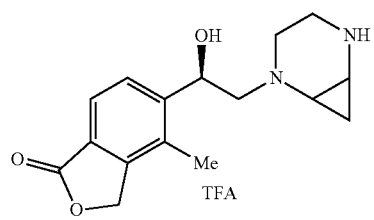 [SMILES: Cc1c([C@@H](O)CN2CCNC3CC32)ccc2c1COC2=O]

5-{(1R)-2-[(±)-2,5-diazabicyclo[4.1.0]hept-2yl]-1-hydroxyethyl}-4-methyl-2-benzofuran-1(3H)-one Step A: 1-tert-butyl 4-(9H-fluoren-9-ylmethyl) 2-oxopiperazine-1,4-dicarboxylate In a pre-dried flask, (9H-fluoren-9-yl)methyl 3-oxopiperazine-1-carboxylate (5.0 g, 15.51 mmol) was dissolved in THF (200 mL) under N2 and was cooled down to −78° C. Then LHMDS (15 mL, 15.00 mmol) was added. Mixture was stirred at −78° C. for 20 minutes, and Boc2O (5.40 mL, 23.27 mmol) was added. Let reaction stir at −78° C. for 1 hour. Then

| INTERME-DIATE | INTERMEDIATE STRUCTURE | | LC/MS (M + H)+ |
|---|---|---|---|
| 171 | | from faster eluting peak of Boc intermediate | 291 |
| 172 | | from slower eluting peak of Boc intermediate | 291 |
| 173 | | from faster eluting peak of Boc intermediate | 291 |
| 174 | | from slower eluting peak of Boc intermediate | 291 | reaction was quenched with distilled water (50 mL) and warmed to room temperature. The reaction mixture was extracted with dichloromethane (200 mL), washed with brine (50 mL) and dried over $Na_2SO_4$. Evaporation of the solvent gave crude product that was purified by silica gel column chromatography (Biotage, 120 gram column, eluting with 0-100% ethyl acetate in hexanes) to afford the title compound. $^1$H NMR (ppm) (500 MHz, CDCl3): δ 7.77 (2H, d, J=7.58 Hz), 7.56 (2H, d, J=7.50 Hz), 7.41 (2H, t, J=7.50 Hz), 7.32 (2H, t, J=7.46 Hz), 4.50 (2H, br), 4.23 (1H, t, J=7.0 Hz, t), 4.16-4.08 (2H, m), 3.75-3.53 (4H, 1.55 (9H, s).

Step B: 1-tert-butyl 4-(9H-fluoren-9-ylmethyl) 2-hydroxypiperazine-1,4-dicarboxylate In a pre-dried RB flask, 1-tert-butyl 4-(9H-fluoren-9-ylmethyl) 2-oxopiperazine-1,4-dicarboxylate (6.5 g, 15.39 mmol) was dissolved in $CH_2Cl_2$ (150 mL) and THF (15 mL) under N2 and was cooled down to −78° C. DIBAL-H (23.08 mL, 23.08 mmol) was added slowly. Let reaction stir at −78° C. for 2 hours. Then saturated Rochelle's salt water solution (150 mL) was added to quenched reaction. Reaction was slowly warmed up to room temperature. Then it was passed through a Celite® pad. Filtering pad was washed with ether (100 mL×2). Then layers were separated and aq. layer was extracted with 50 mL of EtOAc twice. Organic phases were combined and were washed with water and brine (50 mL) respectively. Then it was passed anhydrous $Na_2SO_4$. Concentration gave crude product as white solid that was used directly in next step. LC/MS: $(M+23)^+$=447.16

Step C: tert-butyl 9H-fluoren-9-ylmethyl 2,3-dihydropyrazine-1,4-dicarboxylate

In a round bottom flask charged with stirring bar, 1-tert-butyl 4-(9H-fluoren-9-ylmethyl) 2-hydroxypiperazine-1,4-dicarboxylate (4.34 g, 10.2 mmol) was dissolved in THF (100 mL) and was cooled down to 0° C. under N2. Then TFAA (1.589 mL, 11.25 mmol) was added. After stirring at 0° C. for 20 minutes, reaction was quenched by adding saturated aq. $NaHCO_3$ and warmed up to room temperature. Then reaction was diluted by adding 200 mL of DCM and 100 mL of water. Layers were separated and aqueous layer was extracted with 100 mL of DCM. Organic phases were combined and dried over anhydrous $Na_2SO_4$. Removing solvent gave crude product that was purified by ISCO (120 gram silica gel column, 0-50% EtOAc/Hexane gradient). Concentration gave the title compound. $^1$H NMR (ppm) (500 MHz, CDCl3): δ 7.81 (2H, d, J=7.59 Hz), 7.61 (2H, dd, J=13.92, 7.51 Hz), 7.44 (2H, t, J=7.49 Hz), 7.35 (2H, t, J=7.47 Hz), 6.27-6.14 (2H, m), 4.52 (2H, dd, J=19.02, 6.70 Hz), 4.31 (1H, t, J=6.89 Hz), 3.81-3.68 (4H, m), 1.54 (9H, s); LC/MS $(M+23)^+$=429.13;

Step D: tert-butyl (±)-9H-fluoren-9-ylmethyl 2,5-diazabicyclo[4.1.0]heptane-2,5-dicarboxylate In a pre-dried round bottom flask, tert-butyl 9H-fluoren-9-ylmethyl 2,3-dihydropyrazine-1,4-dicarboxylate (1.5 g, 3.69 mmol) was dissolved in anhydrous ether (80 ml) under $N_2$. Diethylzinc (27.4 ml, 27.4 mmol) in ether (1M) was added in via syringe. Diiodomethane (1.904 ml, 23.60 mmol) was added. Let reaction stir at room temperature overnight. On next day, reaction was quenched by adding 5 mL of saturated aqueous $NH_4Cl$. Reaction mixture was filtered over a pad of Celite® and filtering cake was washed with ether (25 mL×2). Then layers were separated and aqueous portion was extracted with ether (50 mL). The combined organic phases were washed with water (50 mL) and brine (50 mL), dried over anhydrous $Na_2SO_4$. Concentration at reduced pressure afforded crude product that was purified by silica gel column chromatography (40 gram silica gel column, eluted with 0-100% EtOAc/Hexane gradient). Removing solvent gave the title compound. $^1$H NMR (ppm) (500 MHz, CDCl3): δ 7.76 (2H, d, J=7.59 Hz), 7.66-7.53 (2H, m), 7.40 (2H, t, J=7.50 Hz), 7.31 (2H, t, J=7.45 Hz), 4.52-4.44 (2H, m), 4.26 (1H, t, J=7.13 Hz), 3.62-2.90 (6H, m), 1.50 (9H, s), 1.25-0.89 (1H, m). 0.55-0.39 (1H, m); LC/MS $(M+23)^+$=443.13;

Step E: tert-butyl (±)-2,5-diazabicyclo[4.1.0]heptane-2-carboxylate tert-Butyl (±)-9H-fluoren-9-ylmethyl 2,5-diazabicyclo[4.1.0]heptane-2,5-dicarboxylate (1.05 g, 2.50 mmol) was dissolved in Ether (25 mL) and was treated with 1-octanethiol (3.65 g, 24.97 mmol) at room temperature for 10 minutes. Then DBU (0.151 mL, 0.999 mmol) was added. Let mixture stir for 4 hours. Then solvent and extra 1-Octanethiol was removed under reduced pressure. And residue was put on 40 gram silica gel column and eluted on ISCO (0-15% MeOH/EtOAc). Removing solvent gave the title compound. $^1$H NMR (ppm) (500 MHz, CDCl3): δ 3.51-3.45 (1H, m), 3.05-2.58 (5H, m), 1.71 (1H, s), 1.45 (9H, s), 0.88-0.77 (1H, m), 0.53-0.44 (1H, m).

Step F: tert-butyl (±)5-[(2R)-2-hydroxy-2-(4-methyl-1-oxo-1,3-dihydro-2-benzofuran-5-yl)ethyl]-2,5-diazabicyclo[4.1.0]heptane-2-carboxylate In a microwave vial charged with stirring bar, tert-butyl (±)-2,5-diazabicyclo[4.1.0]heptane-2-carboxylate (341 mg, 1.72 mmol) was dissolved in EtOH (20 mL). 4-methyl-5-[(2R)-oxiran-2-yl]-2-benzofuran-1(3H)-one (654 mg, 3.44 mmol) was added. Then mixture was sealed and put on microwave reactor. It was heated up to 145° C. and was stir at 145° C. for 60 minutes. After cooling down to room temperature, solution was transferred to a round bottom flask and was concentrated on rotavapor to give crude product, which was purified by ISCO (80 gram silica gel column, eluted by 0-10% MeOH/DCM gradient). Removing solvent gave the title compound. LC/MS: $(M+1)^+$=389.14;

Step G: 5-{(1R)-2-[(±)-2,5-diazabicyclo[4.1.0]hept-2-yl]-1-hydroxyethyl}-4-methyl-2-benzofuran-1(3H)-one TFA salt In a round bottom flask charged with stirring bar, tert-butyl (±)5-[(2R)-2-hydroxy-2-(4-methyl-1-oxo-1,3-dihydro-2-benzofuran-5-yl)ethyl]-2,5-diazabicyclo[4.1.0]heptane-2-carboxylate (502 mg, 1.292 mmol) was dissolved in DCM (5 mL) and was treated with TFA (2 mL, 26.0 mmol) at room temperature for 3 hours. Then solvent was removed on rotavapor. Residue was re-dissolved in small amount of DCM and evaporated to take out remained TFA. Then it was dried on high vacuum pump for 4 hours to remove extra TFA. Without further purification, crude product was used to make ROMK inhibitors. LC/MS: $(M+1)^+$=289.

Example 1

Route 1; General Method A

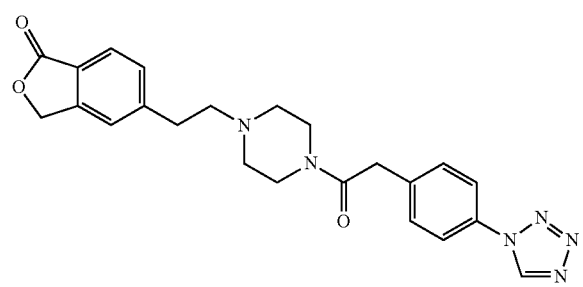 [SMILES: O=C1OCc2cc(CCN3CCN(C(=O)Cc4ccc(-n5cnnn5)cc4)CC3)ccc21]

5-[2-(4-{[4-(1H-tetrazol-1-yl)phenyl]acetyl}piperazin-1-yl)ethyl]-2-benzofurna-1(3H)-one Ozone was bubbled through a cooled (−78° C.) solution of 5-(prop-2-en-1-yl)-2-benzofuran-1(3H)-one (897 mg, 5.15 mmol) in DCM (30 mL) until the color changed to orange. Excess ozone was removed by bubbling $N_2$ through the solution for a minute. A solution of 1-(piperazin-1-yl)-2-[4-(1H-tetrazol-1-yl)phenyl]ethanone hydrochloride (530 mg, 1.72 mmol) and Et₃N (0.287 mL, 2.06 mmol) in DCM (2 mL) was added, followed by NaB(Oac)₃H (2.55 g, 12.0 mmol). The reaction mixture was stirred at rt for 1.5 h. The reaction mixture was diluted with DCM and washed with saturated sodium bicarbonate solution then brine. The organic layer was dried over MgSO₄, filtered and concentrated. The crude product was initially purified by flash chromatography 8% of 1:10 NH₄OH/MeOH in DCM. A more pure sample was obtained by further purification by mass-directed preparative HPLC. The free base was converted to its HCl salt with excess 4 N HCl in dioxane. LC/MS: [(M+1)]⁺=433.

Compounds of the present invention which are exemplified below form another embodiment of the present invention. These compounds can converted to a variety of salts by treatment with any of a number of acids.

Example 1

Route 2; General Method B

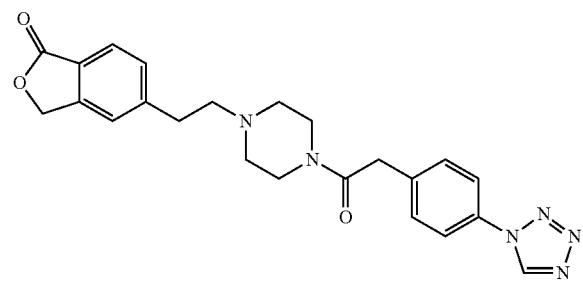 [SMILES: O=C1OCc2cc(CCN3CCN(C(=O)Cc4ccc(-n5cnnn5)cc4)CC3)ccc21]

5-[2-(4-{[4-(1H-tetrazol-1-yl)phenyl]acetyl}piperazin-1-yl)ethyl]-2-benzofuran-1(3H)-one 5-(2-Piperazin-1-ylethyl)-2-benzofuran-1(3M-one hydrochloride (4.02 g, 14.2 mmol) was combined with [4-(1H-tetrazol-1-yl)phenyl]acetic acid (commercially available, 3.63 g, 17.8 mmol), EDC (4.09 g, 21.3 mmol) and triethylamine (3.96 mL, 28.4 mmol) in DCM (30 mL) and stirred overnight at room temperature. The reaction mixture was diluted with DCM and washed with water, then brine. The organic layer was dried over MgSO₄, filtered, and concentrated. Purification by MPLC elutingh with 1:9 NH₄OH:Methanol in DCM (1 L of 4%, 1 L of 5%, 1 L of 5.5%, and 1 L of 6%) afforded 5-[2-(4-{[4-(1H-tetrazol-1-yl)phenyl]acetyl}piperazin-1-yl)ethyl]-2-benzofuran-1(3H)-one.
¹H-NMR (500 MHz, CDCl₃) δ ppm 9.03 (s, 1H), 7.86 (d, J=8 Hz, 1H), 7.71 (d, J=8.5 Hz, 2H), 7.51 (d, J=8.5 Hz, 2H), 7.40 (d, J=8 Hz, 1H), 7.35 (s, 1H), 5.32 (s, 2H), 3.85 (s, 2H), 3.73 (t, J=4.5 Hz, 2H), 3.57 (t, J=5 Hz, 2H), 2.96 (t, J=7 Hz, 2H), 2.68 (t, J=8.5 Hz, 2H), 2.55 (t, J=5 Hz, 2H), 2.48 (t, J=5 Hz, 2H); LC/MS: [(M+1)]⁺=433. The free base product could be converted to its HCl salt by dissolving in DCM (75 mL) and adding 10 mL of 1 M HCl in ether (Aldrich). The mixture was stirred for 5 min then was concentrated and pumped dry under vacuum to give the HCl salt. LC/MS: [(M+1)]⁺=433.

Example 2

General Method C

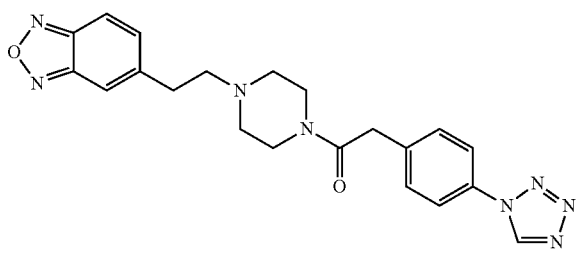 [SMILES: O=C(Cc1ccc(-n2cnnn2)cc1)N1CCN(CCc2ccc3nonc3c2)CC1]

1-{4-[2-(2,1,3-benzoxadiazol-5-yl)ethyl]piperazin-1-yl}-2-[4-(1H-tetrazol-1-yl)phenyl]ethanone 1-(Piperazin-1-yl)-2-[4-(1H-tetrazol-1-yl)phenyl]ethanone (125 mg, 0.405 mmol) was combined with 2,1,3-benzoxadiazol-5-ylacetaldehyde (65.7 mg, 0.405 mmol) in 1,2-dichloroethane (10 mL). Sodium triacetoxyborohydride (258 mg, 1.22 mmol) was added and the mixture was stirred overnight at room temperature. To the reaction mixture was added 1 N NaOH solution (1 mL) and DCM (1 mL). The organic layer was concentrated and purified by mass-directed HPLC to afford the title compound. LC/MS: [(M+1)]⁺=419.

Example 3

General Method D

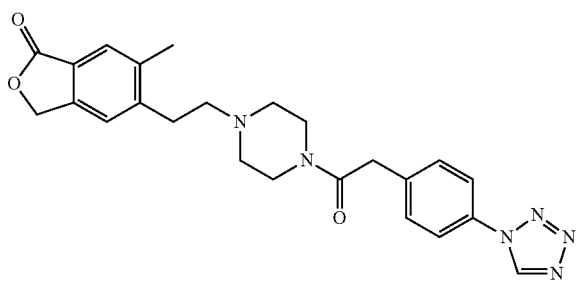 [SMILES: Cc1cc2c(cc1CCN1CCN(C(=O)Cc3ccc(-n4cnnn4)cc3)CC1)COC2=O]

6-methyl-5-[2-(4-{[4-(1h-tetrazol-1-yl)phenyl]acetyl}piperazin-1-yl)ethyl]-2-benzofuran-1(3H)-one To a flask charged with (6-methyl-1-oxo-1,3-dihydro-2-benzofuran-5-yl)acetaldehyde (100 mg, 0.53 mmol) was added 1-{[4-(1H-tetrazol-1-yl)phenyl]acetyl}piperazine hydrochloride (162 mg, 0.53 mmol), sodium cyanoborohydride (165 mg, 2.6 mmol), methanol (10 mL), and a drop of acetic acid. The mixture was allowed to stir at RT for 16 hours. LC showed formation of the desired product. The solvent was removed under reduced pressure. The residue was redissolved in DMSO-water, and purified by mass-directed HPLC. LC/MS: (1E, m/z) (M+1)+=447.3;

Examples 4A and 4B

General Method E, Separation of Diastereomers

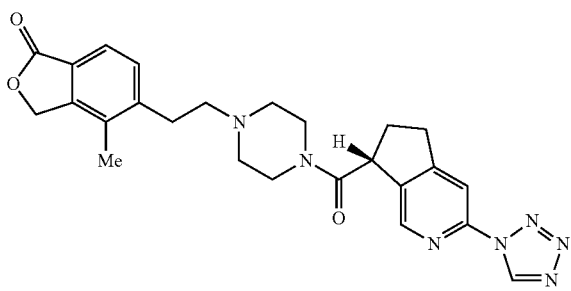

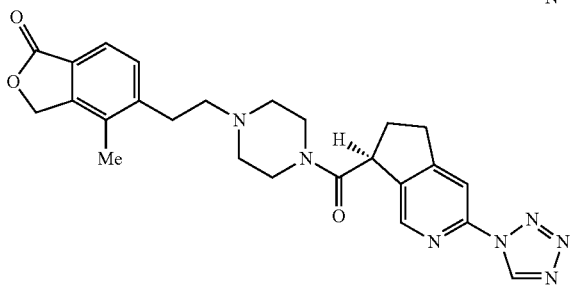

4-methyl-5-[2-(4-{[(7R)-3-(1H-tetrazol-1-yl)-6,7-dihydro-5H-cyclopenta[c]pyridin-7-yl]carbonyl}piperazin-1-yl)ethyl]-2-benzofuran-1(3H)-one, and 4-methyl-5-[2-(4-{[(7S)-3-(1H-tetrazol-1-yl)-6,7-dihydro-5H-cyclopenta[c]pyridin-7-yl]carbonyl}piperazin-1-yl)ethyl]-2-benzofuran-1(3H)-one 4-Methyl-5-[2-(4-{[3-(1H-tetrazol-1-yl)-6,7-dihydro-5H-cyclopenta[c]pyridin-7-yl]carbonyl}piperazin-1-yl)ethyl]-2-benzofuran-1(3H)-one was prepared starting from 3-(1H-tetrazol-1-yl)-6,7-dihydro-5H-cyclopenta[c]pyridine-7-carboxylic acid and 4-methyl-5-(2-piperazin-1-ylethyl)-2-benzofuran-1(3H)-one hydrochloride in an analogous fashion to that described by GENERAL METHOD B. The resulting mixture of two enantiomers was separated by preparative chiral SFC HPLC using a ChiralPak AD-H 250×30 mm I.D. column and eluting with A: SF CO2 and B: ethanol/acetonitrile (2:1) (0.1% DEA) with flow rate of 50 mL/min. The single title isomers were obtained.

Isomer A: LC/MS: (IE, m/z) (M+1)+=475

Isomer B: LC/MS: (IE, m/z) (M+1)+=475

Include in Table (above) to show one isomer is more potent.

The EXAMPLES in Table 1 were prepared in an analogous fashion to that described above in EXAMPLES 1-4 (GENERAL METHODS A, B, C, D, and E). by reductive amination (starting from amines and aldehydes or ketones), ozonolysis then reductive amination (starting from alkenes and amines), or amide coupling (starting from acids, and amines). All intermediates were prepared as described above.

TABLE 1

| example | Structure | General Method | MS: [(M + 1)]+ or HNMR |
|---|---|---|---|
| 5 | (structure) | B | 422 |
| 6 | (structure) | C | 402 |
| 7 | (structure) | B or C | 419 |
| 8 | (structure) | B | 420 |

TABLE 1-continued
| example | Structure | General Method | MS: [(M + 1)]+ or HNMR |
|---|---|---|---|
| 9 | 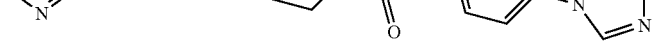 | B | 420 |
| 10 | 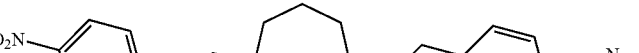 | B | 436 |
| 11 | 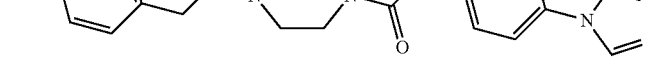 | B | 447 |
| 12 | 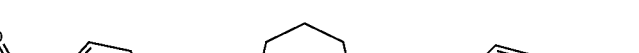 | A or B | 447 |
| 13 | 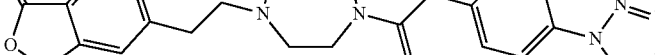 | B | 473 |
| 14 | 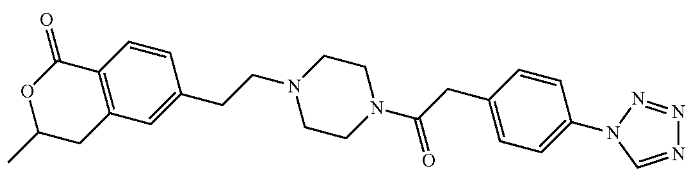 [SMILES: CC1Cc2cc(CCN3CCN(C(=O)Cc4ccc(-n5cnnn5)cc4)CC3)ccc2C(=O)O1] | * | ** |
| 15 | 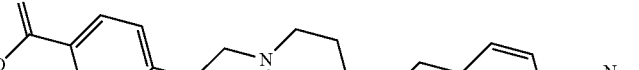 | * | ** |
| 16 | 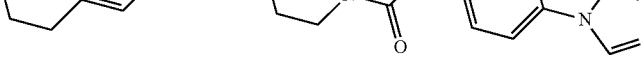 | B | 471 |
| 17 | 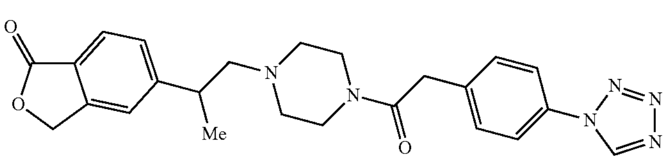 [SMILES: CC(CN1CCN(C(=O)Cc2ccc(-n3cnnn3)cc2)CC1)c1ccc2c(c1)COC2=O] | * | 447 |

TABLE 1-continued

| example | Structure | General Method | MS: [(M + 1)]+ or HNMR |
|---|---|---|---|
| 18 | 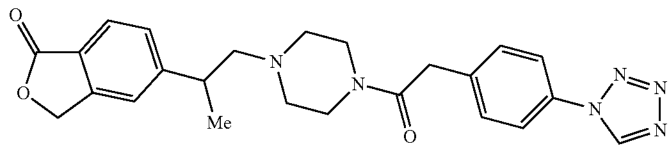 [SMILES: CC(CN1CCN(C(=O)Cc2ccc(-n3cnnn3)cc2)CC1)c1ccc2c(c1)COC2=O] | * | 447 |
| 19 | 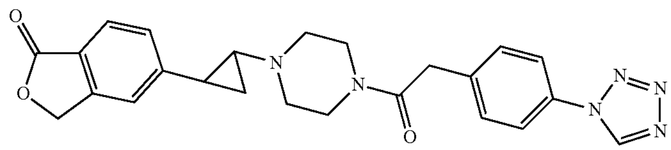 [SMILES: O=C1OCc2cc(C3CC3N3CCN(C(=O)Cc4ccc(-n5cnnn5)cc4)CC3)ccc21] | B | ** |
| 20 | 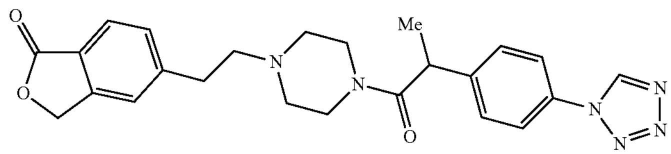 [SMILES: CC(C(=O)N1CCN(CCc2ccc3c(c2)COC3=O)CC1)c1ccc(-n2cnnn2)cc1] | B | 447 |
| 21 | 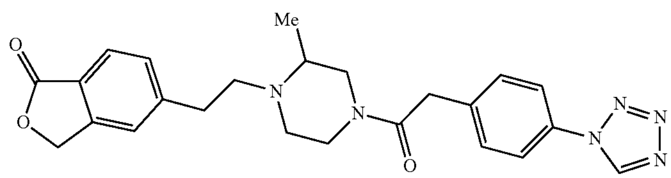 [SMILES: CC1CN(C(=O)Cc2ccc(-n3cnnn3)cc2)CCN1CCc1ccc2c(c1)COC2=O] | B | 447 |
| 22 | 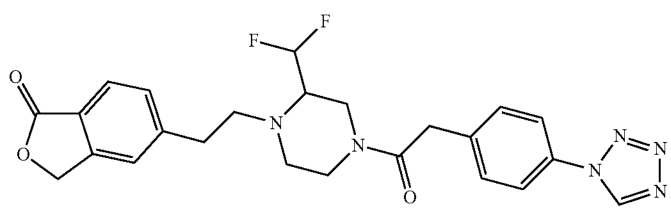 [SMILES: O=C1OCc2cc(CCN3CCN(C(=O)Cc4ccc(-n5cnnn5)cc4)CC3C(F)F)ccc21] | B | 483 |
| 23 | 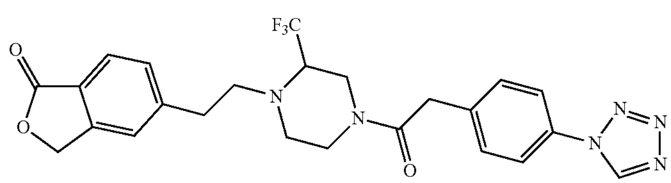 [SMILES: O=C1OCc2cc(CCN3CCN(C(=O)Cc4ccc(-n5cnnn5)cc4)CC3C(F)(F)F)ccc21] | B | 501 |
| 24 | 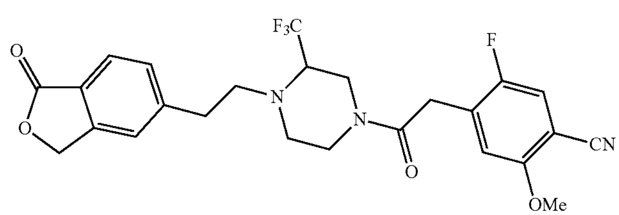 [SMILES: COc1cc(CC(=O)N2CCN(CCc3ccc4c(c3)COC4=O)C(C(F)(F)F)C2)c(F)cc1C#N] | B | 506 |
| 25 | 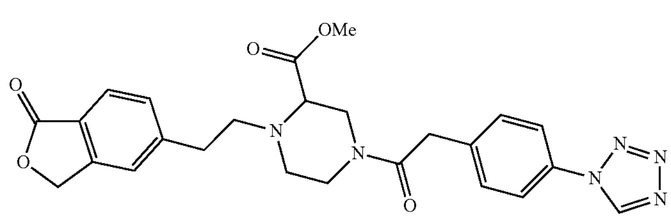 [SMILES: COC(=O)C1CN(C(=O)Cc2ccc(-n3cnnn3)cc2)CCN1CCc1ccc2c(c1)COC2=O] | B | 491 |

TABLE 1-continued
| example | Structure | General Method | MS: [(M + 1)]+ or HNMR |
|---|---|---|---|
| 26 | 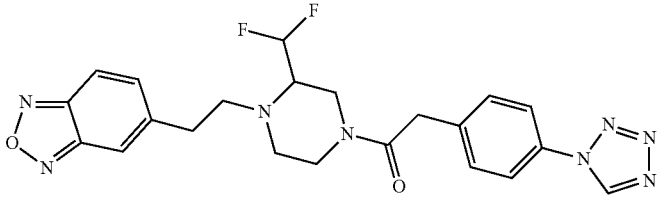 [SMILES: O=C(Cc1ccc(-n2cnnn2)cc1)N1CCN(CCc2ccc3nonc3c2)C(C(F)F)C1] | B | 469 |
| 27 | 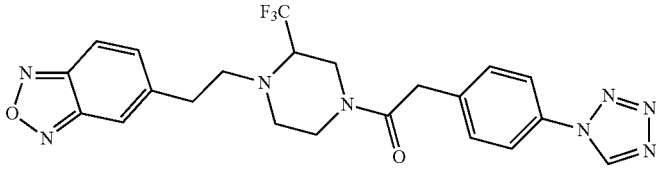 [SMILES: O=C(Cc1ccc(-n2cnnn2)cc1)N1CCN(CCc2ccc3nonc3c2)C(C(F)(F)F)C1] | B | 487 |
| 28 | 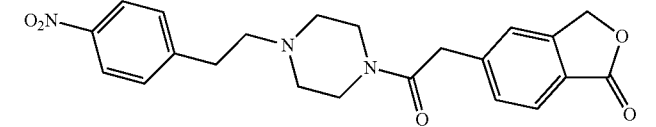 [SMILES: O=C1OCc2cc(CC(=O)N3CCN(CCc4ccc([N+](=O)[O-])cc4)CC3)ccc21] | B | 410 |
| 29 | 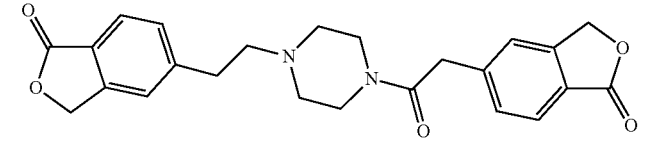 [SMILES: O=C1OCc2cc(CCN3CCN(C(=O)Cc4ccc5c(c4)COC5=O)CC3)ccc21] | B | 421 |
| 30 | 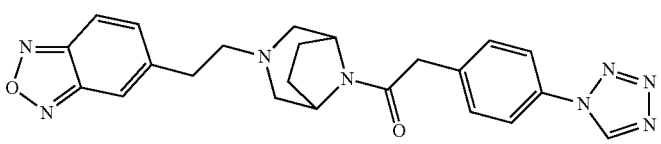 [SMILES: O=C(Cc1ccc(-n2cnnn2)cc1)N1C2CCC1CN(CCc1ccc3nonc3c1)C2] | C | 445 |
| 31 | 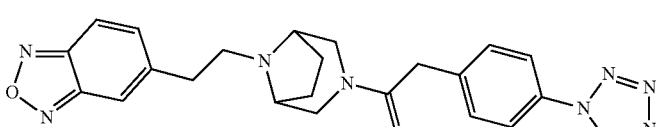 | C | 445 |
| 32 | 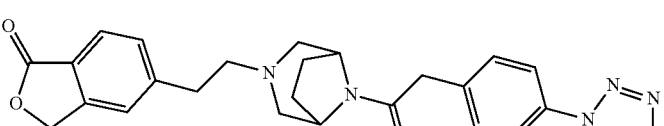 | D | 459 |
| 33 | 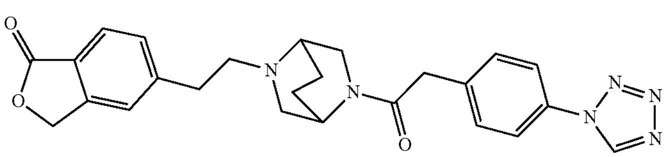 [SMILES: O=C1OCc2cc(CCN3CC4CCC3CN4C(=O)Cc3ccc(-n4cnnn4)cc3)ccc21] | D | 459 |
| 34 | 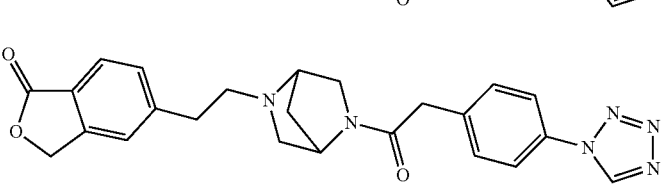 | C | 445 |

TABLE 1-continued
| example | Structure | General Method | MS: [(M + 1)]+ or HNMR |
|---|---|---|---|
| 35 | 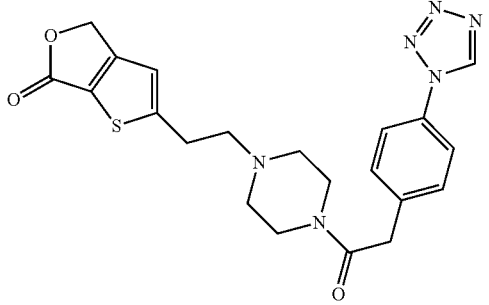 [SMILES: O=C1OCc2cc(CCN3CCN(C(=O)Cc4ccc(-n5cnnn5)cc4)CC3)sc21] | A | 439 |
| 36 | 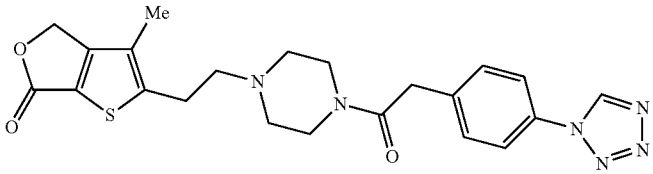 [SMILES: Cc1c(CCN2CCN(C(=O)Cc3ccc(-n4cnnn4)cc3)CC2)sc2c1COC2=O] | A | 453 |
| 37 | 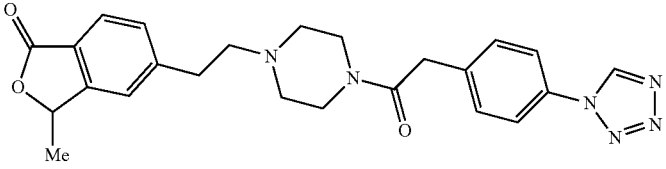 [SMILES: CC1OC(=O)c2ccc(CCN3CCN(C(=O)Cc4ccc(-n5cnnn5)cc4)CC3)cc21] | A | 447 |
| 38 | 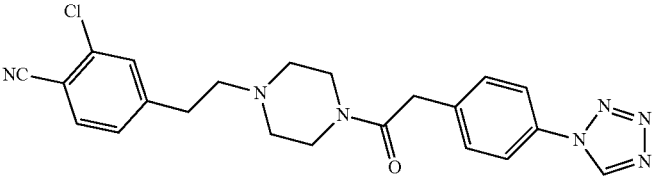 | A | 436 |
| 39 | 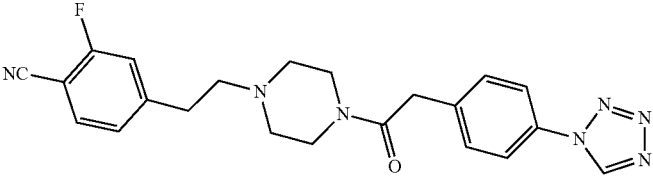 | A | 420 |
| 40 | 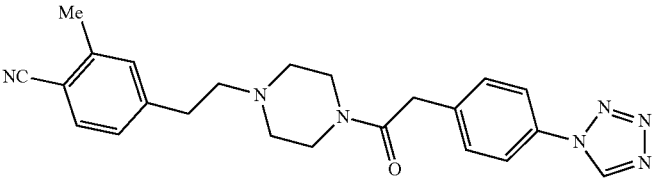 [SMILES: N#Cc1ccc(CCN2CCN(C(=O)Cc3ccc(-n4cnnn4)cc3)CC2)cc1Cl] | A | 416 |
| 41 | 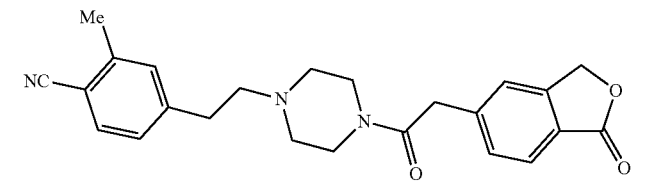 [SMILES: Cc1cc(CCN2CCN(C(=O)Cc3ccc4c(c3)COC4=O)CC2)ccc1C#N] | A | 404 |

TABLE 1-continued

| example | Structure | General Method | MS: [(M + 1)]⁺ or HNMR |
|---|---|---|---|
| 42 | 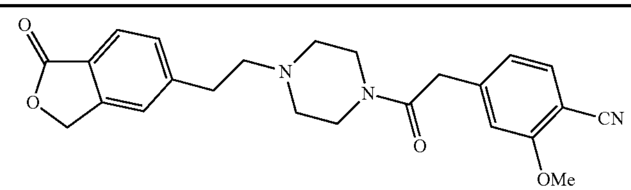 | B | 420 |
| 43 | 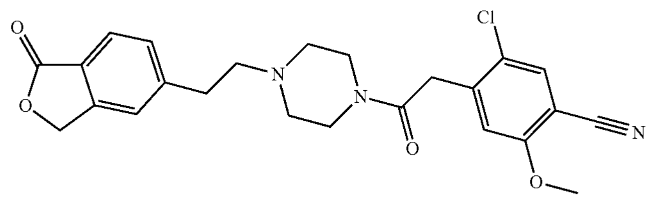 [SMILES: COc1cc(CC(=O)N2CCN(CCc3ccc4c(c3)COC4=O)CC2)c(Cl)cc1C#N] | B | 454 |
| 44 | 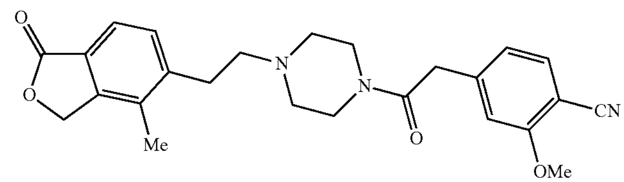 [SMILES: COc1cc(CC(=O)N2CCN(CCc3ccc4c(c3C)COC4=O)CC2)ccc1C#N] | C | 434 |
| 45 | 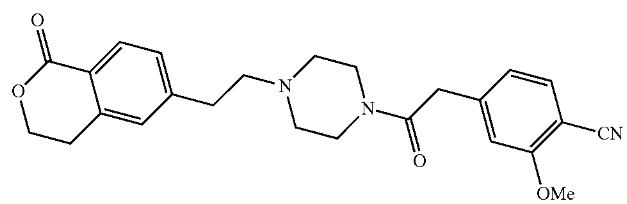 [SMILES: COc1cc(CC(=O)N2CCN(CCc3ccc4c(c3)CCOC4=O)CC2)ccc1C#N] | C | 434 |
| 46 | 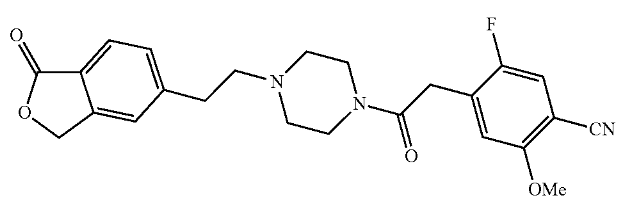 [SMILES: COc1cc(CC(=O)N2CCN(CCc3ccc4c(c3)COC4=O)CC2)c(F)cc1C#N] | B | 438 |
| 47 | 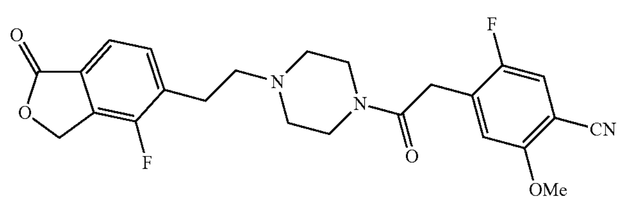 [SMILES: COc1cc(CC(=O)N2CCN(CCc3ccc4c(c3F)COC4=O)CC2)c(F)cc1C#N] | B | 456 |
| 48 | 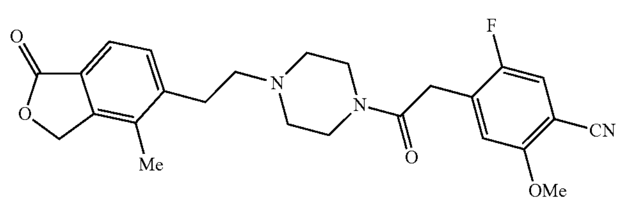 [SMILES: COc1cc(CC(=O)N2CCN(CCc3ccc4c(c3C)COC4=O)CC2)c(F)cc1C#N] | D | 452 |
| 49 | 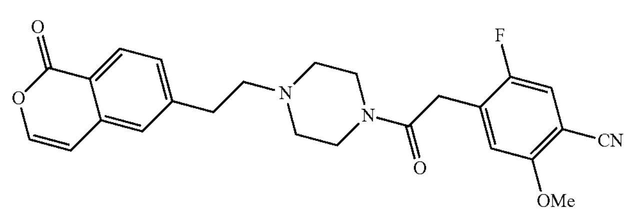 [SMILES: COc1cc(CC(=O)N2CCN(CCc3ccc4c(=O)occc4c3)CC2)c(F)cc1C#N] | B | 450 |

TABLE 1-continued
| example | Structure | General Method | MS: [(M + 1)]+ or HNMR |
|---|---|---|---|
| 50 | 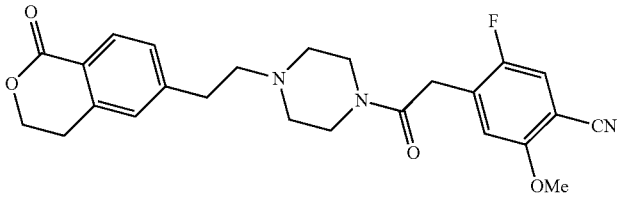 [SMILES: COc1cc(CC(=O)N2CCN(CCc3ccc4c(c3)CCOC4=O)CC2)c(F)cc1C#N] | B | 452 |
| 51 | 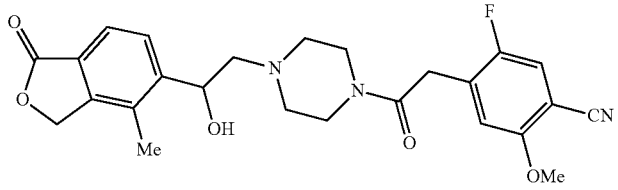 [SMILES: COc1cc(CC(=O)N2CCN(CC(O)c3ccc4c(c3C)COC4=O)CC2)c(F)cc1C#N] | B | 468 |
| 52 | 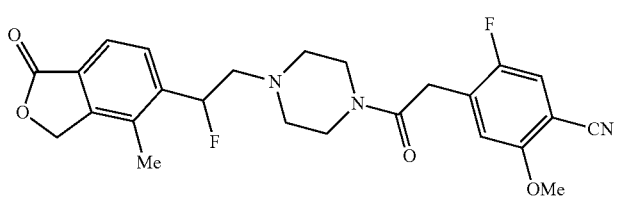 [SMILES: COc1cc(CC(=O)N2CCN(CC(F)c3ccc4c(c3C)COC4=O)CC2)c(F)cc1C#N] | B | 470 |
| 53 | 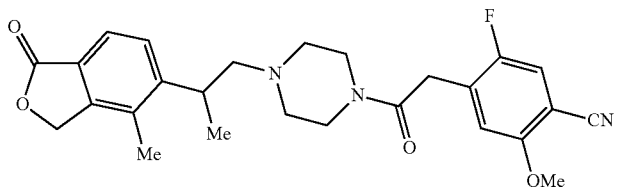 [SMILES: COc1cc(CC(=O)N2CCN(CC(C)c3ccc4c(c3C)COC4=O)CC2)c(F)cc1C#N] | B | 466 |
| 54 | 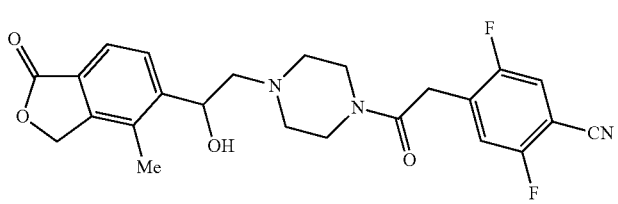 | B | 456 |
| 55 | 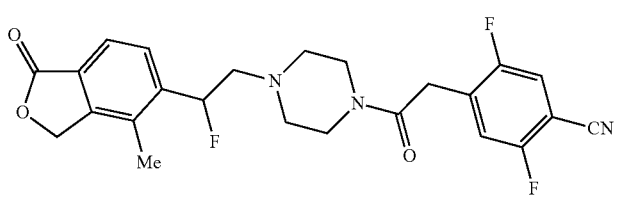 [SMILES: Cc1c(C(F)CN2CCN(C(=O)Cc3cc(F)c(C#N)cc3F)CC2)ccc2c1COC2=O] | B | 458 |
| 56 | 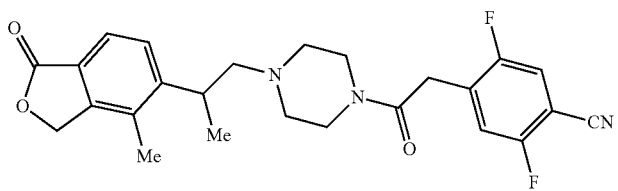 [SMILES: Cc1c(C(C)CN2CCN(C(=O)Cc3cc(F)c(C#N)cc3F)CC2)ccc2c1COC2=O] | B | 454 |

TABLE 1-continued

| example | Structure | General Method | MS: [(M + 1)]⁺ or HNMR |
|---|---|---|---|
| 57 | 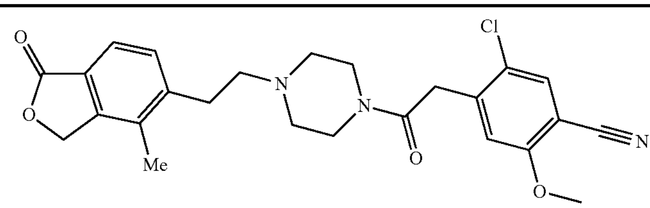 | B | 468 |
| 58 | 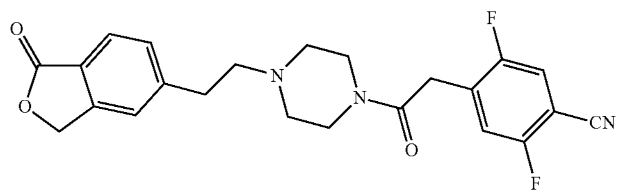 [SMILES: N#Cc1cc(F)c(CC(=O)N2CCN(CCc3ccc4c(c3)COC4=O)CC2)cc1F] | B | 426 |
| 59 | 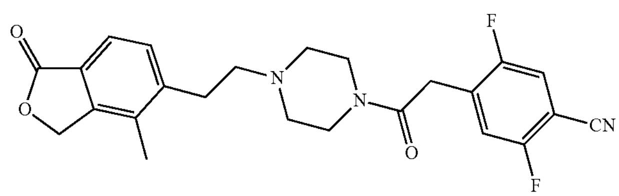 [SMILES: Cc1c(CCN2CCN(C(=O)Cc3cc(F)c(C#N)cc3F)CC2)ccc2c1COC2=O] | B | 440 |
| 60 | 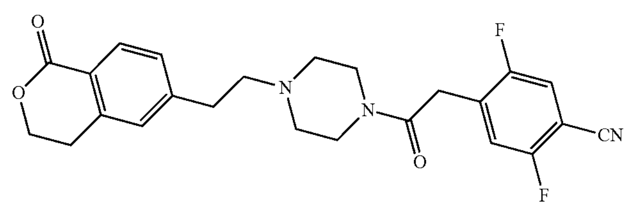 [SMILES: N#Cc1cc(F)c(CC(=O)N2CCN(CCc3ccc4c(c3)CCOC4=O)CC2)cc1F] | B | 440 |
| 61 | 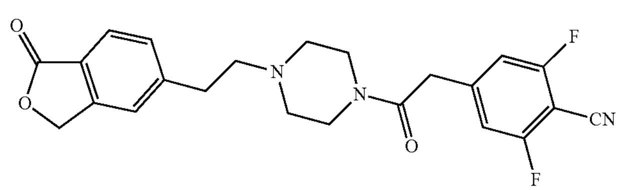 [SMILES: N#Cc1c(F)cc(CC(=O)N2CCN(CCc3ccc4c(c3)COC4=O)CC2)cc1F] | B | 426 |
| 62 | 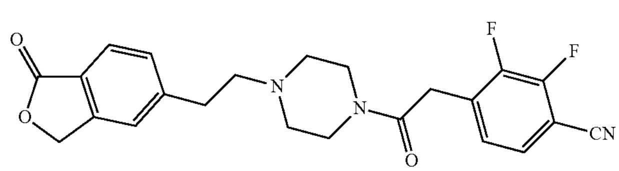 [SMILES: N#Cc1ccc(CC(=O)N2CCN(CCc3ccc4c(c3)COC4=O)CC2)c(F)c1F] | B | 426 |
| 63 | 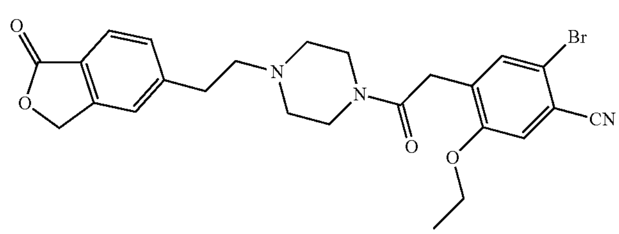 [SMILES: CCOc1cc(C#N)c(Br)cc1CC(=O)N1CCN(CCc2ccc3c(c2)COC3=O)CC1] | B | 512, 514 |
| 64 | 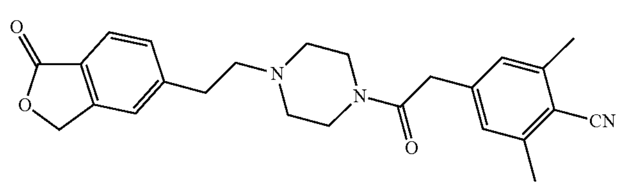 [SMILES: Cc1cc(CC(=O)N2CCN(CCc3ccc4c(c3)COC4=O)CC2)cc(C)c1C#N] | B | 418 |

TABLE 1-continued

| example | Structure | General Method | MS: [(M + 1)]+ or HNMR |
|---|---|---|---|
| 65 | 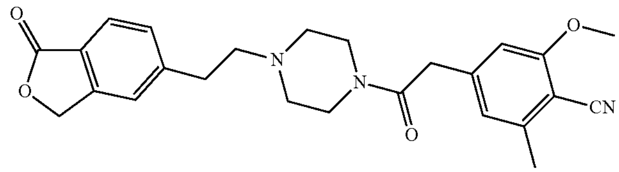 [SMILES: COc1cc(CC(=O)N2CCN(CCc3ccc4c(c3)COC4=O)CC2)cc(C)c1C#N] | B | 433 |
| 66 | 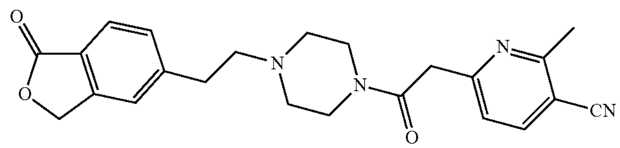 [SMILES: Cc1nc(CC(=O)N2CCN(CCc3ccc4c(c3)COC4=O)CC2)ccc1C#N] | B | 404 |
| 67 | 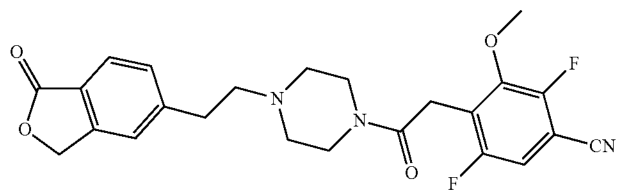 [SMILES: COc1c(F)c(C#N)cc(F)c1CC(=O)N1CCN(CCc2ccc3c(c2)COC3=O)CC1] | B | 456 |
| 68 | 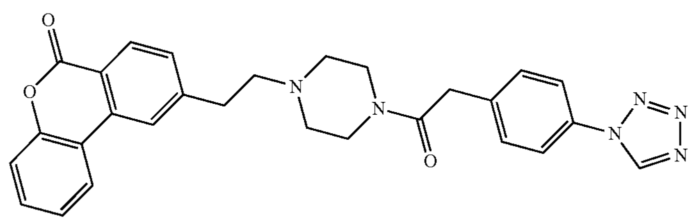 [SMILES: O=C(Cc1ccc(-n2cnnn2)cc1)N1CCN(CCc2ccc3c(=O)oc4ccccc4c3c2)CC1] | C | 495 |
| 69 | 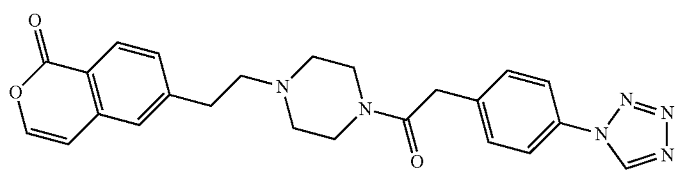 [SMILES: O=C(Cc1ccc(-n2cnnn2)cc1)N1CCN(CCc2ccc3c(=O)occc3c2)CC1] | B | 445 |
| 70 | 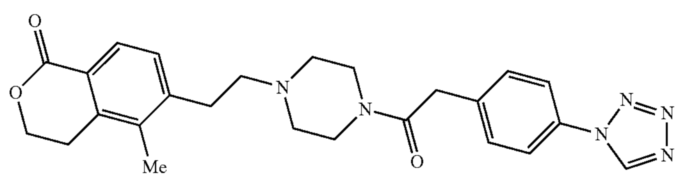 [SMILES: Cc1c(CCN2CCN(C(=O)Cc3ccc(-n4cnnn4)cc3)CC2)ccc2c1CCOC2=O] | D | 461 |
| 71 | 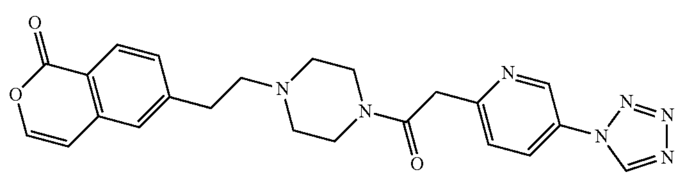 | B | 446 |
| 72 | 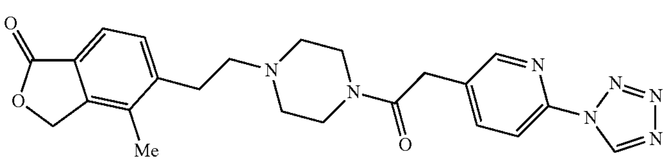 | B | 448 |
| 73 | 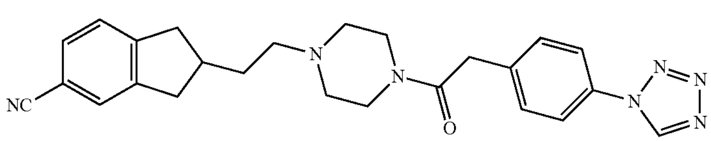 [SMILES: N#Cc1ccc2c(c1)CC(CCN1CCN(C(=O)Cc3ccc(-n4cnnn4)cc3)CC1)C2] | B | 414 |

TABLE 1-continued
| example | Structure | General Method | MS: [(M + 1)]+ or HNMR |
|---|---|---|---|
| 74 | 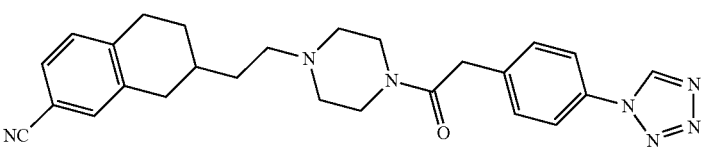 [SMILES: N#Cc1ccc2c(c1)CC(CCN1CCN(C(=O)Cc3ccc(-n4cnnn4)cc3)CC1)CC2] | C | 428 |
| 75 | 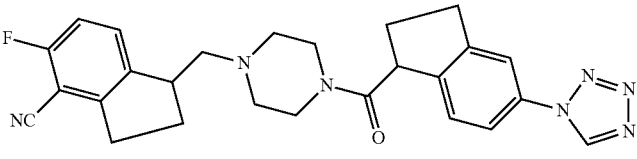 [SMILES: N#Cc1c(F)ccc2c1CCC2CN1CCN(C(=O)C2CCc3cc(-n4cnnn4)ccc32)CC1] | B | 472 |
| 76 | 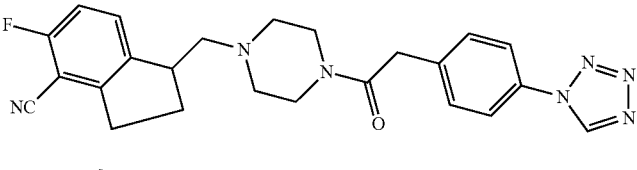 | D | 446 |
| 77 | 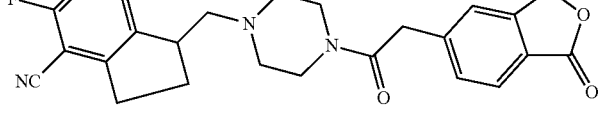 | D | 434 |
| 78 | 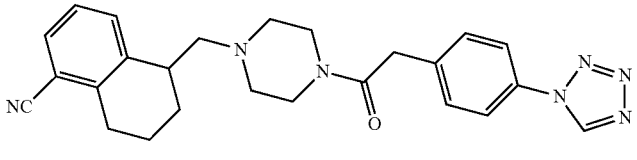 [SMILES: N#Cc1cccc2c1CCCC2CN1CCN(C(=O)Cc2ccc(-n3cnnn3)cc2)CC1] | D | ** |
| 79 | 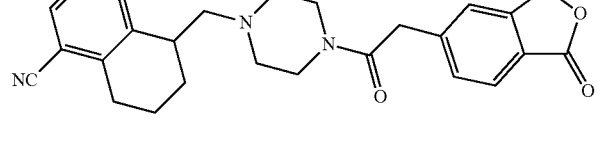 | B | ** |
| 80 | 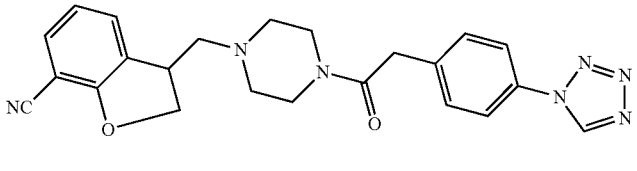 [SMILES: N#Cc1cccc2c1OCC2CN1CCN(C(=O)Cc2ccc(-n3cnnn3)cc2)CC1] | B | 430 |
| 81 | 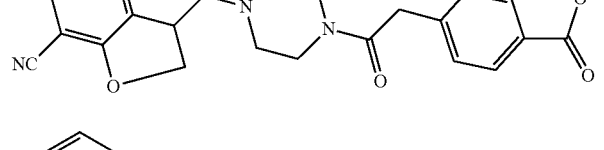 | B | 418 |
| 82 | 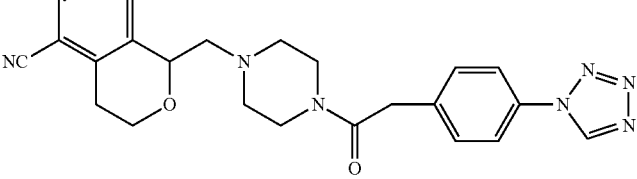 | D | ** |

TABLE 1-continued

| example | Structure | General Method | MS: [(M + 1)]+ or HNMR |
|---|---|---|---|
| 83 | 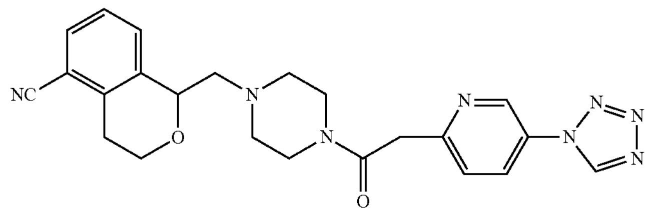 [SMILES: N#Cc1cccc2c1CCOC2CN1CCN(C(=O)Cc2ccc(-n3cnnn3)cn2)CC1] | B | ** |
| 84 | 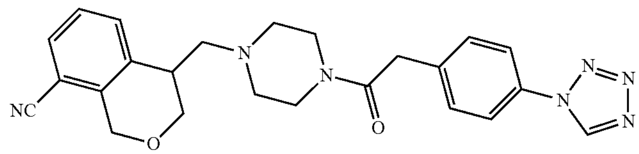 [SMILES: N#Cc1cccc2c1COCC2CN1CCN(C(=O)Cc2ccc(-n3cnnn3)cc2)CC1] | D | ** |
| 85 | 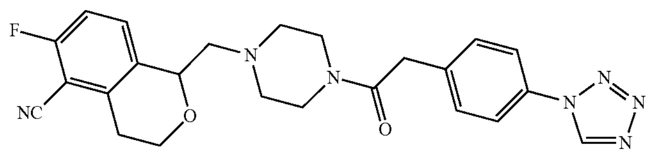 [SMILES: N#Cc1c(F)ccc2c1CCOC2CN1CCN(C(=O)Cc2ccc(-n3cnnn3)cc2)CC1] | B | ** |
| 86 | 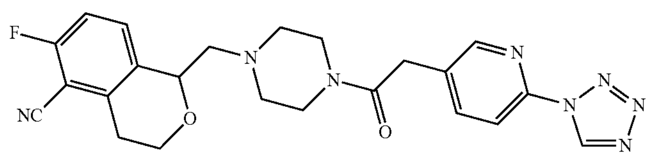 | B | 463 |
| 87 | 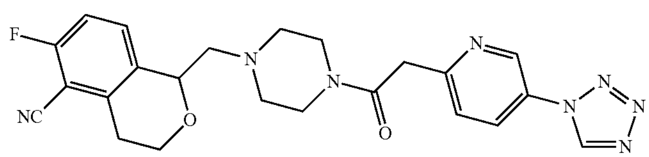 [SMILES: N#Cc1c(F)ccc2c1CCOC2CN1CCN(C(=O)Cc2ccc(-n3cnnn3)cn2)CC1] | B | 463 |
| 88 | 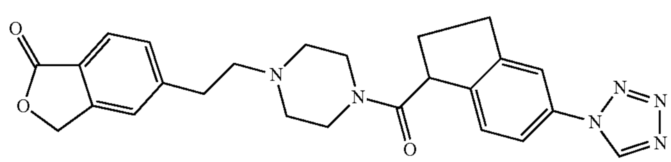 [SMILES: O=C1OCc2cc(CCN3CCN(C(=O)C4CCc5cc(-n6cnnn6)ccc54)CC3)ccc21] | B | 459 |
| 89 | 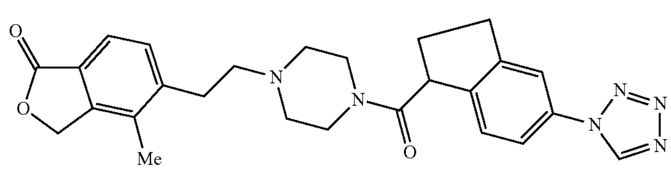 [SMILES: Cc1c(CCN2CCN(C(=O)C3CCc4cc(-n5cnnn5)ccc43)CC2)ccc2c1COC2=O] | * | 473 |
| 90 | 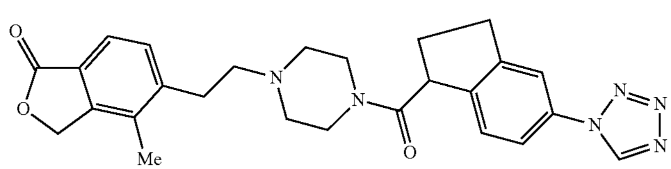 | * | 473 |
| 91 | 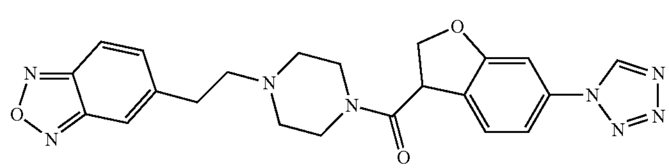 [SMILES: O=C(C1COc2cc(-n3cnnn3)ccc21)N1CCN(CCc2ccc3nonc3c2)CC1] | B | 447 |

TABLE 1-continued

| example | Structure | General Method | MS: [(M + 1)]+ or HNMR |
|---|---|---|---|
| 92 | 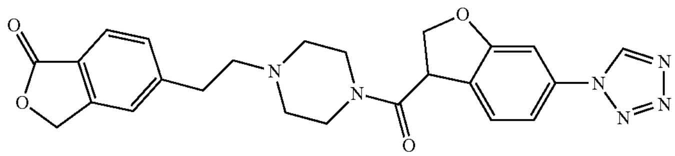 [SMILES: O=C1OCc2cc(CCN3CCN(C(=O)C4COc5cc(-n6cnnn6)ccc54)CC3)ccc21] | B | 461 |
| 93 | 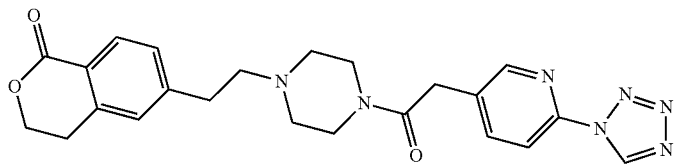 | B | 448 |
| 94 | 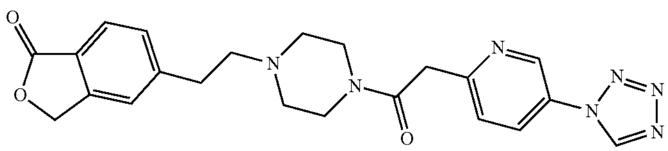 [SMILES: O=C1OCc2cc(CCN3CCN(C(=O)Cc4ccc(-n5cnnn5)cn4)CC3)ccc21] | D | 434 |
| 95 | 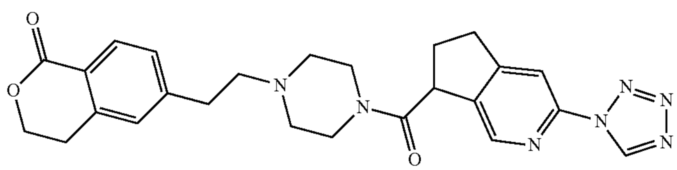 [SMILES: O=C1OCCc2cc(CCN3CCN(C(=O)C4CCc5cc(-n6cnnn6)ncc54)CC3)ccc21] | * | 474 |
| 96 | 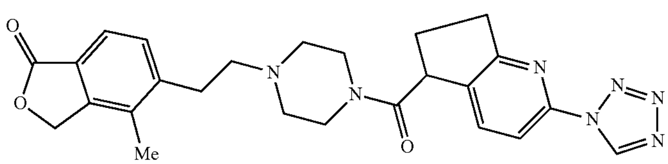 [SMILES: Cc1c(CCN2CCN(C(=O)C3CCc4nc(-n5cnnn5)ccc43)CC2)ccc2c1COC2=O] | * | 474 |
| 97 | 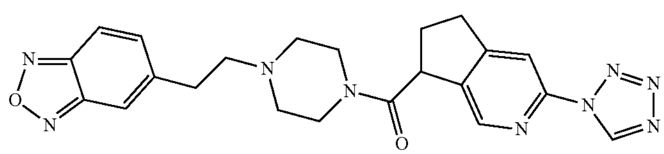 [SMILES: O=C(C1CCc2cc(-n3cnnn3)ncc21)N1CCN(CCc2ccc3nonc3c2)CC1] | * | 446 |
| 98 | 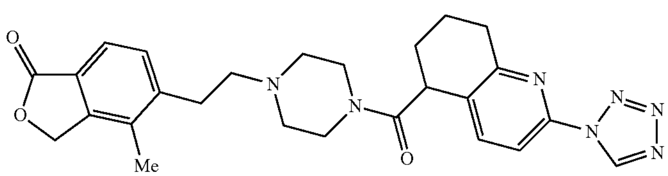 [SMILES: Cc1c(CCN2CCN(C(=O)C3CCCc4nc(-n5cnnn5)ccc43)CC2)ccc2c1COC2=O] | B | 488 |
| 99 | 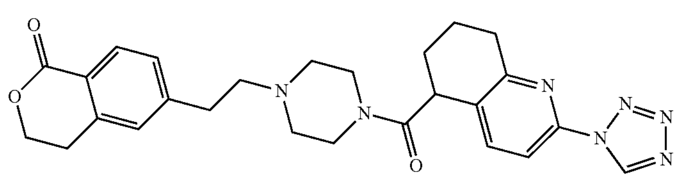 [SMILES: O=C1OCCc2cc(CCN3CCN(C(=O)C4CCCc5nc(-n6cnnn6)ccc54)CC3)ccc21] | B | 488 |
| 100 | 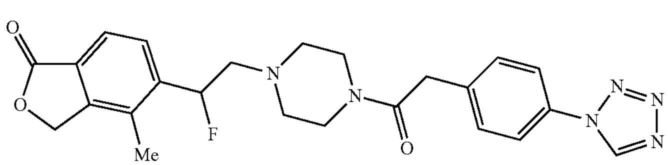 [SMILES: Cc1c(C(F)CN2CCN(C(=O)Cc3ccc(-n4cnnn4)cc3)CC2)ccc2c1COC2=O] | B | 465 |

TABLE 1-continued
| example | Structure | General Method | MS: [(M + 1)]⁺ or HNMR |
|---|---|---|---|
| 101 | 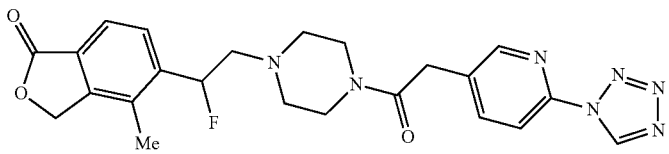 | B | 466 |
| 102 | 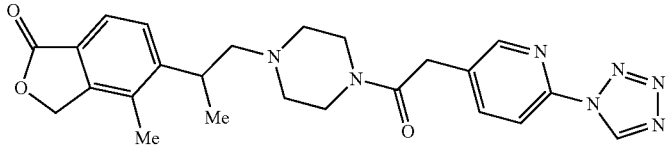 [SMILES: Cc1c(C(C)CN2CCN(C(=O)Cc3ccc(-n4cnnn4)nc3)CC2)ccc2c1COC2=O] | B | 462 |
| 103 | 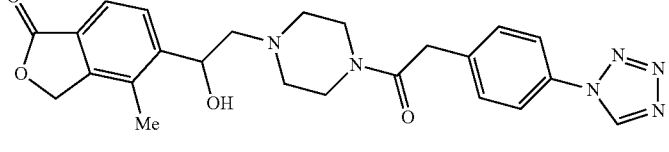 | B | 463 |
| 104 | 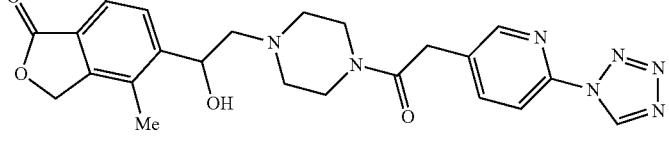 | B | 464 |
| 105 | 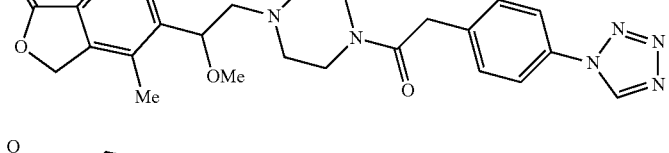 | B | 477 |
| 106 | 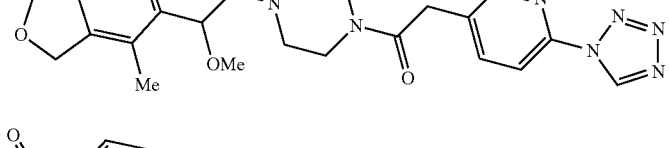 | B | 478 |
| 107 | 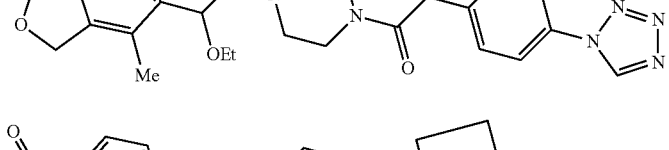 | B | 492 |
| 108 | 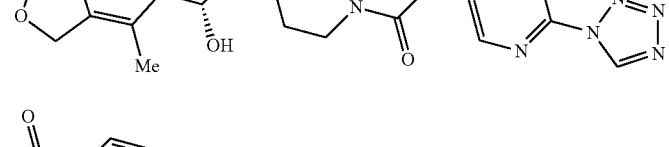 | * | 490 |
| 109 | 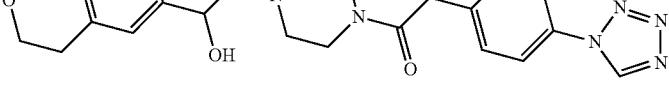 | B | 464 |

TABLE 1-continued

| example | Structure | General Method | MS: [(M + 1)]+ or HNMR |
|---|---|---|---|
| 110 | 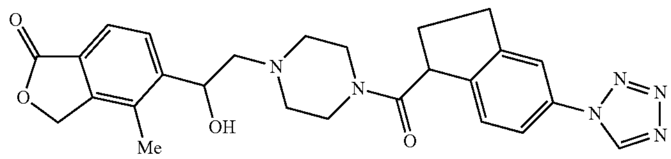 [SMILES: Cc1c(C(O)CN2CCN(C(=O)C3CCc4cc(-n5cnnn5)ccc43)CC2)ccc2c1COC2=O] | B | 489 |
| 111 | 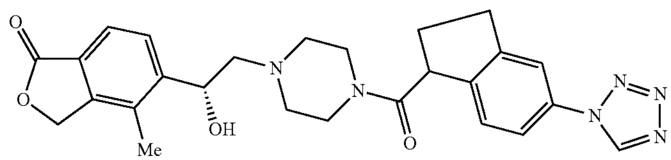 | * | 489 |
| 112 | 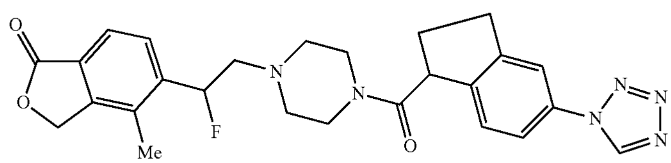 [SMILES: Cc1c(C(F)CN2CCN(C(=O)C3CCc4cc(-n5cnnn5)ccc43)CC2)ccc2c1COC2=O] | B | 491 |
| 113 | 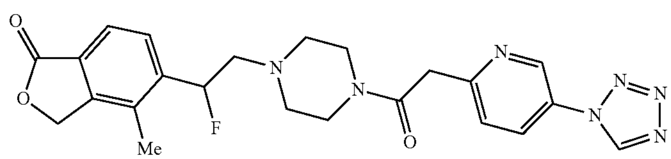 | B | 466 |
| 114 | 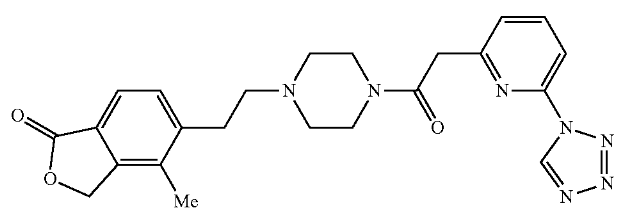 [SMILES: Cc1c(CCN2CCN(C(=O)Cc3cccc(-n4cnnn4)n3)CC2)ccc2c1COC2=O] | B | 420 (M + H − 28)+ Loss of N2 |
| 115 | 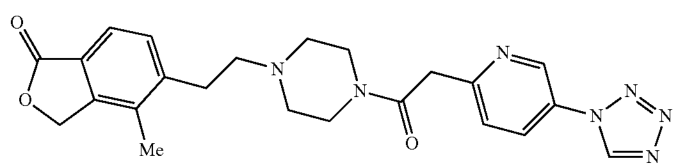 [SMILES: Cc1c(CCN2CCN(C(=O)Cc3ccc(-n4cnnn4)cn3)CC2)ccc2c1COC2=O] | B | 448 |
| 116 | 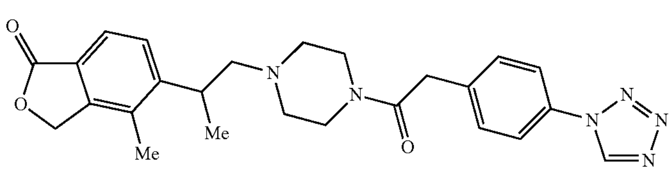 [SMILES: Cc1c(C(C)CN2CCN(C(=O)Cc3ccc(-n4cnnn4)cc3)CC2)ccc2c1COC2=O] | D | 461 |
| 117 | 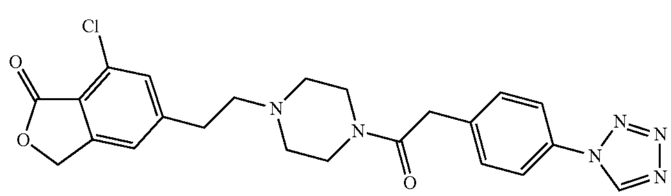 [SMILES: O=C1OCc2cc(CCN3CCN(C(=O)Cc4ccc(-n5cnnn5)cc4)CC3)cc(Cl)c21] | D | 467 |

TABLE 1-continued

| example | Structure | General Method | MS: [(M + 1)]+ or HNMR |
|---|---|---|---|
| 118 | 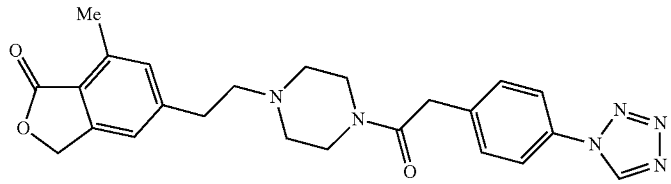 [SMILES: Cc1cc(CCN2CCN(C(=O)Cc3ccc(-n4cnnn4)cc3)CC2)cc2c1C(=O)OC2] | D | 447 |
| 119 | 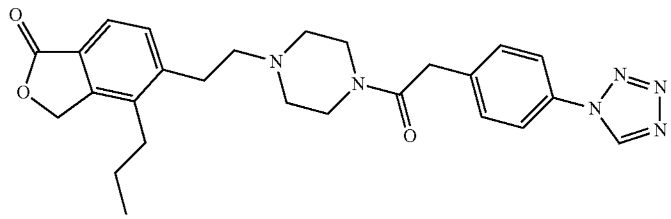 [SMILES: CCCc1c(CCN2CCN(C(=O)Cc3ccc(-n4cnnn4)cc3)CC2)ccc2c1COC2=O] | D | 475 |
| 120 | 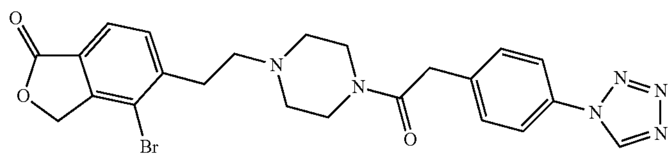 | D | 511, 513 |
| 121 | 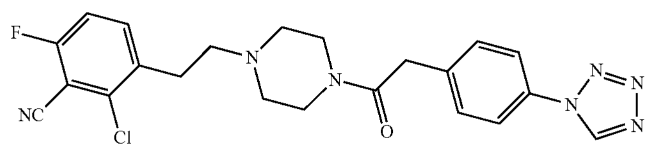 [SMILES: N#Cc1c(F)ccc(CCN2CCN(C(=O)Cc3ccc(-n4cnnn4)cc3)CC2)c1Cl] | D | 454 |
| 122 | 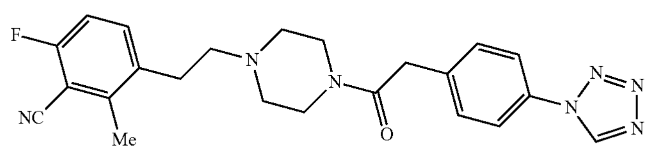 [SMILES: Cc1c(CCN2CCN(C(=O)Cc3ccc(-n4cnnn4)cc3)CC2)ccc(F)c1C#N] | D | ** |
| 123 | 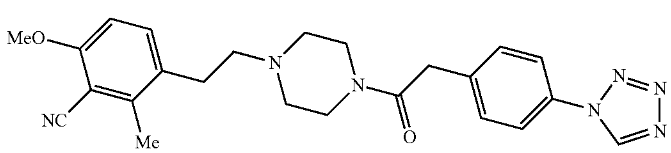 [SMILES: COc1ccc(CCN2CCN(C(=O)Cc3ccc(-n4cnnn4)cc3)CC2)c(C)c1C#N] | D | ** |
| 124 | 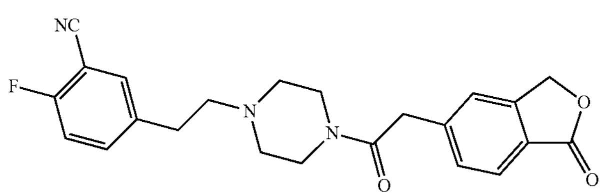 [SMILES: N#Cc1cc(CCN2CCN(C(=O)Cc3ccc4c(c3)COC4=O)CC2)ccc1F] | D | 408 |
| 125 | 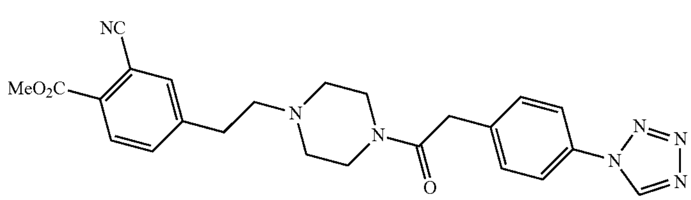 [SMILES: COC(=O)c1ccc(CCN2CCN(C(=O)Cc3ccc(-n4cnnn4)cc3)CC2)cc1C#N] | C | 460 |

TABLE 1-continued

| example | Structure | General Method | MS: [(M + 1)]+ or HNMR |
|---|---|---|---|
| 126 | 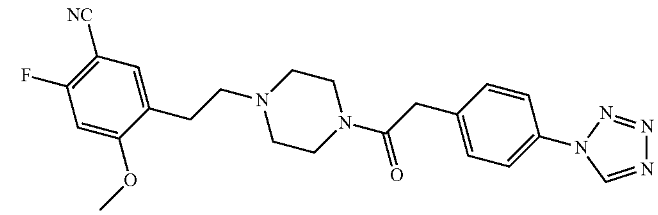 [SMILES: COc1cc(F)c(C#N)cc1CCN1CCN(C(=O)Cc2ccc(-n3cnnn3)cc2)CC1] | C | ** |
| 127 | 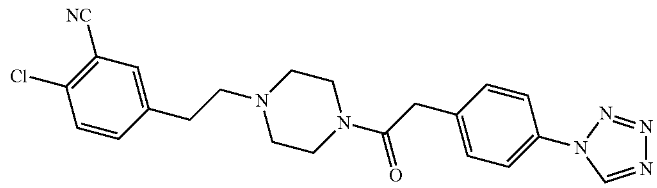 [SMILES: N#Cc1cc(CCN2CCN(C(=O)Cc3ccc(-n4cnnn4)cc3)CC2)ccc1Cl] | C | ** |
| 128 | 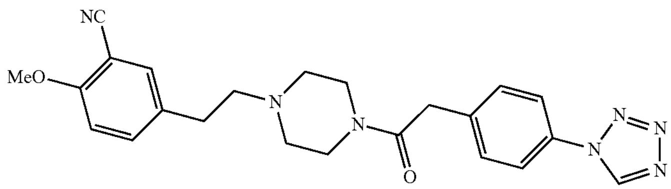 [SMILES: COc1ccc(CCN2CCN(C(=O)Cc3ccc(-n4cnnn4)cc3)CC2)cc1C#N] | C | ** |
| 129 | 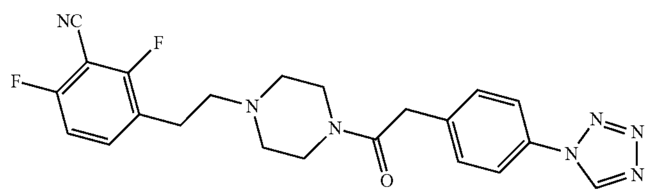 [SMILES: N#Cc1c(F)ccc(CCN2CCN(C(=O)Cc3ccc(-n4cnnn4)cc3)CC2)c1F] | C | ** |
| 130 | 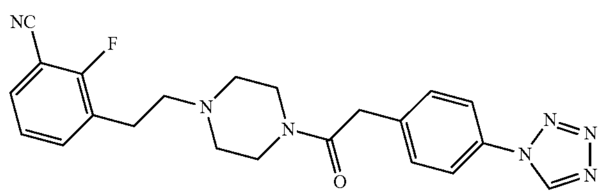 [SMILES: N#Cc1cccc(CCN2CCN(C(=O)Cc3ccc(-n4cnnn4)cc3)CC2)c1F] | C | ** |
| 131 | 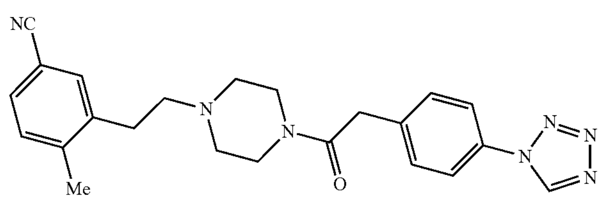 [SMILES: Cc1ccc(C#N)cc1CCN1CCN(C(=O)Cc2ccc(-n3cnnn3)cc2)CC1] | C | ** |
| 132 | 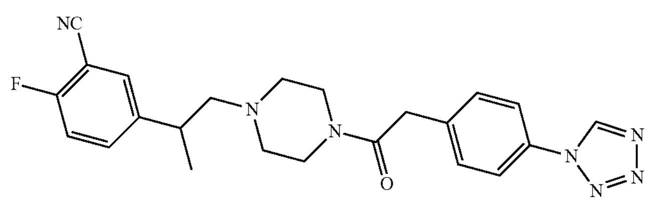 [SMILES: CC(CN1CCN(C(=O)Cc2ccc(-n3cnnn3)cc2)CC1)c1ccc(F)c(C#N)c1] | C | ** |
| 133 | 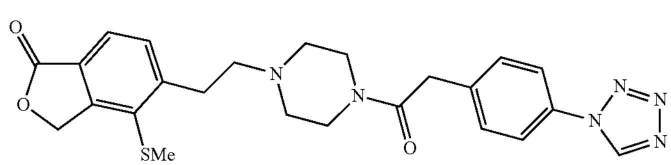 [SMILES: CSc1c(CCN2CCN(C(=O)Cc3ccc(-n4cnnn4)cc3)CC2)ccc2c1COC2=O] | B | 501 |

TABLE 1-continued

| example | Structure | General Method | MS: [(M + 1)]+ or HNMR |
|---|---|---|---|
| 134 | 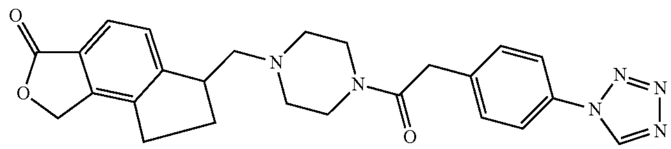 [SMILES: O=C1OCc2c1ccc1c2CCC1CN1CCN(C(=O)Cc2ccc(-n3cnnn3)cc2)CC1] | D | 459 |
| 135 | 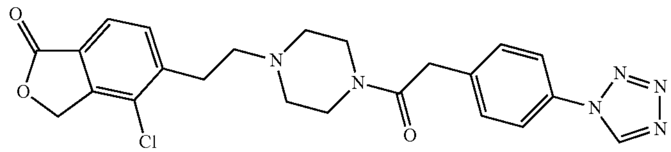 | D | 467 |
| 136 | 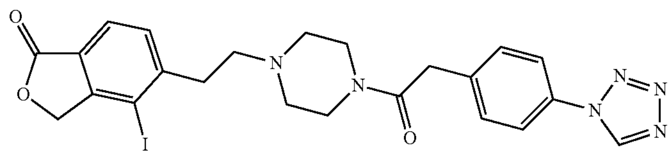 [SMILES: O=C1OCc2c1ccc(CCN1CCN(C(=O)Cc3ccc(-n4cnnn4)cc3)CC1)c2I] | B | 559 |
| 137 | 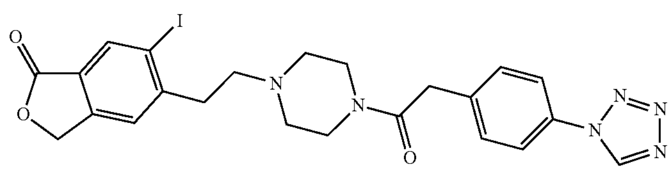 [SMILES: O=C1OCc2cc(CCN3CCN(C(=O)Cc4ccc(-n5cnnn5)cc4)CC3)c(I)cc21] | B | 559 |
| 138 | 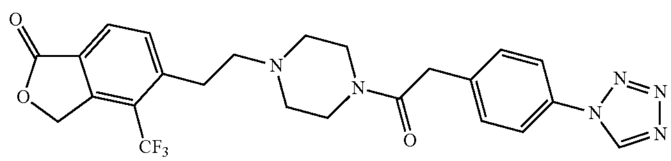 [SMILES: O=C1OCc2c1ccc(CCN1CCN(C(=O)Cc3ccc(-n4cnnn4)cc3)CC1)c2C(F)(F)F] | B | 501 |
| 139 | 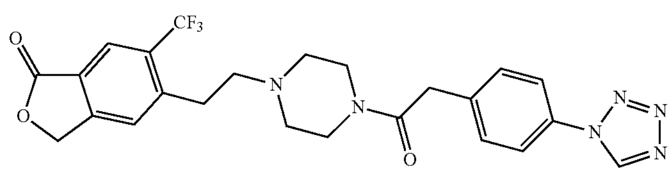 | B | 501 |
| 140 | 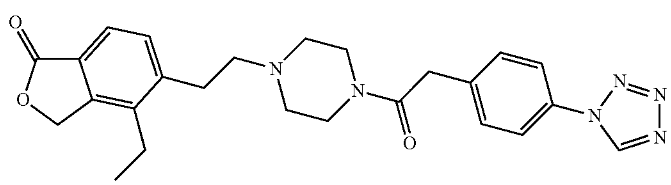 [SMILES: CCc1c(CCN2CCN(C(=O)Cc3ccc(-n4cnnn4)cc3)CC2)ccc2c1COC2=O] | B | 461 |
| 141 | 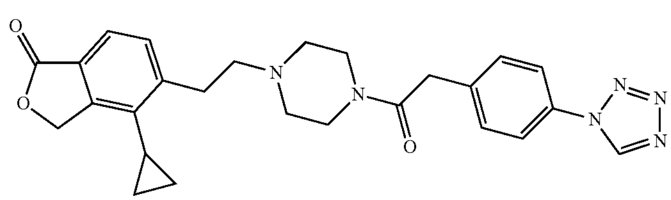 [SMILES: O=C1OCc2c1ccc(CCN1CCN(C(=O)Cc3ccc(-n4cnnn4)cc3)CC1)c2C1CC1] | B | 473 |
| 142 | 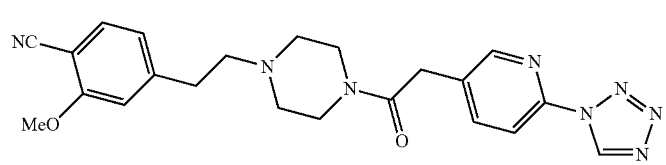 [SMILES: COc1cc(CCN2CCN(C(=O)Cc3ccc(-n4cnnn4)nc3)CC2)ccc1C#N] | B | 433 |

TABLE 1-continued

| example | Structure | General Method | MS: [(M + 1)]+ or HNMR |
|---|---|---|---|
| 143 | 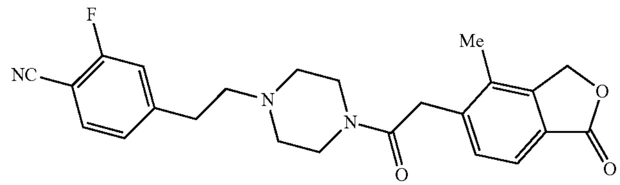 [SMILES: Cc1c(CC(=O)N2CCN(CCc3ccc(C#N)c(F)c3)CC2)ccc2c1COC2=O] | B | ** |
| 144 | 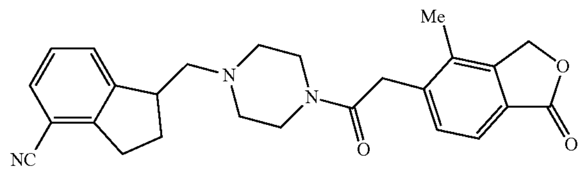 [SMILES: Cc1c(CC(=O)N2CCN(CC3CCc4c(C#N)cccc43)CC2)ccc2c1COC2=O] | B | 430 |
| 145 | 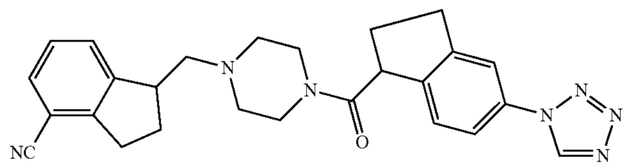 [SMILES: N#Cc1cccc2c1CCC2CN1CCN(C(=O)C2CCc3cc(-n4cnnn4)ccc32)CC1] | B | 454 |
| 146 | 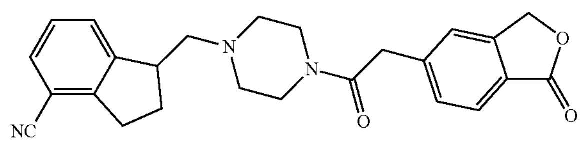 [SMILES: N#Cc1cccc2c1CCC2CN1CCN(C(=O)Cc2ccc3c(c2)COC3=O)CC1] | B | 416 |
| 147 | 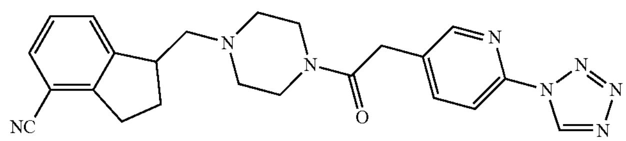 [SMILES: N#Cc1cccc2c1CCC2CN1CCN(C(=O)Cc2ccc(-n3cnnn3)nc2)CC1] | B | 429 |
| 148 | 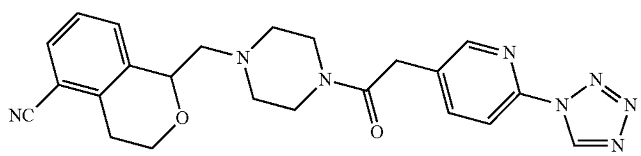 [SMILES: N#Cc1cccc2c1CCOC2CN1CCN(C(=O)Cc2ccc(-n3cnnn3)nc2)CC1] | B | 445 |
| 149 | 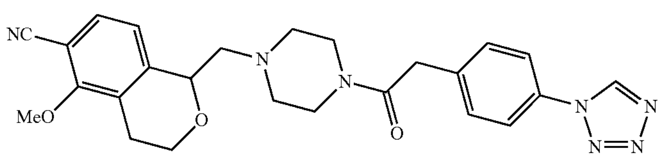 [SMILES: COc1c(C#N)ccc2c1CCOC2CN1CCN(C(=O)Cc2ccc(-n3cnnn3)cc2)CC1] | B | ** |
| 150 | 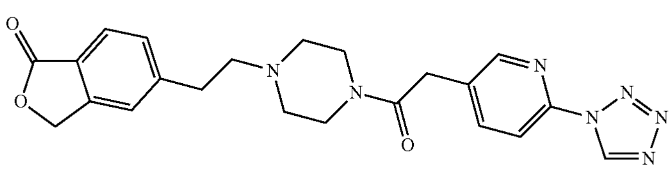 [SMILES: O=C1OCc2cc(CCN3CCN(C(=O)Cc4ccc(-n5cnnn5)nc4)CC3)ccc21] | C | 434 |
| 151 | 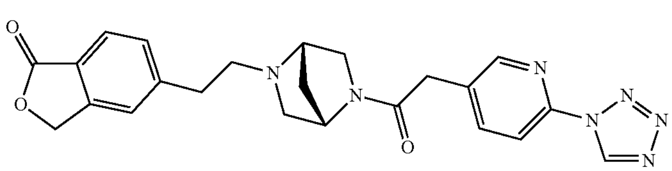 [SMILES: O=C1OCc2cc(CCN3C[C@@H]4C[C@H]3CN4C(=O)Cc3ccc(-n4cnnn4)nc3)ccc21] | C | 446 |

TABLE 1-continued

| example | Structure | General Method | MS: [(M + 1)]+ or HNMR |
|---|---|---|---|
| 152 | 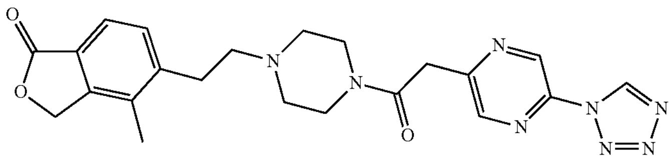 [SMILES: Cc1c(CCN2CCN(C(=O)Cc3cnc(-n4cnnn4)cn3)CC2)ccc2c1COC2=O] | B | ** |
| 153 | 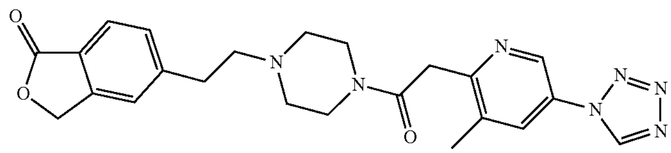 [SMILES: Cc1cc(-n2cnnn2)cnc1CC(=O)N1CCN(CCc2ccc3c(c2)COC3=O)CC1] | B | ** |
| 154 | 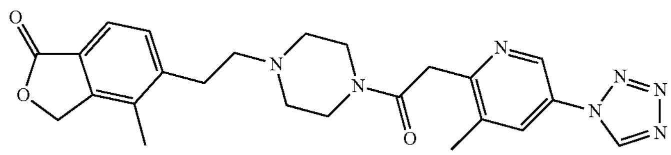 [SMILES: Cc1cc(-n2cnnn2)cnc1CC(=O)N1CCN(CCc2ccc3c(c2C)COC3=O)CC1] | B | 462 |
| 155 | 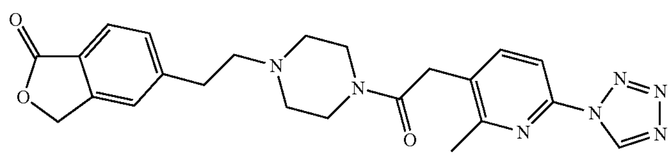 [SMILES: Cc1nc(-n2cnnn2)ccc1CC(=O)N1CCN(CCc2ccc3c(c2)COC3=O)CC1] | B | ** |
| 156 | 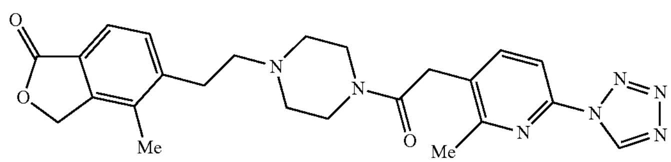 [SMILES: Cc1nc(-n2cnnn2)ccc1CC(=O)N1CCN(CCc2ccc3c(c2C)COC3=O)CC1] | B | 462 |
| 157 | 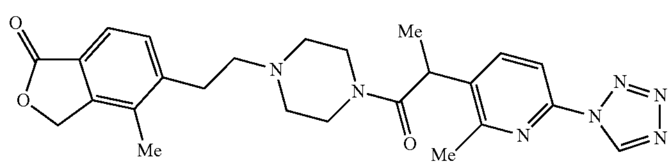 [SMILES: Cc1nc(-n2cnnn2)ccc1C(C)C(=O)N1CCN(CCc2ccc3c(c2C)COC3=O)CC1] | B | ** |
| 158 | 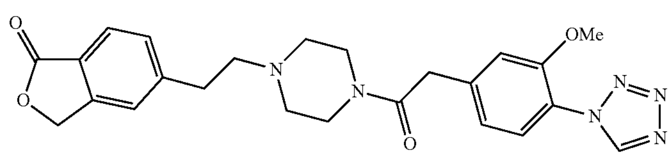 [SMILES: COc1cc(CC(=O)N2CCN(CCc3ccc4c(c3)COC4=O)CC2)ccc1-n1cnnn1] | B | 463 |
| 159 | 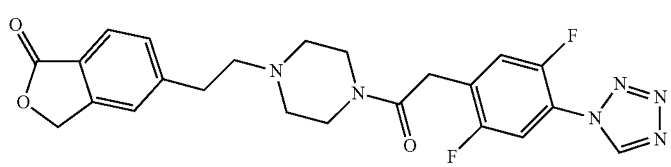 [SMILES: O=C1OCc2cc(CCN3CCN(C(=O)Cc4cc(F)c(-n5cnnn5)cc4F)CC3)ccc21] | B | ** |
| 160 | 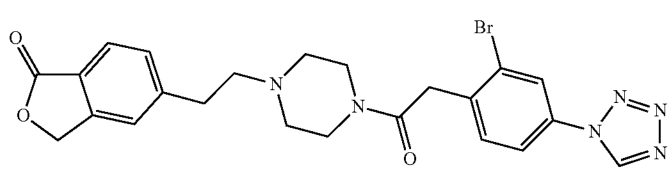 [SMILES: N#Cc1cc(-n2cnnn2)ccc1CC(=O)N1CCN(CCc2ccc3c(c2)COC3=O)CC1] | B | ** |

TABLE 1-continued
| example | Structure | General Method | MS: [(M + 1)]⁺ or HNMR |
|---|---|---|---|
| 161 | 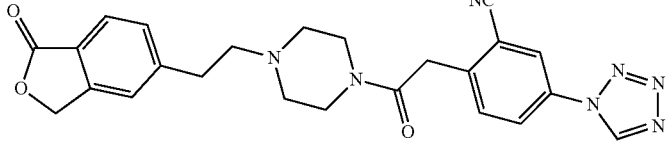 | C | ** |
| 162 | 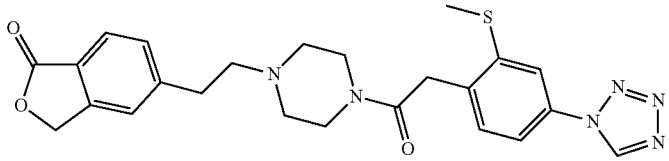 [SMILES: CSc1cc(-n2cnnn2)ccc1CC(=O)N1CCN(CCc2ccc3c(c2)COC3=O)CC1] | B | ** |
| 163 | 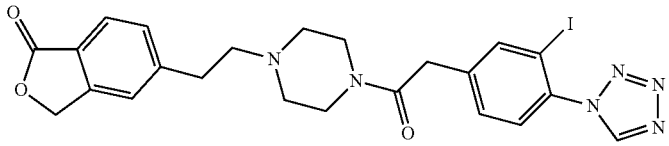 [SMILES: O=C1OCc2cc(CCN3CCN(C(=O)Cc4ccc(-n5cnnn5)c(I)c4)CC3)ccc21] | B | ** |
| 164 | 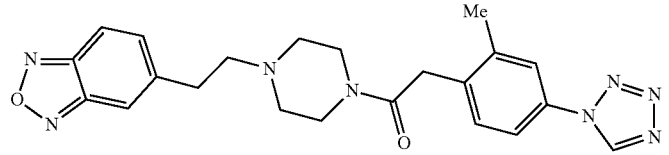 | B | 433 |
| 165 | 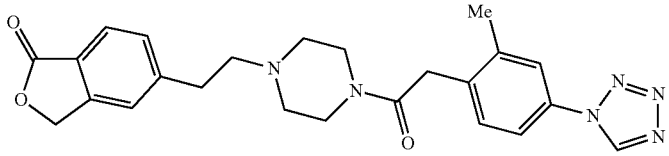 [SMILES: Cc1cc(-n2cnnn2)ccc1CC(=O)N1CCN(CCc2ccc3c(c2)COC3=O)CC1] | B | 447 |
| 166 | 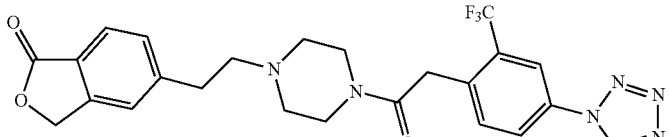 | B | 501 |
| 167 | 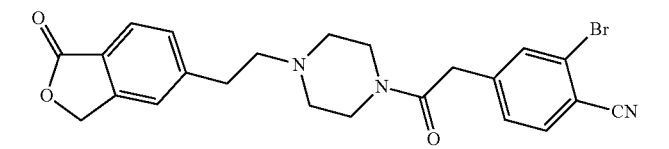 [SMILES: N#Cc1ccc(CC(=O)N2CCN(CCc3ccc4c(c3)COC4=O)CC2)cc1Br] | B | 468, 470 |
| 168 | 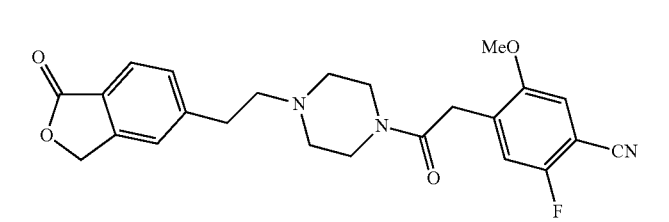 [SMILES: COc1cc(C#N)c(F)cc1CC(=O)N1CCN(CCc2ccc3c(c2)COC3=O)CC1] | B | 438 |

TABLE 1-continued

| example | Structure | General Method | MS: [(M + 1)]+ or HNMR |
|---|---|---|---|
| 169 | 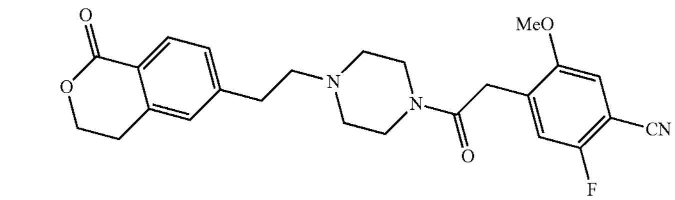 [SMILES: COc1cc(C#N)c(F)cc1CC(=O)N1CCN(CCc2ccc3c(c2)CCOC3=O)CC1] | B | 452 |
| 170 | 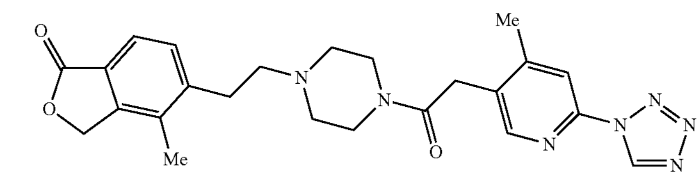 [SMILES: Cc1cc(-n2cnnn2)ncc1CC(=O)N1CCN(CCc2ccc3c(c2C)COC3=O)CC1] | B | 462 |
| 171 | 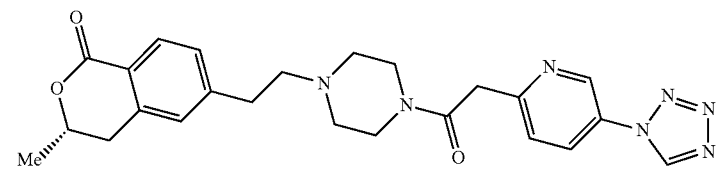 [SMILES: C[C@H]1Cc2cc(CCN3CCN(C(=O)Cc4ccc(-n5cnnn5)cn4)CC3)ccc2C(=O)O1] | B | 462 |
| 172 | 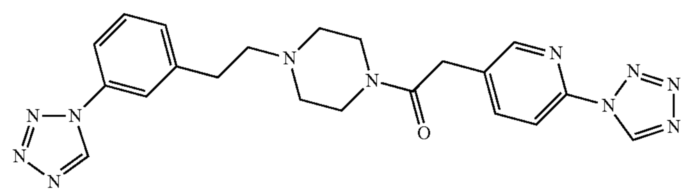 [SMILES: O=C(Cc1ccc(-n2cnnn2)nc1)N1CCN(CCc2cccc(-n3cnnn3)c2)CC1] | B | 446 |
| 173 | 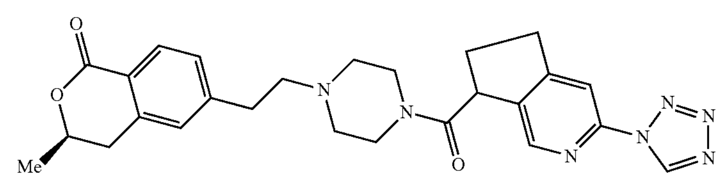 [SMILES: C[C@@H]1Cc2cc(CCN3CCN(C(=O)C4CCc5cc(-n6cnnn6)ncc54)CC3)ccc2C(=O)O1] | * | 488 |
| 174 | 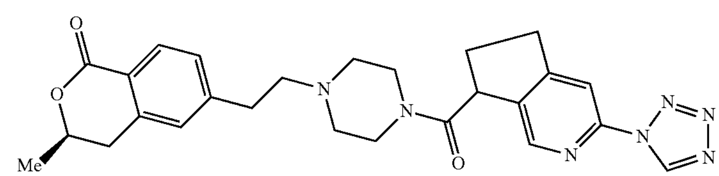 [SMILES: C[C@@H]1Cc2cc(CCN3CCN(C(=O)C4CCc5cc(-n6cnnn6)ncc54)CC3)ccc2C(=O)O1] | * | 488 |
| 175 | 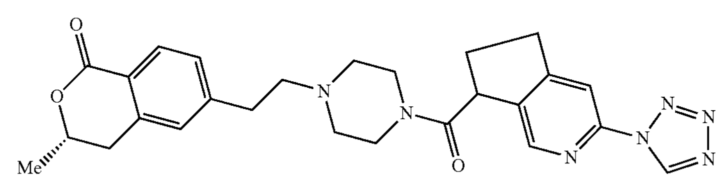 [SMILES: C[C@H]1Cc2cc(CCN3CCN(C(=O)C4CCc5cc(-n6cnnn6)ncc54)CC3)ccc2C(=O)O1] | * | 488 |
| 176 | 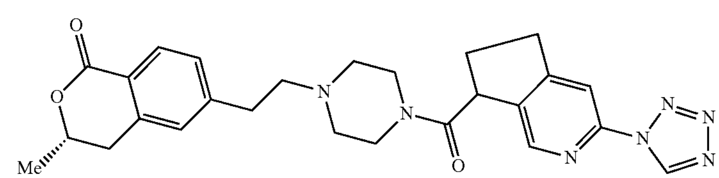 [SMILES: C[C@H]1Cc2cc(CCN3CCN(C(=O)C4CCc5cc(-n6cnnn6)ncc54)CC3)ccc2C(=O)O1] | * | 488 |

TABLE 1-continued

| example | Structure | General Method | MS: [(M + 1)]+ or HNMR |
|---|---|---|---|
| 177 | 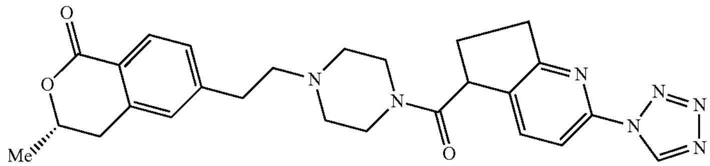 [SMILES: C[C@H]1Cc2cc(CCN3CCN(C(=O)C4CCc5nc(-n6cnnn6)ccc54)CC3)ccc2C(=O)O1] | * | 488 |
| 178 | 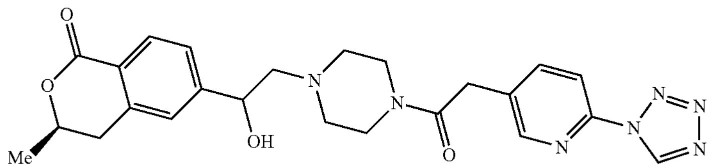 [SMILES: C[C@@H]1Cc2cc(C(O)CN3CCN(C(=O)Cc4ccc(-n5cnnn5)nc4)CC3)ccc2C(=O)O1] | B Single isomer | 478 |
| 179 | 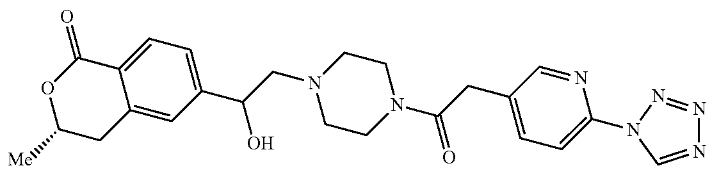 [SMILES: C[C@H]1Cc2cc(C(O)CN3CCN(C(=O)Cc4ccc(-n5cnnn5)nc4)CC3)ccc2C(=O)O1] | * | 478 |
| 180 | 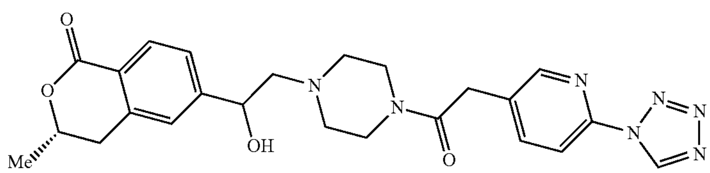 [SMILES: C[C@H]1Cc2cc(C(O)CN3CCN(C(=O)Cc4ccc(-n5cnnn5)nc4)CC3)ccc2C(=O)O1] | * | 478 |

*General Method for examples above:
Example 14: B (single isomer) Chiralpak OD column first peak to elute
Example 15: B (single isomer) Chiralpak OD column second peak to elute
Example 17: C (single isomer) 1st peak to elute, Chiralcel OD column
Example 18: C (single isomer) 2nd peak to elute, Chiralcel OD column
Example 89: B (single isomer) separated on Chiralcel OD column, first peak to elute
Example 90: B (single isomer) separated on Chiralcel OD column, second peak to elute
Example 95: E(Single isomer) ChiralPak IC column, second isomer to elute
Example 96: E Chiralpak IC column, first isomer to elute (single isomer)
Example 97: E ChiralPak IC column, second isomer to elute
Example 108: B (single isomer) ChiralPak AD-H column, first peak to elute
Example 111: B (single isomer) SFC chromatography, ChiralPak AD-H, first peak to elute.
Example 173: B Single isomer, SFC-HPLC ChiralPak AD-H column, faster eluting peak
Example 174: B Single isomer, SFC-HPLC ChiralPak AD-H column, slower eluting peak
Example 175: B Single isomer, SFC-HPLC ChiralCel IA column, faster eluting peak
Example 176: B Single isomer, SFC-HPLC ChiralCel IA column, slower eluting peak
Example 177: B Single isomer, SFC-HPLC ChiralPak OJ-H column, slower eluting peak
Example 179: B Single isomer opposite stereochemistry at hydroxyl carbon than #180
Example 180: B Single isomer opposite stereochemistry at hydroxyl carbon than #179
**MS: [(M + 1)]+ or HNMR for examples above:
Example 14: $^1$H NMR (500 MHz; CDCl$_3$): 8.99 (s, 1H), 8.03 (d, J = 7.8 Hz, 1H), 7.70 (d, J = 8.5 Hz, 2H), 7.49 (d, J = 8.5 Hz, 2H), 7.24 (d, J = 7.8 Hz, 1H), 7.09 (m, 1H), 4.68 (m, 1H), 3839 (s, 2H), 3.72-3.58 (m, 4H), 2.98-2.84 (m, 3H), 2.69-2.48 (m, 4H), 1.59 (m, 4H), 1.54 (d, J = 6.2 Hz, 3H).
Example 15: $^1$H NMR (500 MHz; CDCl$_3$): 8.99 (s, 1H), 8.03 (d, J = 7.8 Hz, 1H), 7.70 (d, J = 8.5 Hz, 2H), 7.49 (d, J = 8.5 Hz, 2H), 7.24 (d, J = 7.8 Hz, 1H), 7.09 (m, 1H), 4.68 (m, 1H), 3839 (s, 2H), 3.72-3.58 (m, 4H), 2.98-2.84 (m, 3H), 2.69-2.48 (m, 4H), 1.59 (m, 4H), 1.54 (d, J = 6.2 Hz, 3H).
Example 19: $^1$H-NMR (400 MHz, CDCl$_3$) δ ppm 8.91 (s, 1H), 7.72 (d, J = 7.8 Hz, 1H), 7.60 (d, J = 8.6 Hz, 1H), 7.10 (d, J = 7.8 Hz, 1H), 7.00 (s, 1H), 5.18 (s, 2H), 3.74 (s, 2H), 3.56~3.62 (m, 2H), 3.40~3.47 (m, 2H), 2.48~2.60 (m, 4H), 2.00~2.09 (m, 1H), 1.89~1.93 (m, 1H), 1.20~1.27 (m, 1H), 1.00~1.04 (m, 1H).
Example 78: $^1$H-NMR (400 MHz, CDCl$_3$) δ ppm 8.97 (s, 1H), 7.67 (d, J = 8.2 Hz, 2H), 7.44~7.48 (m, 4H), 7.14~7.20 (m, 1H), 3.81 (s, 2H), 3.64~3.73 (m, 2H), 3.49~3.57 (m, 2H), 2.86~3.04 (m, 3H), 2.33~2.57 (m, 6H), 1.92~1.99 (m, 1H), 1.76~1.85 (m, 3H).
Example 79: $^1$H-NMR (400 MHz, MeOD) δ ppm 7.82 (d, J = 7.82 Hz, 1H), 7.44~7.61 (m, 4H), 7.24 (d, J = 7.63 Hz, 1H), 5.36 (s, 2H), 3.95 (s, 2H), 3.55~3.75 (m, 4H), 2.78~3.10 (m, 3H), 2.34~2.61 (m, 6H), 1.71~2.08 (m, 4H)
Example 82: $^1$H-NMR (400 MHz, MeOD) δ: 9.74 (s, 1H), 7.84 (d, J = 8.4 Hz, 2H), 7.52 (d, J = 8.8 Hz, 1H), 7.48~7.53 (m, 3H), 7.41~7.45 (m, 1H), 5.30 (d, J = 8.4 Hz, 1H), 4.28~4.33 (m, 2H), 3.97 (s, 2H), 3.88~3.94 (m, 2H), 3.75~3.79 (m, 2H), 3.46~3.52 (m, 4H), 3.29~3.39 (m, 2H), 2.93~3.18 (m, 2H).
Example 83: $^1$H-NMR (400 MHz, MeOD) δ 9.82 (s, 1H), 9.05 (s, 1H), 8.38~8.39 (m, 1H), 7.63~7.68 (m, 2H), 7.54~7.55 (m, 1H), 7.43~7.46 (m, 1H), 5.32~5.35 (m, 1H), 4.30~4.32 (m, 1H), 4.02~4.21 (m, 2H), 3.81~3.95 (m, 3H), 3.45~3.56 (m, 4H), 3.31~3.35 (m, 4H), 2.98~3.25 (m, 2H).
Example 84: $^1$H-NMR (400 MHz, MeOD) δ 9.74 (s, 1H), 7.83 (d, J = 8.0 Hz, 2H), 7.62~7.67 (m, 2H), 7.50 (d, J = 8.0 Hz, 2H), 7.43 (t, J = 4.0 Hz, 1H), 5.51 (d, J = 8.0 Hz, 1H), 4.30 (d, J = 8.0 Hz, 1H), 3.96 (s, 5H), 3.84~3.89 (m, 2H), 3.59~3.65 (m, 5H), 3.37 (m, 5H), 3.24~3.25 (m, 2H).
Example 85: $^1$H-NMR (400 MHz, CDCl$_3$) δ ppm 9.01 (s, 1H), 7.59~7.62 (m, 2H), 7.37~7.42 (m, 3H), 6.94~6.99 (m, 1H), 4.75~4.83 (m, 1H), 4.10~4.16 (m, 1H), 3.60~3.74 (m, 5H), 3.46~3.51 (m, 2H), 2.60~3.04 (m, 4H), 2.43~2.56 (m, 4H).
Example 122: $^1$H-NMR (400 MHz, CD$_3$OD) δ: 9.89 (s, 1H), 7.76~7.78 (m, 2H), 7.51~7.55 (m, 1H), 7.40~7.42 (m, 2H), 7.21~7.25 (m, 1H), 4.44~4.45 (m, 1H), 4.16~4.17 (m, 1H), 3.84 (s, 2H), 3.38~3.56 (m, 2H), 2.98~3.01 (m, 4H).
Example 123: $^1$H-NMR (400 MHz, CD$_3$OD) δ: 10.05 (s, 1H), 7.82~7.84 (m, 2H), 7.45~7.47 (m, 3H), 7.04~7.06 (m, 1H), 4.44 (s, 1H), 4.22~4.24 (m, 1H), 3.85~3.89 (m, 5H), 3.59 (s, 2H), 2.97 (s, 4H), 2.43 (s, 3H).
Example 126: $^1$H-NMR (400 MHz, CDCl$_3$) δ ppm 8.98 (s, 1H), 7.67 (d, J = 8.6 Hz, 2H), 7.47 (d, J = 8.6 Hz, 2H), 7.34 (d, J = 7.6 Hz, 1H), 6.6 (d, J = 10.6 Hz, 1H), 3.87 (s, 3H), 3.80 (s, 2H), 3.65~3.72 (m, 2H), 3.50~3.57 (m, 2H), 2.73~2.79 (m, 2H), 2.43~2.55 (m, 2H).
Example 127: $^1$H-NMR (300 MHz, CDCl$_3$) δ ppm 9.00 (s, 1H), 7.65 (d, J = 8.5 Hz, 2H), 7.36~7.50 (m, 5H), 3.80 (s, 2H), 3.67 (t, J = 5.0 Hz, 2H), 3.54 (t, J = 5.1 Hz, 2H), 3.67 (t, J = 5.0 Hz, 2H), 2.58 (t, J = 8.6 Hz, 2H), 2.39~2.50 (m, 4H).
Example 128: $^1$H-NMR (300 MHz, CDCl$_3$) δ ppm 8.97 (s, 1H), 7.65 (d, J = 8.6 Hz, 2H), 7.46 (d, J = 8.6 Hz, 2H), 7.32~7.38 (m, 2H), 6.88 (d, J = 8.6 Hz, 1H), 3.90 (s, 3H), 3.80 (s, 2H), 3.63~3.71 (m, 2H), 3.49~3.55 (m, 2H), 2.74 (t, J = 7.5 Hz, 2H), 2.56 (t, J = 7.1 Hz, 2H), 2.31~2.52 (m, 4H).

TABLE 1-continued

| example | Structure | General Method | MS: [(M + 1)]⁺ or HNMR |
|---|---|---|---|

Example 129: ¹H-NMR (400 MHz, CDCl₃) δ ppm 8.97 (s, 1H), 7.67 (d, J = 8.5 Hz, 2H), 7.46 (d, J = 8.5 Hz, 3H), 6.96~7.00 (m, 2H), 3.80 (s, 2H), 3.62~3.68 (m, 2H), 3.49~3.54 (m, 2H), 2.79~2.87 (m, 2H), 2.39~2.63 (m, 6H).
Example 130: ¹H-NMR (400 MHz, CDCl₃) δ ppm 9.00 (s, 1H), 7.65 (d, J = 8.5 Hz, 2H), 7.44~7.50 (m, 4H), 7.17 (t, J = 7.9 Hz, 1H), 3.80 (s, 2H), 3.67 (t, J = 5.0 Hz, 2H), 3.54 (t, J = 5.1 Hz, 2H), 2.85 (t, J = 8.5 Hz, 2H), 2.61 (t, J = 8.6 Hz, 2H), 2.39~2.50 (m, 4H).
Example 131: 1H-NMR (300 MHz, CDCl3) δ ppm 9.00 (s, 1H), 7.65 (d, J = 8.5 Hz, 2H), 7.36~7.45 (m, 4H), 7.22 (t, J = 7.9 Hz, 1H), 3.80 (s, 2H), 3.67 (t, J = 5.0 Hz, 2H), 3.54 (t, J = 5.1 Hz, 2H), 2.78 (t, J = 8.6 Hz, 2H), 2.43~2.56 (m, 6H), 2.35 (s, 3H).
Example 132: ¹H-NMR (400 MHz, CDCl₃) δ ppm 8.98 (s, 1H), 7.67 (d, J = 8.0 Hz, 2H), 7.39~7.45 (m, 4H), 7.13 (t, J = 8.5 Hz, 1H), 3.78 (s, 2H), 3.56~3.64 (m, 2H), 3.42~3.46 (m, 2H), 2.91~2.99 (m, 1H), 2.32~2.45 (m, 6H), 1.22 (d, J = 7.0 Hz, 3H).
Example 149: ¹H-NMR (400 MHz, CDCl3) δ ppm 8.92 (s, 1H), 7.61 (d, J = 8.6 Hz, 2H), 7.40 (d, J = 8.6 Hz, 2H), 7.32 (d, J = 7.8 Hz, 1H), 6.91 (d, J = 8.6 Hz, 1H), 4.80~4.83 (m, 1H), 4.07~4.12 (m, 1H), 3.98 (s, 3H), 3.75 (s, 2H), 3.59~3.70 (m, 3H), 3.48~3.51 (m, 2H), 2.62~2.75 (m, 4H), 2.42~2.56 (m, 4H).
Example 152: ¹H-NMR (400 MHz, CDCl3) δ ppm 9.45 (s, 1H), 9.27 (d, J = 1.6 Hz, 1H), 8.52 (d, J = 1.6 Hz, 1H), 7.63 (d, J = 8.0 Hz, 1H), 7.31 (d, J = 8.0 Hz, 1H), 5.23 (s, 2 H), 3.99 (s, 2 H), 3.61-3.68 (m, 4 H), 2.85-2.91 (m, 2 H), 2.42-2.59 (m, 6 H), 2.23 (s, 3 H).
Example 153: ¹H-NMR (400 MHz, CDCl3) δ ppm 9.8 (s, 1H), 8.82 (d, J = 2.3 Hz, 1H), 8.12 (d, J = 2.3 Hz, 1H), 7.97 (d, J = 7.8 Hz, 1H), 7.46~7.5 (m, 2H), 5.34 (s, 2H), 4.08 (s, 2H), 3.64~3.68 (m, 4H), 2.97~3.01 (m, 2H), 2.69~2.73 (m, 2H), 2.56~2.64 (m, 4H), 2.43 (s, 3H).
Example 155: ¹H-NMR (400 MHz, CDCl₃) δ 9.50 (s, 1H), 7.84 (t, J = 7.8 Hz, 2H), 7.66~7.68 (m, 1H), 7.31~7.37 (m, 2H), 5.28 (s, 2H), 3.66~3.73 (m, 4H), 3.53~3.61 (m, 2H), 2.89~2.98 (m, 2H), 2.63~2.72 (m, 2H), 2.48~2.58 (m, 6H).
Example 157: ¹H-NMR (400 MHz, CDCl3) δ ppm 9.44 (s, 1H), 7.83 (d, J = 7.8 Hz, 1H), 7.77 (d, J = 8.6 Hz, 1H), 7.60 (d, J = 7.8 Hz, 1H), 7.22 (d, J = 7.8 Hz, 1H), 5.15 (s, 2H), 3.98-4.03 (m, 1H), 3.71-3.80 (m, 1 H), 3.50-3.58 (m, 1 H), 3.33-3.38 (m, 1 H), 3.18-3.23 (m, 1 H), 2.78-2.82 (m, 2 H), 2.58 (s, 3 H), 2.40-2.47 (m, 4 H), 2.32-2.36 (m, 1 H), 2.18 (s, 3 H), 2.02-2.09 (m, 1 H), 1.40 (d, J = 7.0 Hz, 3H).
Example 159: 1H-NMR (400 MHz, CDCl3) δ ppm 9.67 (d, J = 2.3 Hz, 1H), 7.87 (d, J = 7.9 Hz, 1H), 7.73~7.78 (m, 1H), 7.45~7.61 (m, 3H), 5.39 (s, 2H), 4.04 (s, 3H), 3.43~3.64 (m, 6H), 3.29~3.43 (m, 5H).
Example 160: ¹H-NMR (300 MHz, CDCl3) δ ppm 9.00 (s, 1H), 7.95 (s, 1H), 7.84 (d, J = 7.3 Hz, 1H), 7.63~7.66 (m, 1H), 7.50~7.53 (m, 1H), 7.33~7.39 (m, 2H), 5.30 (s, 2H), 3.90 (s, 2H), 3.56~3.74 (m, 4H), 2.88~3.01 (m, 2H), 2.50~2.74 (m, 6H).
Example 161: ¹H-NMR (400 MHz, CD3CN) δ ppm 9.0 (s, 1H), 8.0 (s, 1H), 7.91~7.95 (m, 1H), 7.83 (d, J = 7.8 Hz, 1H), 7.71 (d, J = 8.3 Hz, 1H), 7.33~7.39 (m, 2H), 5.30 (s, 2H), 4.00 (s, 2H), 3.62~3.74 (m, 4H), 2.88~2.99 (m, 2H), 2.56~2.74 (m, 6H).
Example 162: ¹H-NMR (300 MHz, CDCl3) δ ppm 9.0 (s, 1H), 7.86 (d, J = 7.9 Hz, 1H), 7.6 (s, 1H), 7.33~7.41 (m, 4H), 5.3 (s, 2H), 3.85 (s, 2H), 3.7~3.77 (m, 2H), 3.52~3.59 (m, 2H), 2.92~3.0 (m, 2H), 2.66~2.71 (m, 3H), 2.51~2.58 (m, 6H).
Example 163: ¹H-NMR (300 MHz, CDCl3) δ ppm 8.90 (s, 1H), 7.91 (s, 1H), 7.82 (d, J = 7.9 Hz, 1H), 7.32~7.44 (m, 4H), 5.28 (s, 2H), 3.77 (s, 2H), 3.65~3.73 (m, 2H), 3.51~3.58 (m, 2H), 2.91~2.96 (m, 2H), 2.65~2.70 (m, 2H), 2.48~2.57 (m, 4H).

Example 181

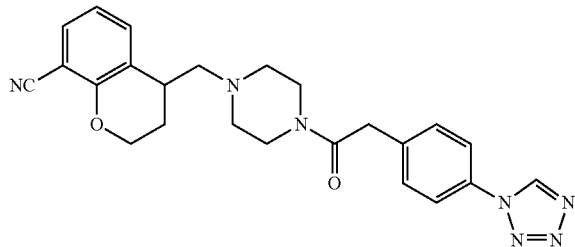 [SMILES: N#Cc1cccc2c1OCCC2CN1CCN(C(=O)Cc2ccc(-n3cnnn3)cc2)CC1]

4-[(4-{[4-(1H-tetrazol-1-yl)phenyl]acetyl}piperazin-1-yl)methyl]-3,4-dihydro-2H-chromene-8-carbonitrile To a solution of 4-formyl-3,4-dihydro-2H-chromene-8-carbonitrile (35 mg, 0.19 mmol) in 6 mL of anhydrous DCM was added 1-(piperazin-1-yl)-2-[4-(1H-tetrazol-1-yl)phenyl]ethanone (61 mg, 0.22 mmol), NaBH(OAc)₃ (161 mg, 0.76 mmol) and the mixture was stirred at ambient temperature overnight. The mixture was diluted with DCM, washed with brine, dried over anhydrous Na₂SO₄ and concentrated. The residue was purified by prep-TLC to afford the title compound. ¹H-NMR (400 MHz, CDCl3) δ ppm 9.0 (s, 1H), 7.67 (d, J=8.4 Hz, 2H), 7.36~7.48 (m, 4H), 6.87 (t, J=7.7 Hz, 1H), 4.17~4.39 (m, 2H), 3.47~3.8 (m, 6H), 2.92~3.03 (m, 1H), 2.3~22.6 (m, 6H), 2.0~2.1 (m, 2H).

Example 182

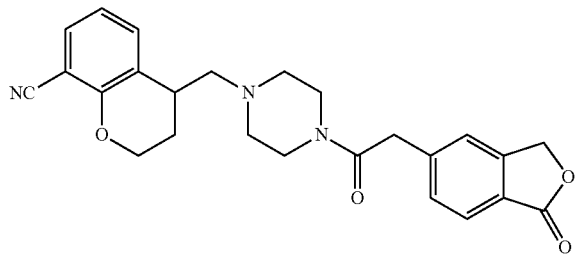 [SMILES: N#Cc1cccc2c1OCCC2CN1CCN(C(=O)Cc2ccc3c(c2)COC3=O)CC1]

4-({4-[(1-oxo-1,3-dihydro-2-benzofuran-5-yl)acetyl]piperazin-1-yl}methyl)-3,4-dihydro-2H-chromene-8-carbonitrile
4-({4-[(1-Oxo-1,3-dihydro-2-benzofuran-5-yl)acetyl]piperazin-1-yl}methyl)-3,4-dihydro-2H-chromene-8-carbonitrile was prepared in an analogous fashion to that described for the synthesis of 4-[(4-{[4-(1H-tetrazol-1-yl)phenyl]acetyl}piperazin-1-yl)methyl]-3,4-dihydro-2H-chromene-8-carbonitrile above starting from 4-formyl-3,4-dihydro-2H-chromene-8-carbonitrile and 5-[2-oxo-2-(piperazin-1-yl)ethyl]-2-benzofuran-1(3H)-one. ¹H-NMR (400 MHz, CDCl3) δ ppm 7.85 (d, J=7.8 Hz, 1H), 7.31~7.38 (m, 4H), 6.8 (t, J=7.8 Hz, 1H), 5.24 (s, 2H), 4.15~4.45 (m, 2H), 3.8 (s, 2H), 3.4~3.73 (m, 4H), 2.88~2.95 (m, 1H), 2.3~2.52 (m, 6H), 1.97~2.1 (m, 2H).

Example 183

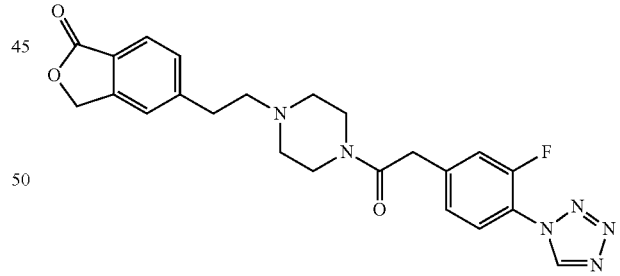

5-[2-(4-{[3-fluoro-4-(1H-tetrazol-1-yl)phenyl]acetyl}piperazin-1-yl)ethyl]-2-benzofuran-1 (3H)-one
To a solution of [3-fluoro-4-(1H-tetrazol-1-yl)phenyl]acetic acid (0.68 mmol) in 10 mL of anhydrous DCM was added 5-(2-piperazin-1-ylethyl)-2-benzofuran-1(3H)-one (191 mg, 0.68 mmol), EDC (200 mg, 1.01 mmol), HOBt (136 mg, 1.01 mmol), TEA (341 mg, 3.38 mmol) was stirred at ambient temperature overnight. The mixture was added DCM, washed with brine, the organic layer was dried over anhydrous Na₂SO₄ and concentrated. The residue was purified via prep-TLC to give the title compound. ¹H-NMR (400 MHz, CDCl3) δ ppm 8.84 (s, 1H), 7.82 (d, J=7.8 Hz, 1H), 7.31~737 (m, 3H), 7.11~7.19 (m, 2H), 5.29 (s, 2H), 3.59 (s, 2H), 3.49~3.52 (m, 2H), 3.37~3.4 (m, 2H), 2.89~2.93 (m, 2H), 2.64~2.68 (m, 2H), 2.4~2.45 (m, 4H).

Example 184

4-[2-(4-{[4-(1H-tetrazol-1-yl)phenyl]acetyl}piperazin-1-yl)ethyl]benzonitrile

Combined 4-(2-bromoethyl)benzonitrile (68 mg, 0.32 mmol) with 1-(piperazin-1-yl)-2-[4-(1H-tetrazol-1-yl)phenyl]ethanone hydrochloride (100 mg, 0.324 mmol), tetrabutyl ammonium iodide (120 mg, 0.324 mmol) and potassium carbonate (179 mg, 1.30 mmol) in DMF (2 mL) and stirred at 80° C. overnight. The reaction mixture was poured into water and extracted twice with ethyl acetate. The combined organic layers were washed with brine, dried over MgSO$_4$, filtered and concentrated. After initial purification by HPLC, repurification by preparative TLC eluting with 5% of 1:9 NH$_4$OH/methanol in DCM afforded the title compound. LC/MS: [(M+1)]$^+$=402.

Example 185

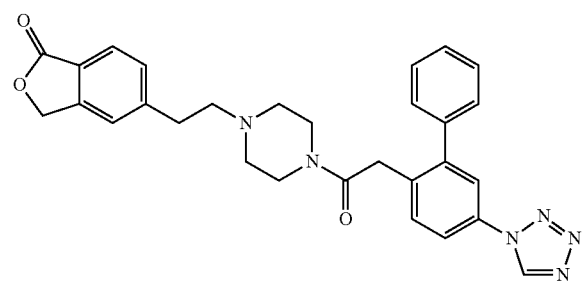 [SMILES: O=C1OCc2cc(CCN3CCN(C(=O)Cc4ccc(-n5cnnn5)cc4-c4ccccc4)CC3)ccc21]

5-[2-(4-{[5-(1H-tetrazol-1-yl)biphenyl-2-yl]acetyl}piperazin-1-yl)ethyl]-2-benzofuran-1(3H)-one A mixture of 5-[2-(4-{[2-bromo-4-(1H-tetrazol-1-yl)phenyl]acetyl}piperazin-1-yl)ethyl]-2-benzofuran-1(3H)-one (40 mg, 0.08 mmol), PhB(OH)$_2$(24 mg, 0.2 mmol), Na$_2$CO$_3$ (42 mg, 0.4 mmol) and Pd(PPh$_3$)$_4$(10 mg) in 3 mL of toluene and 3 mL of ethanol was heated to 80° C. under N$_2$ overnight. The solution was concentrated to get the crude product, which was purified via prep-TLC to afford 5-[2-(4-{[5-(1H-tetrazol-1-yl)biphenyl-2-yl]acetyl}piperazin-1-yl)ethyl]-2-benzofuran-1(3H)-one. $^1$H-NMR (300 MHz, CDCl$_3$) δ ppm 9.0 (s, 1H), 7.84 (d, J=8.0 Hz, 1H), 7.67~7.70 (m, 1H), 7.53~7.63 (m, 2H), 7.44~7.49 (m, 3H), 7.30~7.37 (m, 4H), 5.28 (s, 2H), 3.58~3.74 (m, 4H), 3.17~3.30 (m, 2H), 2.87~2.98 (m, 2H), 2.39~2.69 (m, 4H), 2.22~2.36 (m, 2H).

Example 186

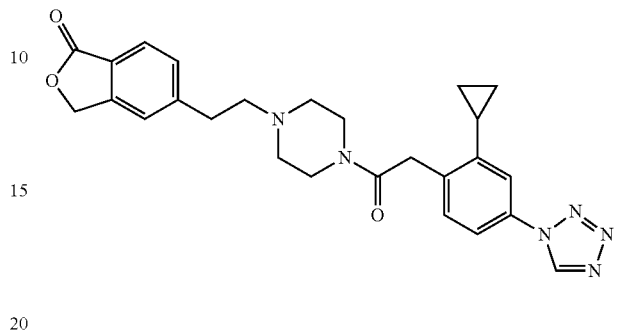

5-[2-(4-{[2-cyclopropyl-4-(1H-tetrazol-1-yl)phenyl]acetyl}piperazin-1-yl)ethyl]-2-benzofuran-1(3H)-one Step A: [2-ethenyl-4-(1H-tetrazol-1-yl)phenyl]acetic acid To a solution of [2-bromo-4-(1H-tetrazol-1-yl)phenyl]acetic acid (100 mg, 0.35 mmol) in 10 mL of toluene was added LiCl (44 mg, 1.05 mmol), Pd(PPh$_3$)$_4$(10 mg), CH$_2$=CHSnBu$_3$ (222 mg, 0.7 mmol), and the mixture was heated to reflux overnight. After the reaction was completed, the reaction solution was diluted with EtOAc and filtered. The filtrate was concentrated and purified by prep-TLC to give [2-ethenyl-4-(1H-tetrazol-1-yl)phenyl]acetic acid.

Step B: 5-[2-(4-{[2-ethenyl-4-(1H-tetrazol-1-yl)phenyl]acetyl}piperazin-1-yl)ethyl]-2-benzofuran-1 (3H)-one A solution of [2-ethenyl-4-(1H-tetrazol-1-yl)phenyl]acetic acid (43 mg, 0.19 mmol) in 10 mL of anhydrous DCM was added 5-[2-(piperazin-1-yl)ethyl]-2-benzofuran-1(3H)-one hydrochloride (53 mg, 0.19 mmol), EDC (56 mg, 0.28 mmol), HOBt (38 mg, 0.28 mmol), TEA (115 mg, 1.14 mmol) and then stirred at ambient temperature overnight. Then DCM was added and then mixture was washed with brine, dried over anhydrous Na$_2$SO$_4$ and concentrated. The residue was purified by prep-TLC to afford 5-[2-(4-{[2-ethenyl-4-(1H-tetrazol-1-yl)phenyl]acetyl}piperazin-1-yl)ethyl]-2-benzofuran-1(3H)-one. $^1$H-NMR (400 MHz, CDCl3) δ ppm 9.0 (s, 1H), 7.75~7.78 (m, 2H), 7.48~7.51 (m, 1H), 7.26~7.31 (m, 3H), 6.76~6.84 (rn, 1H), 5.7 (d, J=17.2 Hz, 1H), 5.44 (d, J=10.9 Hz, 1H), 5.22 (s, 2H), 3.75 (s, 2H), 3.6~3.65 (m, 2H), 3.45~3.48 (m, 2H), 2.86~2.9 (m, 2H), 2.59~2.64 (m, 2H), 2.41~2.5 (m, 4H).

Step C: 5-[2-(4-{[2-cyclopropyl-4-(1H-tetrazol-1-yl)phenyl]acetyl}piperazin-1-yl)ethyl]-2-benzofuran-1(3H)-one A solution of 5-[2-(4-{[2-ethenyl-4-(1H-tetrazol-1-yl)phenyl]acetyl}piperazin-1-yl)ethyl]-2-benzofuran-1(3H)-one (40 mg, 0.08 mmol) in 5 mL of DCM was added a solution of CH$_2$N$_2$ in 2 mL Et$_2$O and Pd(OAc)$_2$ (10 mg) at 0° C. The mixture was stirred at room temperature overnight. The reaction mixture was filtrated and purified by prep-TLC to afford 5-[2-(4-{[2-cyclopropyl-4-(1H-tetrazol-1-yl)phenyl]acetyl}piperazin-1-yl)ethyl]-2-benzofuran-1(3H)-one. $^1$H-NMR (400 MHz, CDCl3) δ ppm 9.0 (s, 1H), 7.76~7.78 (m, 1H), 7.26~7.4 (in, 5H), 5.22 (s, 2H), 3.88 (s, 2H), 3.49~3.66 (m, 4H), 2.83~2.93 (m, 2H), 2.6~2.62 (m, 2H), 2.38~2.48 (m, 4H), 2.0 (s, 1H), 0.94~0.98 (m, 2H), 0.66~0.68 (m, 2H).

Example 187

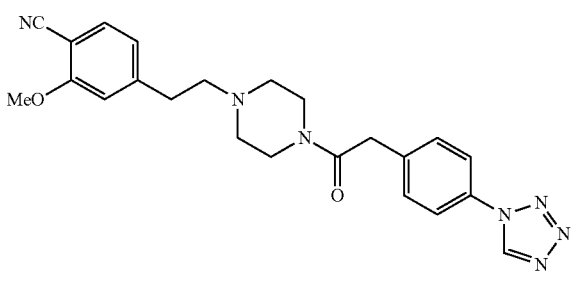 [SMILES: COc1cc(CCN2CCN(C(=O)Cc3ccc(-n4cnnn4)cc3)CC2)ccc1C#N]

2-methoxy-4-[2-(4-{[4-(1H-tetrazol-1-yl)phenyl]acetyl}piperazin-1-yl)ethyl]benzonitrile 2-Methoxy-4-(prop-2-en-1-yl)benzonitrile (100 mg, 0.577 mmol) was dissolved in methanol (13 mL) and the resulting solution was cooled to −78° C. Ozone was bubbled through the solution until a blue color appeared (~15 minutes). 1-(Piperazin-1-yl)-2-[4-(1H-tetrazol-1-yl)phenyl]ethanone hydrochloride (178 mg, 0.577 mmol) was added, followed by sodium cyanoborohydride (363 mg, 5.77 mmol). After stirring the reaction mixture for ~5 minutes 3 drops of acetic acid were added and the mixture was permitted to warm to rt and stir for 2 h. The reaction mixture was concentrated to dryness, dissolved in EtOAc (40 mL) and washed with brine, saturated NaHCO$_3$ solution. The organic layer was dried over Na$_2$SO$_4$, filtered and concentrated to dryness. The residue was then purified by mass directed HPLC to afford the title compound. LC/MS: [(M+1)]$^+$=432.

Example 188

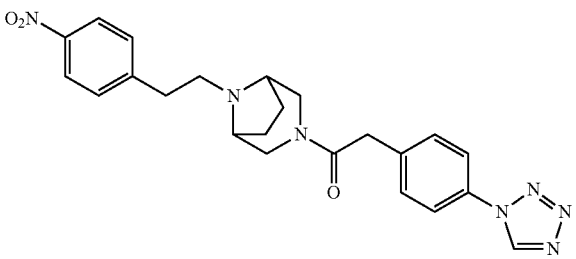 [SMILES: O=C(Cc1ccc(-n2cnnn2)cc1)N1CC2CCC(C1)N2CCc1ccc([N+](=O)[O-])cc1]

1-{8-[2-(4-nitrophenyl)ethyl]-3,8-diazabicyclo[3.2.1]oct-3-yl}-2-[4-(1H-tetrazol-1-yl)phenyl]ethanone 1-(3,8-Diazabicyclo[3.2.1]oct-3-yl)-2-[4-(1H-tetrazol-1-yl)phenyl]ethanone (100 mg, 0.335 mmol) was combined with 1-(2-bromoethyl)-4-nitrobenzene (77 mg, 0.34 mmol) and Hunig's base (43.3 mg, 0.335 mmol) in acetonitrile (1 mL) and stirred at 60° C. for 5 h. Purification by mass-directed HPLC afforded the title compound. LC/MS: [(M+1)]$^+$=448.

Example 189

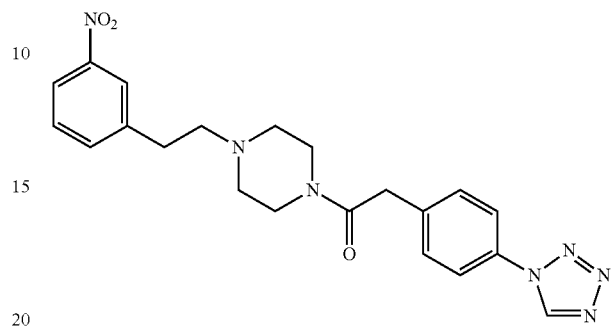

1-{4-[2-(3-nitrophenyl)ethyl]piperazin-1-yl}-2-[4-(1H-tetrazol-1-yl)phenyl]ethanone 1-{4-[2-(3-Nitrophenyl)ethyl]piperazin-1-yl}-2-[4-(1H-tetrazol-1-yl)phenyl]ethanone was prepared from 1-(2-bromoethyl)-3-nitrobenzene and 1-(piperazin-1-yl)-2-[4-(1H-tetrazol-1-ylphenyl]ethanone in an analogous fashion to that described for the synthesis of 1-{8-[2-(4-nitrophenyl)ethyl]-3,8-diazabicyclo[3.2.1]oct-3-yl}-2-[4-(1H-tetrazol-1-yl)phenyl]ethanone. LC/MS: [(M+1)]$^+$=422.

Example 190

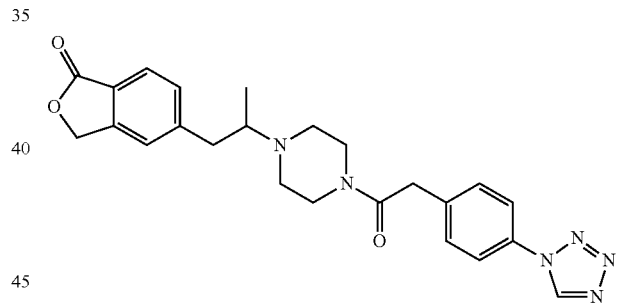

5-[2-(4-{[4-(1H-tetrazol-1-yl)phenyl]acetyl}piperazin-1-yl)propyl]-2-benzofuran-1(3H)-one 1-(Piperazin-1-yl)-2-[4-(1H-tetrazol-1-yl)phenyl]ethanone hydrochloride (141 mg, 0.457 mmol) was combined with 5-(2-oxopropyl)-2-benzofuran-1(3H)-one (87 mg, 0.46 mmol) in titanium (IV) isopropoxide (1.34 mL, 4.57 mmol) and stirred at room temperature for 1 h. Then ethanol (2 mL), sodium cyanoborohydride (86 mg, 1.4 mmol) and several drops of acetic acid were added (Ph ~3) and the reaction mixture was stirred at room temperature under a nitrogen atmosphere overnight. The reaction mixture was filtered through a Celite® pad, diluted with DCM, and washed with brine and water. The organic layer was dried over MgSO$_4$, filtered, and concentrated. The crude product was purified by preparative TLC eluting with 5% methanol/DCM to afford product. LC/MS: [(M+1)]$^+$=447.4.

The following examples were prepared in an analogous fashion to that described for the synthesis of 5-[2-(4-{[4-(1H-tetrazol-1-yl)phenyl]acetyl}piperazin-1-yl)propyl]-2-benzofuran-1(3H)-one starting from aldehyde and acylpiperizine intermediates that were prepared as described above.

| EXAMPLE # | Structure | LC-MS (M + 1)+ |
|---|---|---|
| 191 | 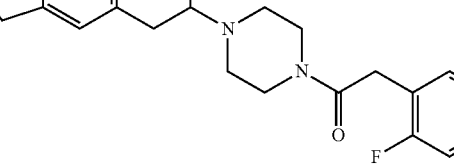 | 440 |
| 192 | 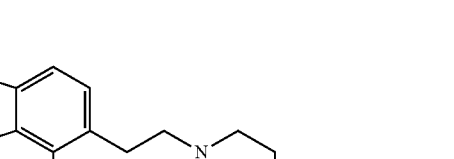 | 451 |
| 193 | 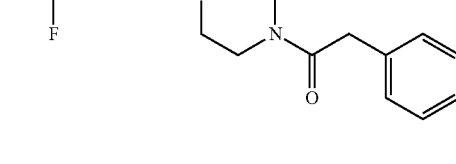 | 451 |
| 194 | 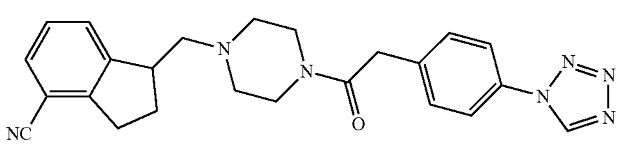 [SMILES: N#Cc1cccc2c1CCC2CN1CCN(C(=O)Cc2ccc(-n3cnnn3)cc2)CC1] | 428 |
| 195 | 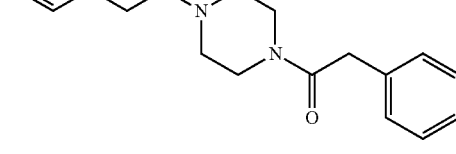 | 447 |

-continued
| EXAMPLE # | Structure | LC-MS (M + 1)+ |
|---|---|---|
| 196 | 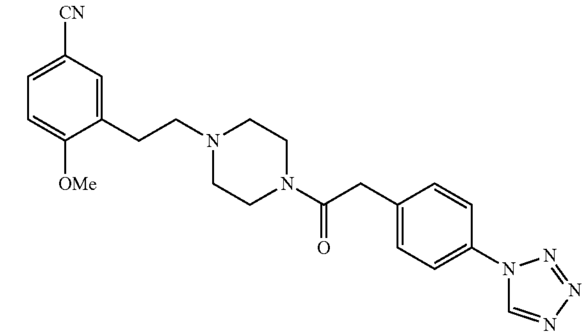 [SMILES: COc1ccc(C#N)cc1CCN1CCN(C(=O)Cc2ccc(-n3cnnn3)cc2)CC1] | |
| 197 | 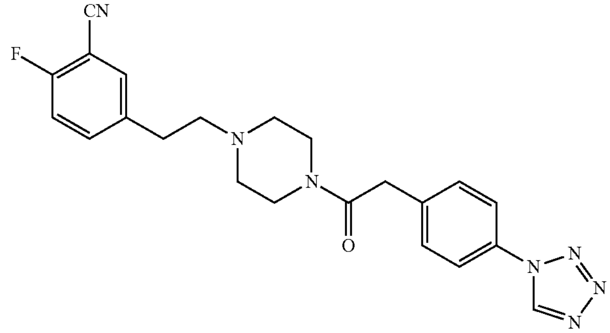 [SMILES: N#Cc1cc(CCN2CCN(C(=O)Cc3ccc(-n4cnnn4)cc3)CC2)ccc1F] | |
| 198 | 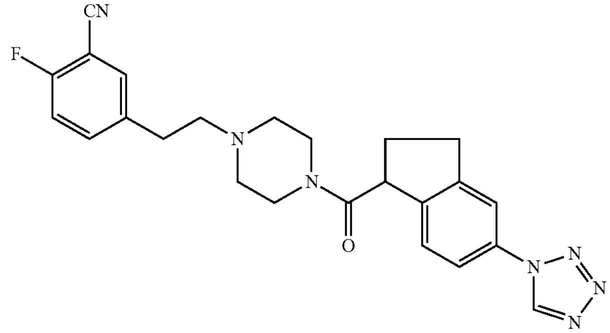 [SMILES: N#Cc1cc(CCN2CCN(C(=O)C3CCc4cc(-n5cnnn5)ccc43)CC2)ccc1F] | 446 |
Examples 199A and 199B
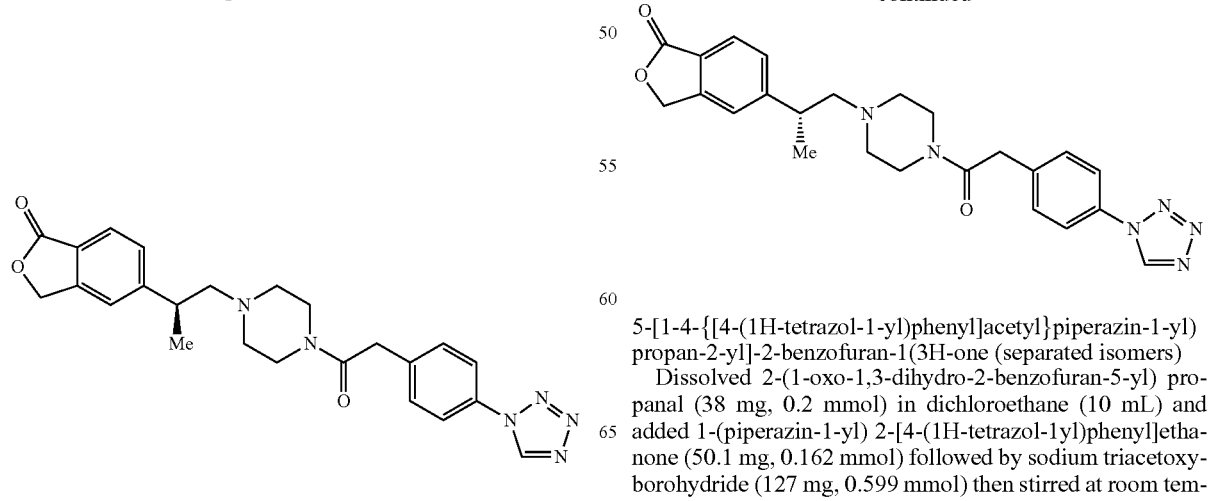
5-[1-4-{[4-(1H-tetrazol-1-yl)phenyl]acetyl}piperazin-1-yl) propan-2-yl]-2-benzofuran-1(3H)-one (separated isomers)
Dissolved 2-(1-oxo-1,3-dihydro-2-benzofuran-5-yl) propanal (38 mg, 0.2 mmol) in dichloroethane (10 mL) and added 1-(piperazin-1-yl) 2-[4-(1H-tetrazol-1yl)phenyl]ethanone (50.1 mg, 0.162 mmol) followed by sodium triacetoxyborohydride (127 mg, 0.599 mmol) then stirred at room temperature for 16 h. The reaction mixture was washed with saturated NaHCO₃ solution, brine, dried and concentrated. Purified by MPLC using a 40 g ISCO Redi-sep column and eluted with 0%-10% methanol/ethyl acetate to yield racemate 5-[1-4-{[4-(1H-tetrazol-1-yl)phenyl]acetyl}piperazin-1-yl)propan-2-yl]-2-benzofuran-1(3H)-one. The isomers were separated on Chiracel OD, 2 cm×25 cm, 10µ column using 45% ethanol: 55% heptane solvent system. The retention times for isomer A was at 42 minutes and for isomer B was at 47 minutes.

Isomer A:
LC-MS (IE, m/z): 447 [M+1]⁺; ¹H-NMR (500 MHz, CDCl₃) δ ppm 9.01 (s, 1H), 7.88 (d, J=8 Hz, 1H), 7.70 (d, J=8.4 Hz, 2H), 7.49 (d, J=8.4 Hz, 2H), 7.40 (d, J=8.1 Hz, 1H), 7.34 (s, 1H), 5.33 (s, 2H), 3.82 (s, 2H), 3.65 (b, 2H), 3.48 (t, J=4.1 Hz, 2H), 3.11-3.14 (m, 1H), 2.50-2.60 (m, 2H), 2.47 (t, J=4.8 Hz, 2H), 2.39 (t, J=4.4 Hz, 2H), 1.34 (d, J=4.8 Hz, 3H).

Isomer B:
LC-MS (IE, m/z): 447 [M+1]⁺; ¹H-NMR (500 MHz, CDCl₃) δ ppm 9.01 (2, 1H), 7.88 (d, J=8 Hz, 1H), 7.70 (d, J=8.2 Hz, 2H), 7.49 (d, J=8.2 Hz, 2H), 7.40 (d, J=6.8 Hz, 1H), 7.34 (s, 1H), 5.33 (s, 2H), 3.83 (s, 2H), 3.65 (t, J=4 Hz, 1H), 3.48 (t, J=4.6 Hz, 1H), 3.10-3.14 (m, 1H), 2.50-2.60 (m, 2H), 2.47 (t, J=4.8 Hz, 1H), 2.39 (t, J=4.4 Hz, 1H), 1.34 (d, J=6.9 Hz, 3H).

Example 200

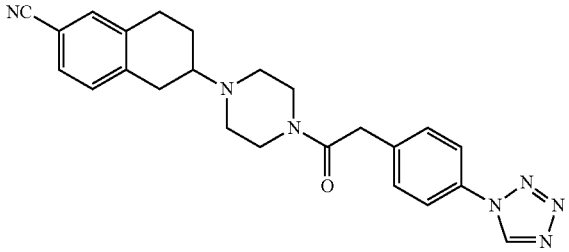 [SMILES: N#Cc1ccc2c(c1)CCC(N1CCN(C(=O)Cc3ccc(-n4cnnn4)cc3)CC1)C2]

6-(4-{[4-(1H-tetrazol-1-yl)phenyl]acetyl}piperazin-1-yl)-5,6,7,8-tetrahydronaphthalene-2-carbonitrile 6-(4-{[4-(1H-Tetrazol-1-yl)phenyl]acetyl}piperazin-1-yl)-5,6,7,8-tetrahydronaphthalene-2-carbonitrile was prepared in an analogous fashion to that described above for the synthesis of 5-[2-(4-{[4-(1H-tetrazol-1-yl)phenyl]acetyl}piperazin-1-yl)propyl]-2-benzofuran-1(3H)-one starting from 1-(piperazin-1-yl)-2-[4-(1H-tetrazol-1-yl)phenyl]ethanone hydrochloride and known compound 6-oxo-5,6,7,8-tetrahydronaphthalene-2-carbonitrile (Ralf Heim, et al. *J. Med. Chem.* 2008, 51(16), 5064-5074). LC/MS: [(M+1)]⁺=428.

Example 201

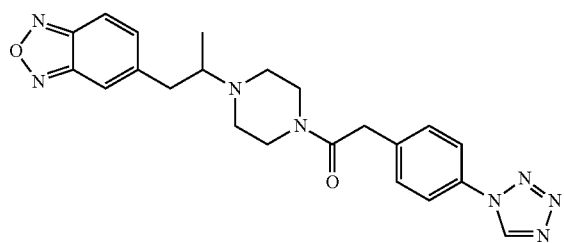 [SMILES: CC(Cc1ccc2nonc2c1)N1CCN(C(=O)Cc2ccc(-n3cnnn3)cc2)CC1]

1-{4-[1-(2,1,3-benzoxadiazol-5-yl)propan-2-yl]piperazin-1-yl}-2-[4-(1H-tetrazol-1-yl)phenyl]ethanone 1-{4-[1-(2,1,3-Benzoxadiazol-5-yl)propan-2-yl]piperazin-1-yl}-2-[4-(1H-tetrazol-1-yl)phenyl]ethanone was prepared in an analogous fashion to that described above for the synthesis of 5-[2-(4-{[4-(1H-tetrazol-1-yl)phenyl]acetyl}piperazin-1-yl)propyl]-2-benzofuran-1(3H)-one starting from 1-(piperazin-1-yl)-2-[4-(1H-tetrazol-1-yl)phenyl]ethanone hydrochloride and 1-(2,1,3-benzoxadiazol-5-yl)propan-2-one. LC/MS: [(M+1)]⁺=433.

Example 202

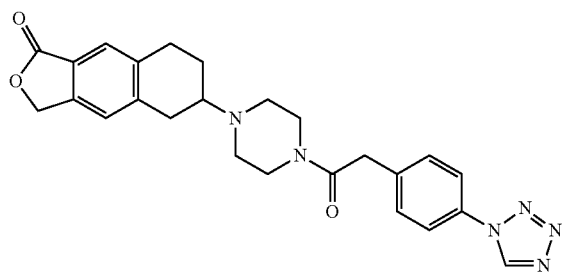 [SMILES: O=C1OCc2cc3c(cc21)CCC(N1CCN(C(=O)Cc2ccc(-n4cnnn4)cc2)CC1)C3]

6-4-{[4-(1H-tetrazol-1-yl)phenyl]acetyl}piperazin-1-yl)-5,6,7,8-tetrahydronaphtho[2,3-c]furan-1(3H)-one 6-(4-{[4-(1H-Tetrazol-1-yl)phenyl]acetyl}piperazin-1-yl)-5,6,7,8-tetrahydronaphtho[2,3-c]furan-1(3H)-one was prepared in an analogous fashion to that described above for the synthesis of 5-[2-(4-{[4-(1H-tetrazol-1-yl)phenyl]acetyl}piperazin-1-yl)propyl]-2-benzofuran-1(3H)-one starting from 1-(piperazin-1-yl)-2-[4-(1H-tetrazol-1-yl)phenyl]ethanone hydrochloride and 7,8-dihydronaphtho[2,3-c]furan-1,6(3H, 5H)-dione. LC/MS: [(M+1)]⁺=459.

Example 203

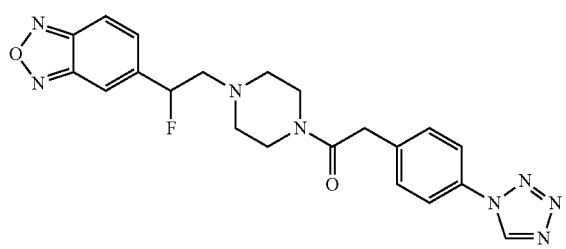 [SMILES: O=C(Cc1ccc(-n2cnnn2)cc1)N1CCN(CC(F)c2ccc3nonc3c2)CC1]

1-{4-[2-(2,1,3-benzoxadiazol-5-yl)-2-fluoroethyl]piperazin-1-yl}-2-[4-(1H-tetrazol-1-yl)phenyl]ethanone Step A: N-methoxy-N-methyl-2,1,3-benzoxadiazole-5-carboxamide 2,1,3-Benzoxadiazole-5-carboxylic acid (1.00 g, 6.09 mmol) was combined with N-methoxymethanamine (594 mg, 6.09 mmol), triethylamine (0.849 mL, 6.09 mmol) and EDC (1.17 g, 6.09 mmol) in acetonitrile (10 mL) and stirred at room temperature overnight. The reaction mixture was concentrated then the resuidue was dissolved in DCM and washed with saturated sodium bicarbonate solution, 5% citric acid, and the organic layer was concentrated and subjected to purification by flash chromatography (50% ethyl acetate/hexames) to afford the title compound. LC/MS: [(M+1)]⁺=208.

Step B: 1-(2,1,3-benzoxadiazol-5-yl)ethanone

To a solution of N-Methoxy-N-methyl-2,1,3-benzoxadiazole-5-carboxamide (630 mg, 3.04 mmol) in THF (5 mL)

cooled to −40° C. was added methyl lithium solution (1.6M, 2.28 mL, 3.65 mmol). The reaction mixture was stirred at the same temperature for 1 h, then was quenched by addition of 1M HCl. The mixture was extracted with ethyl acetate and the organic layer was dried over MgSO₄. Purification my flash chromatography afforded the title compound. ¹H-NMR (500 MHz, CDCl₃) δ ppm 8.48 (s, 1H), 8.02 (d, 1H), 7.91 (d, 1H), 2.72 (s, 3H).

Step C: 1-(2,1,3-benzoxadiazol-5-yl)-2-bromoethanone 1-(2,1,3-Benzoxadiazol-5-yl)ethanone (230 mg, 1.42 mmol) was combined with NBS (265 mg, 1.49 mmol) and ammonium acetate (11 mg, 0.14 mmol) in ether (5 mL) and the resulting mixture was stirred at RT for 1 h. Carbon tetrachloride was added (5 mL) and the mixture was heated at 80° C. for 1 h. An additional 0.2 equivalents of NMS were added and the mixture was heated at 80° C. for an additional 2 h. The reaction mixture was filtered and the filtrate was washed with water and the organic layer was dried over MgSO₄. The crude product which still contained starting material was used without purification in the next step. Step D: 1-(2,1,3-benzoxadiazol-5-yl)-2-(4-{[4-(1H-tetrazol-1-yl)phenyl]acetyl}piperazin-1-yl)ethanone-1-(2,1,3-Benzoxadiazol-5-yl)-2-bromoethanone (crude, 200 mg, 0.830 mmol) was combined with 1-(piperazin-1-yl)-2-[4-(1H-tetrazol-1-yl)phenyl]ethanone hydrochloride (256 mg, 0.830 mmol) in acetonitrile (2 mL) and treated with Hunig's base (0.145 mL, 0.830 mmol). The reaction mixture was stirred at 60° C. for 5 h. The reaction mixture was concentrated and purification by preparative TLC afforded the title compound. LC/MS: [(M+1)]⁺=433.

Step E: 1-{4-[2-(2,1,3-benzoxadiazol-5-yl)-2-hydroxyethyl]piperazin-1-yl}-2-[4-(1H-tetrazol-1-yl)phenyl]ethanone-1-(2,1,3-Benzoxadiazol-5-yl)-2-(4-{[4-(1H-tetrazol-1-yl)phenyl]acetyl}piperazin-1-yl)ethanone (50 mg, 0.12 mmol) was dissolved in methanol (5 mL), cooled to 0° C., and treated with sodium borohydride (4.4 mg, 0.12 mmol). The mixture was stirred at the same temperature for 15 minutes then was quenched by addition of water and extracted with ethyl acetate. The organic layer was dried over MgSO₄ to afford product with good purity. LC/MS: [(M+1)]⁺=435.

Step F: 1-{4-[2-(2,1,3-benzoxadiazol-5-yl)-2-fluoroethyl]piperazin-1-yl}-2-[4-(1H-tetrazol-1-yl)phenyl]ethanone-1-{4-[2-(2,1,3-benzoxadiazol-5-yl)-2-hydroxyethyl]piperazin-1-yl}-2-[4-(1H-tetrazol-1-yl)phenyl]ethanone (15 mg, 0.035 mmol) was dissolved in DCM (2 mL), coiled to 0° C. and treated with DAST (4.6 uL, 0.035 mmol). The mixture was stirred at 0° C. for 1 h then at rt for 1 h. The mixture was quenched with methanol, concentrated, then partitioned between ethyl acetate and water. The organic layer was dried over MgSO₄ and the crude product was purified by HPLC. LC/MS: [(M+1)]⁺=437.

Example 204

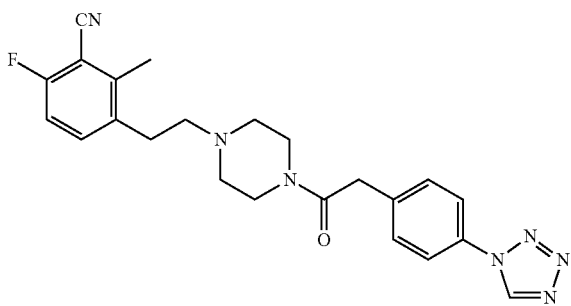 [SMILES: Cc1c(CCN2CCN(C(=O)Cc3ccc(-n4cnnn4)cc3)CC2)ccc(F)c1C#N]

6-fluoro-2-methyl-3-[2-(4-{[4-(1H-tetrazol-1-yl)phenyl]acetyl}piperazin-1-yl)ethyl]benzonitrile 6-Fluoro-2-methyl-3-[2-(4-{[4-(1H-tetrazol-1-yl)phenyl]acetyl}piperazin-1-yl)ethyl]benzonitrile was prepared from 6-fluoro-2-methyl-3-(2-oxoethyl)benzonitrile and 1-(piperazin-1-yl)-2-[4-(1H-tetrazol-1-yl)phenyl]ethanone hydrochloride in an analogous fashion to that described for 1-{4-[2-(2,1,3-benzoxadiazol-5-yl)ethyl]piperazin-1-yl}-2-[4-(1H-tetrazol-1-yl)phenyl]ethanone (General Method C). ¹H-NMR (400 MHz, CD₃OD) δ 9.89 (s, 1H), 7.76~7.78 (m, 2H), 7.51~7.55 (m, 1H), 7.40~7.42 (m, 2H), 7.21~7.25 (m, 1H), 4.44~4.45 (m, 1H), 4.16~4.17 (m, 1H), 3.84 (s, 2H), 3.38~3.56 (m, 2H), 2.98~3.01 (m, 4H).

Example 205

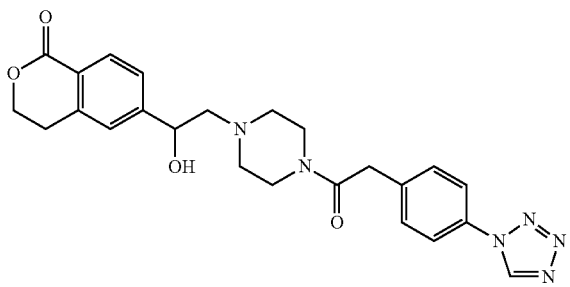 [SMILES: O=C1OCCc2cc(C(O)CN3CCN(C(=O)Cc4ccc(-n5cnnn5)cc4)CC3)ccc21]

6-[1-hydroxy-2-(4-{[4-(1H-tetrazol-1-yl)phenyl]acetyl}piperazin-1-yl)ethyl]-3,4-dihydro-1H-isochromen-1-one A solution of 1-(piperazin-1-yl)-2-[4-(1H-tetrazol-1-yl)phenyl]ethanone (200 mg, 0.734 mmol), 6-(oxiran-2-yl)-3,4-dihydro-1H-isochromen-1-one (140 mg, 0.734 mmol) in ethanol was heated in a microwave reactor at 130° C. for 1 h. The reaction mixture was concentrated and the residue was purified by preparative TLC to afford the title compound. LC/MS: [(M+1]⁺=463.

Example 206

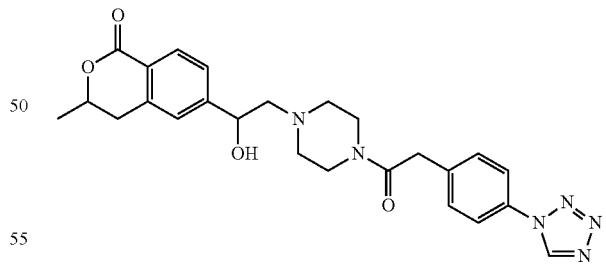

6-[1-hydroxy-2-(4-{[4-(1H-tetrazol-1-yl)phenyl]acetyl}piperazin-1-yl)ethy]-3-methyl-3,4-dihydro-1H-isochromen-1-one A sealed tube containing 3-methyl-6-(oxiran-2-yl)-3,4-dihydro-1H-isochromen-1-one (72 mg, 35 mmol), 1-(piperazin-1-yl)-2-[4-(1H-tetrazol-1-yl)phenyl]ethanone hydrochloride (109 mg, 0.35 mmol), DIEA (0.2 mL) and EtOH (3 mL) was heated to 80 C for 12 hours. The excess solvent was removed and the crude product purified via MPLC (35% EtOAc/Hex-60% EtOAc/Hex) to give 6-[1-hydroxy-2-(4-

{[4-(1H-tetrazol-1-yl)phenyl]acetyl}piperazin-1-yl)ethyl]-3-methyl-3,4-dihydro-1H-isochromen-1-one. LC-MS (IE, m/z): 477 [M+1]+.

Example 207

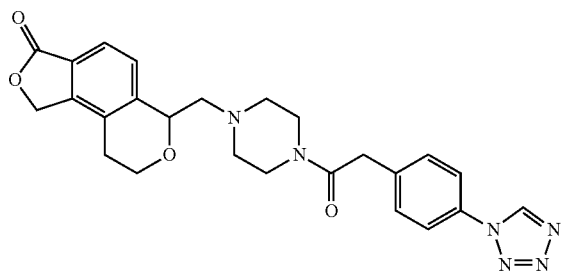 [SMILES: O=C1OCc2c1ccc1c2CCOC1CN1CCN(C(=O)Cc2ccc(-n3cnnn3)cc2)CC1]

6-[(4-{[4-(1H-tetrazol-1-yl)phenyl]acetyl}piperazin-1-yl)methyl]-8,9-dihydro-1H-furo[3,4-f]isochromen-3(6H)-one A solution of (3-oxo-3,6,8,9-tetrahydro-1H-furo[3,4f]isochromen-6-yl)methyl4-methylbenzenesulfonate (20 mg, 0.053 mmol) and 1-(piperazin-1-yl)-2-[4-(1H-tetrazol-1-yl)phenyl]ethanone (17 mg, 0.064 mmol) in CH$_3$CN (2 mL) was heated under microwave conditions (120° C.) for 1 hr. The mixture was purified by prep-TLC (MeOH/DCM=1:15) to give the title product. MS m/e 475 (M+1)+; $^1$H-NMR (400 MHz, MeOD) δ ppm 9.65 (s, 1H), 7.73 (d, J=8.6 Hz, 2H), 7.57 (d, J=8.1 Hz, 1H), 7.43 (d, J=8.6 Hz, 2H), 7.37 (d, J=8.1 Hz, 1H), 5.24 (d, J=3.0 Hz, 2H), 4.97 (t, J=5.6 Hz, 1H), 4.07~4.12 (m, 1H), 3.81 (s, 2H), 3.71~3.77 (m, 1H), 3.53~3.58 (m, 4H), 2.75~2.79 (m, 3H), 2.50~2.66 (m, 5H).

Example 208

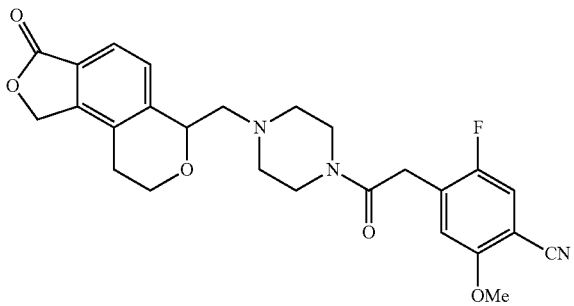 [SMILES: COc1cc(CC(=O)N2CCN(CC3OCCc4c3ccc3c4COC3=O)CC2)c(F)cc1C#N]

5-fluoro-2-methoxy-4-(2-oxo-2-{4-[(3-oxo-3,6,8,9-tetrahydro-1H-furo[3,4-f]isochromen-6-yl)methyl]piperazin-1-yl}ethyl)benzonitrile 5-Fluoro-2-methoxy-4-(2-oxo-2-{4[(3-oxo-3,6,8,9-tetrahydro-1H-furo[3,4-f]isochromen-6-yl)methyl]piperazin-1-yl}ethyl)benzonitrile was prepared from (3-oxo-3,6,8,9-tetrahydro-1H-furo[3,4-f]isochromen-6-yl)methyl4-methylbenzenesulfonate and 5-fluoro-2-methoxy-4-[2-oxo-2-(piperazin-1-yl)ethyl]benzonitrile in an analogous fashion to that described above for the synthesis of 6-[(4-{[4-(1H-tetrazol-1-yl)phenyl]acetyl}piperazin-1-yl)methyl]-8,9-dihydro-1H-furo[3,4-f]isochromen-3(6H)-one. MS m/e 480 (M+1)+.

Example 209

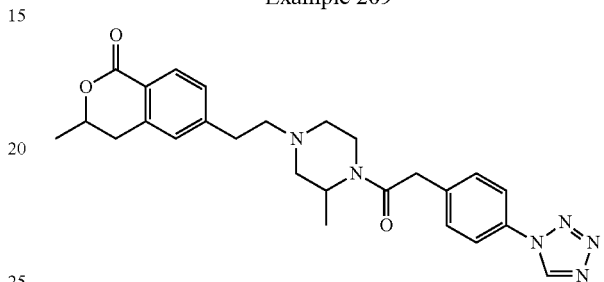

3-methyl-6-[2-(3-methyl-4-{[4-(1H-tetrazol-1-yl)phenyl]acetyl}piperazin-1-yl)ethyl]-3,4-dihydro-1H-isochromen-1-one A solution of [4-(1H-tetrazol-1-yl)phenyl]acetic acid (101 mg, 0.49 mmol) in DCM (1271 µl) was treated with HATU (189 mg, 0.49 mmol) at room temp. After 5 minutes a solution of of 3-methyl-6-[2-(3-methylpiperazin-1-yl)ethyl]-3,4-dihydro-1H-isochromen-1-one (110 mg, 0.38 mmol) and DIEA (167 µl, 0.954 mmol) in DCM (1271 µl) was added and the reaction allowed to stir overnight at room temp. The reaction was quenched with water and SPE purification gives crude product which was purified via reverse phase HPLC (5-85% gradient elution ACN/H$_2$O with 0.5% TFA) to obtain 3-methyl-6-[2-(3-methyl-4-{[4-(1H-tetrazol-1-yl)phenyl]acetyl}piperazin-1-yl)ethyl]-3,4-dihydro-1H-isochromen-1-one. LC-MS (IE, m/z): 475 [M+1]+.

The following EXAMPLES (Table) were prepared in an analogous fashion to that described for the synthesis of 3-methyl-6-[2-(3-methyl-4-{[4-(1H-tetrazol-1-yl)phenyl]acetyl}piperazin-1-yl)ethyl]-3,4-dihydro-1H-isochromen-1-one from [4-(1H-tetrazol-1-yl)phenyl]acetic acid and the appropriate substituted piperazines which were described previously.

| EXAMPLE | Structure of EXAMPLE | LC/MS (M + 1)+ |
|---|---|---|
| 210 | 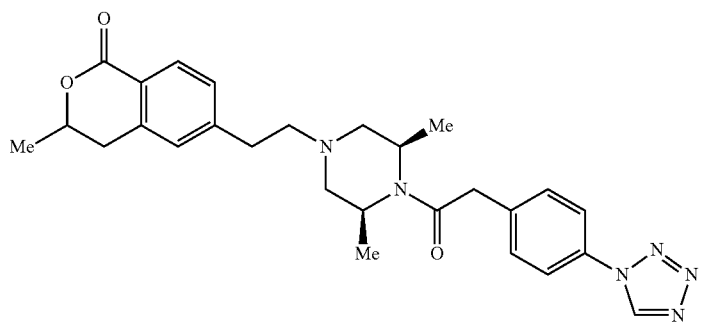 [SMILES: CC1Cc2cc(CCN3C[C@@H](C)N(C(=O)Cc4ccc(-n5cnnn5)cc4)[C@@H](C)C3)ccc2C(=O)O1] | 489 |

| EXAMPLE | Structure of EXAMPLE | LC/MS (M + 1)+ |
|---|---|---|
| 211 | 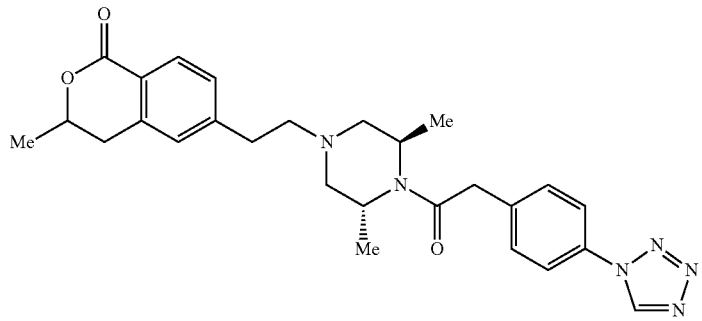 [SMILES: CC1Cc2cc(CCN3C[C@@H](C)N(C(=O)Cc4ccc(-n5cnnn5)cc4)[C@H](C)C3)ccc2C(=O)O1] | 489 |
| 212 | 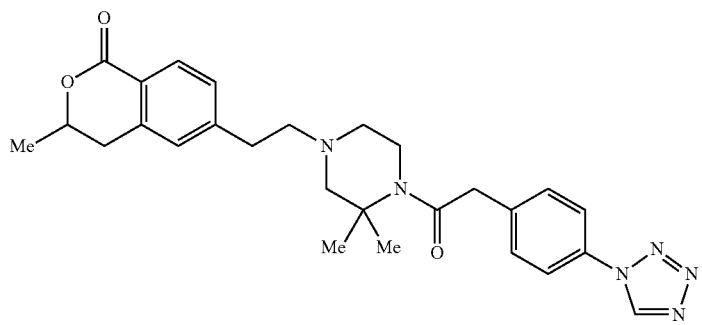 [SMILES: CC1Cc2cc(CCN3CCN(C(=O)Cc4ccc(-n5cnnn5)cc4)C(C)(C)C3)ccc2C(=O)O1] | 489 |
| 213 | 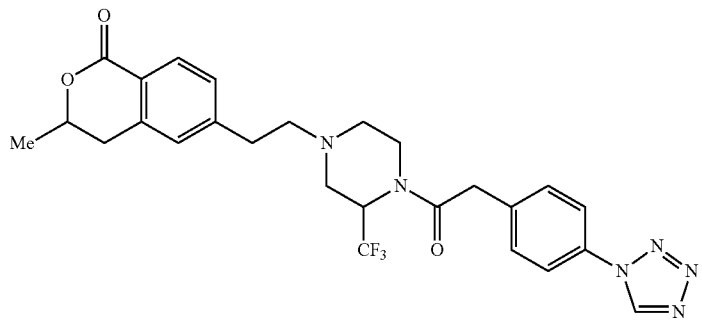 [SMILES: CC1Cc2cc(CCN3CCN(C(=O)Cc4ccc(-n5cnnn5)cc4)C(C(F)(F)F)C3)ccc2C(=O)O1] | 529 |
| 214 | 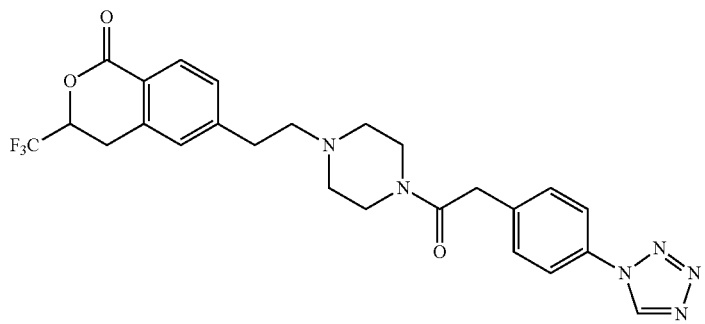 [SMILES: O=C1OC(C(F)(F)F)Cc2cc(CCN3CCN(C(=O)Cc4ccc(-n5cnnn5)cc4)CC3)ccc21] | 515 |

Examples 215A and 215B

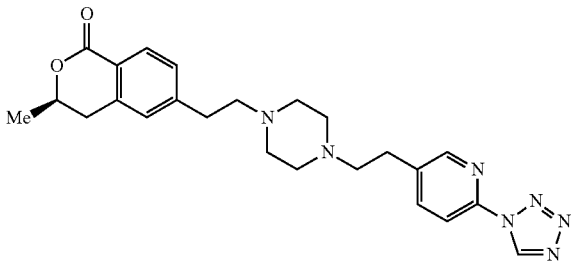

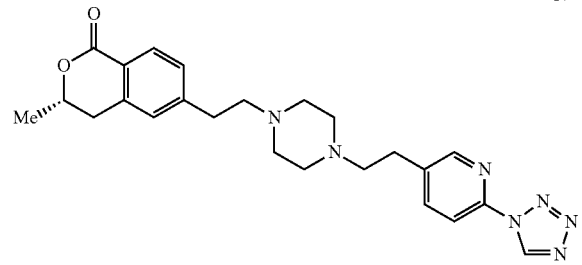

(3R)-3-methyl-6-[2-(4-{[6-(1H-tetrazol-1-yl)pyridin-3-yl]acetyl}piperazin-1-yl)ethyl]-3,4-dihydro-1H-isochromen-1-one and (3S)-3-methyl-6-[2-(4-{[6-(1H-tetrazol-1-yl)pyridin-3-yl]acetyl}piperazin-1-yl)ethyl]-3,4-dihydro-1H-isochromen-1-one 3-Methyl-6-[2-(4-{[6-(1H-tetrazol-1-yl)pyridin-3-yl]acetyl}piperazin-1-yl)ethyl]-3,4-dihydro-1H-isochromen-1-one was synthesized according to the procedure described for 3-methyl-6-[2-(3-methyl-4-{[4-(1H-tetrazol-1-yl)phenyl]acetyl}piperazin-1-yl)ethyl]-3,4-dihydro-1H-isochromen-1-one, utilizing [6-(1H-tetrazol-1-yl)pyridin-3-yl]acetic acid and 3-methyl-6-[2-(piperazin-1-yl)ethyl]-3,4-dihydro-1H-isochromen-1-one hydrochloride. LC-MS (IE, m/z): 462 [M+1]⁺. Separation of the two enantiomers was achieved by chiral preparative HPLC using a Chiralcel OD column eluting with 75% EtOH/Heptane to afford (3R)-3-methyl-6-[2-(4-{[6-(1H-tetrazol-1-yl)pyridin-3-yl]acetyl}piperazin-1-yl)ethyl]-3,4-dihydro-1H-isochromen-1-one and (3S)-3-methyl-6-[2-(4-{[6-(1H-tetrazol-1-yl)pyridin-3-yl]acetyl}piperazin-1-yl)ethyl]-3,4-dihydro-1H-isochromen-1-one both having LC-MS (IE, m/z): 462 [M+1]⁺.

Example 216

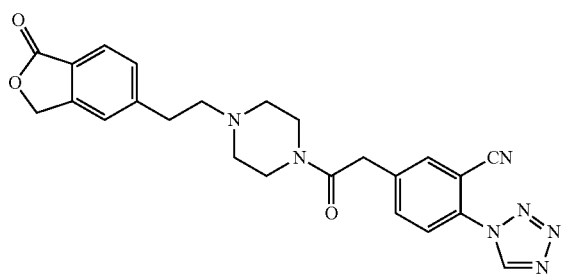

5-(2-oxo-2-{4-[2-(1-oxo-1,3-dihydro-2-benzofuran-5-yl)ethyl]piperazin-1-yl}ethyl)-2-(1H-tetrazol-1-yl)benzonitrile A mixture of 5-[2-(4-{[3-iodo-4-(1H-tetrazol-1-yl)phenyl]acetyl}piperazin-1-yl)ethyl]-2-benzofuran-1(3H)-one (190 mg, 034 mmol) and CuCN (47 mg, 0.52 mmol) in 2 ml of anhydrous DMF was heated to 110° C. under N₂ for 30 min. The reaction was cooled to ambient temperature, and then 15 ml of water was added. Extracted with DCM and the organic layer was dried over anhydrous sodium sulfate and concentrated. The crude product was purified via prep-TLC to afford 5-(2-oxo-2-{4-[2-(1-oxo-1,3-dihydro-2-benzofuran-5-yl)ethyl]piperazin-1-yl}ethyl)-2-(1H-tetrazol-1-yl)benzonitrile. ¹H-NMR (400 MHz, CD₃CN) δ ppm 9.36 (s, 1H), 7.85 (s, 1H), 7.72~7.79 (m, 3H), 7.44~7.50 (m, 2H), 5.30 (s, 2H), 3.87 (s, 2H), 2.49 (t, J=7.5 Hz, 21H), 2.64 (t, J=7.2 Hz, 2H), 2.65~2.70 (m, 2H), 2.46~2.53 (m, 4H).

Example 217

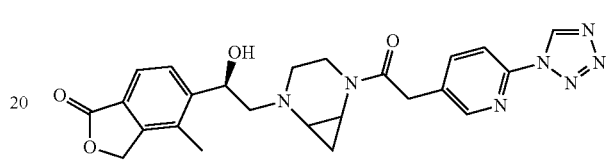

5-[(1R)-1-hydroxy-2-(5-{[6-(1H-tetrazol-1-yl)pyridin-3-yl]acetyl}-2,5-diazabicyclo[4.1.0]hept-2-yl)ethyl]-4-methyl-2-benzofuran-1(3H)-one In a round bottom flask, 5-{(1R)-2-[(±)-2,5-diazabicyclo[4.1.0]hept-2-yl]-1-hydroxyethyl}-4-methyl-2-benzofuran-1(3H)-one TFA salt (66 mg, 0.126 mmol) was dissolved in DMF (2 mL). DIEA (66 mg, 0.511 mmol) was added, followed by [6-(1H-tetrazol-1-yl)pyridin-3-yl]acetic acid (32 mg, 0.153 mmol). HATU (73 mg, 0.192 mmol) was added and let reaction stir at room temperature for 6 hours. Then reaction was diluted by adding small amount of water and was put on prep-HPLC for purification (Sunfire-C18 column, eluted by 10-75% AcCN/H₂O+0.1% formic acid). Lyophilization gave the title compound. ¹H NMR (ppm) (500 MHz, CD₃OD): δ 9.90 (1H, s), 8.50 (1H, s), 8.07-8.00 (2H, m), 7.80 (1H, m), 7.72 (1H, d, J=8.0 Hz), 5.36 (2H, d, J=3.10 Hz), 5.40-5.31 (1H, m), 4.10 (2H, s), 4.08-3.95 (1H, m), 3.20-3.07 (1H, in), 3.06-2.83 (3H, m), 2.80 (2H, s), 2.78-2.68 (2H, m), 2.54-2.39 (1H, m), 2.36 (3H, s), 0.95 (1H, t, J=6.39 Hz), 0.81 (1H, t, J=4.98 Hz); LC/MS: (M+23)⁺ =498.

Example 218

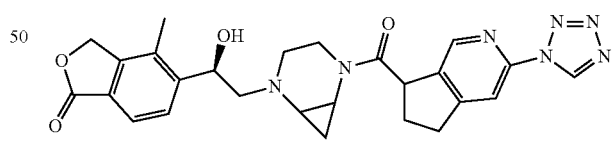

5-[(1R)-1-hydroxy-2-(5-{[3-(1H-tetrazol-1yl)-6,7-dihydro-5H-cycloclopenta[c]pyridin-7-yl]carbonyl}-2,5-diazabicyclo[4.1.0]hept-2-yl)ethyl]-4-methyl-2-benzofuran-1(3H)-one In a round bottom flask, 5-{(1R)-2-[(±)-2,5-diazabicyclo[4.1.0]hept-2-yl]-1-hydroxyethyl}-4-methyl-2-benzofuran-1(3H)-one TFA salt (135 mg, 0.261 mmol) was dissolved in DMF (2 mL). DIEA (135 mg, 1.05 mmol) was added, followed by 3-(1H-tetrazol-1-yl)-6,7-dihydro-5H-cyclopenta[c]pyridine-7-carboxylic acid (72.5 mg, 0.314 mmol). HATU (149 mg, 0.392 mmol) was added and let reaction stir at room temperature for 6 hours. Then reaction was diluted by adding small amount of water and was put on prep-HPLC for purification (Sunfire-C18 column, eluted by 10-75% AcCN/H$_2$O+0.1% formic acid). Lyophilization gave white solid as formic acid salt of title compound as a mixture of four diastereomers. $^1$H NMR (ppm) (500 MHz, Acetone-d$_6$): 9.76-9.73 (1H, m), 8.40 (1H, s), 7.97 (1H, s), 7.86 (1H, dd, J=7.96, 3.28 Hz), 7.69 (1H, d, J=7.94 Hz), 5.50-5.38 (1H, m), 5.40 (2H, d, J=9.85 Hz), 5.36 (2H, s), 4.95 (1H, m), 4.10 (1H, m) 3.31-3.23 (1H, m), 3.18-2.98 (4H, m), 2.74-2.58 (3H, m), 2.40 (3H, d, J=9.0 Hz), 2.38-2.28 (1H., m), 1.16-0.96 (2H, m); LC/MS: (M+23)$^+$=524.

Several assays may be used to measure functional inhibition of the ROMK channel by compounds of the instant invention. One primary assay that can be used is a functional $^{86}$Rb$^+$ efflux assay that measures the ability of ROMK to permeate $^{86}$Rb$^+$, in the absence or presence of test compound. Under control conditions, cells loaded with $^{86}$Rb$^+$ and incubated in Rb$^+$-free medium display a time-dependent efflux of the isotope, the rate of which depends on number of functional channels. When cells are incubated in the presence of a channel inhibitor, efflux of $^{86}$Rb$^+$ is prevented in a concentration-dependent manner, and IC$_{50}$ values of inhibition by compounds can be accurately determined. This assay has been established with cell lines expressing either human, rat or dog ROMK channels, and can operate in 96- or 384-well format. Importantly, the human, rat, and dog $^{86}$Rb$^+$ efflux assays can be carried out in the presence of up to 100% serum allowing, therefore, an accurate estimation of the effect of protein binding on the inhibitory activity of compounds of interest. Another ROMK functional assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and IC$_{50}$ values of inhibition by compounds can be accurately determined. This assay has been established with cell lines expressing either human, or rat ROMK channels, and operates in 384-well format. Another assay for evaluation of the compounds of the instant invention and for evaluation of mechanism of action of compounds of Formula I relies on the measurement of the electrical current that is generated as potassium permeates through the channel. For these electrophysiological experiments, three different platforms, IonWorks, QPatch, or manual patch clamp, are used, depending on the experimental protocol under consideration. IonWorks operates in a 384-well format and allows accurate determination of IC$_{50}$ values for inhibitors. Examples of compounds of the present invention (listed above) all had potencies of at least 1 µM or lower in one or more of the three assays described herein.

The following Thallium Flux Assay and/or the $^{86}$Rb$^+$ Efflux Assay and/or Electrophysiology Assay were performed on the final product compounds in the Examples.

$^{86}$Rb$^+$ Efflux Assay

Cell Culture Conditions—CHO-DHFR-cells stably expressing hROMK1 (K$_{ir}$1.1) are grown at 37° C. in a 10% CO$_2$ humidified incubator in Iscoves Modified Dulbecco's Medium (Gibco 12440) supplemented with HT Supplement, Penicillin/Streptomycin/Glutamine, G418 (500 µg/ml) and 10% FBS. Cells are seeded in Sterile and Tissue Culture Treated Packard CulturPlate White Opaque Microplates at a concentration of 5.0E5-7.0E5 cells/ml-PerkinElmer 6005680 (96-well); Corning 3707 (384 well) in complete media containing 1.5 µCi/ml Rubidium-86. Cells are incubated in 37° C.-10% CO$_2$ incubator overnight. On the day of the experiment, the media is removed and cells are washed with low K assay buffer. $^{86}$Rb$^+$ efflux is initiated after addition of assay buffer±test compound followed by 35 min incubation at room temperature. ROMK-sensitive component of efflux is defined in the presence of 10 mM BaCl$_2$. Assay buffer is removed and transferred to a plate and cells are solubilized in the presence of SDS. Radioactivity associated with assay and cell plate is determined.

Step Protocol
1. Remove cell media and wash cells with low K assay buffer (126.9 mM NaCl, 4.6 mM KCl, 2 mM CaCl$_2$, 1 mM MgCl$_2$, 10 mM Hepes/NaOH; pH 7.4)
   200 µl for 96-well plate; 70 µl for 384-well plate
2. Add assay buffer (121.5 mM NaCl, 10 mM KCl, 2 mM CaCl$_2$, 1 mM MgCl$_2$, 10 mM Hepes/NaOH; pH 7.4)±test compound to cells
   100 µl for 96-well plate; 50 µl for 384-well plate
3. Incubate at ambient temperature (22-24° C.) for 35 min
4. Remove assay buffer add it to a 96- or 384-well plate containing Microscint-20
   96-well Plate: 100 µl buffer, 170 µl MicroScint 20 (for TopCount)
   384-well plate: 20 µl buffer, 50 µl Optiphiase (for MicroLux)
5. Completely remove remaining assay buffer from cell plate
6. Solubilize cells with 1% SDS; than add MicroScint or Optiphase
   96-well Plate: 30 µl SDS, 170 µl MicroScint 20 (for TopCount)
   384-well plate: 20 µl SDS, 50 µl Optiphiase (for MicroLux)
7. Seal both cell and supernatant plates and count Data Calculation—Radioactivity associated with the assay plate is normalized to the total radioactivity (assay+cell plates) to provide % efflux, under each condition. % efflux in the presence of 10 mM BaCl$_2$ is subtracted from each experimental point to provide the ROMK-sensitive component of $^{86}$Rb$^+$ efflux. In the absence of test compound, this number corresponds to 100% control efflux. IC$_{50}$ values represent the concentration of compound that inhibits 50% of ROMK efflux. Normally, a control compound is included to support that the assay is giving consistent results compared to previous measurements, although the control is not required to obtain the results for the test compounds. The control can be any compound of Formula I of the present invention, preferably with an IC$_{50}$ potency of less than 1 µM in this assay. Alternatively, the control could be another compound (outside the scope of Formula I) that has an IC$_{50}$ potency in this assay of less than 1 µM.

Thallium Flux Assay

Cell Culture Conditions—HEK293 cells stably expressing hROMK (hK$_{ir}$1.1) are grown at 37° C. in a 10% CO$_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 ml Calcium/Magnesium-free PBS. Add 5 ml of 1× trypsin (prepared in Ca/Mg Free PBS) to T-225 flask and return flask to 37° C./CO$_2$ incubator for 2-3 minutes. To dislodge the cell, gently bang the side of the flask with your hand. Triturate the cells completely and then transfer the cells to 25 ml complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
- FluxOR™ Reagent (Component A)
- FluxOR™ Assay Buffer (Component B)—10× Concentrate
- PowerLoad™ Concentrate (Component C)—100× Concentrate
- Probenecid (Component D)—Lyophilized sample is kept at −20° C. Water soluble, 100× after solubilization in 1 ml water. Store at 4° C.
- FluxOR™ Chloride-free Buffer (Component E)—5× Concentrate
- Potassium sulfate ($K_2SO_4$) Concentrate (Component F)—125 mM in water. Store at 4° C.
- Thallium sulfate ($Tl_2SO_4$) Concentrate (Component G)—50 mM in water. Store at 4° C.
- DMSO (dimethyl sulfoxide, Component H)—1 ml (100%)

Reagent Preparation—
FluxOR Working Solutions
- 1000× FluxOR™ Reagent: Reconstitute a vial of component A in 100 µl DMSO; Mix well; Store 10 µl aliquots at −20° C.
- 1+FluxOR™ Assay Buffer: Dilute Component B 10-fold with water; Adjust pH to 7.4 with Hepes/NaOH; Filter and store at 4° C.
- Probenecid/Assay Buffer: 100 ml of 1× FluxOR™ Assay Buffer; 1 ml of reconstituted component D; Store at 4° C.
- Loading Buffer (per microplate): 10 µl 1000× FluxOR™ Reagent; 100 µl component C; 10 ml Probenecid/Assay Buffer
- Compound Buffer (per microplate): 20 ml Probenecid/Assay Buffer; 0.3 mM ouabain (10 mM ouabain in water can be stored in amber bottle/aluminum foil at room temperature); Test compound
- 1× FluxOR™ Chloride-Free Buffer: Prepare IX working solution in water. Can be stored at room temperature
- Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer± test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer± test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1µM.

Electrophysiology Assay

Block of Kir1.1 (ROMKI) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 ml of Versene (Invitrogen 15040-066) for approximately 6 min at 37° C. and suspended in 10 ml of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 ml of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/ml amphotericin B for 4 min. Amphotericin B (Sigma A-4888) was prepared as a 40 mg/ml solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Representative examples of data collected for compounds of the present invention using the ROMK electrophysiology assay titrations are shown in the Table 1 below.

TABLE 1

| EXAMPLE # | ROMK Electrophysiology Assay $IC_{50}$ (µM) |
|---|---|
| 1 | 0.065 |
| 11 | 0.012 |
| 12 | 0.061 |
| 39 | 0.063 |
| 48 | 0.035 |
| 59 | 0.094 |
| 72 | 0.020 |
| 96 | 0.061 |
| 122 | 0.037 |
| 177 | 0.100 |
| 217 | 0.056 |

Compounds of the Examples were tested in the electrophysiology assay and found to have a therapeutic level of potency.

Rat Diuresis Assay

Experimental protocols for evaluating diuretic efficacy of compounds of the present invention in Sprague-Dawley (SD) rats:
1. Adult male SD rats are acclimated to single housing in metabolism cages for at least three (3) days before their use in the diuresis screen. Rats have at lib access to food and water.
2. For most studies the procedure will be to remove food hoppers and water bottles from the metabolic cages 1-2 h before the start of the diuresis screen. Rats will be dosed with compound (see below) and 30 minutes later dosed with water or saline orally at 18 mL/kg to induce voiding and placed in the metabolic cage where urine is collected over the next 4 hours.
For selected studies an overnight fast may be necessary if saline/water loads larger than those described above are required. For these studies a saline or water dose of up to 27 mL/kg will be given.
3. Following the fasting period (usually 1-2 hours but sometimes overnight), animals are removed from the metabolism cages and temporarily housed in shoebox cages for dosing. Compound or vehicle is dosed in 70% PEG200 or Imwitor:Tween (depending on the physical properties of the compound) at 1 mL/Kg PO.
4. The 30 min time period between compound dosing and water/saline loading may be modified depending on the bioavailability of the compound being tested.
5. Urine is collected from each animal for up to 4 hrs at room temperature.
6. The urine volume collected from each animal is measured and recorded. Urine is centrifuged, aliquoted and frozen (−20° C.) until analyzed.
7. Blood (150-200 µl) can be obtained from treated animals by jugular vein bleed for compound plasma exposure levels.
Note: Rats can be re-tested with additional compounds after 1 week of recovery while housed in metabolism cages. Data=Mean/sem. Data analyzed by one way ANOVA and Dunnett's comparison of treatments to vehicle. The known diuretic, hydrochlorothiazide, dosed PO at 10 or 25 mg/kg, can be used as a positive control in this model.

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneuously hypertensive rats (SHR): Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis.

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:
1. A compound 1 selected from the group consisting of:
5-[2-(4-{[4-(1H-tetrazol-1-yl)phenyl]acetyl}piperazin-1-yl)ethyl]-2-benzofuran-1(3H)-one,
1-{4-[2-(2,1,3-benzoxadiazol-5-yl)ethyl]piperazin-1-yl}-2-[4-(1H-tetrazol-1-yl)phenyl]ethanone,
6-methyl-5-[2-(4-{[4-(1H-tetrazol-1-yl)phenyl]acetyl}piperazin-1-yl)ethyl]-2-benzofuran-1(3H)-one,
4-methyl-5-[2-(4-{[(7R)-3-(1H-tetrazol-1-yl)-6,7-dihydro-5H-cyclopenta[c]pyridin-7-yl]carbonyl}piperazin-1-yl)ethyl]-2-benzofuran-1(3H)-one,
4-methyl-5-[2-(4-{[(7S)-3-(1H-tetrazol-1-yl)-6,7-dihydro-5H-cyclopenta[c]pyridin-7-yl]carbonyl}piperazin-1-yl)ethyl]-2-benzofuran-1(3H)-one,
4-[(4-{[4-(1H-tetrazol-1-yl)phenyl]acetyl}piperazin-1-yl)methyl]-3,4-dihydro-2H-chromene-8-carbonitrile,
4-({4-[(1-oxo-1,3-dihydro-2-benzofuran-5-yl)acetyl]piperazin-1-yl}methyl)-3,4-dihydro-2H-chromene-8-carbonitrile,

5-[2-(4-{[3-fluoro-4-(1H-tetrazol-1-yl)phenyl]
acetyl}piperazin-1-yl)ethyl]-2-benzofuran-1(3H)-one,
4-[2-(4-{[4-(1H-tetrazol-1-yl)phenyl]acetyl}piperazin-1-
yl)ethyl]benzonitrile,
5-[2-(4-{[5-(1H-tetrazol-1-yl)biphenyl-2-yl]
acetyl}piperazin-1-yl)ethyl]-2-benzofuran-1(3H)-one,
5-[2-(4-{[2-cyclopropyl-4-(1H-tetrazol-1-yl)phenyl]
acetyl}piperazin-1-yl)ethyl]-2-benzofuran-1(3H)-one,
2-methoxy-4-[2-(4-{[4-(1H-tetrazol-1-yl)phenyl]
acetyl}piperazin-1-yl)ethyl]benzonitrile,
1-{4-[2-(3-nitrophenyl)ethyl]piperazin-1-yl}-2-[4-(1H-
tetrazol-1-yl)phenyl]ethanone,
5-[2-(4-{[4-(1H-tetrazol-1-yl)phenyl]acetyl}piperazin-1-
yl)propyl]-2-benzofuran-1(3H)-one,
5-[1-4-{[4-(1H-tetrazol-1-yl)phenyl]acetyl}piperazin-1-
yl)propan-2-yl]-2-benzofuran-1(3H)-one,
6-(4-{[4-(1H-tetrazol-1-yl)phenyl]acetyl}piperazin-1-
yl)-5,6,7,8-tetrahydronaphthalene-2-carbonitrile,
1-{4-[1-(2,1,3-benzoxadiazol-5-yl)propan-2-yl]piper-
azin-1-yl}-2-[4-(1H-tetrazol-1-yl)phenyl]ethanone,
6-(4-{[4-(1H-tetrazol-1-yl)phenyl]acetyl}piperazin-1-
yl)-5,6,7,8-tetrahydronaphtho[2,3-c]furan-1(3H)-one,
1-{4-[2-(2,1,3-benzoxadiazol-5-yl)-2-fluoro ethyl]piper-
azin-1-yl}-2-[4-(1H-tetrazol-1-yl)phenyl]ethanone,
6-fluoro-2-methyl-3-[2-(4-{[4-(1H-tetrazol-1-yl)phenyl]
acetyl}piperazin-1-yl)ethyl]benzonitrile,
6-[1-hydroxy-2-(4-{[4-(1H-tetrazol-1-yl)phenyl]
acetyl}piperazin-1-yl)ethyl]-3,4-dihydro-1H-isoch-
romen-1-one,
6-[1-hydroxy-2-(4-{[4-(1H-tetrazol-1-yl)phenyl]
acetyl}piperazin-1-yl)ethyl]-3-methyl-3,4-dihydro-
1H-isochromen-1-one,
6-[(4-{[4-(1H-tetrazol-1-yl)phenyl]acetyl}piperazin-1-
yl)methyl]-8,9-dihydro-1H-furo[3,4-j]isochromen-3
(614)-one,
5-fluoro-2-methoxy-4-(2-oxo-2-{4-[(3-oxo-3,6,8,9-tet-
rahydro-1H-furo[3,4-j]isochromen-6-yl)methyl]piper-
azin-1-yl}ethyl)benzonitrile,
3-methyl-6-[2-(3-methyl-4-{[4-(1H-tetrazol-1-yl)phenyl]
acetyl}piperazin-1-yl)ethyl]-3,4-dihydro-1H-isoch-
romen-1-one,
(3R)-3-methyl-6-[2-(4-{[6-(1H-tetrazol-1-yl)pyridin-3-
yl]acetyl}piperazin-1-yl)ethyl]-3,4-dihydro-1H-isoch-
romen-1-one,
(3S)-3-methyl-6-[2-(4-{[6-(1H-tetrazol-1-yl)pyridin-3-
yl]acetyl}piperazin-1-yl)ethyl]-3,4-dihydro-1H-isoch-
romen-1-one, or
5-(2-oxo-2-{4-[2-(1-oxo-1,3-dihydro-2-benzofuran-5-yl)
ethyl]piperazin-1-yl}ethyl)-2-(1H-tetrazol-1-yl)ben-
zonitrile,
or a pharmaceutically acceptable salt thereof.

2. A compound selected from the group consisting of:

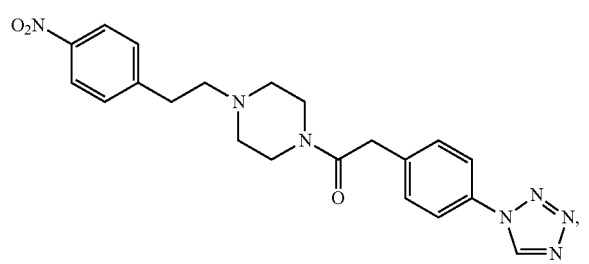

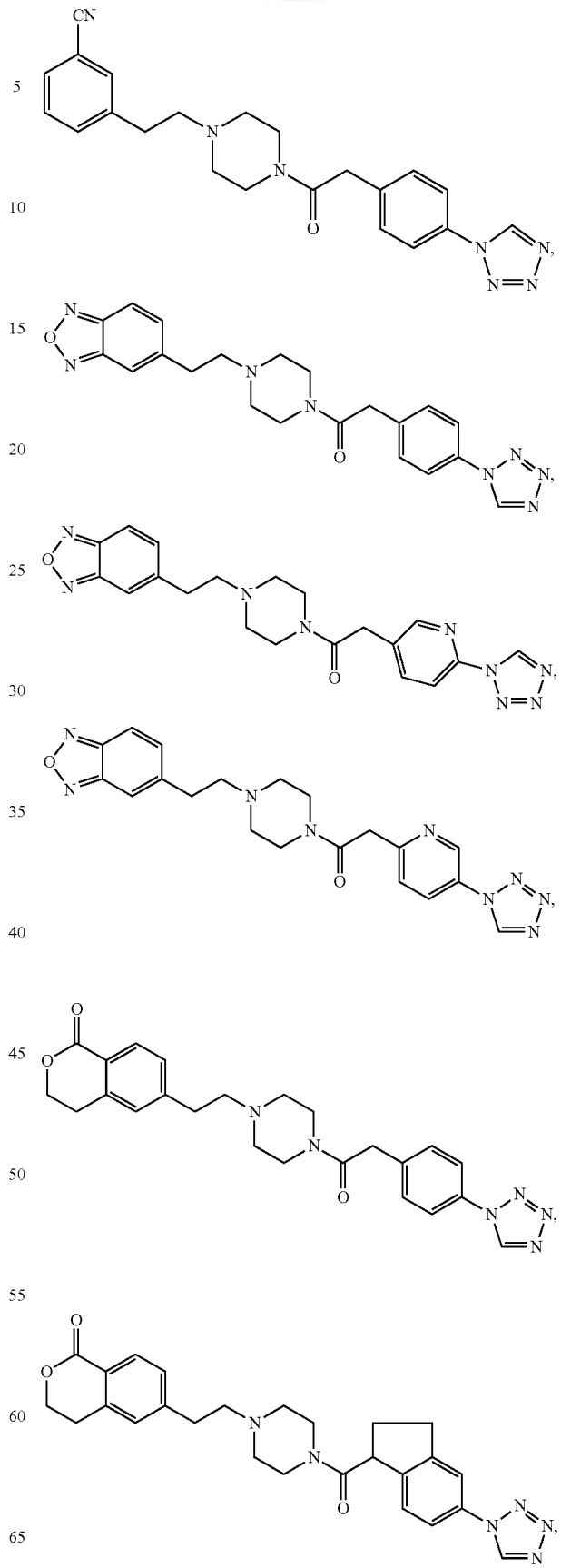

233
-continued
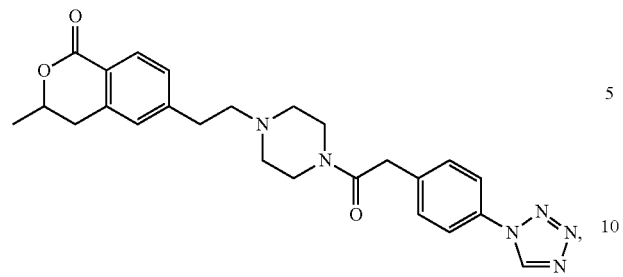
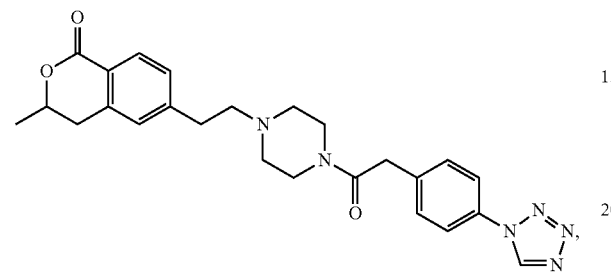
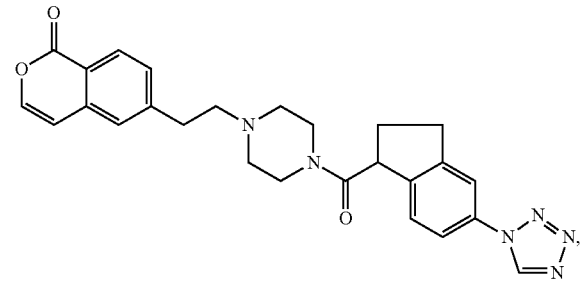
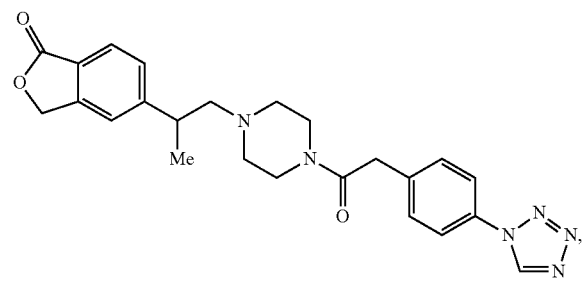
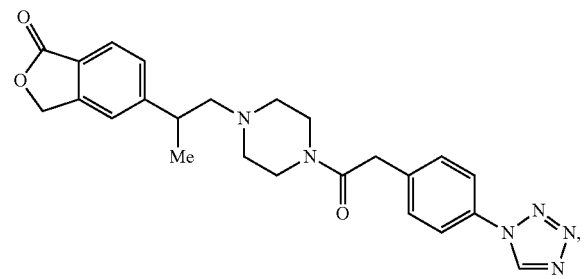
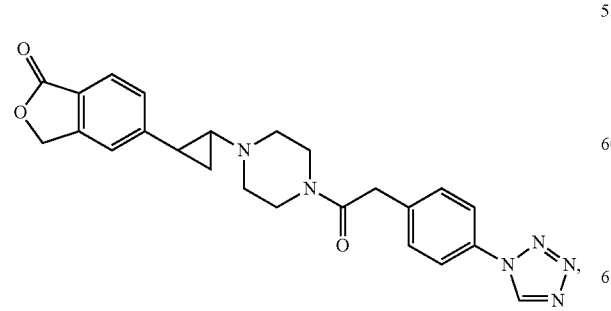
234
-continued
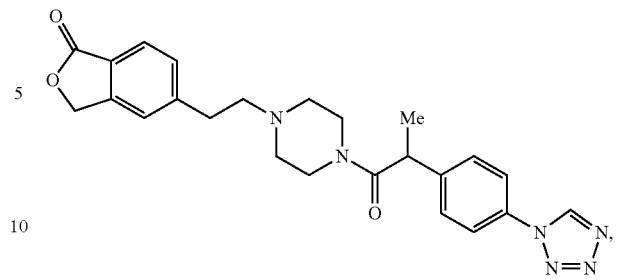
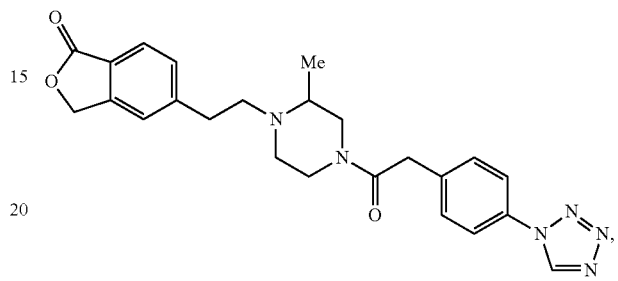
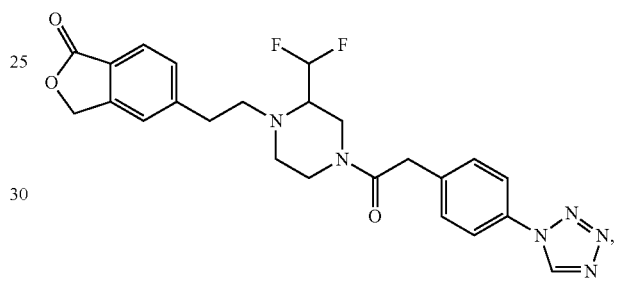
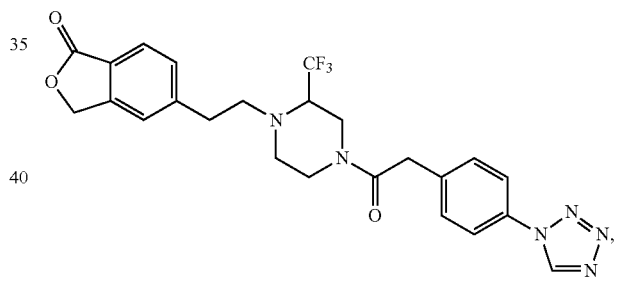
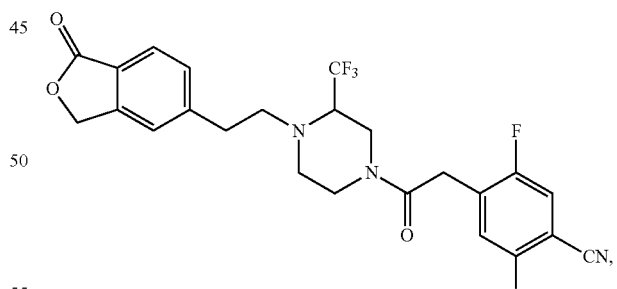
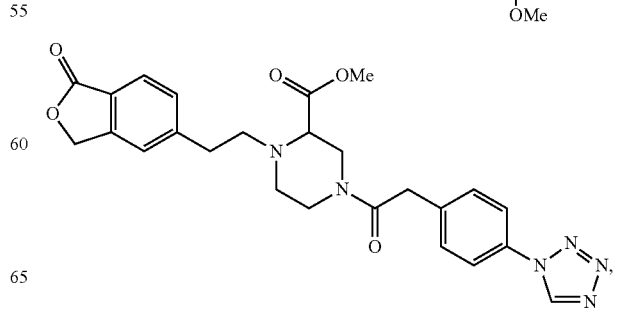

235
-continued
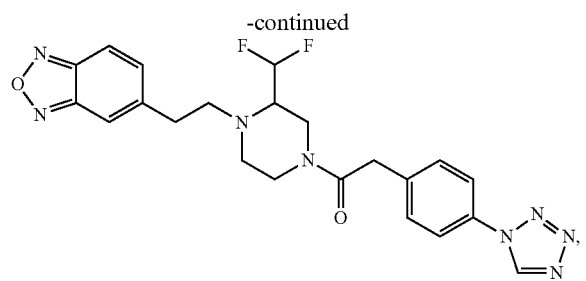
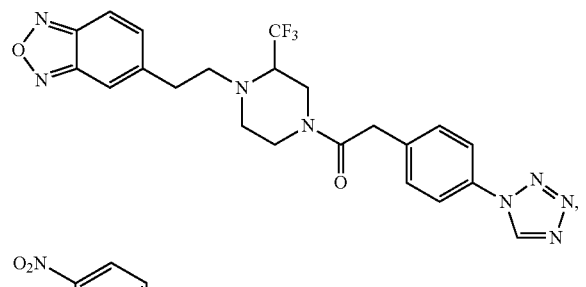
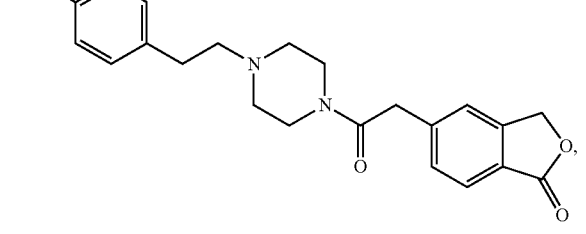
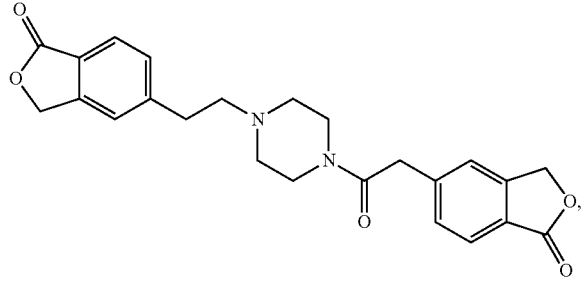 [SMILES: O=C1OCc2cc(CCN3CCN(C(=O)Cc4ccc5c(c4)COC5=O)CC3)ccc21]
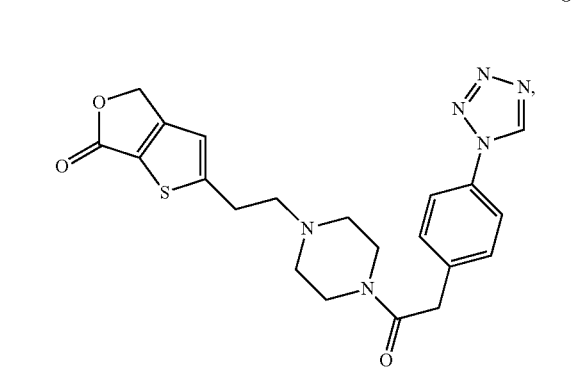
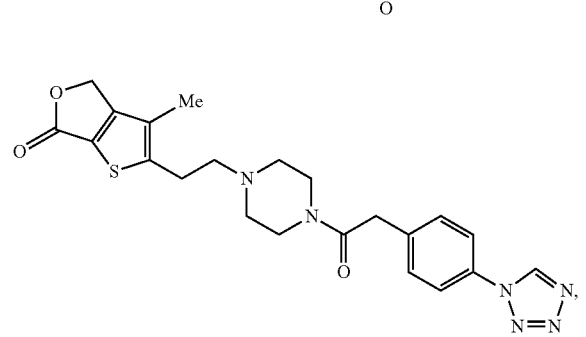
236
-continued
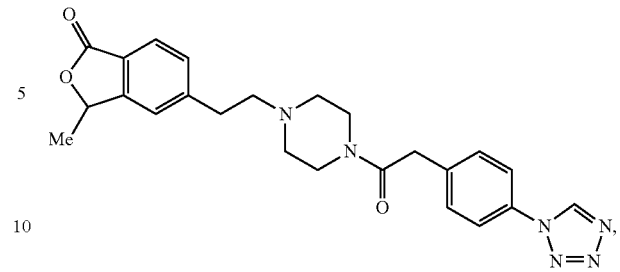
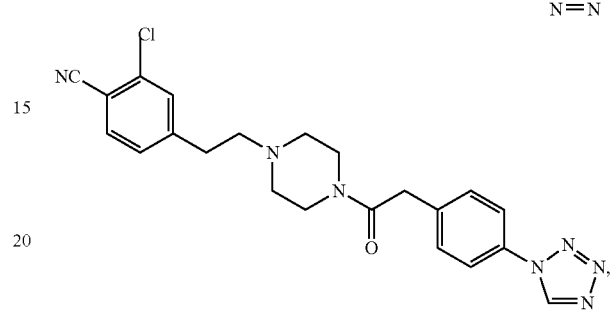
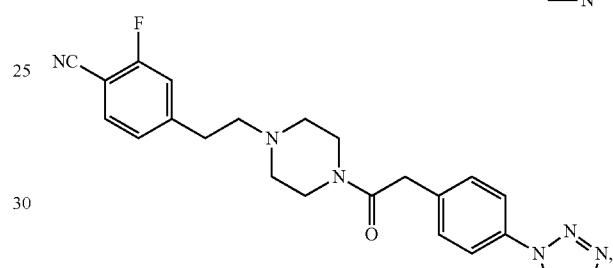
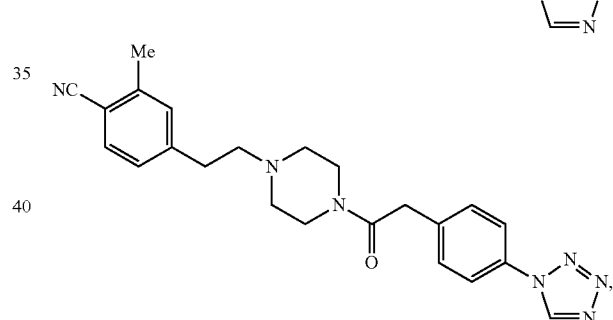
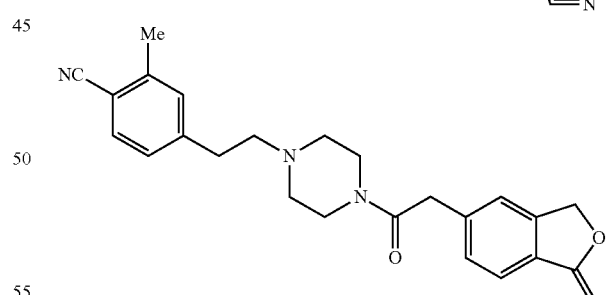
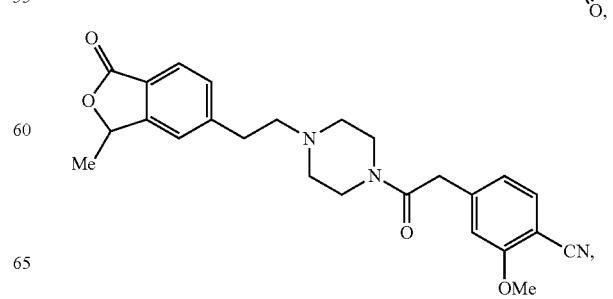

237
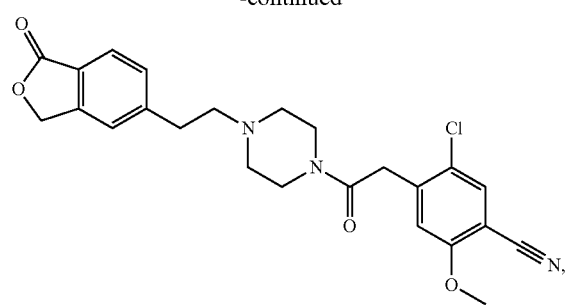
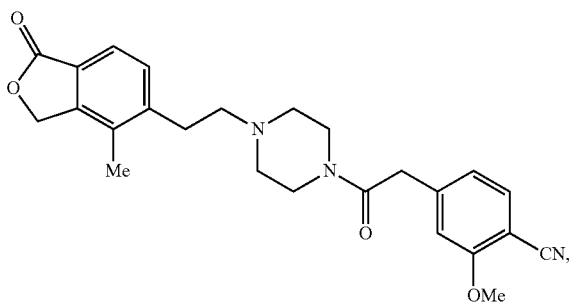
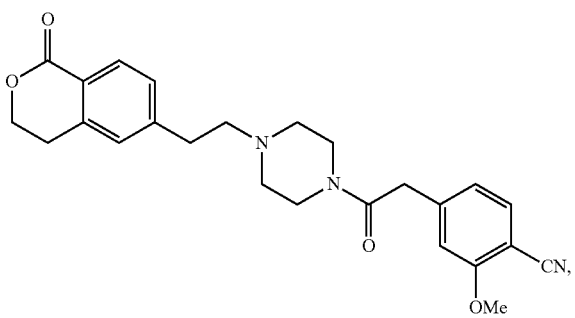
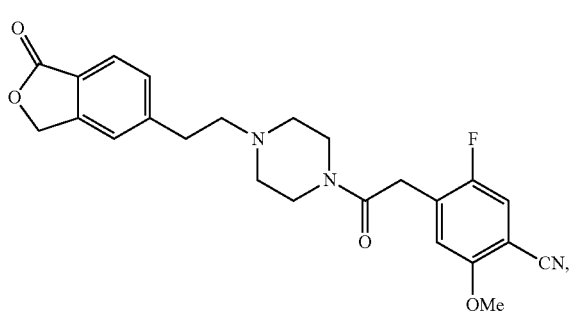
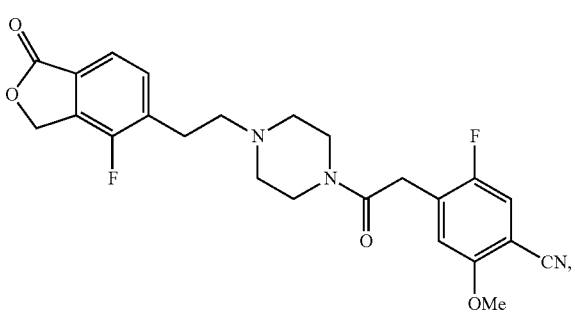
238
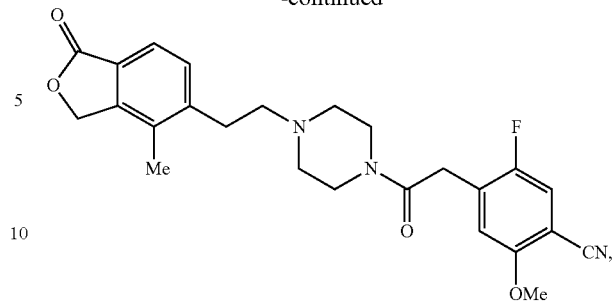
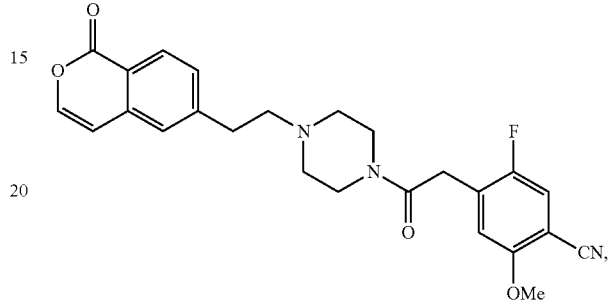
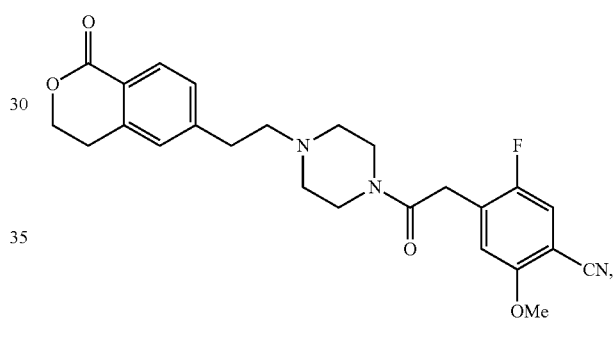
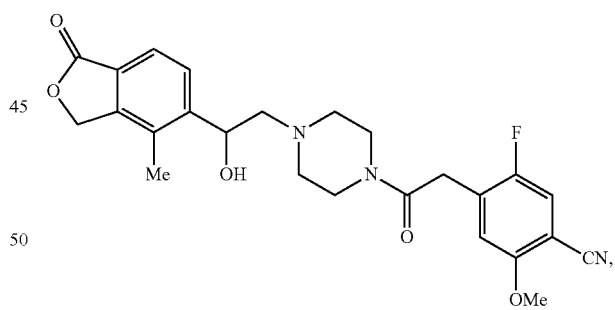
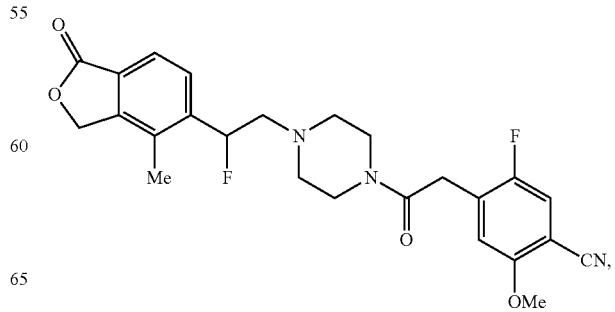

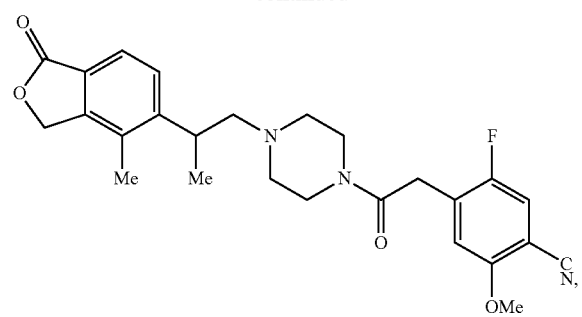
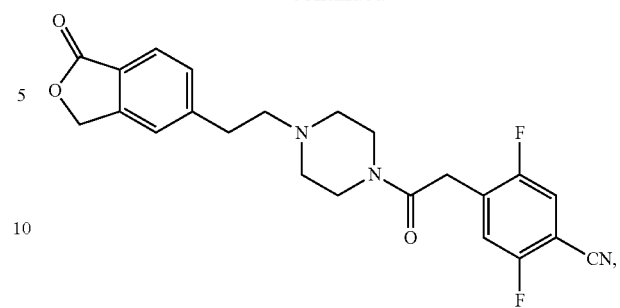
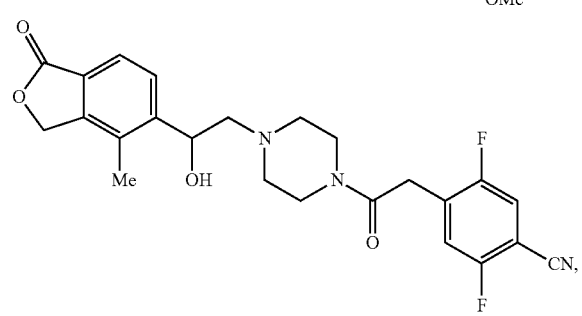
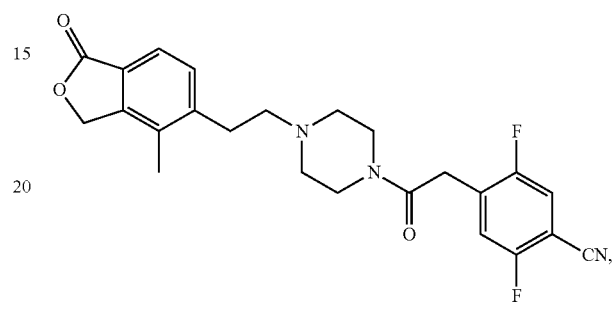
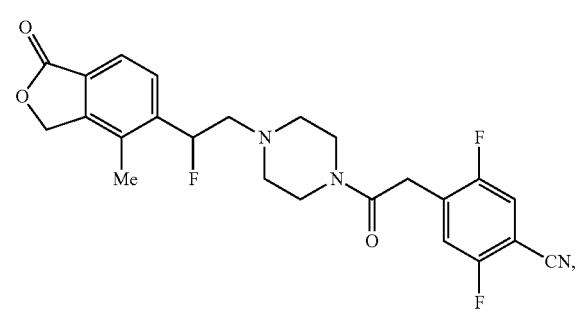
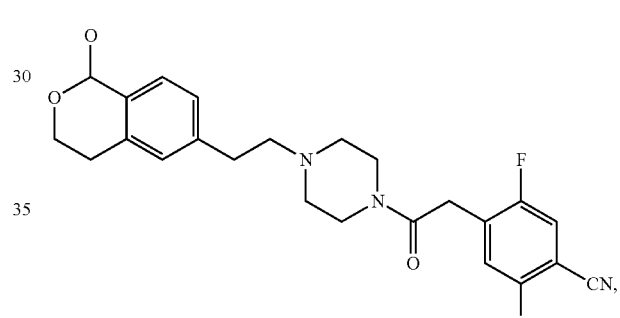
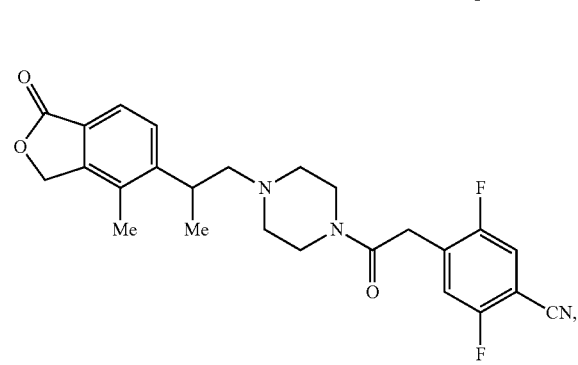
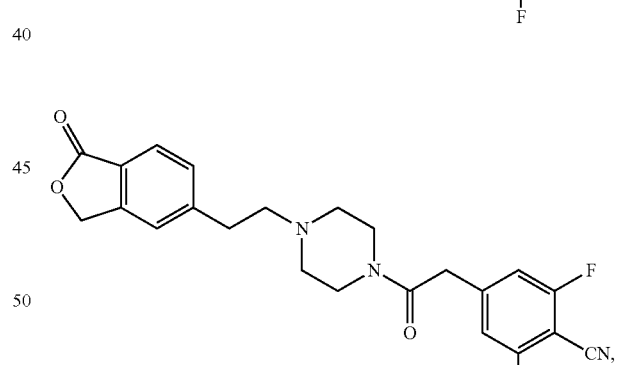
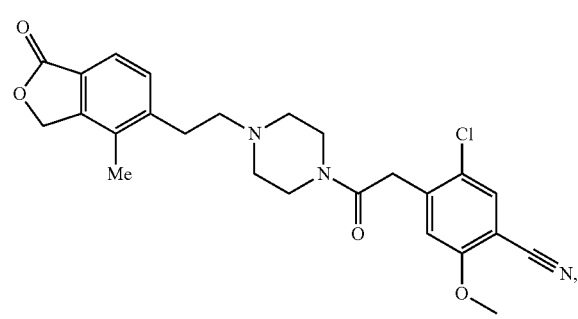
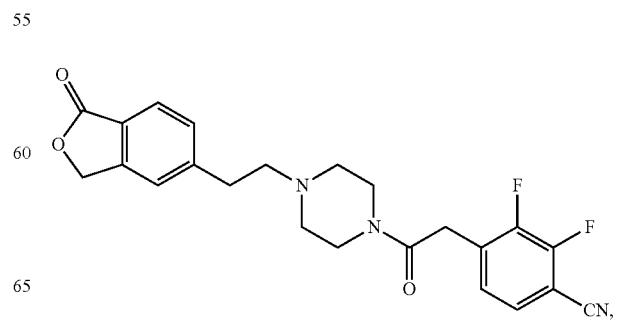

241
-continued
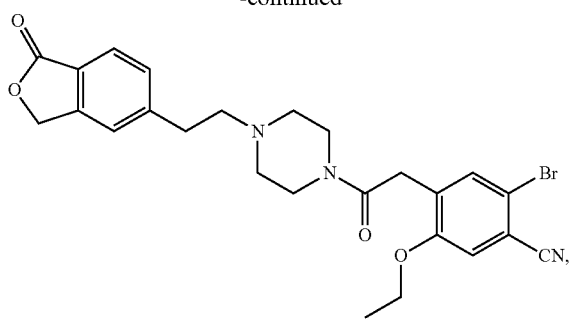
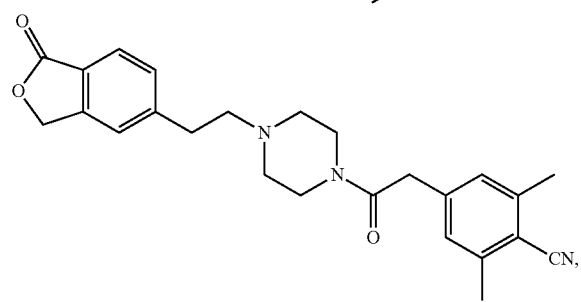
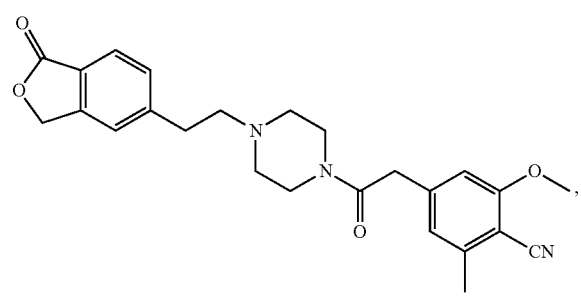
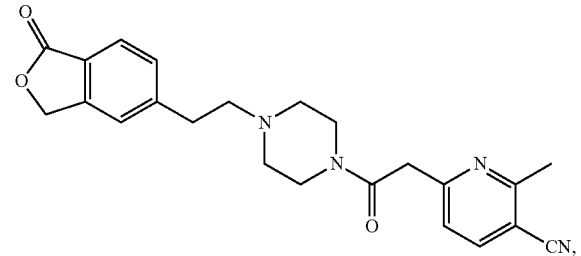
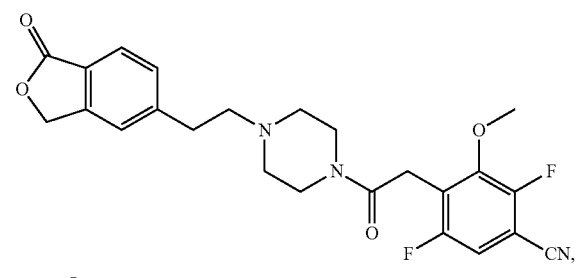
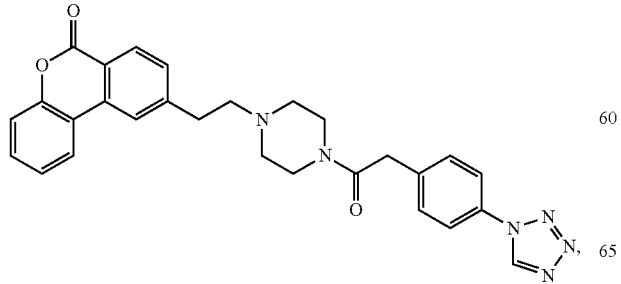
242
-continued
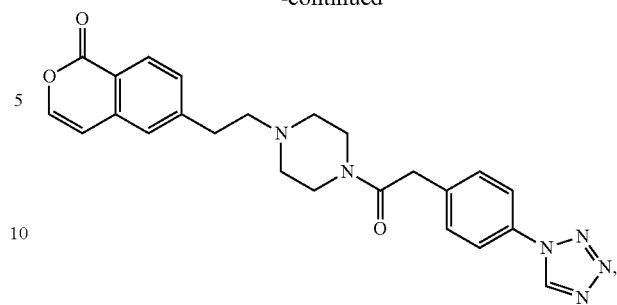
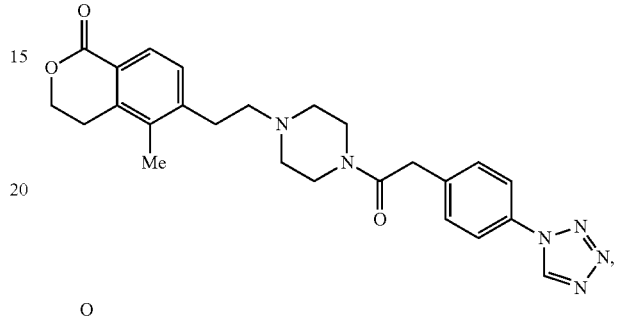
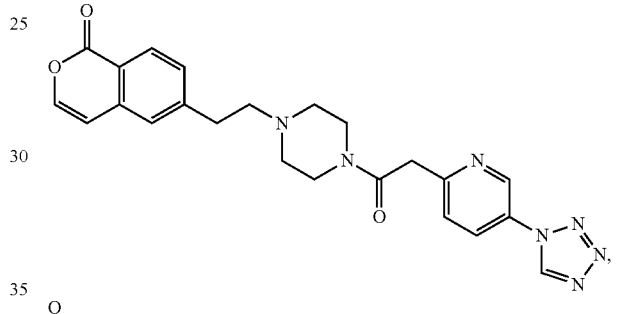
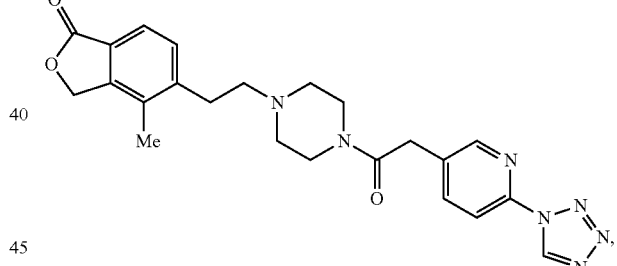
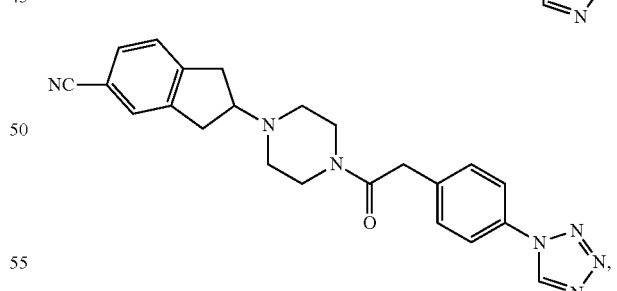
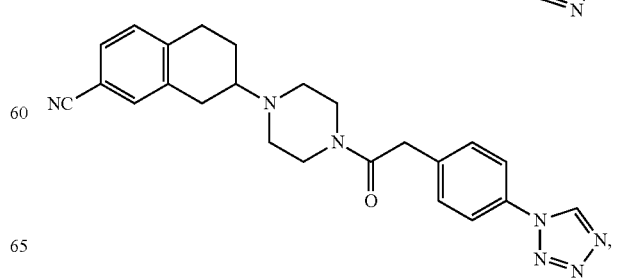

243
-continued
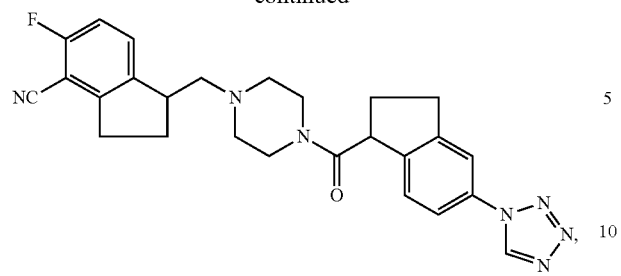
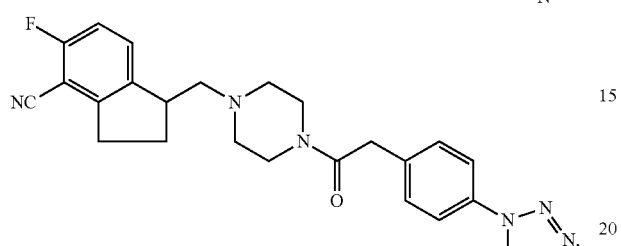
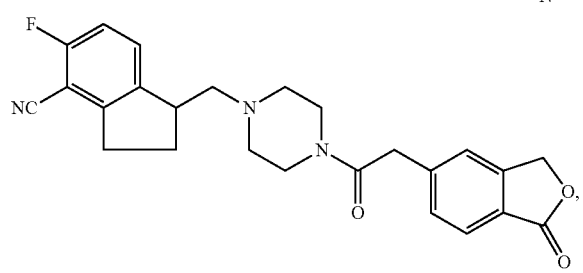
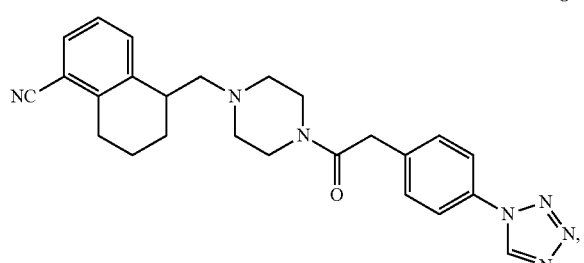
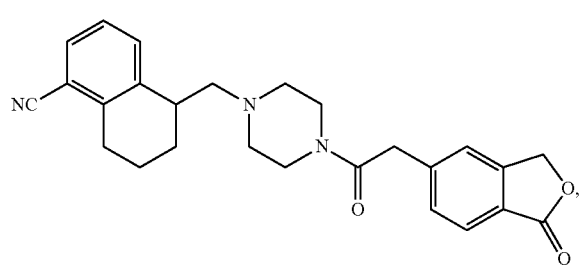
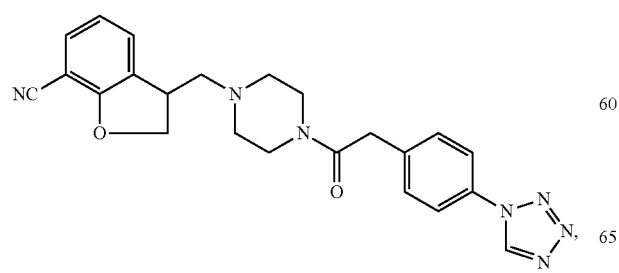
244
-continued
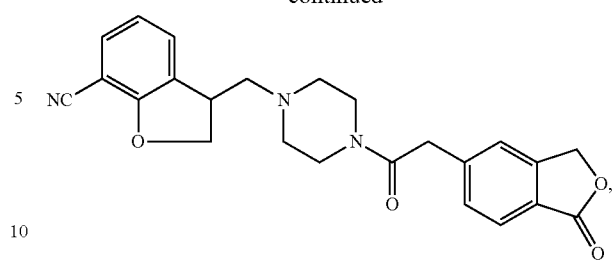
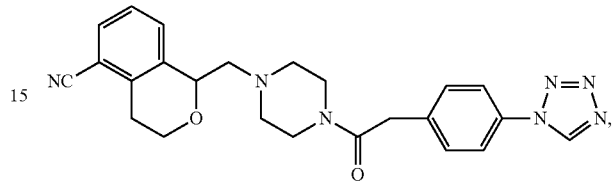
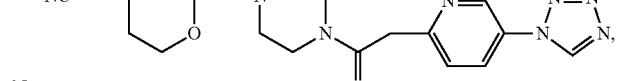
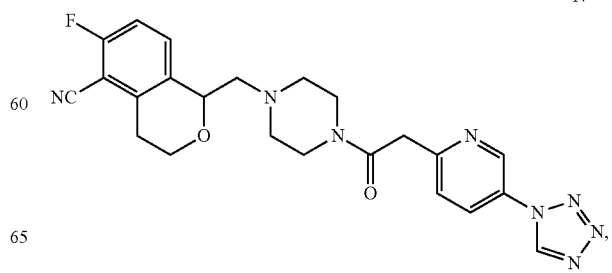

245
-continued
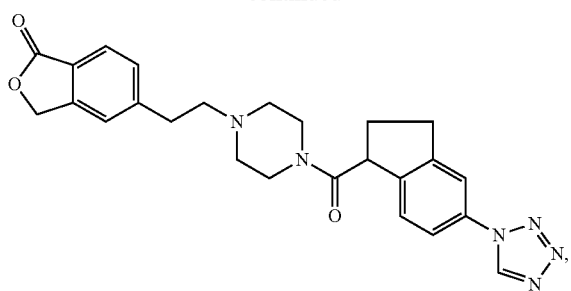
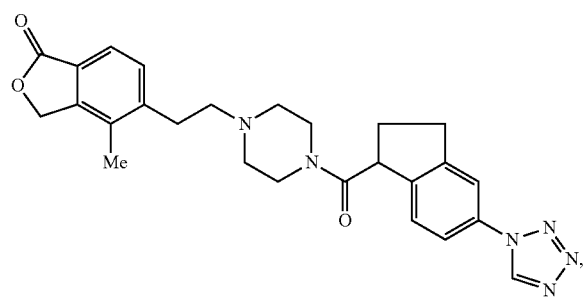
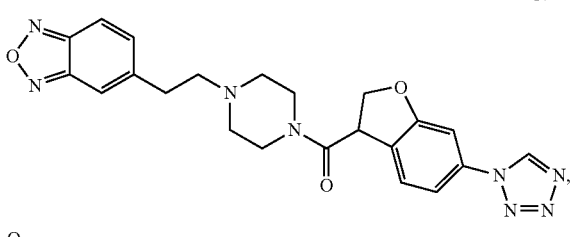
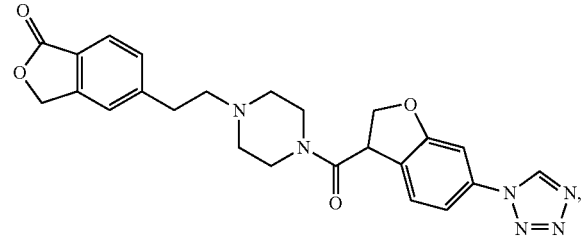
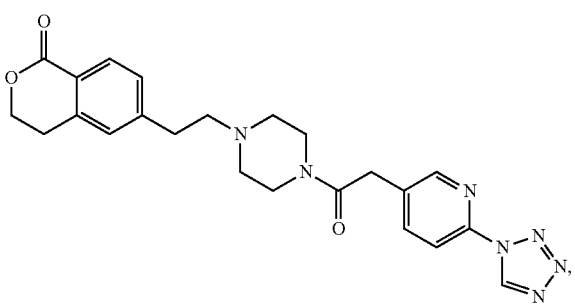
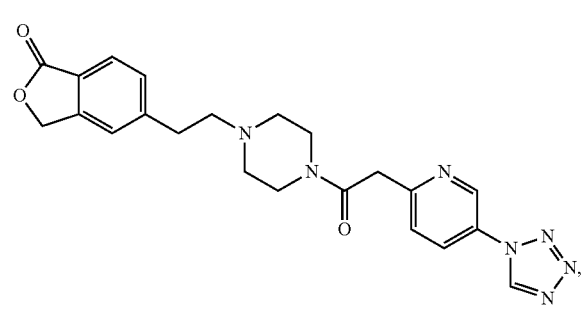
246
-continued
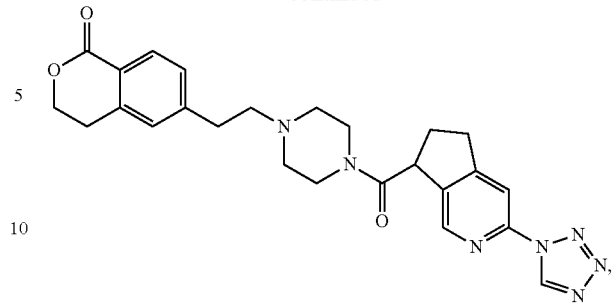
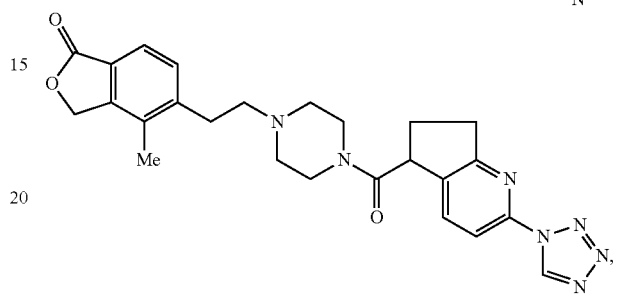
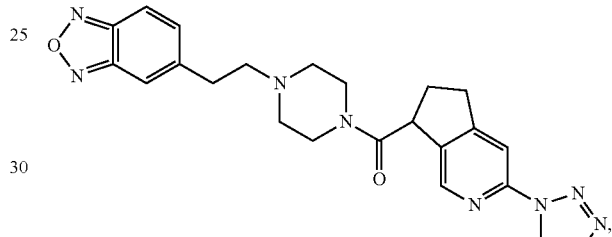
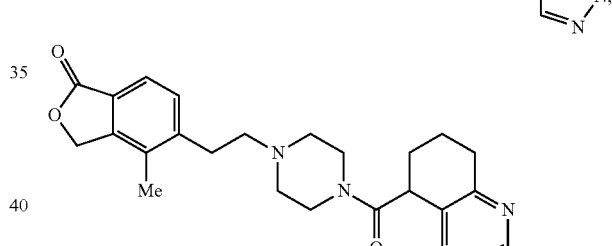
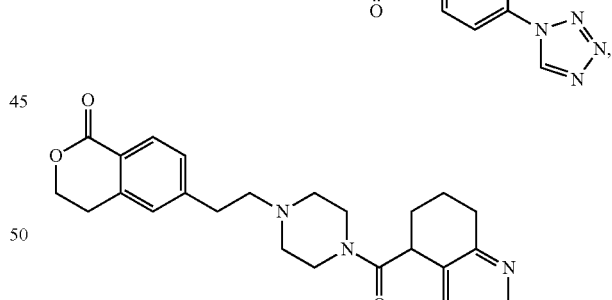
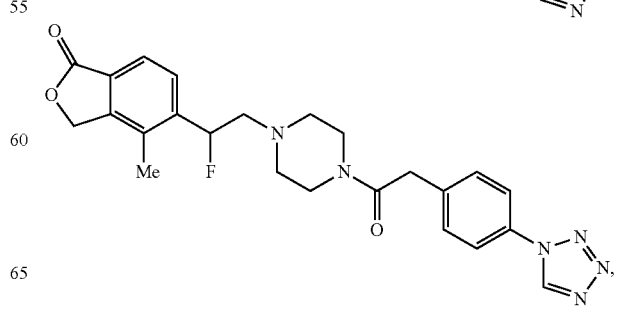

247
-continued
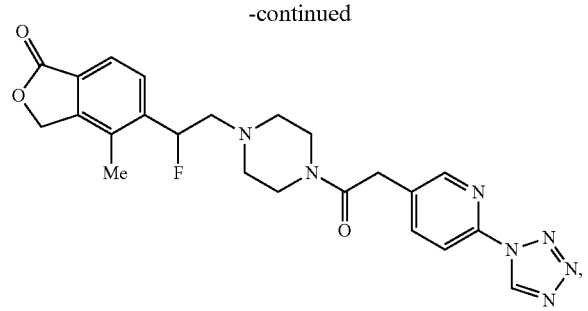
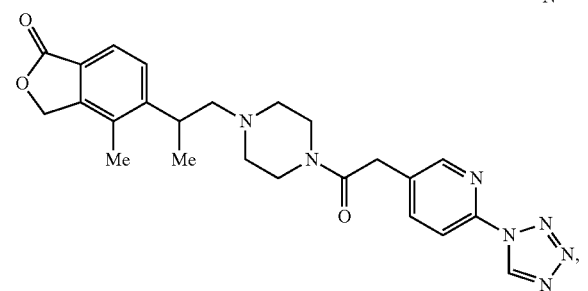
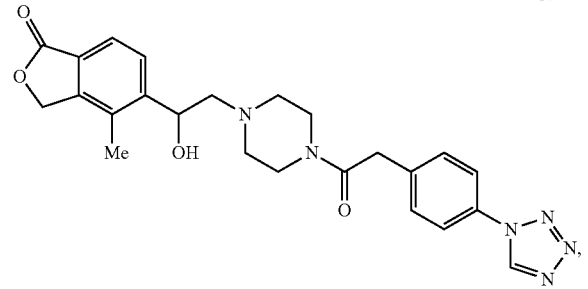
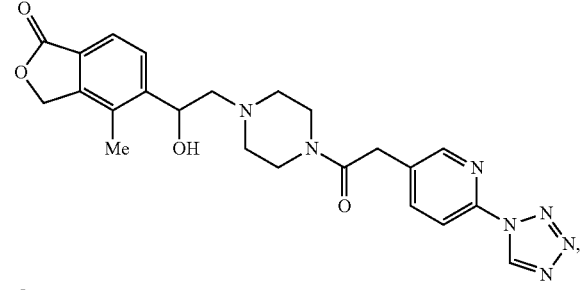
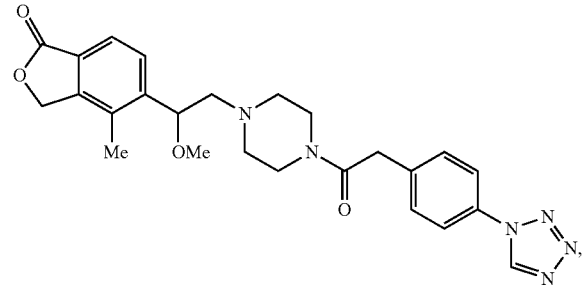
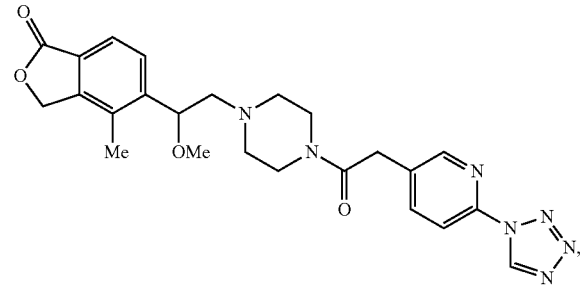
248
-continued
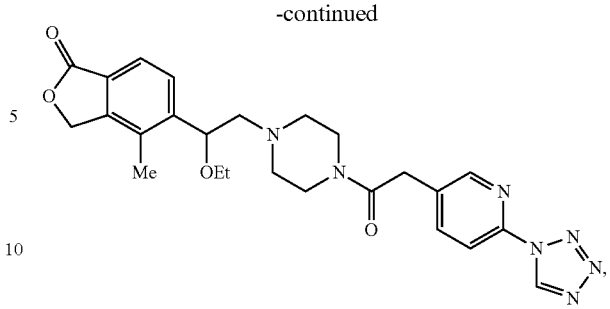
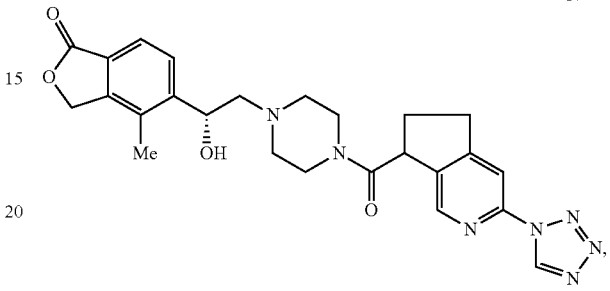
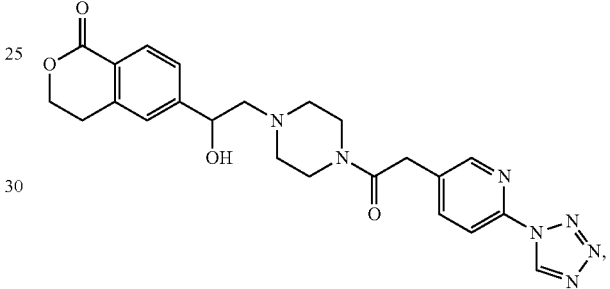
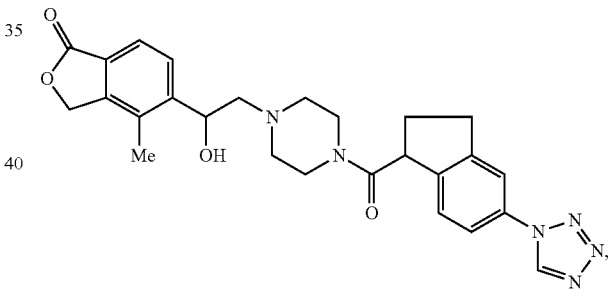
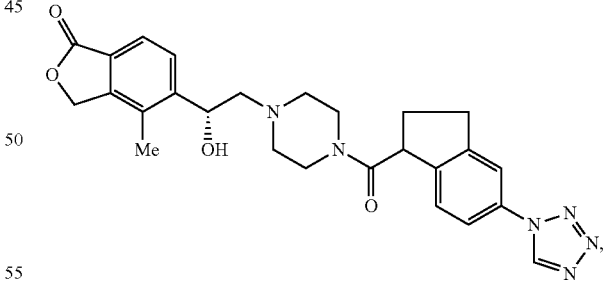
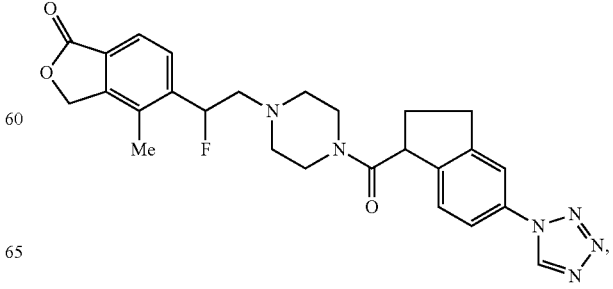

249
-continued
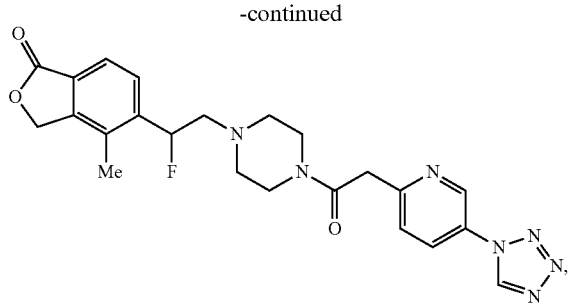
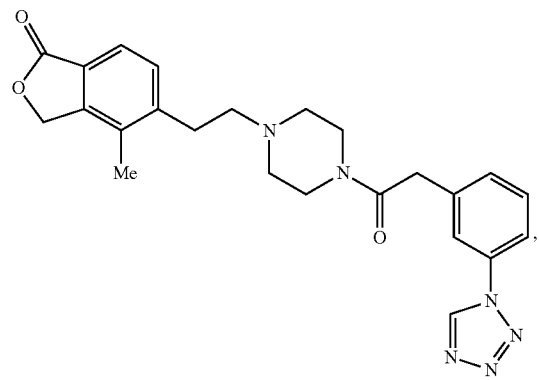
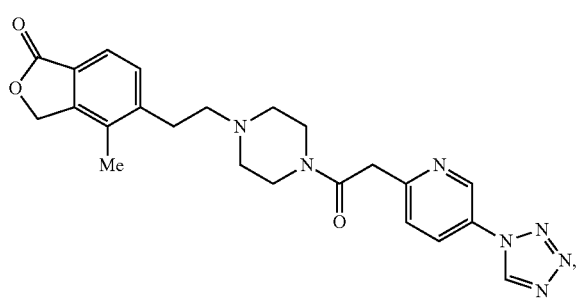
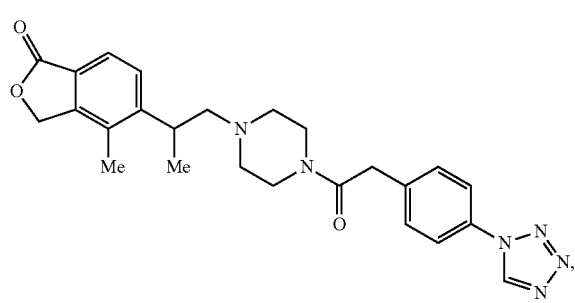
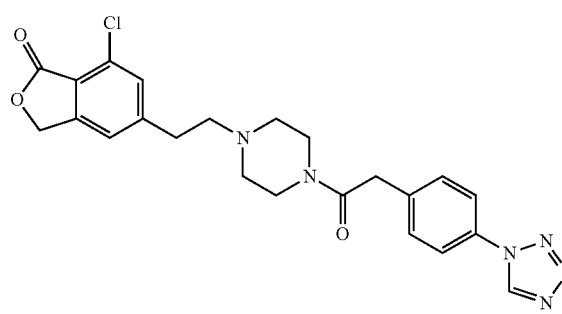
250
-continued
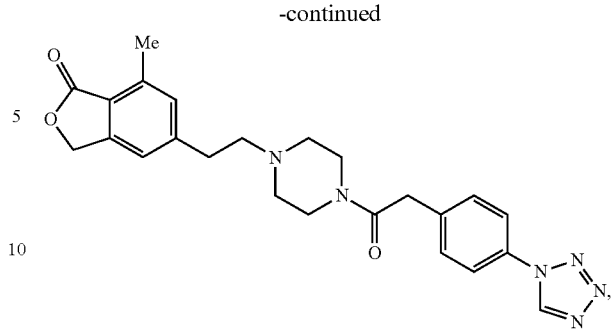
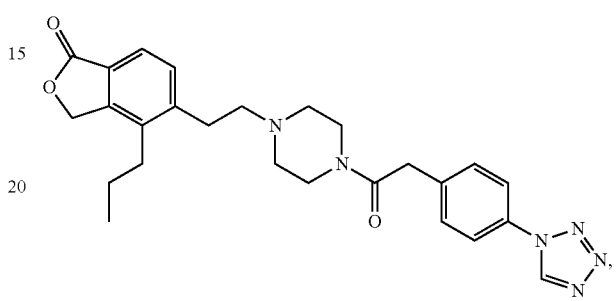
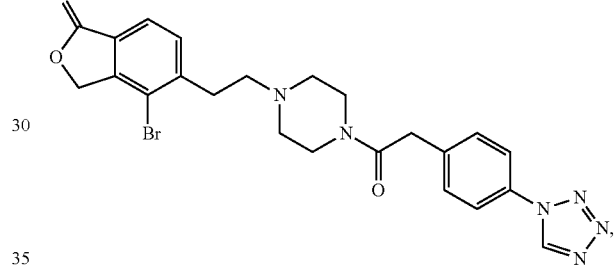
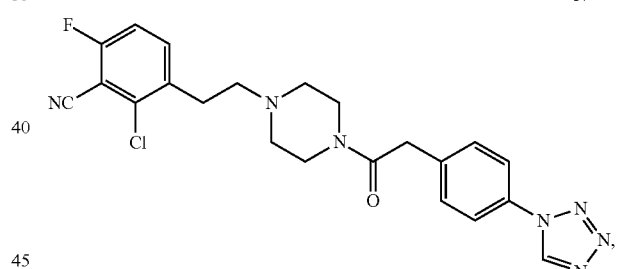
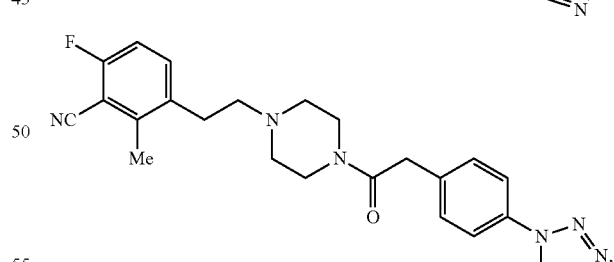
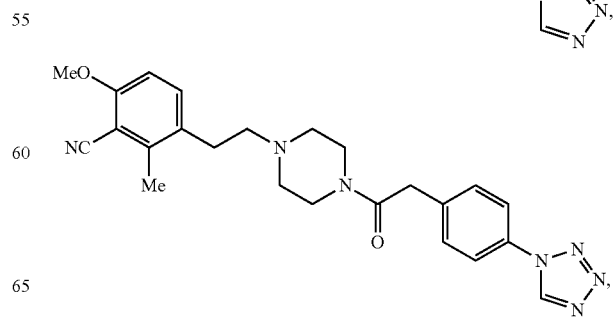

251
-continued
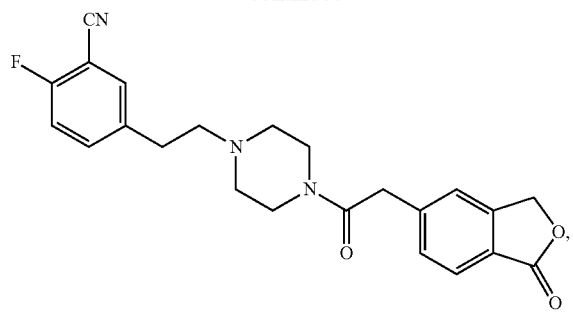
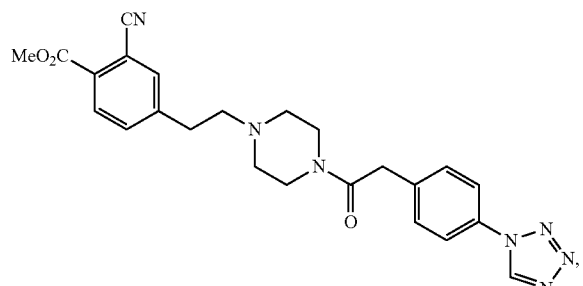
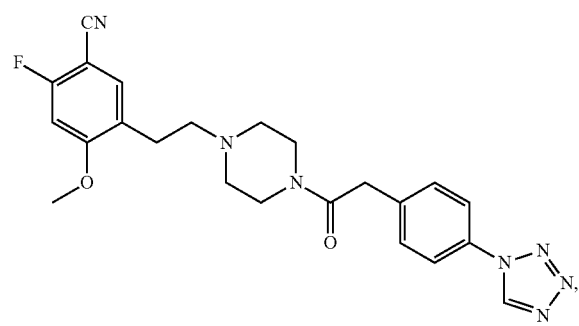
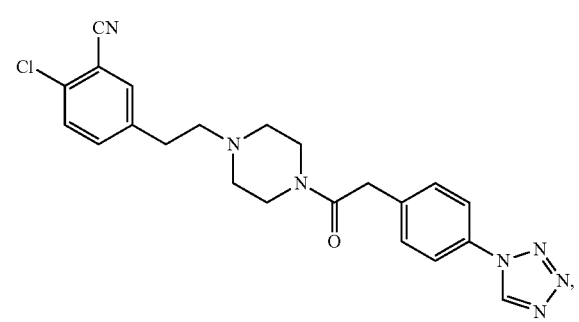
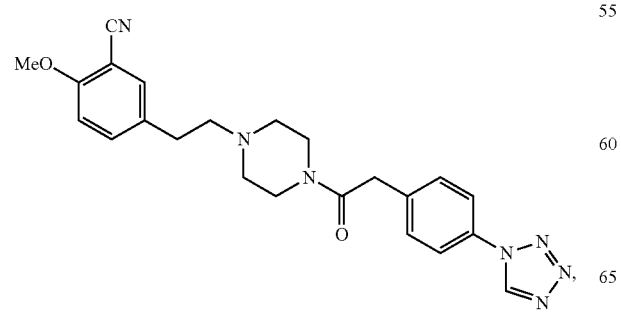
252
-continued
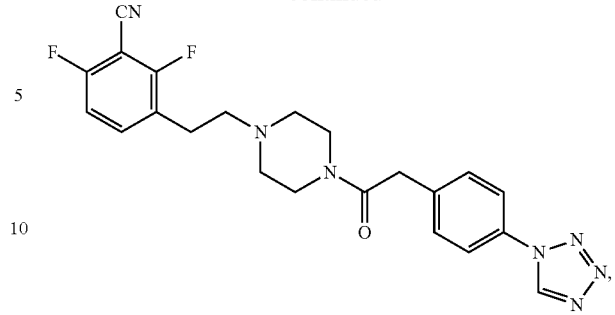
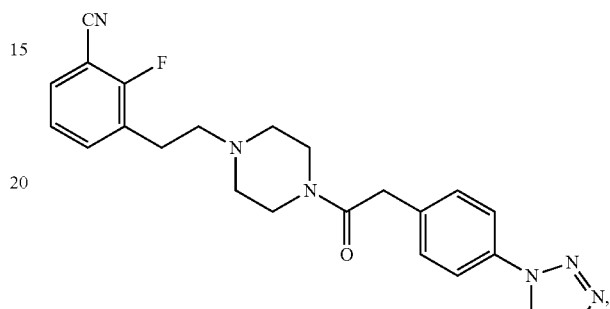
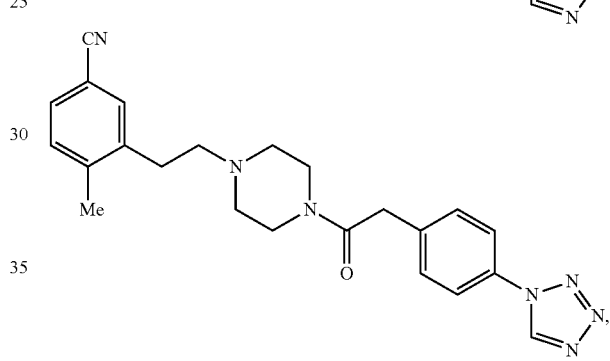
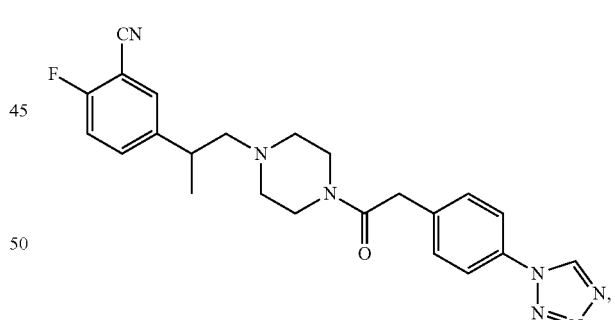
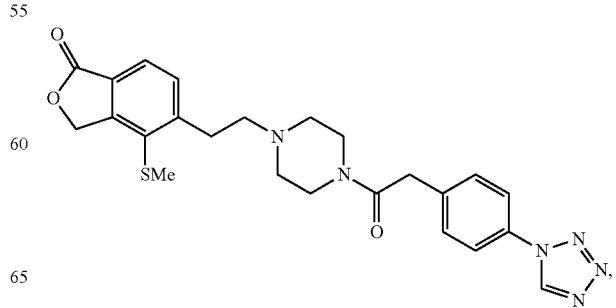

253
-continued
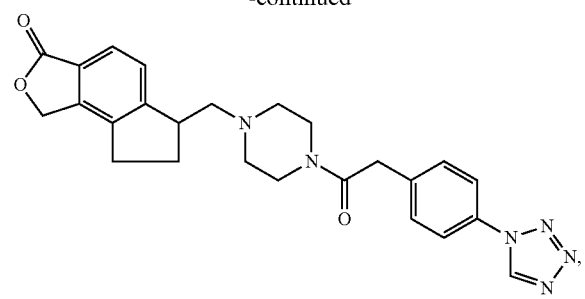
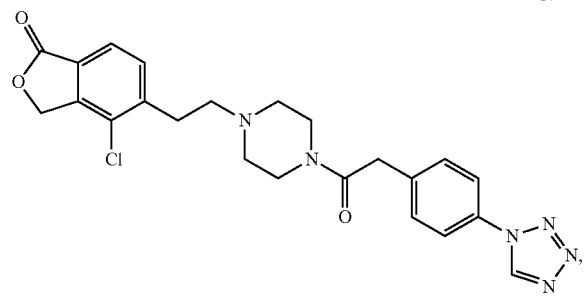
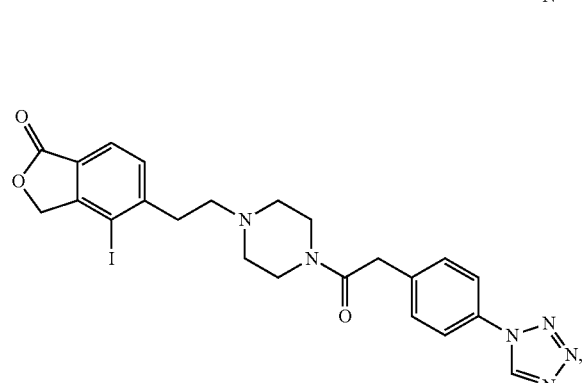
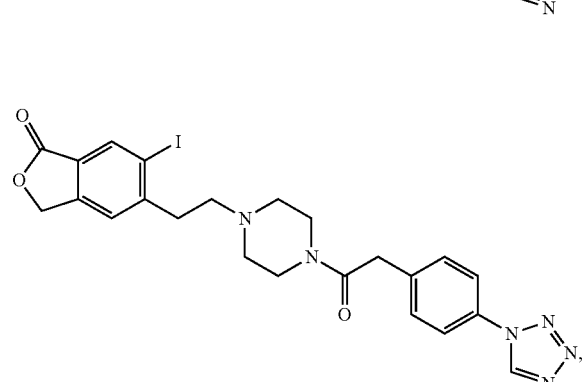
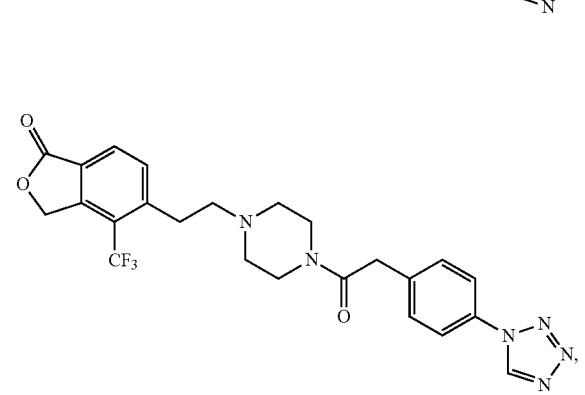
254
-continued
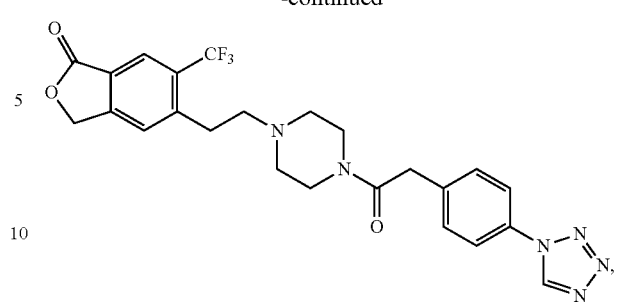
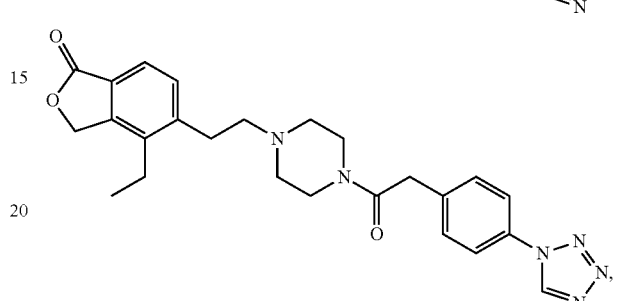
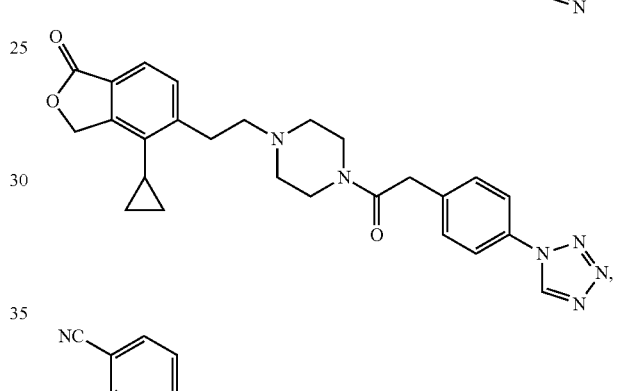
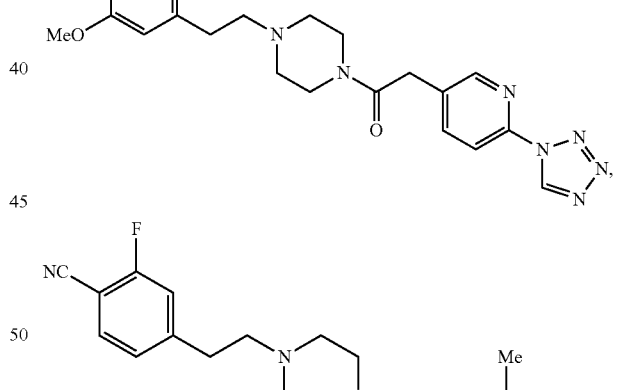
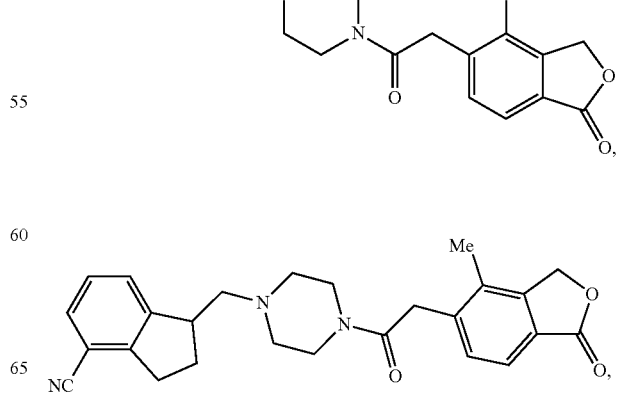

255
-continued
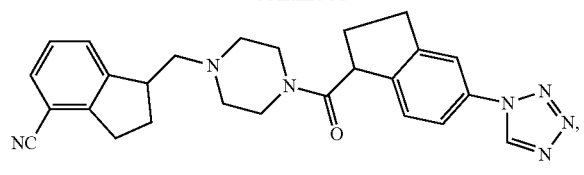
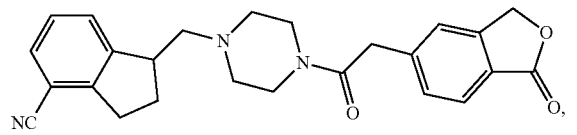
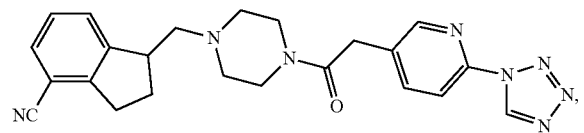
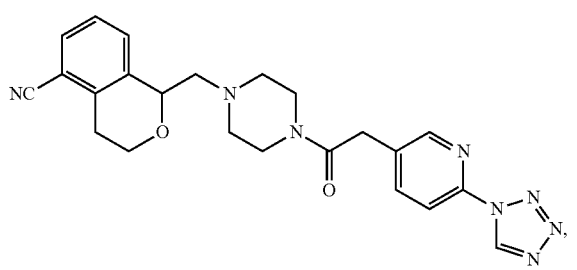
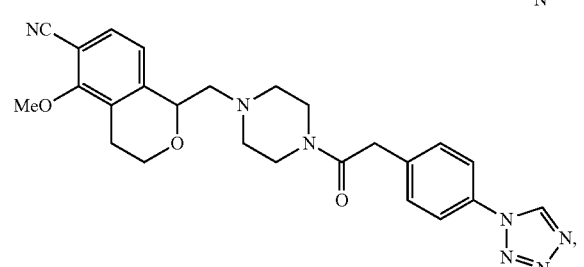
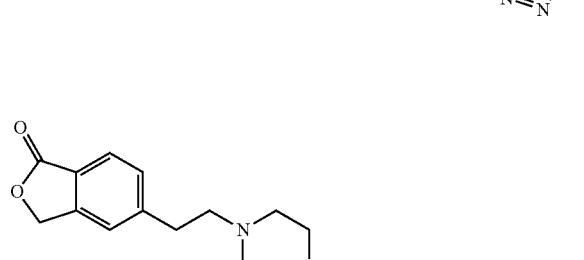
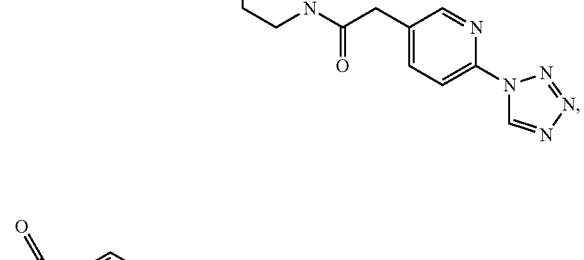
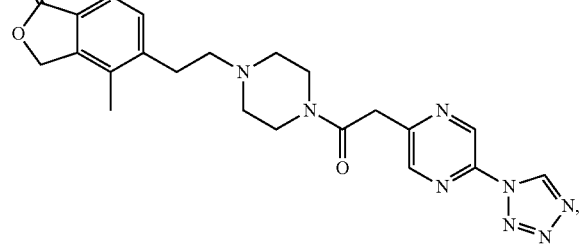
256
-continued
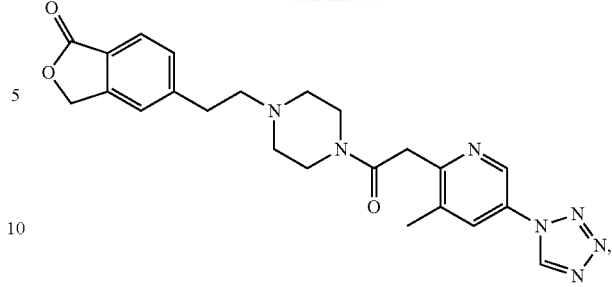
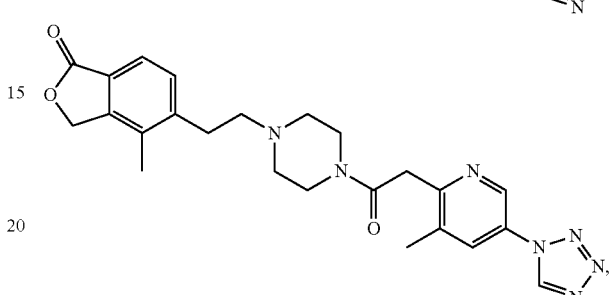
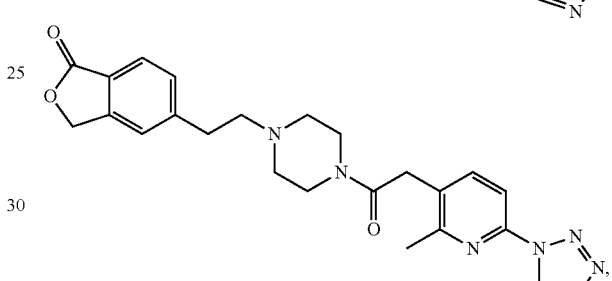
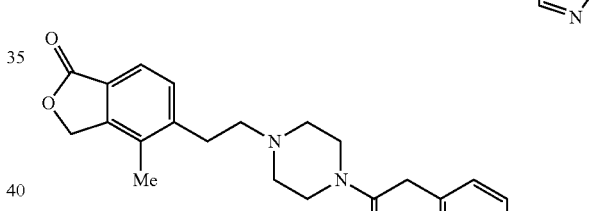
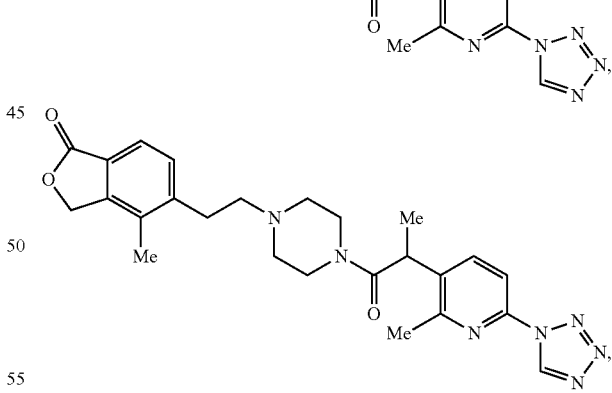
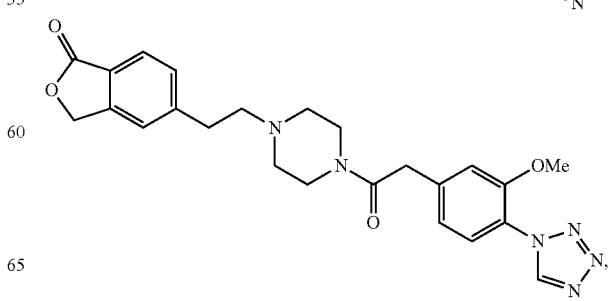

257
-continued
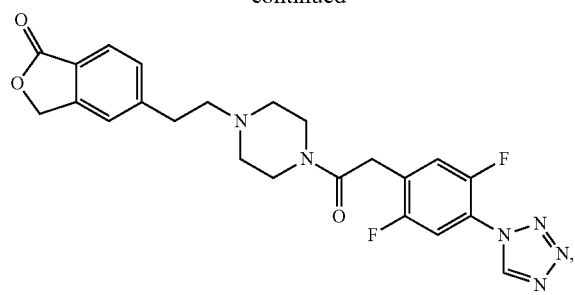
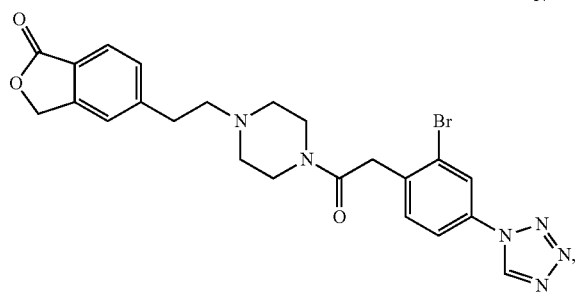
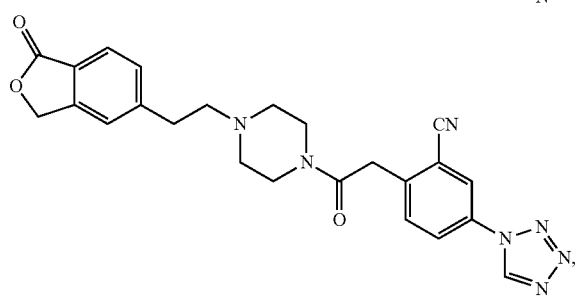
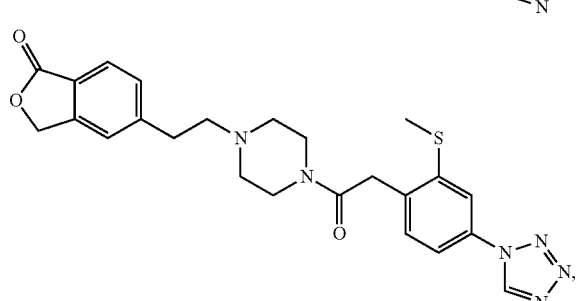
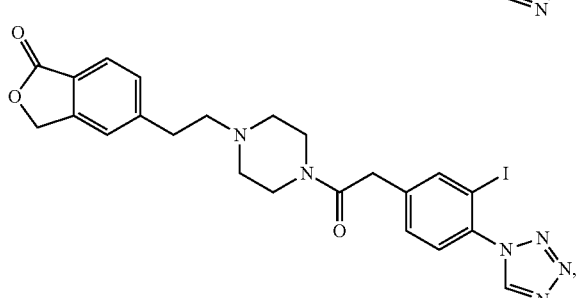
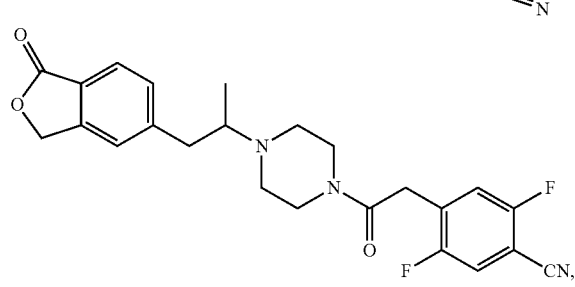
258
-continued
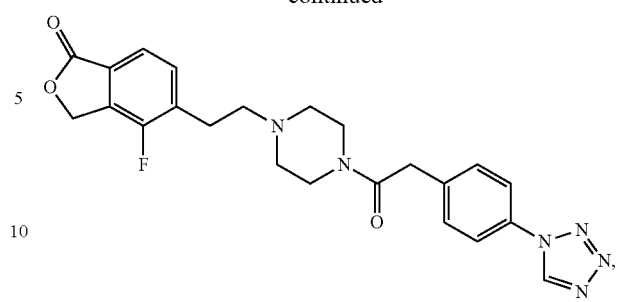
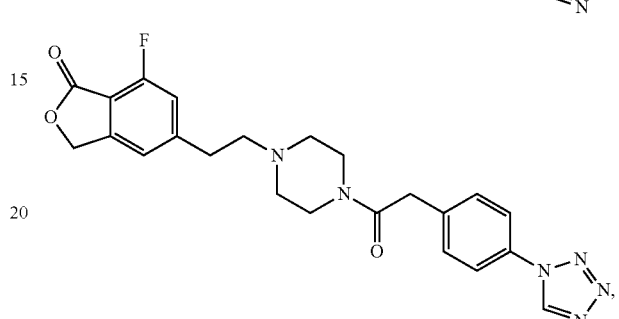
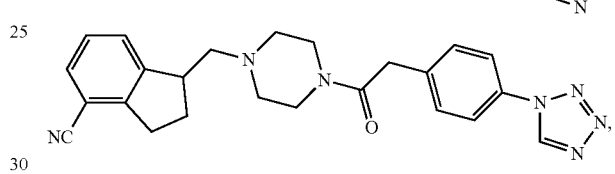
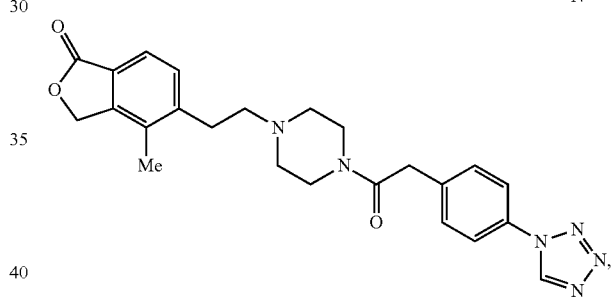
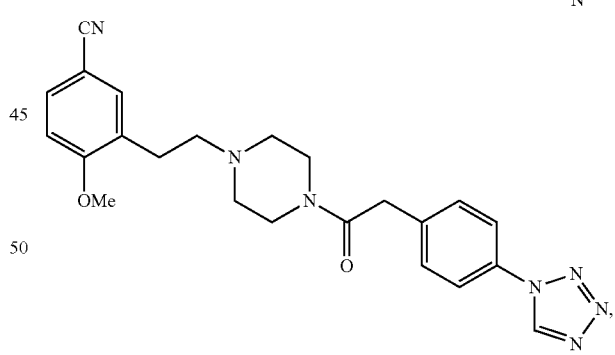
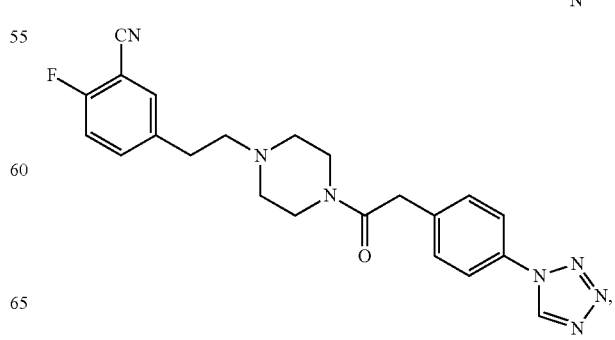

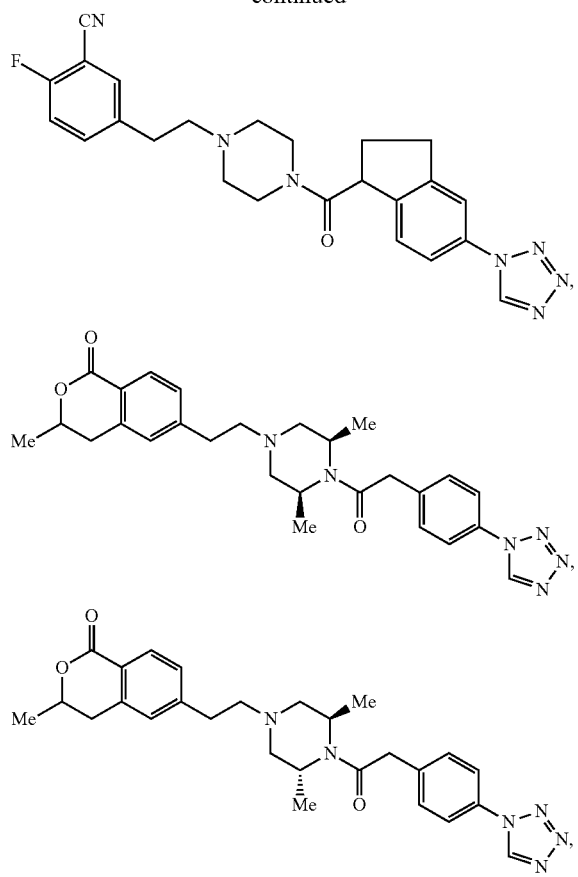
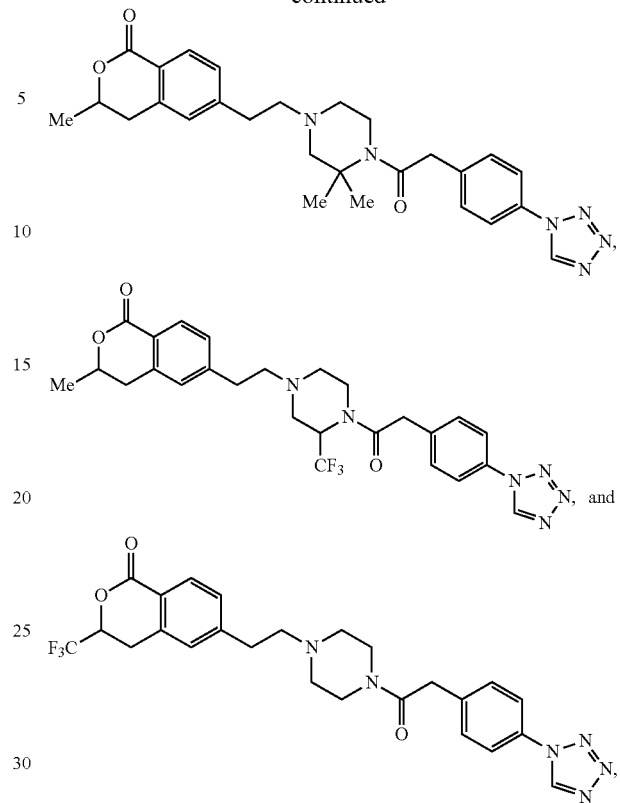
or a pharmaceutically acceptable salt thereof.
* * * * *